US010663474B2

United States Patent
Sidhu et al.

(10) Patent No.: US 10,663,474 B2
(45) Date of Patent: May 26, 2020

(54) ANTIBODIES WHICH SPECIFICALLY BIND αKLOTHO POLYPEPTIDE

(71) Applicants: The Governing Council of the University of Toronto, Toronto (CA); Board of Regents, The University of Texas System, Austin, TX (US)

(72) Inventors: Sachdev S. Sidhu, Toronto (CA); Sarah L. Barker, Toronto (CA); Orson W. Moe, Dallas, TX (US); Makoto Kuro-o, Tochigi (JP); Johanne Pastor, Flower Mound, TX (US)

(73) Assignees: The Governing Council of the University of Toronto, Toronto (CA); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/075,033

(22) PCT Filed: Feb. 3, 2017

(86) PCT No.: PCT/CA2017/050127
§ 371 (c)(1),
(2) Date: Aug. 2, 2018

(87) PCT Pub. No.: WO2017/132772
PCT Pub. Date: Aug. 10, 2017

(65) Prior Publication Data
US 2019/0041402 A1 Feb. 7, 2019

Related U.S. Application Data

(60) Provisional application No. 62/290,776, filed on Feb. 3, 2016.

(51) Int. Cl.
| | |
|---|---|
| *C07K 16/18* | (2006.01) |
| *C07K 16/28* | (2006.01) |
| *G01N 33/68* | (2006.01) |
| *G01N 33/74* | (2006.01) |
| *G01N 33/573* | (2006.01) |
| *G01N 33/541* | (2006.01) |

(52) U.S. Cl.
CPC ......... *G01N 33/6893* (2013.01); *C07K 16/18* (2013.01); *C07K 16/28* (2013.01); *G01N 33/573* (2013.01); *G01N 33/74* (2013.01); *C07K 2317/21* (2013.01); *C07K 2317/33* (2013.01); *C07K 2317/55* (2013.01); *C07K 2317/92* (2013.01); *C07K 2319/32* (2013.01); *G01N 33/541* (2013.01); *G01N 2800/347* (2013.01); *G01N 2800/52* (2013.01); *G01N 2800/56* (2013.01)

(58) Field of Classification Search
CPC .............. G01N 33/573; G01N 33/541; G01N 33/6893; G01N 2800/347; G01N 2800/52; G01N 2800/56; G01N 33/74; C07K 16/18; C07K 16/28; C07K 2317/21; C07K 2317/33; C07K 2317/55; C07K 2317/92
See application file for complete search history.

(56) References Cited

U.S. PATENT DOCUMENTS

2017/0219582 A1 8/2017 Sidhu et al.

FOREIGN PATENT DOCUMENTS

| WO | 2013/184218 | 12/2013 |
| WO | 2016/015162 A1 | 7/2015 |
| WO | 2016019456 A1 | 2/2016 |
| WO | 2016145536 | 9/2016 |
| WO | 2017132772 A1 | 8/2017 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Kuro-o M, Matsumura Y, Aizawa H, et al. (1997) Mutation of the mouse klotho gene leads to a syndrome resembling ageing. Nature 390: 45-51.
Nabeshima Y. (2002) Klotho: a fundamental regulator of aging. Ageing Res Rev 1: 627-638.
Matsumura Y, Aizawa H, Shiraki-Iida T, Nagai R, Kuro-o M, Nabeshima Y. (1998) Identification of the human klotho gene and its two transcripts encoding membrane and secreted klotho protein. Biochem Biophys Res Commun 242: 626-630.

(Continued)

*Primary Examiner* — Robert S Landsman
(74) *Attorney, Agent, or Firm* — Fitch Even Tabin & Flannery LLP

(57) ABSTRACT

An antibody and/or binding fragment thereof, wherein the antibody and/or binding fragment thereof comprises a light chain variable region and a heavy chain variable region, the light chain variable region comprising complementarity determining region (CDR) CDR-L3 and the heavy chain variable region comprising CDR-H1, CDR-H2 and CDR-H3, with the amino acid sequences of said CDRs comprising one or more of the sequences set forth below: CDR-L3; selected from any one of SEQ ID NOs: 123, 126-130, 142, 148 or 149; CDR-H1: SEQ ID NOs: 121 or 124; CDR-H2; SEQ ID NOs: 122 or 125; and/or CDR-H3: selected from any one of SEQ ID NOs: 196-226.

12 Claims, 34 Drawing Sheets

Specification includes a Sequence Listing.

(56) References Cited

OTHER PUBLICATIONS

Ben-Dov IZ, Galitzer H, Lavi-Moshayoff V, Goetz R, Kuro-o M, Mohammadi M, Sirkis R, Naveh-Many T, Silver J. (2007) The parathyroid is a target organ for FGF23 in rats. J Clin Invest 117: 4003-4008.
Ito S, Kinoshita S, Shiraishi N, Nakagawa S, Sekine S, Fujimori T, Nabeshima YI. Molecular cloning and expression analyses of mouse betaklotho, which encodes a novel Klotho family protein. (2000) Mech Dev 98: 115-119.
Kuro-o M. (2012) Klotho and betaKlotho. Adv Exp Med Biol 728: 25-40.
Hu MC, Shi M, Zhang J, et al. Klotho: a novel phosphaturic substance acting as an autocrine enzyme in the renal proximal tubule. FASEB J 2010;24(9):3438-3450.
Kato Y, Arakawa E, Kinoshita S, et al. Establishment of the anti-Klotho monoclonal antibodies and detection of Klotho protein in kidneys. Biochem Biophys Res Commun 2000;267(2):597-602.
Goetz R, Nakada Y, Hu MC, et al. Isolated C-terminal tail of FGF23 alleviates hypophosphatemia by inhibiting FGF23-FGFR-Klotho complex formation. Proc Natl Acad Sci USA 2010;107(1):407-412.
Kurosu H, Ogawa Y, Miyoshi M, et al. Regulation of fibroblast growth factor-23 signaling by klotho. J Biol Chem 2006;281(10):6120-6123.
Urakawa I, Yamazaki Y, Shimada T, et al. Klotho converts canonical FGF receptor into a specific receptor for FGF23. Nature 2006;444(7120):770-774.
Hu MC, Shi M, Zhang J, et al. Klotho deficiency causes vascular calcification in chronic kidney disease. J Am Soc Nephrol 2011;22(1):124-136.
Imura A, Iwano A, Tohyama 0, et al. Secreted Klotho protein in sera and CSF: implication for post-translational cleavage in release of Klotho protein from cell membrane. FEBS Lett 2004;565(1-3):143-147.
Bloch L, Sineshchekova 0, Reichenbach D, et al. Klotho is a substrate for alpha-, beta- and gamma-secretase. FEBS Lett 2009;583(19):3221-3224.
Chen CD, Podvin S, Gillespie E, et al. Insulin stimulates the cleavage and release of the extracellular domain of Klotho by ADAM10 and ADAM17. Proc Natl Acad Sci U S A 2007;104(50):19796-19801.
Hu MC, Shi M, Zhang J, et at., Renal production, uptake, and handling of circulating alpha-klotho. J Am Soc Nephrol 27(1): Jan. 2016, pp. 79-90.
Hu MC, Kuro-o M, Moe OW. Secreted klotho and chronic kidney disease. Adv Exp Med Biol 2012;728:126-157.
Aizawa H, Saito Y, Nakamura T, et al. Downregulation of the Klotho gene in the kidney under sustained circulatory stress in rats. Biochem Biophys Res Commun 1998;249(3):865-871.
Cheng MF, Chen LJ, Cheng JT. Decrease of Klotho in the kidney of streptozotocin-induced diabetic rats. J Biomed Biotechnol 2010;2010:513853.
Haruna Y, Kashihara N, Satoh M, et al. Amelioration of progressive renal injury by genetic manipulation of Klotho gene. Proc Natl Acad Sci U S A 2007;104(7):2331-2336.
Koh N, Fujimori T, Nishiguchi S, et al. Severely reduced production of klotho in human chronic renal failure kidney. Biochem Biophys Res Commun 2001;280(4)1 015-1020.
Mitani H, Ishizaka N, Aizawa T, et al. In vivo klotho gene transfer ameliorates angiotensin II-induced renal damage. Hypertension 2002;39(4):838-843.
Wang Y, Sun Z. Klotho gene delivery prevents the progression of spontaneous hypertension and renal damage. Hypertension 2009;54:810-817.
Zhao Y, Banerjee S, Dey N, et al. Klotho depletion contributes to increased inflammation in kidney of the db/db mouse model of diabetes via RelA (serine)536 phosphorylation. Diabetes 2011;60(7)1 907-1916.
Hu MC, Shi M, Zhang J, et al. Klotho deficiency is an early biomarker of renal ischemia-reperfusion injury and its replacement is protective. Kidney Int 2010;78(12):1240-1251.
Hu MC, Moe OW. Klotho as a potential biomarker and therapy for acute kidney injury. Nat Rev Nephrol 2012;8(7):423-429.
Goetz R, Beenken A, Ibrahim' OA, et al. (2007) Molecular insights into the klotho-dependent, endocrine mode of action of fibroblast growth factor 19 subfamily members. Mol Cell Biol 27:3417-3428.
Shimada T, Kakitani M, Yamazaki Y, Hasegawa H, Takeuchi Y, Fujita T, Fukumoto S, Tomizuka K, Yamashita T. (2004) Targeted ablation of Fgf23 demonstrates an essential physiological role of FGF23 in phosphate and vitamin D metabolism. J Clin Invest 113: 561-568.
Ichikawa S, Imel EA, Kreiter ML, et al. (2007) A homozygous missense mutation in human Klotho causes severe tumoral calcinosis. J Clin Invest 117: 2684-2691.
Kuro-o M. (2010) Overview of the FGF23-Klotho axis. Pediatr Nephrol 25: 583-590.
Kurosu H, Kuro OM. (2009) The Klotho gene family as a regulator of endocrine fibroblast growth factors. Mol Cell Endocrinol 299: 72-78.
Ayodele OE, Alebiosu CO. (2010) Burden of chronic kidney disease: an international perspective. Adv Chronic Kidney Dis 17: 215-224.
Soni RK, Weisbord SD, Unruh ML (2010) Health-related quality of life outcomes in chronic kidney disease. Curr Opin Nephrol Hypertens 19: 153-159.
Trivedi H. (2010) Cost implications of caring for chronic kidney disease: are interventions cost-effective? Adv Chronic Kidney Dis 17: 265-270.
Ganesh SK, Stack AG, Levin NW, Hulbert-Shearon T, Port FK. (2001) Association of elevated serum P0(4), Ca x P0(4) product, and parathyroid hormone with cardiac mortality risk in chronic hemodialysis patients. J Am Soc Nephrol 12: 2131-2138.
Tonelli M, Curhan G, Pfeffer M, Sacks F, Thadhani R, Melamed ML, Wiebe N, Muntner P. (2009) Relation between alkaline phosphatase, serum phosphate, and all-cause or cardiovascular mortality. Circulation 120: 1784-1792.
Gutierrez 0, Isakova T, Rhee E, Shah A, Holmes J, Collerone G, Juppner H, Wolf M. (2005) Fibroblast growth actor-23 mitigates hyperphosphatemia but accentuates calciticl deficiency in chronic kidney disease. J Am Soc Nephrol 16: 2205-2215.
Asai 0, Nakatani K, Tanaka T, et al. Decreased renal alpha-Klotho expression in early diabetic nephropathy in humans and mice and its possible role in urinary calcium excretion. Kidney Int 2012; 81 (6): 539-547.
Akimoto T, Kimura T, Watanabe Y, et al. The impact of nephrectomy and renal transplantation on serum levels of soluble Klotho protein. Transplant Proc 2013;45(1):134-136.
Akimoto T, Shiizaki K, Sugase T, et al. The relationship between the soluble Klotho protein and the residual renal function among peritoneal dialysis patients. Clin Exp Nephrol 2012;16(3):442-447.
Akimoto T, Yoshizawa H, Watanabe Y, et al. Characteristics of urinary and serum soluble Klotho protein in patients with different degrees of chronic kidney disease. BMC Nephrol 2012;13:155.
Carpenter TO, Insogna KL, Zhang JH, et al. Circulating Levels of Soluble Klotho and FGF23 in X-Linked Hypophosphatemia: Circadian Variance, Effects of Treatment, and Relationship to Parathyroid Status. J Clin Endocrinol Metab 2010;95(11):E352-357.
Crasto CL, Semba RD, Sun K, et al. Relationship of low-circulating "anti-aging" klotho hormone with disability in activities of daily living among older community-dwelling adults. Rejuvenation Res 2012;15(3):295-301.
Devaraj S, Syed B, Chien A, et al. Validation of an immunoassay for soluble klotho protein: decreased levels in diabetes and increased levels in chronic kidney disease. Am J Clin Pathol 2012;137(3):479-485.
Fliser D, Seiler S, Heine GH, et al. Measurement of serum soluble Klotho levels in CKD 5D patients: useful tool or dispensable biomarker? Nephrol Dial Transplant 2012;27(5):1702-1703.
Heijboer AC, Blankenstein MA, Hoenderop J, et al. Laboratory aspects of circulating alpha-Klotho. Nephrol Dial Transplant 2013;28(9):2283-2287.

(56) References Cited

OTHER PUBLICATIONS

Kacso IM, Bondor CI, Kacso G. Soluble serum Klotho in diabetic nephropathy: relationship to VEGF-A. Clin Biochem 2012;45(16-17)1 415-1420.

Kim HR, Nam BY, Kim DW, et al. Circulating alpha-Klotho levels in CKD and relationship to progression. Am J Kidney Dis 2013;61(6):899-909.

Kitagawa M, Sugiyama H, Morinaga H, et a/. A decreased level of serum soluble Klotho is an independent biomarker associated with arterial stiffness in patients with chronic kidney disease. PLoS One 2013;8(2):e56695.

Komaba H, Koizumi M, Tanaka H, et al. Effects of cinacalcet treatment on serum soluble Klotho levels in haemodialysis patients with secondary hyperparathyroidism. Nephrol Dial Transplant 2012;27(5)1 967-1969.

Pavik I, Jaeger P, Ebner L, et al. Soluble klotho and autosomal dominant polycystic kidney disease. Clin J Am Soc Nephrol 2012;7(2):248-257.

Pavik I, Jaeger P, Ebner L, et al. Secreted Klotho and FGF23 in chronic kidney disease Stage 1 to 5: a sequence suggested from a cross-sectional study. Nephrol Dial Trarisplant 2013;28(2):352-359.

Seiler S, Wen M, Roth HJ, et al. Plasma Klotho is not related to kidney function and does not predict adverse outcome in patients with chronic kidney disease. Kidney Int 2013;83(1):121-128.

Shimamura Y, Hamada K, Inoue K, et al. Serum levels of soluble secreted alpha-Klotho are decreased in the early stages of chronic kidney disease, making it a probable novel biomarker for early diagnosis. Clin Exp Nephrol 2012;16(5):722-729.

Siahanidou T, Garatzioti M, Lazaropoulou C, et at. Plasma soluble alpha-Klotho protein levels in premature and term neonates: correlations with growth and metabolic parameters. Eur J Endocrinol 2012;167(3):433-440.

Sugiura H, Tsuchiya K, Nitta K. Circulating levels of soluble alpha-Klotho in patients with chronic kidney disease. Clin Exp Nephrol 2011 ;1 5(5):795-796.

Wan M, Smith C, Shah V, et a/. Fibroblast growth factor 23 and soluble klotho in children with chronic kidney disease. Nephrol Dial Transplant 2013;28(1)153-161.

Yamazaki Y, Imura A, Urakawa I, et al. Establishment of sandwich ELISA for soluble alpha-Klotho measurement: Age-dependent change of soluble alpha-Klotho levels in healthy subjects. Biochem Biophys Res Commun 2010;398(3):513-518.

Yokoyama K, Imura A, Ohkido I, et al. Serum soluble alpha-Klotho in hemodialysis patients. Clinical Nephrology, vol. 77—No. 5/2012 (347-351). DOI 10.5414/CN107204. e-pub: Dec. 21, 2011.

Semba RD, Cappola AR, Sun K, et al. Plasma klotho and mortality risk in older community-dwelling adults. J Gerontol A Biol Sci Med Sci 2011;66(7):794-800.

Doi S, Zou Y, Togao 0, et al. Klotho inhibits transforming growth factor-beta1 (TGF-beta1) signaling and suppresses renal fibrosis and cancer metastasis in mice. J Biol Chem 2011;286(10):8655-8665.

Ohyama Y, Kurabayashi M, Masuda H, et at Molecular cloning of rat klotho cDNA: markedly decreased expression of klotho by acute inflammatory stress. Biochemical and Biophysical Research Communications 1998;251(3):920-925.

Sugiura H, Yoshida T, Mitobe M, et al. Klotho reduces apoptosis in experimental ischaemic acute kidney injury via HSP-70. Nephrol Dial Transplant 2010;25(1):60-68.

Sugiura H, Yoshida T, Tsuchiya K, et al. Klotho reduces apoptosis in experimental ischaemic acute renal failure. Nephrol Dial Transplant 2005;20(12):2636-2645.

Moreno JA, Izquierdo MC, Sanchez-Nino MD, et al. The inflammatory cytokines TWEAK and TNFalpha reduce renal klotho expression through NFkappaB. J Am Soc Nephrol 2011;22(7):1315-1325.

Fellouse FA, Esaki K, Birtalan S, et al. High-throughput generation of synthetic antibodies from highly functional minimalist phage-displayed libraries. J Mol Biol 2007;373(4):924-940.

Gao J, Sidhu SS, Wells JA. Two-state selection of conformation-specific antibodies. Proc Natl Acad Sci U S A 2009:106(9):3071-3076.

Koellhoffer JF, Chen G, Sandesara RG, et al. Two synthetic antibodies that recognize and neutralize distinct proteolytic forms of the ebola virus envelope glycoprotein. Chembiochem 2012;13(17):2549-2557.

Li B, Russell SJ, Compaan DM, et al. Activation of the proapoptotic death receptor DR5 by oligomeric peptide and antibody agonists. J Mol Biol 2006;361(3):522-536.

Uysal S, Vasquez V, Tereshko V, et al. Crystal structure of full-length KcsA in its closed conformation. Proc Natl Acad Sci U S A 2009;106(16):6644-6649.

Ibrahim' OA, Zhang F, Eliseenkova AV, et al. Biochemical analysis of pathogenic ligand-dependent FGFR2 mutations suggests distinct pathophysiological mechanisms for craniofacial and limb abnormalities. Hum Mol Genet 2004;13(19):2313-2324.

Plotnikov AN, Hubbard SR, Schlessinger J, et al. Crystal structures of two FGF-FGFR complexes reveal the determinants of ligand-receptor specificity. Cell 2000;101(4):413-424.

Persson H, Ye W, Wemimont A, et a/. CDR-H3 diversity is not required for antigen recognition by synthetic antibodies. J Mol Biol 2013;425(4):803-811.

Rajan S, Sidhu SS. Simplified synthetic antibody libraries. Methods Enzymol 2012;502:3-21.

Colwill K, Graslund S. A roadmap to generate renewable protein binders to the human proteome. Nat Methods 2011;8(7):551-558.

Olsen SK, Garbi M, Zampieri N, et al. Fibroblast growth factor (FGF) homologous factors share structural but not functional homology with FGFs. J Biol Chem 2003;278(36):34226-34236.

Kurosu H, Choi M, Ogawa Y, et al. Tissue-specific expression of betaKlotho and fibroblast growth factor (FGF) receptor isoforms determines metabolic activity of FGF19 and FGF21. J Biol Chem 2007;282(37):26687-26695.

Kurosu H, Yamamoto M, Clark JD, et a/. Suppression of aging in mice by the hormone Klotho. Science 2005; 309(5742):1829-1833.

Hu MC, Shiizaki K, Kuro-o M, et al. Physiology and pathophysiology of an endocrine network of mineral metabolism. Ann Rev Phys 2013;75:503-533.

Hu MC, Kuro-o M, Moe OW. Renal and extrarenal actions of Klotho. Semin Nephrol 2013;33(2):118-129.

Pedersen L, Pedersen SM, Brasen CL, et al. Soluble serum Klotho levels in healthy subjects. Comparison of two different immunoassays. Clin Biochem 2013;46(12):1079-1083.

Grams ME, Chow EK, Segev DL, Coresh J.Lifetime incidence of CKD stages 3-5 in the United States. Am J Kidney Dis. Aug. 2013;62(2):245-52.

Lefranc et al. IMGT unique numbering for immunoglobulin and T cell receptor variable domains and Ig superfamily V-like domains. Development and Comparative Immunology. 2003;27:55-77.

Barker, Sarah L. et al., The demonstration of aKlotho deficiency in human chronic kidney disease with a novel synthetic antibody. Nephrol Dial Transplant (2015) 30:223-233.

Goldstein, Stuart L., Acute kidney injury biomarkers: renal angina and the need for a renal troponin I. BMC Med (2011) 9:135.

Hu, Ming Chang et al., The Emerging Role of Klotho in Clinical Nephrology. Nephrology Dialysis Transplantation, 2012, vol. 27, pp. 2650-2657.

Seo, Min Young et al., Renal Klotho Expression in Patients with Acute Kidney Injury is Associated with the Severity of the Injury. The Korean Journal of Internal Medicine, 2015, vol. 30, No. 4, pp. 489-495.

International Search Report, International Patent Application No. PCT/CA2015/050728, dated Oct. 30, 2015, 7 pages.

Written Opinion, International Patent Application No. PCT/CA2015/050728, dated Oct. 30, 2015, 7 pages.

International Search Report, International Patent Application No. PCT/CA2017/050127, dated May 10, 2017, 8 pages.

Written Opinion, International Patent Application No. PCT/CA2017/050127, dated May 10, 2017, 8 pages.

Mencke, Rik et al. "Membrane-bound Klotho is not expressed endogenously in healthy or uraemic human vascular tissue." Cardiovascular Research (2015) 108, 220-31.

(56) References Cited

OTHER PUBLICATIONS

Rudikoff, Stuart et al. "Single Amino Acid Substitution Altering Antigen-Binding Specificity." Proc. Natl. Acad. Sci. USA. vol. 79, pp. 1979-1983, Mar. 1982, Immunology. (XP007901436).

Scholze, Alexandra et al. "Soluble a-Klotho and its Relation to Kidney Function and Fibroblast Growth Factor-23." J Clin Endocrinol Metal., May 2014, 99(5) : E855-E861.

Ravikumar, Priya et al. aKlotho deficiency in acute kidney injury contributes to lung damage. J Appl Physiol 120: 723-732, 2016.

Richter, Beatrice et al. FGF23 Actions on Target Tissues With and Without Klotho. Front. Endocrinol. 9:189, May 2018.

Lu, Xiang et al. Klotho/FGF23 Axis in Chronic Kidney Disease and Cardiovascular Disease. Chronic Kidney Disease-Mineral and Bone Disorder: Review. Kidney Dis 2017;3:15-23. DOI: 10.1159/000452880.

J.A. Neyra and M.C. Hu. αKlotho and Chronic Kidney Disease. Vitamins and Hormones, vol. 101, p. 257-310, 2016.

Javier A. Neyra, Ming Chang Hu. Potential application of klotho in human chronic kidney disease. Bone 100 (2017) 41-49. http://dx.doi.org/10.1016/j.bone.2017.01.017.

Nordholm, A. Klotho and activin A in kidney injury: plasma Klotho is maintained in unilateral obstruction despite no upregulation of Klotho biosynthesis in the contralateral kidney. Am J Physiol Renal Physiol 314: F753-F762, 2018.

Pastor-Arroyo, Eva-Maria et al. The elevation of circulating fibroblast growth factor 23 without kidney disease does not increase cardiovascular disease risk. Kidney International (2018) 94, 49-59.

Pedraza-Chaverri, José et al. New Pathogenic Concepts and Therapeutic Approaches to Oxidative Stress in Chronic Kidney Disease. Hindawi Publishing Corporation. Oxidative Medicine and Cellular Longevity. vol. 2016, Article ID 6043601, 21 pages.

Andrad, Lucia et al. Acute Kidney Injury as a Condition of Renal Senescence. Cell Transplantation 2018, vol. 27(5) 739-753.

Zhou, Ning et al. A Metabolomics-Based Strategy for the Mechanism Exploration of Traditional Chinese Medicine: Descurainia sophia Seeds Extract and Fractions as a Case Study. Hindawi, Evidence-Based Complementary and Alternative Medicine, vol. 2017, Article ID 2845173, 11 pages.

Bian, Ao et al. Klotho, stem cells, and aging. Clinical Interventions in Aging. Aug. 4, 2015:10 1233-1243.

Chang, Alex R. et al. Dietary Phosphorus Intake and the Kidney. Annual Review of Nutrition, 2017 37:321-346.

Drew, David A. et al. Association between Soluble Klotho and Change in Kidney Function: The Health Aging and Body Composition Study. Am Soc Nephrol 28: 1859-1866, 2017.

Faul, Christian et al. Hunt for the culprit of cardiovascular injury in kidney disease. Cardiovascular Research (Sep. 22, 2015) 108, 209-211.

Gazdhar, Amiq et al. Alpha-Klotho Enrichment in Induced Pluripotent Stem Cell Secretome Contributes to Antioxidative Protection in Acute Lung Injury. Stem Cells (2018) 36:616-625.

Garbner, Alexander et al. The role of fibroblast growth factor 23 and Klotho in uremic cardiomyopathy. Curr Opin Nephrol Hypertens. vol. 25, No. 4, pp. 314-324. Jul. 2016.

Ravikumar, Priya et al. a-Klotho protects against oxidative damage in pulmonary epithelia. Am J Physiol Lung Cell Mol Physiol 307: L566-L575, Jul. 25, 2014.

Hu, Ming Chang et al. Renal Production, Uptake, and Handling of Circulating aKlotho. J Am Soc Nephrol 27: 79-90, 2016.

Hu, Ming Chang et al. Recombinant a-Klotho may be prophylactic and therapeutic for acute to chronic kidney disease progression and uremic cardiomyopathy. Kidney Int. May 2017; 91(5): 1104-1114.

Ritter, Cynthia S. et al. Phosphate Toxicity in CKD: The Killer among Us. Clin J Am Soc Nephrol 11: 1088-1100, 2016.

Rutkowski, Joseph M. et al. Adiponectin alters renal calcium and phosphate excretion through regulation of klotho expression. Kidney Int. Feb. 2017; 91(2): 324-337.

Paul, WE. Fundamental Immunology, 3rd ed. Raven Press, NY, Chap. 9, pp. 292-295, 1993.

Colman, PM. Research in Immunology, Elsevier, NY, 145(1):33-36, 1994.

Maltare, Astha et al. "Development and Characterization of Monoclonal Antibodies to Detect Klotho." Monoclonal Antibodies in Immundiagnosis and Immunotherapy . vol. 33 (6) (2014).

\* cited by examiner

A

| | | |
|---|---|---|
| CDR-L1 | Q S V S S A | (SEQ ID NO: 9) |
| CDR-L2 | S A S | (SEQ ID NO: 10) |
| CDR-L3 | Q Q A G Y S P I T | (SEQ ID NO: 5) |
| CDR-H1 | G F N I S Y Y S I | (SEQ ID NO: 6) |
| CDR-H2 | Y I S P S Y G Y T S | (SEQ ID NO: 7) |
| CDR-H3 | A R Y Y V Y A S H G W A G Y G M D Y | (SEQ ID NO: 8) |

A.

C.

Fig. 3
A.
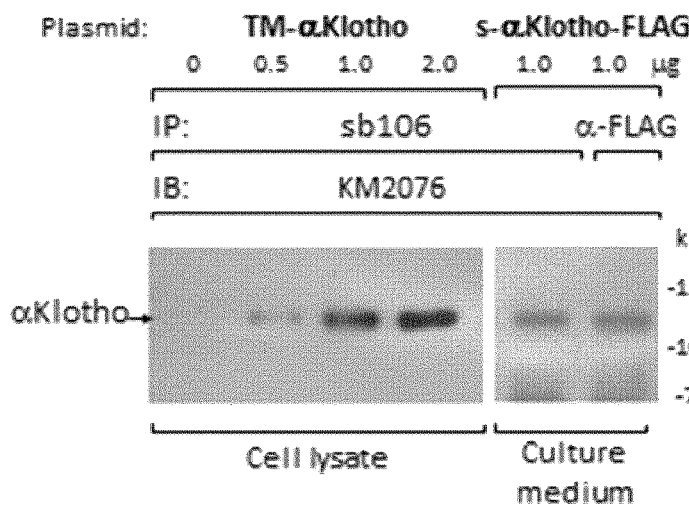
B.
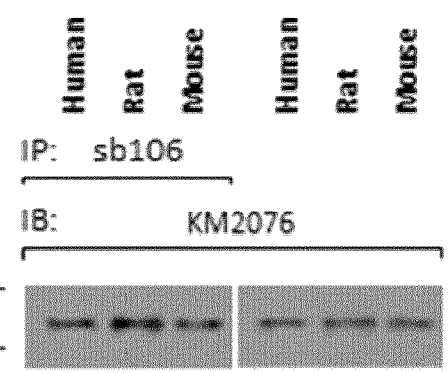
C.
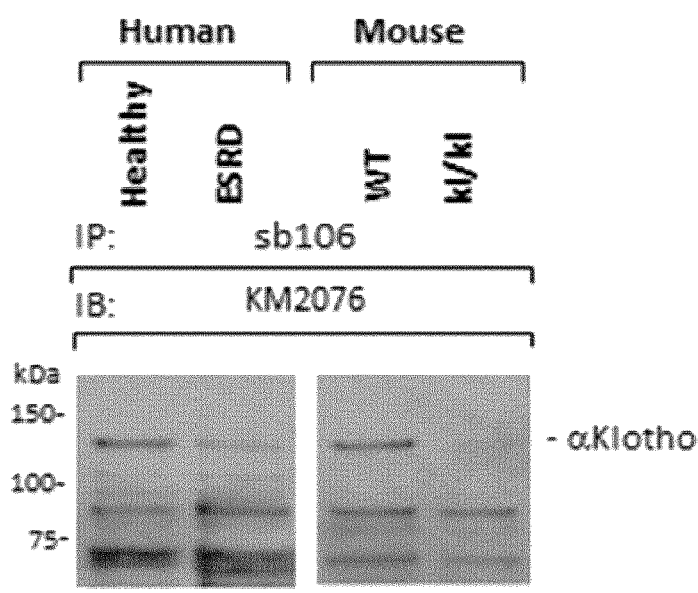

Fig. 4
A.
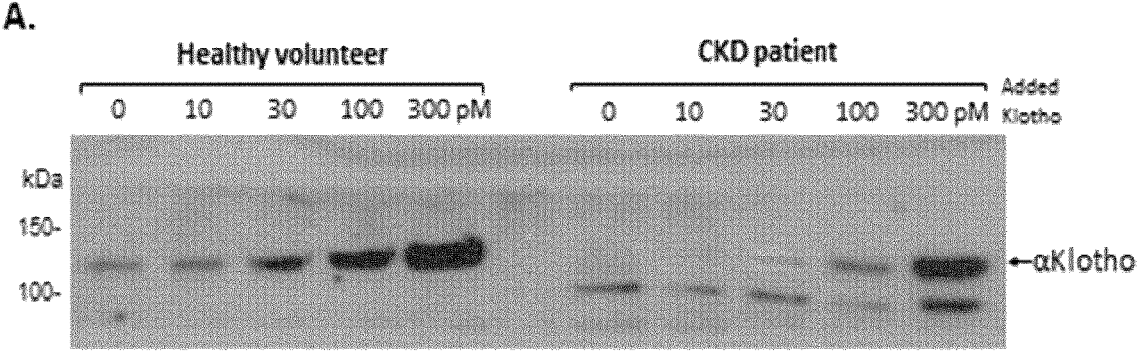
B. Healthy volunteer
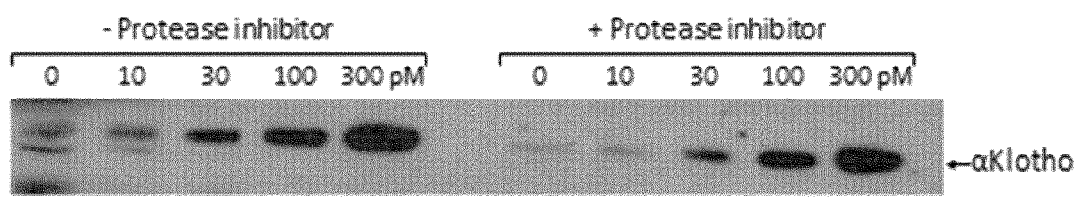
CKD patient
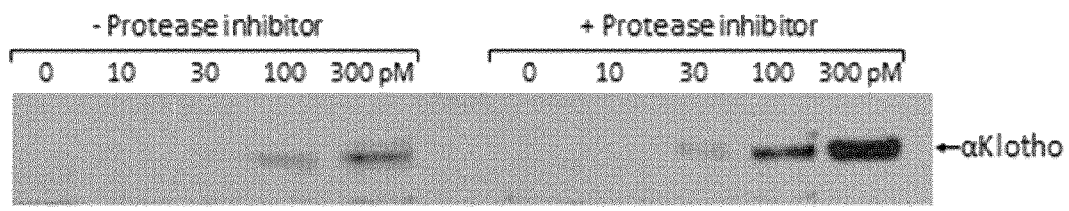

C.

A.

B.

C.

Fig. 6
A.
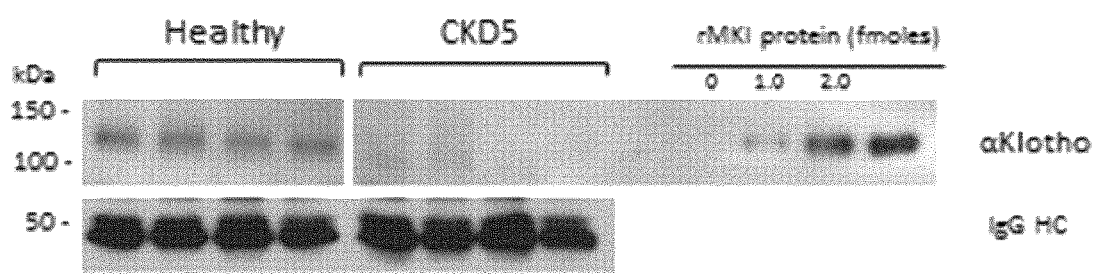
B.
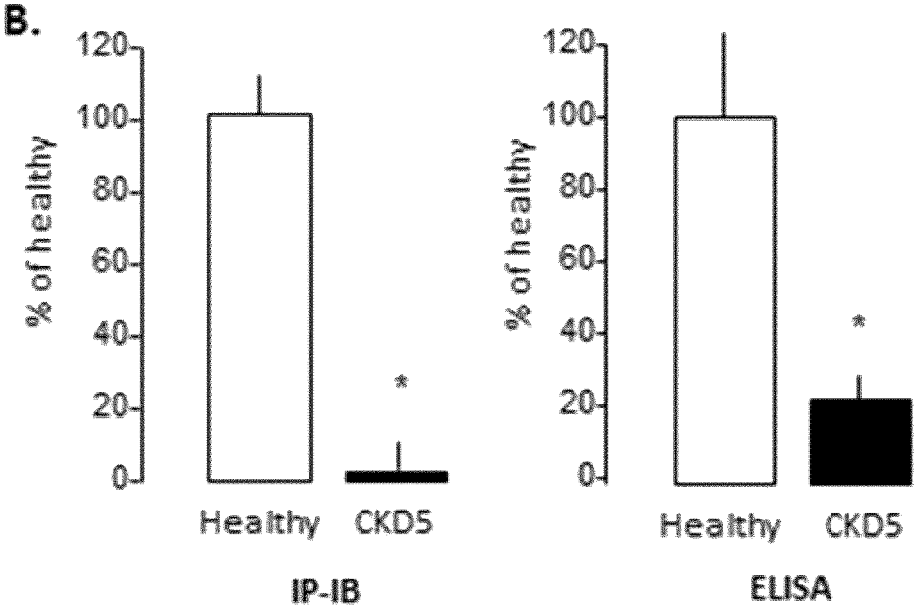

Fig. 8

A. Light chain sequence (SEQ ID NO: 11)

DIQMTQSPSSLSASVGDRVTITCRAS<u>QSVSSA</u>VAWYQQKPGKAPKLLIY<u>SASS</u>LYSGV
PSRFSGSRSGTDFTLTISSLQPEDFATYYC<u>QQAGYSPI</u>TFGQGTKVEIK*RTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC*

B. Heavy chain sequence – Fab (SEQ ID NO: 12)

EVQLVESGGGLVQPGGSLRLSCAAS<u>GFNISYYSI</u>HWVRQAPGKGLEWVA**YISPSY
GYTSYADSVKGRFTISADTSKNTAYLQMNSLRAEDTAVYYC<u>ARYYVYASHGWA
GYGM**</u>DYWGQGTLVTVSS*ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKK
VEPKSCDKTHT*

C. Heavy chain sequence – IgG1 (SEQ ID NO: 13)

EVQLVESGGGLVQPGGSLRLSCAAS<u>GFNISYYSI</u>HWVRQAPGKGLEWVA**YISPSY
GYTSYADSVKGRFTISADTSKNTAYLQMNSLRAEDTAVYYC<u>ARYYVYASHGWA
GYGM**</u>DYWGQGTLVTVSS*ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSLSL
SPGK*

D. Heavy chain sequence – IgG4 (SEQ ID NO: 14)

EVQLVESGGGLVQPGGSLRLSCAAS<u>GFNISYYSI</u>HWVRQAPGKGLEWVA**YISPSY
GYTSYADSVKGRFTISADTSKNTAYLQMNSLRAEDTAVYYC<u>ARYYVYASHGWA
GYGM**</u>DYWGQGTLVTVSS*ASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKVDK
RVESKYGPPCPSCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYTQKSLSLSP
GK*

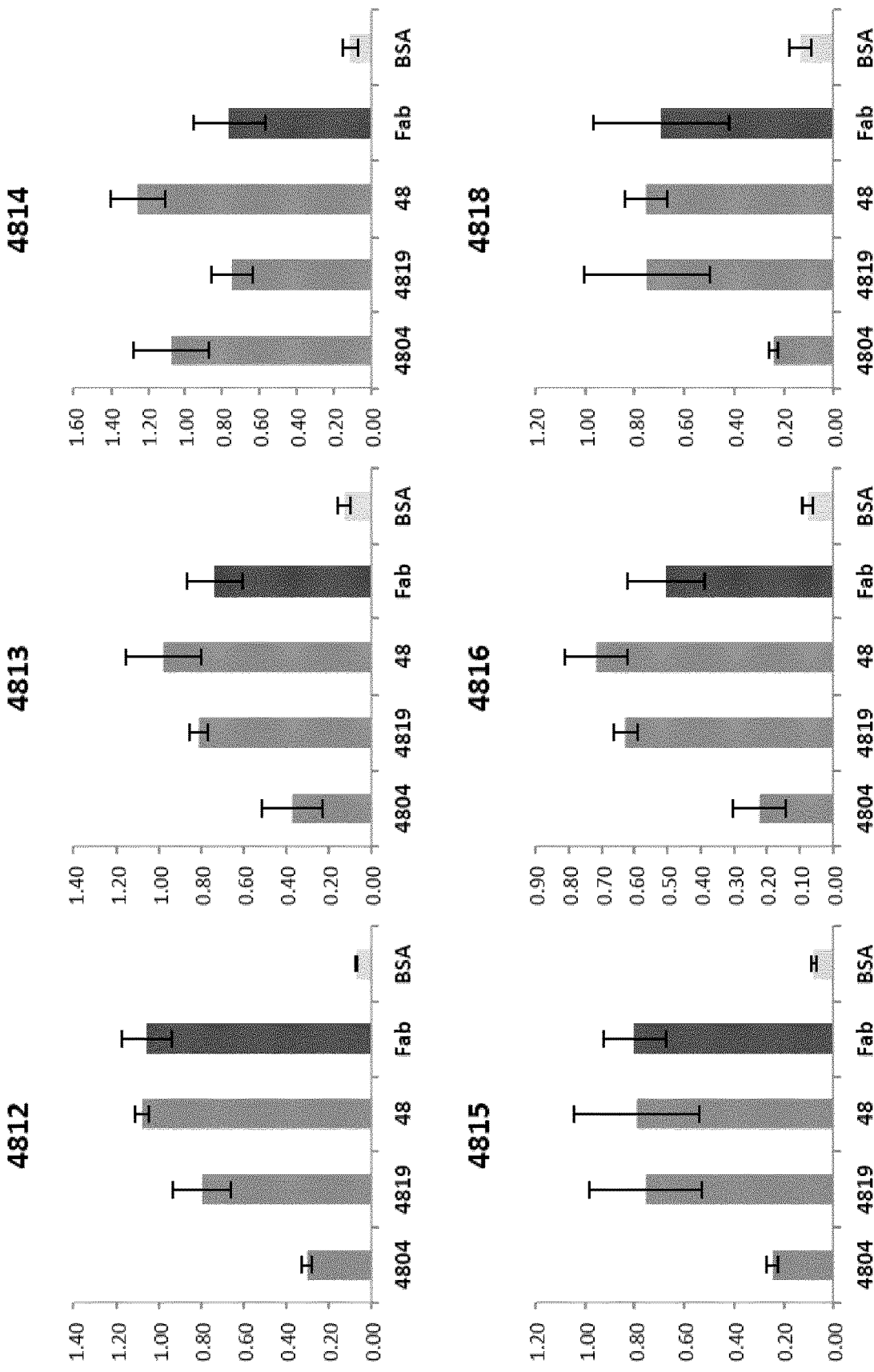
Fig. 11 – (continued)

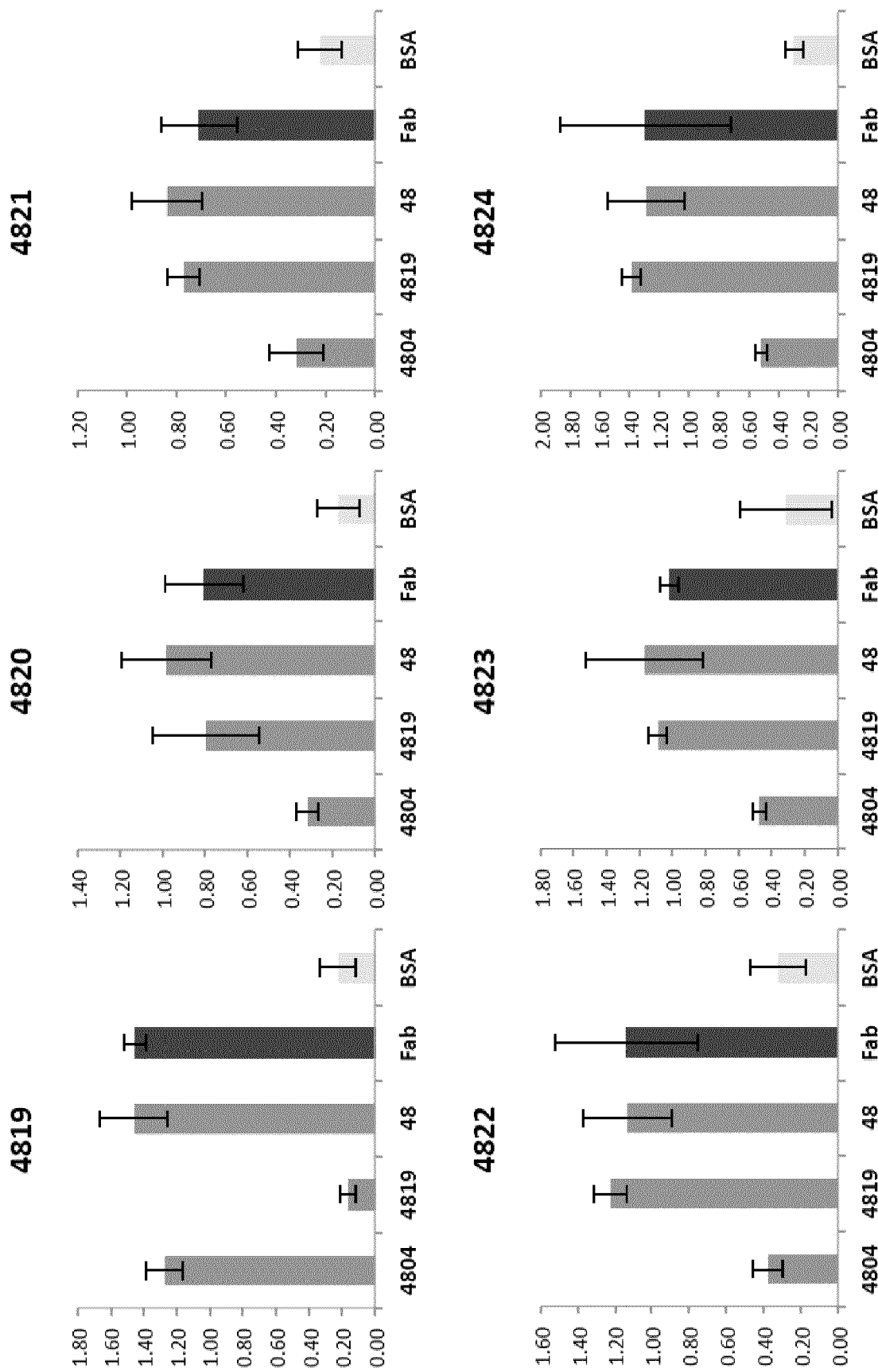
Fig. 11 – (continued)

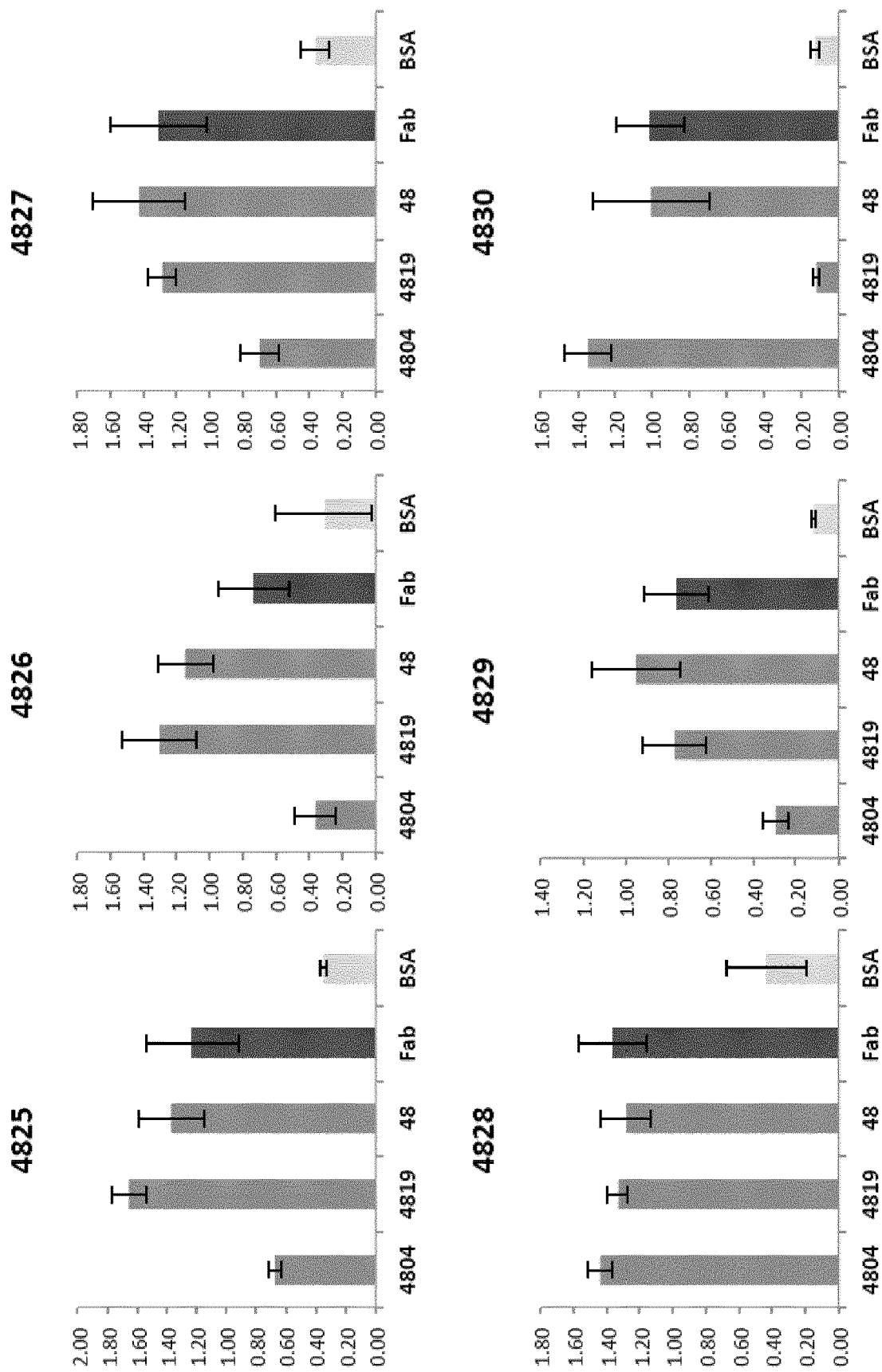
Fig. 11 – (continued)

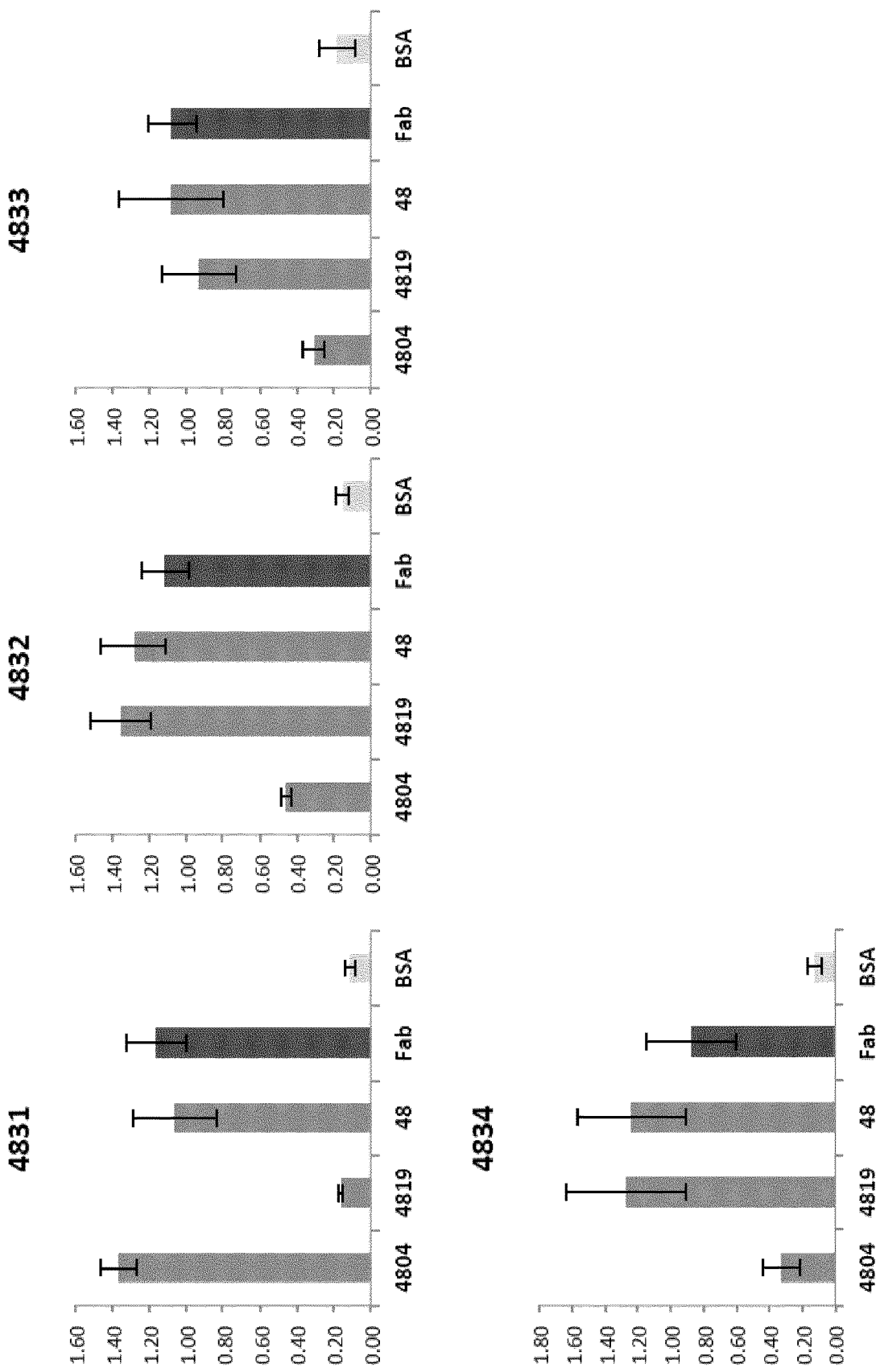
Fig. 11 – (continued)

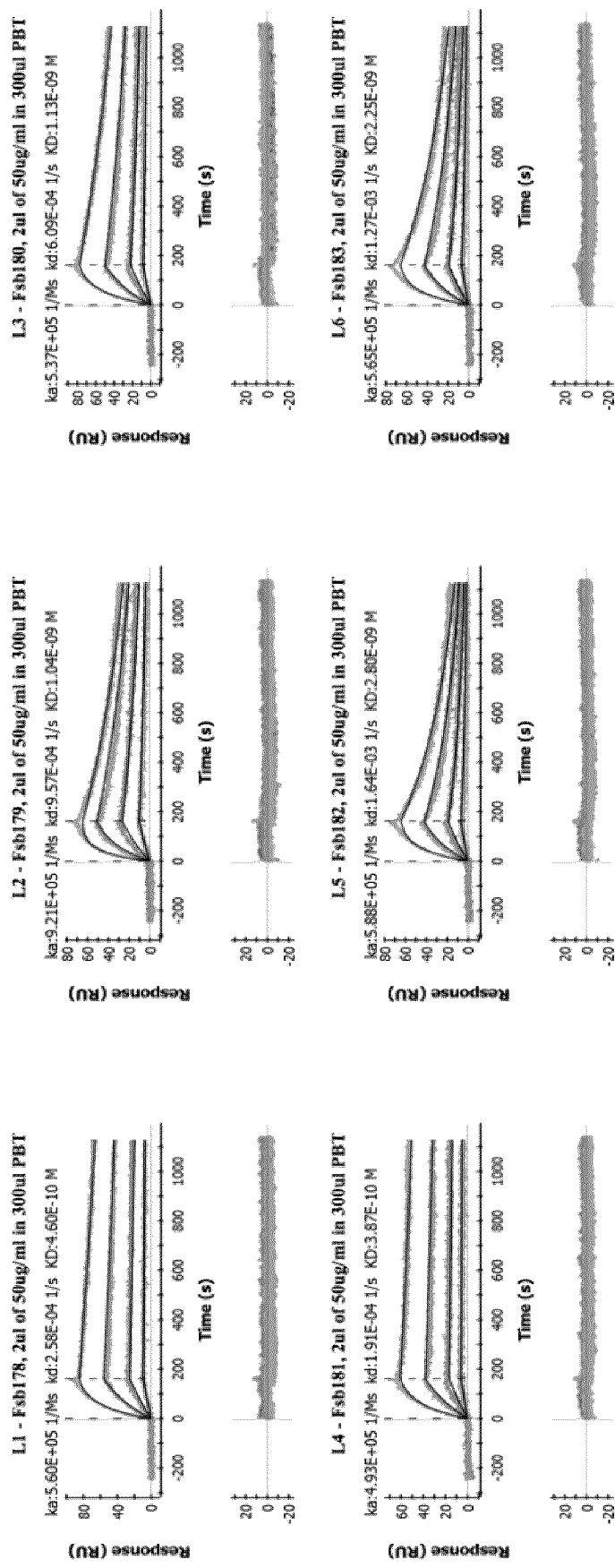
Fig. 12 – (continued)

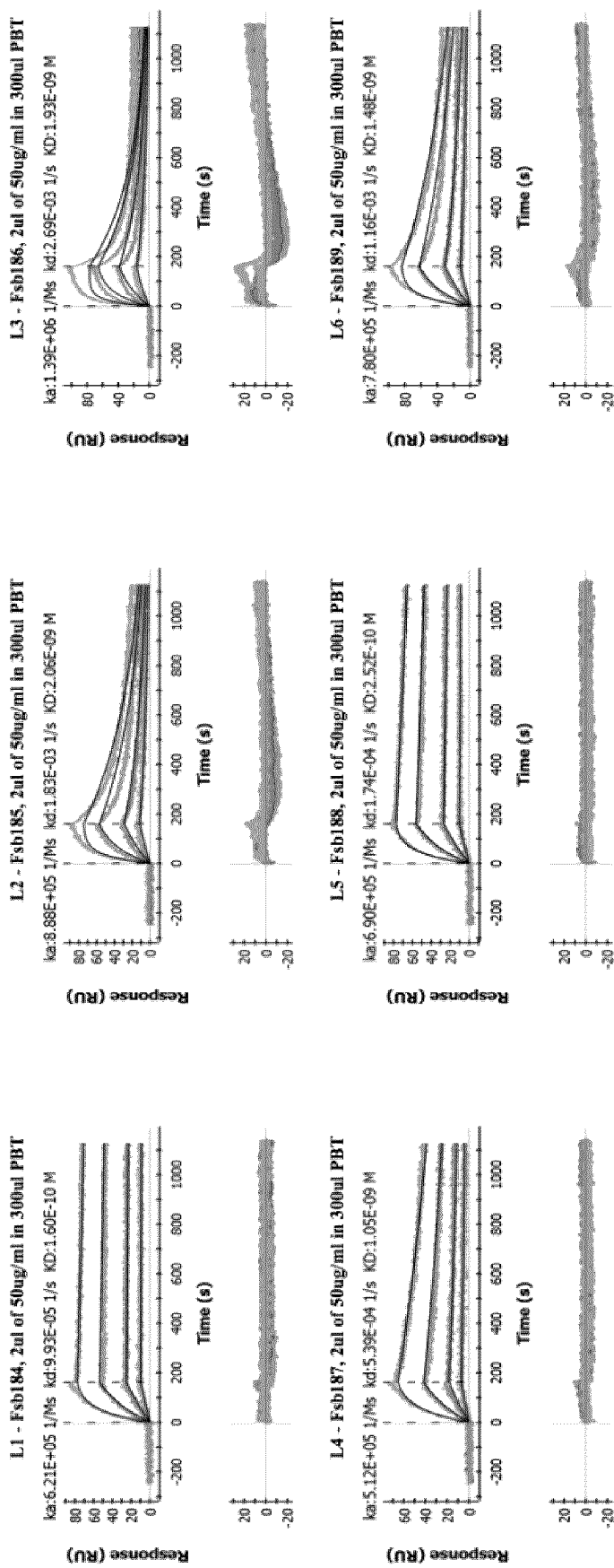
Fig. 12 – (continued)

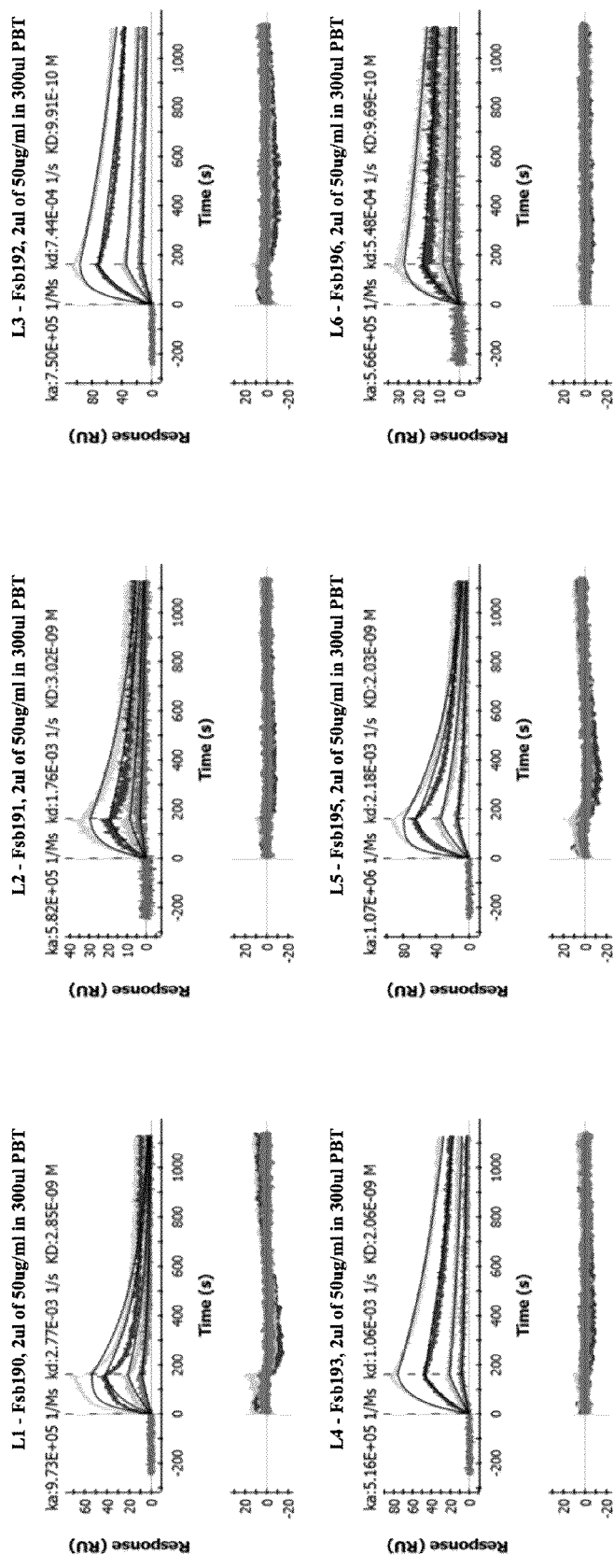
Fig. 12 – (continued)

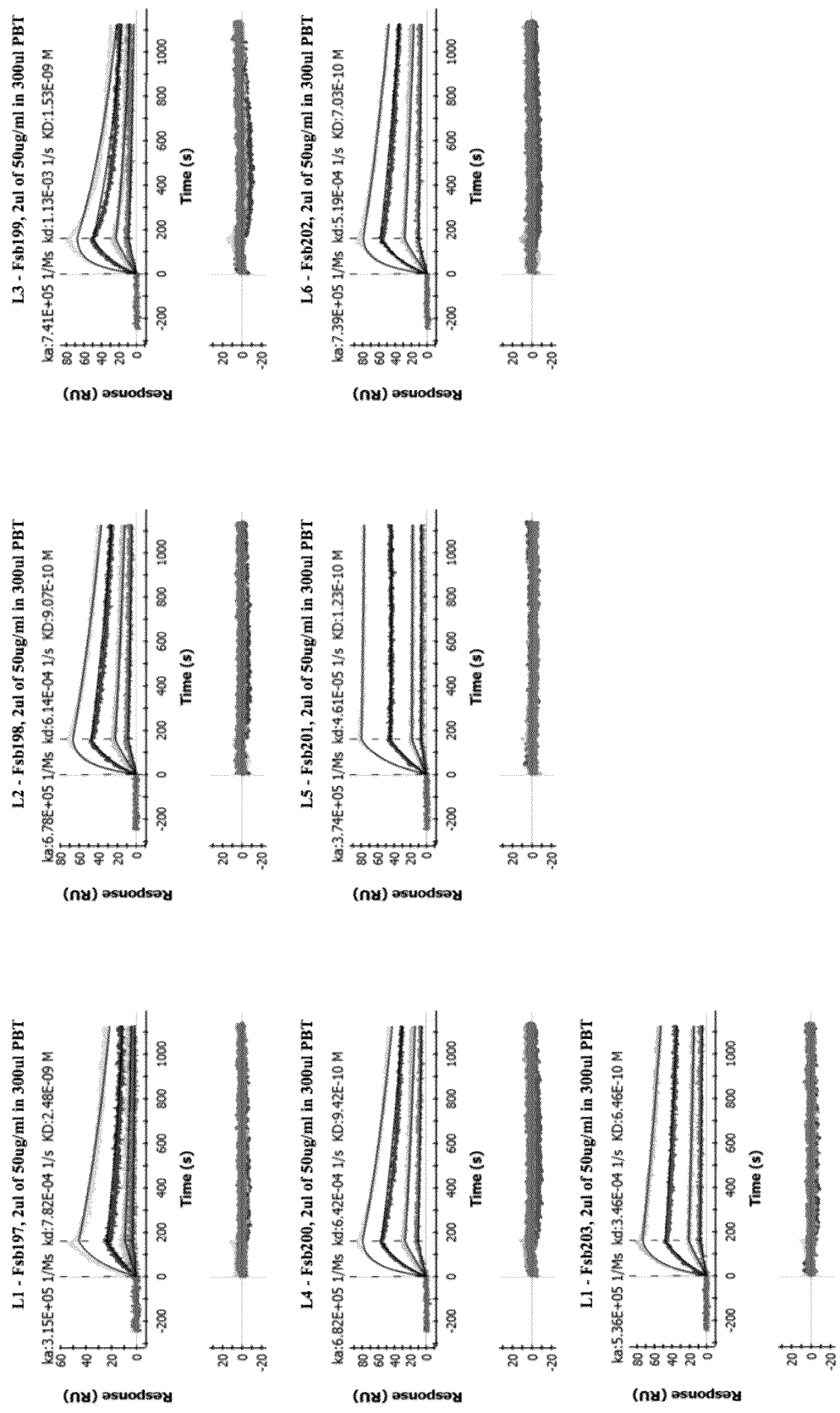
Fig. 12 – (continued)

| ID | name | human αKlotho | | | mouse αKlotho | | |
|---|---|---|---|---|---|---|---|
| | | $K_{on}$ | $K_{off}$ | $K_D$ | $K_{on}$ | $K_{off}$ | $K_D$ |
| 48 | sb106 | 3.08E+05 | 3.15E-04 | 1.02E-09 | 2.02E+05 | 1.59E-04 | 7.84E-10 |
| 4808 | sb177 | 8.61E+05 | 1.41E-03 | 1.64E-09 | 2.93E+05 | 1.12E-02 | 3.82E-08 |
| 4811 | sb180 | 3.49E+05 | 5.16E-04 | 1.48E-09 | 2.73E+05 | 5.45E-03 | 1.99E-08 |
| 4827 | sb196 | 1.54E+05 | 4.82E-04 | 3.13E-09 | 1.03E+05 | 3.75E-03 | 3.64E-08 |
| 4831 | sb200 | 4.99E+05 | 6.00E-04 | 1.20E-09 | 3.21E+05 | 1.21E-02 | 3.77E-08 |

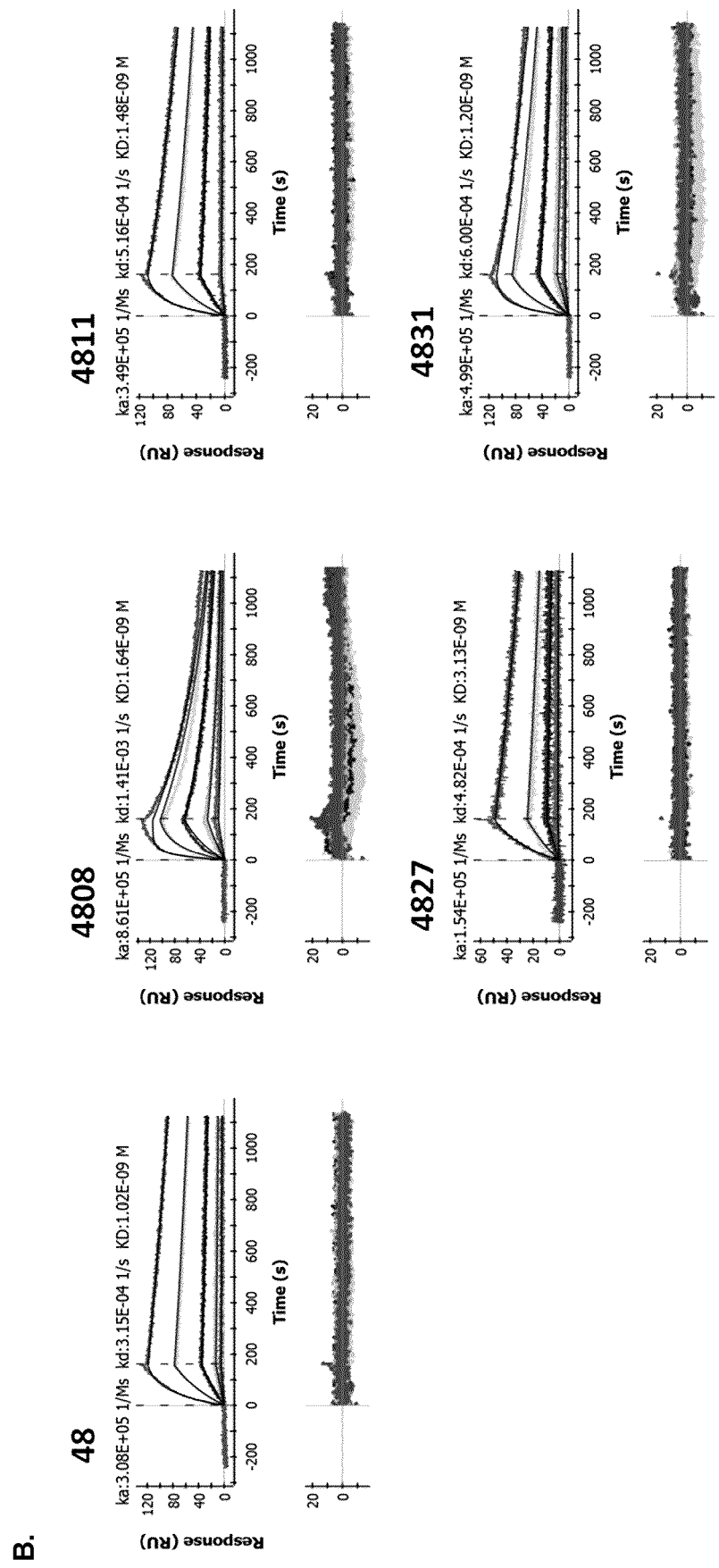
Fig. 17 – (continued)

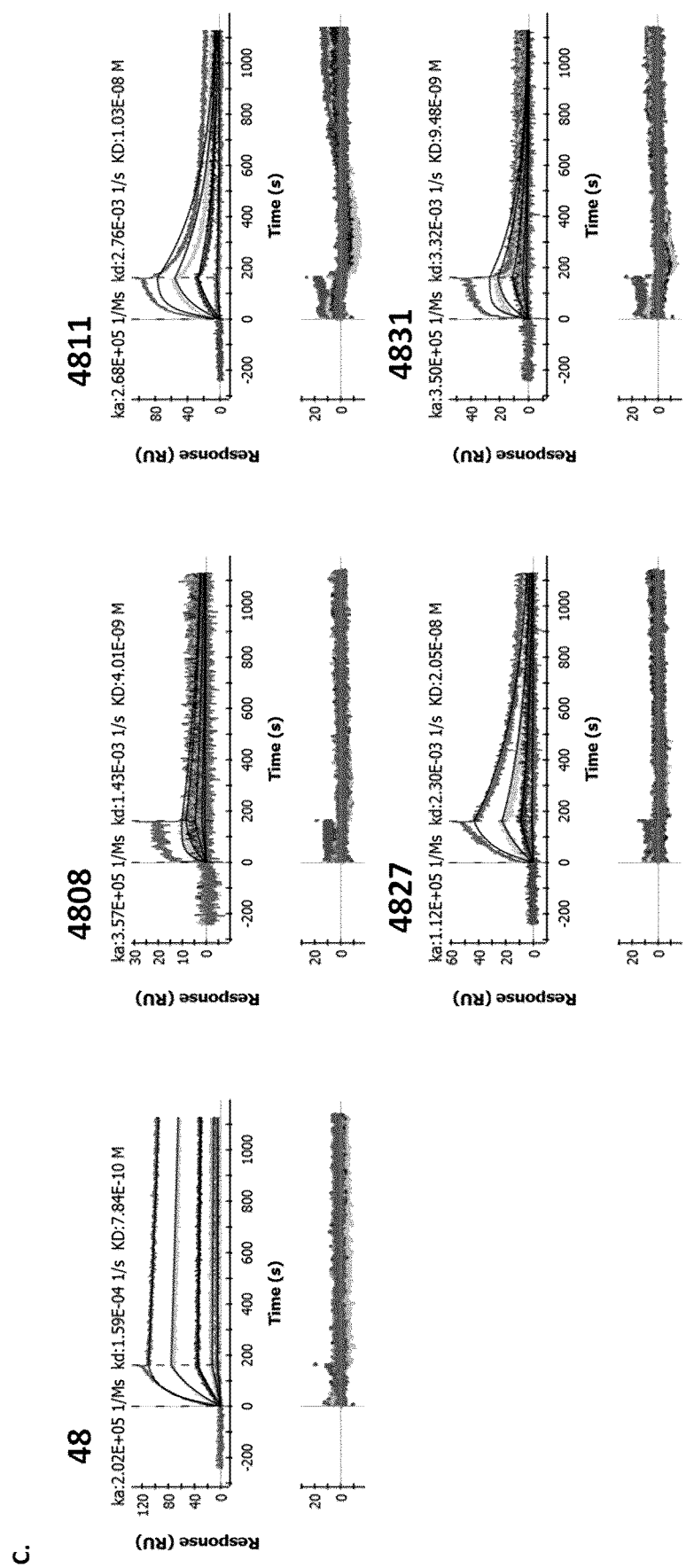
Fig. 17 – (continued)

SEQUENCE LISTING

```
<160> NUMBER OF SEQ ID NOS: 320

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is A or S
<220> FEATURE:
<221> NAME/KEY: MISC_FEATURE
<222> LOCATION: (2)..(2)
<223> OTHER INFORMATION: Xaa is G or A
<220> FEATURE:
<221> NAME/KEY: MISC_FEATURE
<222> LOCATION: (3)..(3)
<223> OTHER INFORMATION: Xaa is Y or F
<220> FEATURE:
<221> NAME/KEY: MISC_FEATURE
<222> LOCATION: (4)..(4)
<223> OTHER INFORMATION: Xaa is S or A
<220> FEATURE:
<221> NAME/KEY: MISC_FEATURE
<222> LOCATION: (6)..(6)
<223> OTHER INFORMATION: Xaa is I or V

<400> SEQUENCE: 1

Xaa Xaa Xaa Xaa Pro Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (2)..(2)
<223> OTHER INFORMATION: Xaa is S or A
<220> FEATURE:
<221> NAME/KEY: MISC_FEATURE
<222> LOCATION: (3)..(3)
<223> OTHER INFORMATION: Xaa is Y, F or S
<220> FEATURE:
<221> NAME/KEY: MISC_FEATURE
<222> LOCATION: (4)..(4)
<223> OTHER INFORMATION: Xaa is Y, F or S
<220> FEATURE:
<221> NAME/KEY: MISC_FEATURE
<222> LOCATION: (5)..(5)
<223> OTHER INFORMATION: Xaa is S or A
<220> FEATURE:
<221> NAME/KEY: MISC_FEATURE
<222> LOCATION: (6)..(6)
<223> OTHER INFORMATION: Xaa is I or V

<400> SEQUENCE: 2

Xaa Xaa Xaa Xaa Xaa Xaa
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Y, F or S
<220> FEATURE:
<221> NAME/KEY: MISC_FEATURE
<222> LOCATION: (2)..(2)
<223> OTHER INFORMATION: Xaa is I or V
<220> FEATURE:
<221> NAME/KEY: MISC_FEATURE
<222> LOCATION: (3)..(3)
<223> OTHER INFORMATION: Xaa is S or A
<220> FEATURE:
<221> NAME/KEY: MISC_FEATURE
<222> LOCATION: (4)..(4)
<223> OTHER INFORMATION: Xaa is P or S
<220> FEATURE:
<221> NAME/KEY: MISC_FEATURE
<222> LOCATION: (5)..(5)
<223> OTHER INFORMATION: Xaa is S or A
<220> FEATURE:
<221> NAME/KEY: MISC_FEATURE
<222> LOCATION: (6)..(6)
<223> OTHER INFORMATION: Xaa is Y or F
<220> FEATURE:
<221> NAME/KEY: MISC_FEATURE
<222> LOCATION: (7)..(7)
<223> OTHER INFORMATION: Xaa is G or A
<220> FEATURE:
<221> NAME/KEY: MISC_FEATURE
<222> LOCATION: (8)..(8)
<223> OTHER INFORMATION: Xaa is Y or F
<220> FEATURE:
<221> NAME/KEY: MISC_FEATURE
<222> LOCATION: (9)..(9)
<223> OTHER INFORMATION: Xaa is T or S
<220> FEATURE:
<221> NAME/KEY: MISC_FEATURE
<222> LOCATION: (10)..(10)
<223> OTHER INFORMATION: Xaa is S, A or Y
```

<400> SEQUENCE: 3

Xaa Xaa Xaa Xaa Xaa Xaa Xaa Xaa Xaa Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Y or F
<220> FEATURE:
<221> NAME/KEY: MISC_FEATURE
<222> LOCATION: (2)..(2)
<223> OTHER INFORMATION: Xaa is Y or F
<220> FEATURE:
<221> NAME/KEY: MISC_FEATURE
<222> LOCATION: (5)..(5)
<223> OTHER INFORMATION: Xaa is A or S
<220> FEATURE:
<221> NAME/KEY: MISC_FEATURE
<222> LOCATION: (6)..(6)
<223> OTHER INFORMATION: Xaa is S or A
<220> FEATURE:
<221> NAME/KEY: MISC_FEATURE
<222> LOCATION: (7)..(7)
<223> OTHER INFORMATION: Xaa is H or N
<220> FEATURE:
<221> NAME/KEY: MISC_FEATURE
<222> LOCATION: (8)..(8)
<223> OTHER INFORMATION: Xaa is G or A
<220> FEATURE:
<221> NAME/KEY: MISC_FEATURE
<222> LOCATION: (10)..(10)
<223> OTHER INFORMATION: Xaa is A or S
<220> FEATURE:
<221> NAME/KEY: MISC_FEATURE
<222> LOCATION: (12)..(12)
<223> OTHER INFORMATION: Xaa is Y or F

<400> SEQUENCE: 4

Xaa Xaa Val Tyr Xaa Xaa Xaa Xaa Trp Xaa Gly Xaa Gly Met
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Gln Gln Ala Gly Tyr Ser Pro Ile Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gly Phe Asn Ile Ser Tyr Tyr Ser Ile
1               5

<210> SEQ ID NO 7

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Tyr Ile Ser Pro Ser Tyr Gly Tyr Thr Ser
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Synthetic Construct

<400> SEQUENCE: 8

Ala Arg Tyr Tyr Val Tyr Ala Ser His Gly Trp Ala Gly Tyr Gly Met
1               5                   10                  15

Asp Tyr

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Gln Ser Val Ser Ser Ala
1               5

<210> SEQ ID NO 10
<211> LENGTH: 3
<212> TYPE: PRT
<213> ORGANISM: Artificial Sequence
<220> FEATURE:
<223> OTHER INFORMATION: Synthetic Construct

<400> SEQUENCE: 10

Ser Ala Ser
1

<210> SEQ ID NO 11
<211> LENGTH: 214
<212> TYPE: PRT
<213> ORGANISM: Artificial Sequence
<220> FEATURE:
<223> OTHER INFORMATION: Synthetic Construct

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gly Tyr Ser Pro Ile
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 233
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Ile His Trp Val Arg Gln Ala Pro Gly Lys Gly Leu Glu Trp Val
        35                  40                  45

Ala Tyr Ile Ser Pro Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Val Tyr Ala Ser His Gly Trp Ala Tyr Gly Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230
```

<210> SEQ ID NO 13
<211> LENGTH: 455
<212> TYPE: PRT
<213> ORGANISM: Artificial Sequence
<220> FEATURE:
<223> OTHER INFORMATION: Synthetic Construct

<400> SEQUENCE: 13

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Ile His Trp Val Arg Gln Ala Pro Gly Lys Gly Leu Glu Trp Val
        35                  40                  45

Ala Tyr Ile Ser Pro Ser Tyr Gly Tyr Thr Ser Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Val Tyr Ala Ser His Gly Trp Ala Gly Tyr Gly Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365
```

```
Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
        435                 440                 445

Leu Ser Leu Ser Pro Gly Lys
        450                 455

<210> SEQ ID NO 14
<211> LENGTH: 452
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Ile His Trp Val Arg Gln Ala Pro Gly Lys Gly Leu Glu Trp Val
        35                  40                  45

Ala Tyr Ile Ser Pro Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Val Tyr Ala Ser His Gly Trp Ala Gly Tyr Gly Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Ser Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Ala Gly Tyr Ala Pro Ile
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Ile Ala Tyr Tyr Ala Val
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Phe Ile Ala Pro Ser Tyr Gly Tyr Ser Ser
1               5                   10

<210> SEQ ID NO 18
<211> LENGTH: 14
```

```
<212> TYPE: PRT
<213> ORGANISM: Artificial Sequence
<220> FEATURE:
<223> OTHER INFORMATION: Synthetic Construct

<400> SEQUENCE: 18

Phe Tyr Val Tyr Ala Ser Asn Ala Trp Ala Gly Tyr Gly Met
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Ala Gly Phe Ala Pro Ile
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Ile Ser Tyr Phe Ser Val
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Phe Ile Ser Pro Ala Tyr Gly Phe Thr Ala
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic Construct

<400> SEQUENCE: 22

Phe Tyr Val Tyr Ala Ala Asn Gly Trp Ala Gly Tyr Gly Met
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

Ala Ala Phe Ala Pro Val
1               5

<210> SEQ ID NO 24
<211> LENGTH: 6
<212> TYPE: PRT
```

```
<213> ORGANISM: Artificial Sequence
<220> FEATURE:
<223> OTHER INFORMATION: Synthetic Construct

<400> SEQUENCE: 24

Ile Ala Phe Tyr Ala Val
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Phe Val Ser Ala Ser Tyr Gly Tyr Thr Ser
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Phe Tyr Val Tyr Ala Ala Asn Gly Trp Ala Gly Tyr Gly Met
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Ser Ala Phe Ser Pro Val
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Val Ser Phe Tyr Ser Ile
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Tyr Val Ala Pro Ala Tyr Gly Tyr Ser Ala
1               5                   10

<210> SEQ ID NO 30
<211> LENGTH: 14
<212> TYPE: PRT
<213> ORGANISM: Artificial Sequence
```

```
<220> FEATURE:
<223> OTHER INFORMATION: Synthetic Construct

<400> SEQUENCE: 30

Phe Tyr Val Tyr Ala Ala His Gly Trp Ala Gly Tyr Gly Met
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Synthetic Construct

<400> SEQUENCE: 31

Ala Ala Phe Ser Pro Val
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Construct

<400> SEQUENCE: 32

Val Ser Phe Phe Ser Ile
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Tyr Ile Ser Pro Ser Tyr Gly Tyr Ser Ser
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic Construct

<400> SEQUENCE: 34

Phe Tyr Val Tyr Ala Ala Asn Gly Trp Ala Gly Tyr Gly Met
1               5                   10

<210> SEQ ID NO 35
<211> LENGTH: 6
<212> TYPE: PRT
<213> ORGANISM: Artificial Sequence
<220> FEATURE:
<223> OTHER INFORMATION: Synthetic Construct

<400> SEQUENCE: 35

Ala Gly Phe Ala Pro Ile
1               5

<210> SEQ ID NO 36
<211> LENGTH: 6
<212> TYPE: PRT
<213> ORGANISM: Artificial Sequence
<220> FEATURE:
```

```
<223> OTHER INFORMATION: Synthetic Construct

<400> SEQUENCE: 36

Ile Ser Tyr Tyr Ala Val
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Phe Val Ser Pro Ala Tyr Gly Phe Ser Ser
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic Construct

<400> SEQUENCE: 38

Phe Phe Val Tyr Ala Ala His Gly Trp Ala Gly Tyr Gly Met
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Synthetic Construct

<400> SEQUENCE: 39

Ala Ala Phe Ala Pro Val
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Construct

<400> SEQUENCE: 40

Phe Ser Ser Ser Ser Ile
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Phe Val Ser Pro Ala Tyr Gly Phe Thr Ala
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic Construct
```

```
<400> SEQUENCE: 42

Phe Phe Val Tyr Ser Ser His Gly Trp Ala Gly Tyr Gly Met
1               5                   10

<210> SEQ ID NO 43
<211> LENGTH: 6
<212> TYPE: PRT
<213> ORGANISM: Artificial Sequence
<220> FEATURE:
<223> OTHER INFORMATION: Synthetic Construct

<400> SEQUENCE: 43

Ala Gly Tyr Ala Pro Val
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44

Ile Ser Tyr Tyr Ser Ile
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Tyr Ile Ser Pro Ser Phe Gly Tyr Thr Ala
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetic Construct

<400> SEQUENCE: 46

Phe Tyr Val Tyr Ser Ser His Gly Trp Ala Gly Tyr Gly Met
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Synthetic Construct

<400> SEQUENCE: 47

Ala Ala Phe Ala Pro Val
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 48

Ile Ser Tyr Tyr Ser Ile
1               5

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Phe Ile Ala Pro Ala Phe Gly Tyr Ser Ser
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic Construct

<400> SEQUENCE: 50

Phe Tyr Val Tyr Ala Ala Asn Gly Trp Ala Gly Tyr Gly Met
1               5                   10

<210> SEQ ID NO 51
<211> LENGTH: 6
<212> TYPE: PRT
<213> ORGANISM: Artificial Sequence
<220> FEATURE:
<223> OTHER INFORMATION: Synthetic Construct

<400> SEQUENCE: 51

Ala Ala Phe Ser Pro Ile
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Construct

<400> SEQUENCE: 52

Ile Ala Tyr Phe Ser Ile
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Tyr Val Ser Pro Ala Tyr Gly Tyr Thr Ser
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic Construct

<400> SEQUENCE: 54
```

Phe Tyr Val Tyr Ser Ala Asn Gly Trp Ala Gly Tyr Gly Met
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Ala Gly Tyr Ala Pro Ile
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Construct

<400> SEQUENCE: 56

Ile Ala Phe Tyr Ser Ile
1               5

<210> SEQ ID NO 57
<211> LENGTH: 10
<212> TYPE: PRT
<213> ORGANISM: Artificial Sequence
<220> FEATURE:
<223> OTHER INFORMATION: Synthetic Construct

<400> SEQUENCE: 57

Tyr Val Ser Pro Ala Tyr Ala Tyr Thr Ala
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetic Construct

<400> SEQUENCE: 58

Phe Tyr Val Tyr Ala Ala His Gly Trp Ala Gly Tyr Gly Met
1               5                   10

<210> SEQ ID NO 59
<211> LENGTH: 6
<212> TYPE: PRT
<213> ORGANISM: Artificial Sequence
<220> FEATURE:
<223> OTHER INFORMATION: Synthetic Construct

<400> SEQUENCE: 59

Ala Gly Phe Ala Pro Ile
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic Construct

<400> SEQUENCE: 60

```
Val Ser Phe Tyr Ser Ile
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Ser Ile Ser Ser Ser Tyr Gly Tyr Thr Tyr
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthetic Construct

<400> SEQUENCE: 62

Phe Tyr Val Tyr Ala Ser Asn Gly Trp Ala Gly Tyr Gly Met
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Synthetic Construct

<400> SEQUENCE: 63

Ala Gly Phe Ala Pro Val
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Construct

<400> SEQUENCE: 64

Val Ser Phe Phe Ser Ile
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Ser Ile Ser Ser Ser Tyr Gly Tyr Thr Tyr
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic Construct

<400> SEQUENCE: 66

Phe Tyr Val Tyr Ser Ser His Gly Trp Ala Gly Tyr Gly Met
```

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct

<400> SEQUENCE: 67

Ser Ala Tyr Ala Pro Val
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Construct

<400> SEQUENCE: 68

Val Ala Phe Tyr Ser Ile
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Phe Ile Ala Pro Ser Tyr Gly Tyr Ser Ala
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic Construct

<400> SEQUENCE: 70

Phe Phe Val Tyr Ala Ala His Gly Trp Ala Gly Tyr Gly Met
1               5                   10

<210> SEQ ID NO 71
<211> LENGTH: 6
<212> TYPE: PRT
<213> ORGANISM: Artificial Sequence
<220> FEATURE:
<223> OTHER INFORMATION: Synthetic Construct

<400> SEQUENCE: 71

Ala Gly Phe Ala Pro Val
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Construct

<400> SEQUENCE: 72

Ile Ala Phe Phe Ser Ile
1               5

<210> SEQ ID NO 73
<211> LENGTH: 10
<212> TYPE: PRT
<213> ORGANISM: Artificial Sequence
<220> FEATURE:
<223> OTHER INFORMATION: Synthetic Construct

<400> SEQUENCE: 73

Phe Val Ser Pro Ala Tyr Gly Tyr Thr Ala
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Phe Tyr Val Tyr Ser Ala Asn Gly Trp Ala Gly Tyr Gly Met
1               5                   10

<210> SEQ ID NO 75
<211> LENGTH: 6
<212> TYPE: PRT
<213> ORGANISM: Artificial Sequence
<220> FEATURE:
<223> OTHER INFORMATION: Synthetic Construct

<400> SEQUENCE: 75

Ser Ala Tyr Ser Pro Val
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Construct

<400> SEQUENCE: 76

Ile Ala Phe Tyr Ser Ile
1               5

<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Phe Val Ser Pro Ala Tyr Ala Tyr Ser Ala
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Construct

<400> SEQUENCE: 78

Phe Tyr Val Tyr Ser Ala Asn Gly Trp Ala Gly Tyr Gly Met
1               5                   10

<210> SEQ ID NO 79
<211> LENGTH: 6
<212> TYPE: PRT
<213> ORGANISM: Artificial Sequence
<220> FEATURE:
<223> OTHER INFORMATION: Synthetic Construct

<400> SEQUENCE: 79

Ala Ala Phe Ala Pro Val
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic Construct

<400> SEQUENCE: 80

Phe Ser Ser Ser Ser Ile
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Tyr Ile Ser Pro Ala Tyr Gly Tyr Ser Ala
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic Construct

<400> SEQUENCE: 82

Phe Phe Val Tyr Ser Ala Asn Ala Trp Ser Gly Tyr Gly Met
1               5                   10

<210> SEQ ID NO 83
<211> LENGTH: 6
<212> TYPE: PRT
<213> ORGANISM: Artificial Sequence
<220> FEATURE:
<223> OTHER INFORMATION: Synthetic Construct

<400> SEQUENCE: 83

Val Ser Tyr Tyr Ser Ile
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct

<400> SEQUENCE: 84

Ser Ile Ser Ser Ser Tyr Gly Tyr Thr Ser
1               5                   10

```
<210> SEQ ID NO 85
<211> LENGTH: 14
<212> TYPE: PRT
<213> ORGANISM: Artificial Sequence
<220> FEATURE:
<223> OTHER INFORMATION: Synthetic Construct

<400> SEQUENCE: 85

Phe Phe Val Tyr Ala Ala His Gly Trp Ala Gly Tyr Gly Met
1               5                   10

<210> SEQ ID NO 86
<211> LENGTH: 6
<212> TYPE: PRT
<213> ORGANISM: Artificial Sequence
<220> FEATURE:
<223> OTHER INFORMATION: Synthetic Construct

<400> SEQUENCE: 86

Ser Ala Phe Ser Pro Val
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic Construct

<400> SEQUENCE: 87

Ile Ala Phe Phe Ala Val
1               5

<210> SEQ ID NO 88
<211> LENGTH: 10
<212> TYPE: PRT
<213> ORGANISM: Artificial Sequence
<220> FEATURE:
<223> OTHER INFORMATION: Synthetic Construct

<400> SEQUENCE: 88

Phe Val Ser Pro Ser Phe Gly Tyr Ser Ser
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic Construct

<400> SEQUENCE: 89

Phe Tyr Val Tyr Ala Ala His Gly Trp Ala Gly Tyr Gly Met
1               5                   10

<210> SEQ ID NO 90
<211> LENGTH: 6
<212> TYPE: PRT
<213> ORGANISM: Artificial Sequence
<220> FEATURE:
<223> OTHER INFORMATION: Synthetic Construct

<400> SEQUENCE: 90

Ala Ala Phe Ala Pro Val
1               5

<210> SEQ ID NO 91
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 91

Val Ala Phe Tyr Ser Ile
1               5

<210> SEQ ID NO 92
<211> LENGTH: 10
<212> TYPE: PRT
<213> ORGANISM: Artificial Sequence
<220> FEATURE:
<223> OTHER INFORMATION: Synthetic Construct

<400> SEQUENCE: 92

Tyr Ile Ser Pro Ala Tyr Ala Tyr Ser Ala
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Synthetic Construct

<400> SEQUENCE: 93

Tyr Phe Val Tyr Ala Ser Asn Gly Trp Ala Gly Tyr Gly Met
1               5                   10

<210> SEQ ID NO 94
<211> LENGTH: 6
<212> TYPE: PRT
<213> ORGANISM: Artificial Sequence
<220> FEATURE:
<223> OTHER INFORMATION: Synthetic Construct

<400> SEQUENCE: 94

Ile Ser Tyr Phe Ser Val
1               5

<210> SEQ ID NO 95
<211> LENGTH: 10
<212> TYPE: PRT
<213> ORGANISM: Artificial Sequence
<220> FEATURE:
<223> OTHER INFORMATION: Synthetic Construct

<400> SEQUENCE: 95

Tyr Val Ser Pro Ser Phe Ala Phe Ser Ser
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetic Construct

<400> SEQUENCE: 96

Phe Phe Val Tyr Ser Ala His Gly Trp Ala Gly Tyr Gly Met
1               5                   10

<210> SEQ ID NO 97
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 97

Ala Ala Tyr Ala Pro Val
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic Construct

<400> SEQUENCE: 98

Val Ala Phe Tyr Ser Val
1               5

<210> SEQ ID NO 99
<211> LENGTH: 10
<212> TYPE: PRT
<213> ORGANISM: Artificial Sequence
<220> FEATURE:
<223> OTHER INFORMATION: Synthetic Construct

<400> SEQUENCE: 99

Ser Ile Ser Ser Ser Tyr Gly Tyr Thr Ala
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic Construct

<400> SEQUENCE: 100

Phe Tyr Val Tyr Ala Ala His Gly Trp Ala Gly Tyr Gly Met
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Synthetic Construct

<400> SEQUENCE: 101

Ala Ala Tyr Ala Pro Val
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic Construct

<400> SEQUENCE: 102

Ile Ala Tyr Tyr Ala Val
1               5

<210> SEQ ID NO 103
<211> LENGTH: 10
<212> TYPE: PRT
```

<213> ORGANISM: Artificial Sequence
<220> FEATURE:
<223> OTHER INFORMATION: Synthetic Construct

<400> SEQUENCE: 103

Phe Val Ser Pro Ala Tyr Gly Phe Thr Ser
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Synthetic Construct

<400> SEQUENCE: 104

Phe Tyr Val Tyr Ser Ser His Gly Trp Ala Gly Phe Gly Met
1               5                   10

<210> SEQ ID NO 105
<211> LENGTH: 6
<212> TYPE: PRT
<213> ORGANISM: Artificial Sequence
<220> FEATURE:
<223> OTHER INFORMATION: Synthetic Construct

<400> SEQUENCE: 105

Ala Ala Phe Ala Pro Val
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic Construct

<400> SEQUENCE: 106

Ile Ala Phe Tyr Ala Val
1               5

<210> SEQ ID NO 107
<211> LENGTH: 10
<212> TYPE: PRT
<213> ORGANISM: Artificial Sequence
<220> FEATURE:
<223> OTHER INFORMATION: Synthetic Construct

<400> SEQUENCE: 107

Tyr Val Ala Pro Pro Tyr Ala Tyr Ser Ala
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetic Construct

<400> SEQUENCE: 108

Phe Tyr Val Tyr Ser Ala His Gly Trp Ala Gly Tyr Gly Met
1               5                   10

<210> SEQ ID NO 109
<211> LENGTH: 6
<212> TYPE: PRT
<213> ORGANISM: Artificial Sequence

```
<220> FEATURE:
<223> OTHER INFORMATION: Synthetic Construct

<400> SEQUENCE: 109

Ala Ala Tyr Ala Pro Val
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic Construct

<400> SEQUENCE: 110

Val Ser Phe Tyr Ser Ile
1               5

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

Tyr Ile Ser Pro Ala Tyr Gly Tyr Thr Ser
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Synthetic Construct

<400> SEQUENCE: 112

Phe Tyr Val Tyr Ser Ala His Gly Trp Ala Gly Tyr Gly Met
1               5                   10

<210> SEQ ID NO 113
<211> LENGTH: 6
<212> TYPE: PRT
<213> ORGANISM: Artificial Sequence
<220> FEATURE:
<223> OTHER INFORMATION: Synthetic Construct

<400> SEQUENCE: 113

Ser Ala Tyr Ser Pro Val
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic Construct

<400> SEQUENCE: 114

Val Ala Tyr Tyr Ser Ile
1               5

<210> SEQ ID NO 115
<211> LENGTH: 10
<212> TYPE: PRT
<213> ORGANISM: Artificial Sequence
<220> FEATURE:
```

<223> OTHER INFORMATION: Synthetic Construct

<400> SEQUENCE: 115

Tyr Ile Ser Pro Ala Phe Gly Tyr Ser Ser
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Synthetic Construct

<400> SEQUENCE: 116

Phe Tyr Val Tyr Ala Ala Asn Gly Trp Ala Gly Tyr Gly Met
1               5                   10

<210> SEQ ID NO 117
<211> LENGTH: 6
<212> TYPE: PRT
<213> ORGANISM: Artificial Sequence
<220> FEATURE:
<223> OTHER INFORMATION: Synthetic Construct

<400> SEQUENCE: 117

Ala Ala Tyr Ala Pro Ile
1               5

<210> SEQ ID NO 118
<211> LENGTH: 6
<212> TYPE: PRT
<213> ORGANISM: Artificial Sequence
<220> FEATURE:
<223> OTHER INFORMATION: Synthetic Construct

<400> SEQUENCE: 118

Val Ala Phe Tyr Ala Val
1               5

<210> SEQ ID NO 119
<211> LENGTH: 10
<212> TYPE: PRT
<213> ORGANISM: Artificial Sequence
<220> FEATURE:
<223> OTHER INFORMATION: Synthetic Construct

<400> SEQUENCE: 119

Ser Ile Ser Ser Ser Tyr Gly Tyr Thr Tyr
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Synthetic Construct

<400> SEQUENCE: 120

Tyr Tyr Val Tyr Ala Ala His Gly Trp Ala Gly Tyr Gly Met
1               5                   10

<210> SEQ ID NO 121
<211> LENGTH: 9
<212> TYPE: PRT
<213> ORGANISM: Artificial Sequence
<220> FEATURE:
<223> OTHER INFORMATION: Synthetic Construct

```
<220> FEATURE:
<221> NAME/KEY: MISC_FEATURE
<222> LOCATION: (4)..(4)
<223> OTHER INFORMATION: Xaa is Leu, Phe or Ile
<220> FEATURE:
<221> NAME/KEY: MISC_FEATURE
<222> LOCATION: (5)..(5)
<223> OTHER INFORMATION: Xaa is Tyr or Ser
<220> FEATURE:
<221> NAME/KEY: MISC_FEATURE
<222> LOCATION: (6)..(6)
<223> OTHER INFORMATION: Xaa is Ser or Tyr
<220> FEATURE:
<221> NAME/KEY: MISC_FEATURE
<222> LOCATION: (7)..(7)
<223> OTHER INFORMATION: Xaa is Ser or Tyr
<220> FEATURE:
<221> NAME/KEY: MISC_FEATURE
<222> LOCATION: (8)..(8)
<223> OTHER INFORMATION: Xaa is Ser or Tyr
<220> FEATURE:
<221> NAME/KEY: MISC_FEATURE
<222> LOCATION: (9)..(9)
<223> OTHER INFORMATION: Xaa is Ile or Met

<400> SEQUENCE: 121

Gly Phe Asn Xaa Xaa Xaa Xaa Xaa Xaa
1               5

<210> SEQ ID NO 122
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Tyr or Ser
<220> FEATURE:
<221> NAME/KEY: MISC_FEATURE
<222> LOCATION: (3)..(3)
<223> OTHER INFORMATION: Xaa is Tyr or Ser
<220> FEATURE:
<221> NAME/KEY: MISC_FEATURE
<222> LOCATION: (4)..(4)
<223> OTHER INFORMATION: Xaa is Ser or Pro
<220> FEATURE:
<221> NAME/KEY: MISC_FEATURE
<222> LOCATION: (5)..(5)
<223> OTHER INFORMATION: Xaa is Ser or Tyr
<220> FEATURE:
<221> NAME/KEY: MISC_FEATURE
<222> LOCATION: (6)..(6)
<223> OTHER INFORMATION: Xaa is Ser or Tyr
<220> FEATURE:
<221> NAME/KEY: MISC_FEATURE
<222> LOCATION: (7)..(7)
<223> OTHER INFORMATION: Xaa is Gly or Ser
<220> FEATURE:
<221> NAME/KEY: MISC_FEATURE
<222> LOCATION: (8)..(8)
<223> OTHER INFORMATION: Xaa is Tyr or Ser
<220> FEATURE:
<221> NAME/KEY: MISC_FEATURE
<222> LOCATION: (10)..(10)
<223> OTHER INFORMATION: Xaa is Tyr or Ser

<400> SEQUENCE: 122

Xaa Ile Xaa Xaa Xaa Xaa Xaa Xaa Thr Xaa
1               5                   10

<210> SEQ ID NO 123
<211> LENGTH: 12
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Gly or Tyr
<220> FEATURE:
<221> NAME/KEY: MISC_FEATURE
<222> LOCATION: (5)..(5)
<223> OTHER INFORMATION: Xaa is Tyr or Trp
<220> FEATURE:
<221> NAME/KEY: MISC_FEATURE
<222> LOCATION: (7)..(7)
<223> OTHER INFORMATION: Xaa is Trp or Tyr
<220> FEATURE:
<221> NAME/KEY: MISC_FEATURE
<222> LOCATION: (8)..(8)
<223> OTHER INFORMATION: Xaa is Trp, Tyr or Ala

<400> SEQUENCE: 123

Gln Gln Xaa Ser Xaa Tyr Xaa Xaa Ser Pro Ile Thr
1               5                   10

<210> SEQ ID NO 124
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Ile or Leu
<220> FEATURE:
<221> NAME/KEY: MISC_FEATURE
<222> LOCATION: (6)..(6)
<223> OTHER INFORMATION: Xaa is Tyr or Ser
<220> FEATURE:
<221> NAME/KEY: MISC_FEATURE
<222> LOCATION: (7)..(7)
<223> OTHER INFORMATION: Xaa is Ser or Tyr
<220> FEATURE:
<221> NAME/KEY: MISC_FEATURE
<222> LOCATION: (9)..(9)
<223> OTHER INFORMATION: Xaa is Ile or Met

<400> SEQUENCE: 124

Gly Phe Asn Xaa Tyr Xaa Xaa Ser Xaa
1               5

<210> SEQ ID NO 125
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Ser or Tyr
<220> FEATURE:
<221> NAME/KEY: MISC_FEATURE
<222> LOCATION: (5)..(5)
<223> OTHER INFORMATION: Xaa is Ser or Tyr
<220> FEATURE:
<221> NAME/KEY: MISC_FEATURE
<222> LOCATION: (6)..(6)
<223> OTHER INFORMATION: Xaa is Ser or Tyr
<220> FEATURE:
<221> NAME/KEY: MISC_FEATURE
<222> LOCATION: (7)..(7)
<223> OTHER INFORMATION: Xaa is Ser or Gly

<400> SEQUENCE: 125
```

```
Ser Ile Xaa Pro Xaa Xaa Xaa Tyr Thr Tyr
1               5                   10
```

```
<210> SEQ ID NO 126
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Tyr or Gly
<220> FEATURE:
<221> NAME/KEY: MISC_FEATURE
<222> LOCATION: (5)..(5)
<223> OTHER INFORMATION: Xaa is Trp, Ala or Gly
<220> FEATURE:
<221> NAME/KEY: MISC_FEATURE
<222> LOCATION: (7)..(7)
<223> OTHER INFORMATION: Xaa is Phe or Ile

<400> SEQUENCE: 126

Gln Gln Gly Xaa Xaa Leu Xaa Thr
1               5
```

```
<210> SEQ ID NO 127
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Ala or Gly
<220> FEATURE:
<221> NAME/KEY: MISC_FEATURE
<222> LOCATION: (5)..(5)
<223> OTHER INFORMATION: Xaa is Trp or Phe
<220> FEATURE:
<221> NAME/KEY: MISC_FEATURE
<222> LOCATION: (6)..(6)
<223> OTHER INFORMATION: Xaa is Gly or Phe
<220> FEATURE:
<221> NAME/KEY: MISC_FEATURE
<222> LOCATION: (7)..(7)
<223> OTHER INFORMATION: Xaa is Gly or Ser
<220> FEATURE:
<221> NAME/KEY: MISC_FEATURE
<222> LOCATION: (8)..(8)
<223> OTHER INFORMATION: Xaa is Ala or Tyr

<400> SEQUENCE: 127

Gln Gln Ala Xaa Xaa Xaa Xaa Xaa Pro Ile Thr
1               5                   10
```

```
<210> SEQ ID NO 128

<400> SEQUENCE: 128

000
```

```
<210> SEQ ID NO 129
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
```

```
<223> OTHER INFORMATION: Xaa is Ser or Pro
<220> FEATURE:
<221> NAME/KEY: MISC_FEATURE
<222> LOCATION: (5)..(5)
<223> OTHER INFORMATION: Xaa is His or Trp
<220> FEATURE:
<221> NAME/KEY: MISC_FEATURE
<222> LOCATION: (7)..(7)
<223> OTHER INFORMATION: Xaa is His or Ala
<220> FEATURE:
<221> NAME/KEY: MISC_FEATURE
<222> LOCATION: (9)..(9)
<223> OTHER INFORMATION: Xaa is Pro or Leu

<400> SEQUENCE: 129

Gln Gln Ser Xaa Xaa Gly Xaa Tyr Xaa Ile Thr
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Synthetic Consrtuct
<220> FEATURE:
<221> NAME/KEY: MISC_FEATURE
<222> LOCATION: (4)..(4)
<223> OTHER INFORMATION: Xaa is Ser or Gly
<220> FEATURE:
<221> NAME/KEY: MISC_FEATURE
<222> LOCATION: (5)..(5)
<223> OTHER INFORMATION: Xaa is Gly or Trp
<220> FEATURE:
<221> NAME/KEY: MISC_FEATURE
<222> LOCATION: (6)..(6)
<223> OTHER INFORMATION: Xaa is Trp or Ala
<220> FEATURE:
<221> NAME/KEY: MISC_FEATURE
<222> LOCATION: (9)..(9)
<223> OTHER INFORMATION: Xaa is Phe or Pro
<220> FEATURE:
<221> NAME/KEY: MISC_FEATURE
<222> LOCATION: (10)..(10)
<223> OTHER INFORMATION: Xaa is Leu or Ile
<220> FEATURE:
<221> NAME/KEY: MISC_FEATURE
<222> LOCATION: (11)..(11)
<223> OTHER INFORMATION: Xaa is Phe or absent

<400> SEQUENCE: 130

Gln Gln Ser Xaa Xaa Xaa Tyr His Xaa Xaa Xaa Thr
1               5                   10

<210> SEQ ID NO 131

<400> SEQUENCE: 131

000

<210> SEQ ID NO 132

<400> SEQUENCE: 132

000

<210> SEQ ID NO 133
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (5)..(5)
<223> OTHER INFORMATION: Xaa is Tyr or Ser
<220> FEATURE:
<221> NAME/KEY: MISC_FEATURE
<222> LOCATION: (6)..(6)
<223> OTHER INFORMATION: Xaa is Tyr or Ser
<220> FEATURE:
<221> NAME/KEY: MISC_FEATURE
<222> LOCATION: (7)..(7)
<223> OTHER INFORMATION: Xaa is Tyr or Ser
<220> FEATURE:
<221> NAME/KEY: MISC_FEATURE
<222> LOCATION: (8)..(8)
<223> OTHER INFORMATION: Xaa is Tyr or Ser

<400> SEQUENCE: 133

Gly Phe Asn Ile Xaa Xaa Xaa Xaa Ile
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Tyr or Ser
<220> FEATURE:
<221> NAME/KEY: MISC_FEATURE
<222> LOCATION: (6)..(6)
<223> OTHER INFORMATION: Xaa is Tyr or Ser
<220> FEATURE:
<221> NAME/KEY: MISC_FEATURE
<222> LOCATION: (7)..(7)
<223> OTHER INFORMATION: Xaa is Tyr or Ser
<220> FEATURE:
<221> NAME/KEY: MISC_FEATURE
<222> LOCATION: (8)..(8)
<223> OTHER INFORMATION: Xaa is Tyr or Ser
<220> FEATURE:
<221> NAME/KEY: MISC_FEATURE
<222> LOCATION: (9)..(9)
<223> OTHER INFORMATION: Xaa is Met or Ile

<400> SEQUENCE: 134

Gly Phe Asn Leu Xaa Xaa Xaa Xaa Xaa
1               5

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Ser or Tyr
<220> FEATURE:
<221> NAME/KEY: MISC_FEATURE
<222> LOCATION: (6)..(6)
<223> OTHER INFORMATION: Xaa is Ser or Tyr
<220> FEATURE:
<221> NAME/KEY: MISC_FEATURE
<222> LOCATION: (8)..(8)
<223> OTHER INFORMATION: Xaa is Ser or Tyr
<220> FEATURE:
<221> NAME/KEY: MISC_FEATURE
<222> LOCATION: (10)..(10)
<223> OTHER INFORMATION: Xaa is Ser or Tyr

<400> SEQUENCE: 135
```

```
Tyr Ile Xaa Ser Ser Xaa Gly Xaa Thr Xaa
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Ser or Tyr
<220> FEATURE:
<221> NAME/KEY: MISC_FEATURE
<222> LOCATION: (4)..(4)
<223> OTHER INFORMATION: Xaa is Ser or Pro
<220> FEATURE:
<221> NAME/KEY: MISC_FEATURE
<222> LOCATION: (5)..(5)
<223> OTHER INFORMATION: Xaa is Tyr or Ser
<220> FEATURE:
<221> NAME/KEY: MISC_FEATURE
<222> LOCATION: (6)..(6)
<223> OTHER INFORMATION: Xaa is Tyr or Ser
<220> FEATURE:
<221> NAME/KEY: MISC_FEATURE
<222> LOCATION: (7)..(7)
<223> OTHER INFORMATION: Xaa is Gly or Ser
<220> FEATURE:
<221> NAME/KEY: MISC_FEATURE
<222> LOCATION: (8)..(8)
<223> OTHER INFORMATION: Xaa is Ser or Tyr
<220> FEATURE:
<221> NAME/KEY: MISC_FEATURE
<222> LOCATION: (10)..(10)
<223> OTHER INFORMATION: Xaa is Tyr or Ser

<400> SEQUENCE: 136

Ser Ile Xaa Xaa Xaa Xaa Xaa Xaa Thr Xaa
1               5                   10

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140
<211> LENGTH: 6
<212> TYPE: PRT
<213> ORGANISM: Artificial Sequence
<220> FEATURE:
<223> OTHER INFORMATION: Synthetic Construct

<400> SEQUENCE: 140

Gln Ser Val Ser Ser Ala
1               5
```

```
<210> SEQ ID NO 141
<211> LENGTH: 3
<212> TYPE: PRT
<213> ORGANISM: Artificial Sequence
<220> FEATURE:
<223> OTHER INFORMATION: Synthetic Construct

<400> SEQUENCE: 141

Ser Ala Ser
1

<210> SEQ ID NO 142
<211> LENGTH: 9
<212> TYPE: PRT
<213> ORGANISM: Artificial Sequence
<220> FEATURE:
<223> OTHER INFORMATION: Synthetic Construct

<400> SEQUENCE: 142

Gln Gln Ser Ser Tyr Ser Leu Ile Thr
1               5

<210> SEQ ID NO 143
<211> LENGTH: 12
<212> TYPE: PRT
<213> ORGANISM: Artificial Sequence
<220> FEATURE:
<223> OTHER INFORMATION: Synthetic Construct

<400> SEQUENCE: 143

Gln Gln Ser Ser Gly Trp Tyr His Phe Leu Phe Thr
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Synthetic Construct

<400> SEQUENCE: 144

Gln Gln Ser Gly Trp Ala Tyr His Pro Ile Thr
1               5                   10

<210> SEQ ID NO 145
<211> LENGTH: 8
<212> TYPE: PRT
<213> ORGANISM: Artificial Sequence
<220> FEATURE:
<223> OTHER INFORMATION: Synthetic Construct

<400> SEQUENCE: 145

Gln Gln Gly Tyr Ala Leu Phe Thr
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic Construct

<400> SEQUENCE: 146

Gln Gln Gly Tyr Trp Leu Phe Thr
1               5

<210> SEQ ID NO 147
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 147

Gln Gln Ala Ala Trp Gly Gly Ala Pro Ile Thr
1               5                   10

<210> SEQ ID NO 148
<211> LENGTH: 8
<212> TYPE: PRT
<213> ORGANISM: Artificial Sequence
<220> FEATURE:
<223> OTHER INFORMATION: Synthetic Construct

<400> SEQUENCE: 148

Gln Gln Ser Ser Pro Pro Ile Thr
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic Construct

<400> SEQUENCE: 149

Gln Gln Pro Tyr Ser Pro Ile Thr
1               5

<210> SEQ ID NO 150
<211> LENGTH: 12
<212> TYPE: PRT
<213> ORGANISM: Artificial Sequence
<220> FEATURE:
<223> OTHER INFORMATION: Synthetic Construct

<400> SEQUENCE: 150

Gln Gln Gly Ser Tyr Tyr Trp Trp Ser Pro Ile Thr
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Synthetic Construct

<400> SEQUENCE: 151

Gln Gln Ser Pro Trp Gly Ala Tyr Leu Ile Thr
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Synthetic Construct

<400> SEQUENCE: 152

Gln Gln Ala Gly Phe Phe Ser Tyr Pro Ile Thr
1               5                   10

<210> SEQ ID NO 153
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 153

Gln Gln Gly Gly Gly Leu Ile Thr
1               5

<210> SEQ ID NO 154
<211> LENGTH: 12
<212> TYPE: PRT
<213> ORGANISM: Artificial Sequence
<220> FEATURE:
<223> OTHER INFORMATION: Synthetic Construct

<400> SEQUENCE: 154

Gln Gln Tyr Ser Trp Tyr Trp Tyr Ser Pro Ile Thr
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Synthetic Construct

<400> SEQUENCE: 155

Gln Gln Tyr Ser Tyr Tyr Tyr Ala Ser Pro Ile Thr
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Synthetic Construct

<400> SEQUENCE: 156

Gln Gln Ser Ser His Gly His Tyr Pro Ile Thr
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Synthetic Construct

<400> SEQUENCE: 157

Gly Phe Asn Leu Tyr Ser Tyr Ser Ile
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct

<400> SEQUENCE: 158

Gly Phe Asn Leu Ser Tyr Tyr Ser Met
1               5

<210> SEQ ID NO 159
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 159

Gly Phe Asn Ile Ser Ser Ser Ser Ile
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic Construct

<400> SEQUENCE: 160

Gly Phe Asn Leu Ser Ser Ser Tyr Met
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic Construct

<400> SEQUENCE: 161

Gly Phe Asn Phe Ser Ser Ser Ser Ile
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Construct

<400> SEQUENCE: 162

Gly Phe Asn Ile Tyr Ser Tyr Tyr Ile
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic Construct

<400> SEQUENCE: 163

Gly Phe Asn Leu Ser Ser Ser Ser Ile
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic Construct

<400> SEQUENCE: 164

Gly Phe Asn Leu Tyr Tyr Ser Tyr Met
1               5

<210> SEQ ID NO 165
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 165

Gly Phe Asn Leu Ser Ser Tyr Ser Met
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Construct

<400> SEQUENCE: 166

Gly Phe Asn Leu Tyr Ser Ser Ser Ile
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic Construct

<400> SEQUENCE: 167

Gly Phe Asn Leu Tyr Ser Tyr Ser Met
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic Construct

<400> SEQUENCE: 168

Gly Phe Asn Ile Ser Tyr Ser Ser Ile
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic Construct

<400> SEQUENCE: 169

Gly Phe Asn Ile Tyr Ser Tyr Ser Met
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic Construct

<400> SEQUENCE: 170

Gly Phe Asn Ile Ser Ser Tyr Tyr Met
1               5

<210> SEQ ID NO 171
<211> LENGTH: 9
<212> TYPE: PRT
<213> ORGANISM: Artificial Sequence
<220> FEATURE:
```

```
<223> OTHER INFORMATION: Synthetic Construct

<400> SEQUENCE: 171

Gly Phe Asn Ile Ser Ser Tyr Tyr Ile
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Construct

<400> SEQUENCE: 172

Gly Phe Asn Ile Tyr Tyr Ser Ser Ile
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic Construct

<400> SEQUENCE: 173

Gly Phe Asn Ile Tyr Ser Ser Ser Ile
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic Construct

<400> SEQUENCE: 174

Gly Phe Asn Leu Ser Ser Tyr Tyr Met
1               5

<210> SEQ ID NO 175
<211> LENGTH: 10
<212> TYPE: PRT
<213> ORGANISM: Artificial Sequence
<220> FEATURE:
<223> OTHER INFORMATION: Synthetic Construct

<400> SEQUENCE: 175

Tyr Ile Ser Ser Ser Ser Gly Ser Thr Tyr
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Synthetic Construct

<400> SEQUENCE: 176

Ser Ile Ser Ser Tyr Tyr Gly Ser Thr Tyr
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 177

Tyr Ile Ser Ser Ser Tyr Ser Ser Thr Ser
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic Construct

<400> SEQUENCE: 178

Ser Ile Tyr Pro Ser Tyr Gly Ser Thr Ser
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Synthetic Construct

<400> SEQUENCE: 179

Ser Ile Ser Ser Ser Tyr Gly Tyr Thr Tyr
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Synthetic Construct

<400> SEQUENCE: 180

Ser Ile Tyr Ser Tyr Tyr Gly Ser Thr Ser
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Synthetic Construct

<400> SEQUENCE: 181

Tyr Ile Ser Pro Ser Tyr Gly Ser Thr Ser
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Synthetic Construct

<400> SEQUENCE: 182

Ser Ile Tyr Ser Ser Ser Ser Tyr Thr Ser
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 183

Ser Ile Ser Ser Tyr Ser Gly Tyr Thr Ser
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Synthetic Construct

<400> SEQUENCE: 184

Ser Ile Ser Pro Tyr Ser Gly Tyr Thr Tyr
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Synthetic Construct

<400> SEQUENCE: 185

Ser Ile Tyr Pro Ser Ser Ser Tyr Thr Tyr
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic Construct

<400> SEQUENCE: 186

Ser Ile Tyr Ser Ser Tyr Ser Ser Thr Tyr
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Synthetic Construct

<400> SEQUENCE: 187

Ser Ile Ser Pro Tyr Ser Gly Ser Thr Tyr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Synthetic Construct

<400> SEQUENCE: 188

Tyr Ile Tyr Ser Ser Tyr Gly Tyr Thr Tyr
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Synthetic Construct

<400> SEQUENCE: 189
```

```
Ser Ile Ser Pro Tyr Tyr Ser Tyr Thr Tyr
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Synthetic Construct

<400> SEQUENCE: 190

Tyr Ile Ser Ser Ser Ser Gly Ser Thr Ser
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Synthetic Construct

<400> SEQUENCE: 191

Ser Ile Tyr Ser Ser Tyr Gly Tyr Thr Ser
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Synthetic Construct

<400> SEQUENCE: 192

Ser Ile Tyr Pro Tyr Tyr Ser Tyr Thr Tyr
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic Construct

<400> SEQUENCE: 193

Ser Ile Tyr Pro Tyr Ser Gly Tyr Thr Tyr
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Synthetic Construct

<400> SEQUENCE: 194

Tyr Ile Ser Ser Ser Tyr Gly Tyr Thr Ser
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Synthetic Construct

<400> SEQUENCE: 195
```

```
Ser Ile Tyr Pro Ser Tyr Ser Ser Thr Tyr
1               5                   10
```

<210> SEQ ID NO 196
<211> LENGTH: 18
<212> TYPE: PRT
<213> ORGANISM: Artificial Sequence
<220> FEATURE:
<223> OTHER INFORMATION: Synthetic Construct

<400> SEQUENCE: 196

```
Ala Arg Gly Trp Gly Gly Gly Tyr Trp Phe Tyr Pro Val Tyr Gly Ile
1               5                   10                  15

Asp Tyr
```

<210> SEQ ID NO 197
<211> LENGTH: 16
<212> TYPE: PRT
<213> ORGANISM: Artificial Sequence
<220> FEATURE:
<223> OTHER INFORMATION: Synthetic Construct

<400> SEQUENCE: 197

```
Ala Arg Gly Gly Gly Tyr Tyr Ser Gly Pro Tyr Ala Gly Phe Asp Tyr
1               5                   10                  15
```

<210> SEQ ID NO 198
<211> LENGTH: 20
<212> TYPE: PRT
<213> ORGANISM: Artificial Sequence
<220> FEATURE:
<223> OTHER INFORMATION: Synthetic Construct

<400> SEQUENCE: 198

```
Ala Arg Ser Ser Gly Gly Gly Tyr Tyr His Trp Trp Val Val Pro Tyr
1               5                   10                  15

Ala Met Asp Tyr
            20
```

<210> SEQ ID NO 199
<211> LENGTH: 20
<212> TYPE: PRT
<213> ORGANISM: Artificial Sequence
<220> FEATURE:
<223> OTHER INFORMATION: Synthetic Construct

<400> SEQUENCE: 199

```
Ala Arg Gly Val Val Pro Ser Tyr Tyr Trp Phe Trp Pro Tyr Gly
1               5                   10                  15

Ala Ile Asp Tyr
            20
```

<210> SEQ ID NO 200
<211> LENGTH: 20
<212> TYPE: PRT
<213> ORGANISM: Artificial Sequence
<220> FEATURE:
<223> OTHER INFORMATION: Synthetic Construct

<400> SEQUENCE: 200

```
Ala Arg Pro Tyr Ser Ala Tyr Tyr Trp Ala Trp Tyr Gly Pro Gly Gly
1               5                   10                  15

Ala Leu Asp Tyr
            20
```

<210> SEQ ID NO 201
<211> LENGTH: 13
<212> TYPE: PRT
<213> ORGANISM: Artificial Sequence
<220> FEATURE:
<223> OTHER INFORMATION: Synthetic Construct

<400> SEQUENCE: 201

Ala Arg Ser Gly Pro Trp Ala Trp Tyr Gly Leu Asp Tyr
1               5                   10

<210> SEQ ID NO 202
<211> LENGTH: 22
<212> TYPE: PRT
<213> ORGANISM: Artificial Sequence
<220> FEATURE:
<223> OTHER INFORMATION: Synthetic Construct

<400> SEQUENCE: 202

Ala Arg Ser Gly Tyr Tyr Ser Gly Ala Tyr Trp His Trp Trp Val Val
1               5                   10                  15

Pro Tyr Ala Met Asp Tyr
            20

<210> SEQ ID NO 203
<211> LENGTH: 16
<212> TYPE: PRT
<213> ORGANISM: Artificial Sequence
<220> FEATURE:
<223> OTHER INFORMATION: Synthetic Construct

<400> SEQUENCE: 203

Ala Arg Ser Pro Ser Trp Trp Val Ser Tyr His Ser Ala Leu Asp Tyr
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: Synthetic Construct

<400> SEQUENCE: 204

Ala Arg Ser Pro Ser Trp Trp Val Ser Tyr His Ser Ala Leu Asp Tyr
1               5                   10                  15

<210> SEQ ID NO 205
<211> LENGTH: 18
<212> TYPE: PRT
<213> ORGANISM: Artificial Sequence
<220> FEATURE:
<223> OTHER INFORMATION: Synthetic Construct

<400> SEQUENCE: 205

Ala Arg Tyr Tyr Ser Gly Trp Tyr Ser Pro Ala Trp Trp Tyr Gly Ile
1               5                   10                  15

Asp Tyr

<210> SEQ ID NO 206
<211> LENGTH: 18
<212> TYPE: PRT
<213> ORGANISM: Artificial Sequence
<220> FEATURE:
<223> OTHER INFORMATION: Synthetic Construct

<400> SEQUENCE: 206

```
Ala Arg Ser Phe Phe Pro Tyr Ser Tyr Trp Val Tyr Gly Gly Gly Met
1               5                   10                  15

Asp Tyr

<210> SEQ ID NO 207
<211> LENGTH: 23
<212> TYPE: PRT
<213> ORGANISM: Artificial Sequence
<220> FEATURE:
<223> OTHER INFORMATION: Synthetic Construct

<400> SEQUENCE: 207

Ala Arg Gly Phe Ser Ser Ser Ala His Trp Tyr Trp Ser Trp Tyr Gly
1               5                   10                  15

Pro Gly Gly Gly Phe Asp Tyr
            20

<210> SEQ ID NO 208
<211> LENGTH: 23
<212> TYPE: PRT
<213> ORGANISM: Artificial Sequence
<220> FEATURE:
<223> OTHER INFORMATION: Synthetic Construct

<400> SEQUENCE: 208

Ala Arg Gly Trp Tyr Ala Ala Tyr Ser Val Tyr Trp Phe Gly His
1               5                   10                  15

Ala Ser Tyr Gly Leu Asp Tyr
            20

<210> SEQ ID NO 209
<211> LENGTH: 23
<212> TYPE: PRT
<213> ORGANISM: Artificial Sequence
<220> FEATURE:
<223> OTHER INFORMATION: Synthetic Construct

<400> SEQUENCE: 209

Ala Arg Gly Tyr Pro Ser Ser Gly Ala Ala Trp Phe Trp Phe Ser His
1               5                   10                  15

Pro Gly Ser Ala Met Asp Tyr
            20

<210> SEQ ID NO 210
<211> LENGTH: 18
<212> TYPE: PRT
<213> ORGANISM: Artificial Sequence
<220> FEATURE:
<223> OTHER INFORMATION: Synthetic Construct

<400> SEQUENCE: 210

Ala Arg Ser Gly His Ser Val Tyr Trp Trp Trp Ser His Phe Gly Met
1               5                   10                  15

Asp Tyr

<210> SEQ ID NO 211
<211> LENGTH: 18
<212> TYPE: PRT
<213> ORGANISM: Artificial Sequence
<220> FEATURE:
<223> OTHER INFORMATION: Synthetic Construct

<400> SEQUENCE: 211
```

Ala Arg Ala Gly Tyr Phe Ser Ala Tyr Tyr Ser Ser Trp Gly Ala Met
1               5                   10                  15

Asp Tyr

<210> SEQ ID NO 212
<211> LENGTH: 9
<212> TYPE: PRT
<213> ORGANISM: Artificial Sequence
<220> FEATURE:
<223> OTHER INFORMATION: Synthetic Construct

<400> SEQUENCE: 212

Ala Arg Gly Ala Trp Ala Met Asp Tyr
1               5

<210> SEQ ID NO 213
<211> LENGTH: 18
<212> TYPE: PRT
<213> ORGANISM: Artificial Sequence
<220> FEATURE:
<223> OTHER INFORMATION: Synthetic Construct

<400> SEQUENCE: 213

Ala Arg Ser Gly Phe Ser Ser Trp Trp Trp Val Val Ser Tyr Ala Phe
1               5                   10                  15

Asp Tyr

<210> SEQ ID NO 214
<211> LENGTH: 22
<212> TYPE: PRT
<213> ORGANISM: Artificial Sequence
<220> FEATURE:
<223> OTHER INFORMATION: Synthetic Construct

<400> SEQUENCE: 214

Ala Arg Ala Gly Trp Tyr Ser Ser Trp Trp Trp Ser Ala Trp Gly Ala
1               5                   10                  15

Gly Gly Gly Leu Asp Tyr
            20

<210> SEQ ID NO 215
<211> LENGTH: 16
<212> TYPE: PRT
<213> ORGANISM: Artificial Sequence
<220> FEATURE:
<223> OTHER INFORMATION: Synthetic Construct

<400> SEQUENCE: 215

Ala Arg Ala Ala His Tyr Gly Tyr Tyr Val His Ser Gly Leu Asp Tyr
1               5                   10                  15

<210> SEQ ID NO 216
<211> LENGTH: 21
<212> TYPE: PRT
<213> ORGANISM: Artificial Sequence
<220> FEATURE:
<223> OTHER INFORMATION: Synthetic Construct

<400> SEQUENCE: 216

Ala Arg His Gly Tyr Gly Tyr Phe Phe Trp Gly Tyr Tyr Gly Pro Gly
1               5                   10                  15

Ser Ala Met Asp Tyr
            20

```
<210> SEQ ID NO 217
<211> LENGTH: 20
<212> TYPE: PRT
<213> ORGANISM: Artificial Sequence
<220> FEATURE:
<223> OTHER INFORMATION: Synthetic Construct

<400> SEQUENCE: 217

Ala Arg Ser Val Tyr Ser Trp Tyr Trp Ser Ser Trp Gly Pro Gly Ser
1               5                   10                  15

Ala Leu Asp Tyr
            20

<210> SEQ ID NO 218
<211> LENGTH: 18
<212> TYPE: PRT
<213> ORGANISM: Artificial Sequence
<220> FEATURE:
<223> OTHER INFORMATION: Synthetic Construct

<400> SEQUENCE: 218

Ala Arg Gly Tyr Pro Ala Ser Ser Tyr Tyr Tyr Pro Ser Ser Ala Leu
1               5                   10                  15

Asp Tyr

<210> SEQ ID NO 219
<211> LENGTH: 23
<212> TYPE: PRT
<213> ORGANISM: Artificial Sequence
<220> FEATURE:
<223> OTHER INFORMATION: Synthetic Construct

<400> SEQUENCE: 219

Ala Arg Ala Tyr His Ser Tyr Phe Tyr Gly Ser Tyr Trp Ser Tyr Gly
1               5                   10                  15

Trp Ala Gly Ala Leu Asp Tyr
            20

<210> SEQ ID NO 220
<211> LENGTH: 16
<212> TYPE: PRT
<213> ORGANISM: Artificial Sequence
<220> FEATURE:
<223> OTHER INFORMATION: Synthetic Construct

<400> SEQUENCE: 220

Ala Arg Tyr Val Val Gly Gly Trp Trp Tyr His Tyr Gly Met Asp Tyr
1               5                   10                  15

<210> SEQ ID NO 221
<211> LENGTH: 18
<212> TYPE: PRT
<213> ORGANISM: Artificial Sequence
<220> FEATURE:
<223> OTHER INFORMATION: Synthetic Construct

<400> SEQUENCE: 221

Ala Arg Tyr Ser Trp Ser Pro Tyr Trp Trp Trp Ala Tyr Ser Gly Leu
1               5                   10                  15

Asp Tyr

<210> SEQ ID NO 222
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 222

Ala Arg Ser Val Ala Ser Ala Leu Asp Tyr
1               5                   10

<210> SEQ ID NO 223
<211> LENGTH: 17
<212> TYPE: PRT
<213> ORGANISM: Artificial Sequence
<220> FEATURE:
<223> OTHER INFORMATION: Synthetic Construct

<400> SEQUENCE: 223

Ala Arg Tyr Ser Trp Gly Ser Ser Phe Trp Pro Gly Tyr Gly Phe Asp
1               5                   10                  15

Tyr

<210> SEQ ID NO 224
<211> LENGTH: 20
<212> TYPE: PRT
<213> ORGANISM: Artificial Sequence
<220> FEATURE:
<223> OTHER INFORMATION: Synthetic Construct

<400> SEQUENCE: 224

Ala Arg Ala Ser Gly Trp Phe Ser His Phe Tyr Pro Ala Ala Val Ser
1               5                   10                  15

Gly Met Asp Tyr
            20

<210> SEQ ID NO 225
<211> LENGTH: 18
<212> TYPE: PRT
<213> ORGANISM: Artificial Sequence
<220> FEATURE:
<223> OTHER INFORMATION: Synthetic Construct

<400> SEQUENCE: 225

Ala Arg Ser Ser Tyr Ser Val Tyr Phe Trp Trp Tyr Val Ser Ala Met
1               5                   10                  15

Asp Tyr

<210> SEQ ID NO 226
<211> LENGTH: 20
<212> TYPE: PRT
<213> ORGANISM: Artificial Sequence
<220> FEATURE:
<223> OTHER INFORMATION: Synthetic Construct

<400> SEQUENCE: 226

Ala Arg Ala Val Ser Phe Tyr Tyr Trp Ala Trp Tyr Gly Pro Gly Phe
1               5                   10                  15

Ala Met Asp Tyr
            20

<210> SEQ ID NO 227
<211> LENGTH: 18
<212> TYPE: DNA
<213> ORGANISM: Artificial Sequence
<220> FEATURE:
<223> OTHER INFORMATION: Synthetic Construct

<400> SEQUENCE: 227
```
cagtccgtgt ccagcgct                                                       18

<210> SEQ ID NO 228
<211> LENGTH: 9
<212> TYPE: DNA
<213> ORGANISM: Artificial Sequence
<220> FEATURE:
<223> OTHER INFORMATION: Synthetic Construct

<400> SEQUENCE: 228 tcggcatcc                                                                  9

<210> SEQ ID NO 229
<211> LENGTH: 27
<212> TYPE: DNA
<213> ORGANISM: Artificial Sequence
<220> FEATURE:
<223> OTHER INFORMATION: Synthetic Construct

<400> SEQUENCE: 229
cagcaatctt cttattctct gatcacg                                             27

<210> SEQ ID NO 230
<211> LENGTH: 36
<212> TYPE: DNA
<213> ORGANISM: Artificial Sequence
<220> FEATURE:
<223> OTHER INFORMATION: Synthetic Construct

<400> SEQUENCE: 230
cagcaatctt ctggttggta ccatttcctg ttcacg                                   36

<210> SEQ ID NO 231
<211> LENGTH: 33
<212> TYPE: DNA
<213> ORGANISM: Artificial Sequence
<220> FEATURE:
<223> OTHER INFORMATION: Synthetic Construct

<400> SEQUENCE: 231
cagcaatctg gttgggctta ccatccgatc acg                                      33

<210> SEQ ID NO 232
<211> LENGTH: 24
<212> TYPE: DNA
<213> ORGANISM: Artificial Sequence
<220> FEATURE:
<223> OTHER INFORMATION: Synthetic Construct

<400> SEQUENCE: 232
cagcaaggtt acgctctgtt cacg                                                24

<210> SEQ ID NO 233
<211> LENGTH: 24
<212> TYPE: DNA
<213> ORGANISM: Artificial Sequence
<220> FEATURE:
<223> OTHER INFORMATION: Synthetic Construct

<400> SEQUENCE: 233
cagcaaggtt actggctgtt cacg                                                24

<210> SEQ ID NO 234
<211> LENGTH: 33
<212> TYPE: DNA

```
<213> ORGANISM: Artificial Sequence
<220> FEATURE:
<223> OTHER INFORMATION: Synthetic Construct

<400> SEQUENCE: 234
cagcaagctg cttggggtgg tgctccgatc acg                                  33

<210> SEQ ID NO 235
<211> LENGTH: 24
<212> TYPE: DNA
<213> ORGANISM: Artificial Sequence
<220> FEATURE:
<223> OTHER INFORMATION: Synthetic Construct

<400> SEQUENCE: 235
cagcaatctt ctccgccgat cacg                                            24

<210> SEQ ID NO 236
<211> LENGTH: 24
<212> TYPE: DNA
<213> ORGANISM: Artificial Sequence
<220> FEATURE:
<223> OTHER INFORMATION: Synthetic Construct

<400> SEQUENCE: 236
cagcaaccgt actctccgat cacg                                            24

<210> SEQ ID NO 237
<211> LENGTH: 36
<212> TYPE: DNA
<213> ORGANISM: Artificial Sequence
<220> FEATURE:
<223> OTHER INFORMATION: Synthetic Construct

<400> SEQUENCE: 237
cagcaaggtt cttactactg gtggtctccg atcacg                               36

<210> SEQ ID NO 238
<211> LENGTH: 33
<212> TYPE: DNA
<213> ORGANISM: Artificial Sequence
<220> FEATURE:
<223> OTHER INFORMATION: Synthetic Construct

<400> SEQUENCE: 238
cagcaatctc cgtggggtgc ttacctgatc acg                                  33

<210> SEQ ID NO 239
<211> LENGTH: 33
<212> TYPE: DNA
<213> ORGANISM: Artificial Sequence
<220> FEATURE:
<223> OTHER INFORMATION: Synthetic Construct

<400> SEQUENCE: 239
cagcaagctg gtttcttctc ttacccgatc acg                                  33

<210> SEQ ID NO 240
<211> LENGTH: 24
<212> TYPE: DNA
<213> ORGANISM: Artificial Sequence
<220> FEATURE:
<223> OTHER INFORMATION: Synthetic Construct

<400> SEQUENCE: 240
cagcaaggtg gtggtctgat cacg                                            24
```

<210> SEQ ID NO 241
<211> LENGTH: 36
<212> TYPE: DNA
<213> ORGANISM: Artificial Sequence
<220> FEATURE:
<223> OTHER INFORMATION: Synthetic Construct

<400> SEQUENCE: 241
cagcaatact cttggtactg gtactctccg atcacg                                 36

<210> SEQ ID NO 242
<211> LENGTH: 36
<212> TYPE: DNA
<213> ORGANISM: Artificial Sequence
<220> FEATURE:
<223> OTHER INFORMATION: Synthetic Construct

<400> SEQUENCE: 242
cagcaatact cttactacta cgcttctccg atcacg                                 36

<210> SEQ ID NO 243
<211> LENGTH: 33
<212> TYPE: DNA
<213> ORGANISM: Artificial Sequence
<220> FEATURE:
<223> OTHER INFORMATION: Synthetic Construct

<400> SEQUENCE: 243
cagcaatctt ctcatggtca ttacccgatc acg                                    33

<210> SEQ ID NO 244
<211> LENGTH: 27
<212> TYPE: DNA
<213> ORGANISM: Artificial Sequence
<220> FEATURE:
<223> OTHER INFORMATION: Synthetic Construct

<400> SEQUENCE: 244
ggcttcaacc tctattctta ttctatc                                           27

<210> SEQ ID NO 245
<211> LENGTH: 27
<212> TYPE: DNA
<213> ORGANISM: Artificial Sequence
<220> FEATURE:
<223> OTHER INFORMATION: Synthetic Construct

<400> SEQUENCE: 245
ggcttcaacc tctcttatta ttctatg                                           27

<210> SEQ ID NO 246
<211> LENGTH: 27
<212> TYPE: DNA
<213> ORGANISM: Artificial Sequence
<220> FEATURE:
<223> OTHER INFORMATION: Synthetic Construct

<400> SEQUENCE: 246
ggcttcaaca tctcttcttc ttctatc                                           27

<210> SEQ ID NO 247
<211> LENGTH: 27
<212> TYPE: DNA
<213> ORGANISM: Artificial Sequence
<220> FEATURE:

<223> OTHER INFORMATION: Synthetic Construct

<400> SEQUENCE: 247
ggcttcaacc tctcttcttc ttatatg        27

<210> SEQ ID NO 248
<211> LENGTH: 27
<212> TYPE: DNA
<213> ORGANISM: Artificial Sequence
<220> FEATURE:
<223> OTHER INFORMATION: Synthetic Construct

<400> SEQUENCE: 248
ggcttcaact tttcttcttc ttctata        27

<210> SEQ ID NO 249
<211> LENGTH: 27
<212> TYPE: DNA
<213> ORGANISM: Artificial Sequence
<220> FEATURE:
<223> OTHER INFORMATION: Synthetic Construct

<400> SEQUENCE: 249
ggcttcaaca tctattctta ttatatc        27

<210> SEQ ID NO 250
<211> LENGTH: 27
<212> TYPE: DNA
<213> ORGANISM: Artificial Sequence
<220> FEATURE:
<223> OTHER INFORMATION: Synthetic Construct

<400> SEQUENCE: 250
ggcttcaacc tctcttcttc ttctatc        27

<210> SEQ ID NO 251
<211> LENGTH: 27
<212> TYPE: DNA
<213> ORGANISM: Artificial Sequence
<220> FEATURE:
<223> OTHER INFORMATION: Synthetic Construct

<400> SEQUENCE: 251
ggcttcaacc tctattattc ttatatg        27

<210> SEQ ID NO 252
<211> LENGTH: 27
<212> TYPE: DNA
<213> ORGANISM: Artificial Sequence
<220> FEATURE:
<223> OTHER INFORMATION: Synthetic Construct

<400> SEQUENCE: 252
ggcttcaacc tctcttctta ttctatg        27

<210> SEQ ID NO 253
<211> LENGTH: 27
<212> TYPE: DNA
<213> ORGANISM: Artificial Sequence
<220> FEATURE:
<223> OTHER INFORMATION: Synthetic Construct

<400> SEQUENCE: 253
ggcttcaacc tctattcttc ttctatc        27

```
<210> SEQ ID NO 254
<211> LENGTH: 27
<212> TYPE: DNA
<213> ORGANISM: Artificial Sequence
<220> FEATURE:
<223> OTHER INFORMATION: Synthetic Construct

<400> SEQUENCE: 254
ggcttcaacc tctattctta ttctatg                                           27

<210> SEQ ID NO 255
<211> LENGTH: 27
<212> TYPE: DNA
<213> ORGANISM: Artificial Sequence
<220> FEATURE:
<223> OTHER INFORMATION: Synthetic Construct

<400> SEQUENCE: 255
ggcttcaaca tttcttactc ttctatt                                           27

<210> SEQ ID NO 256
<211> LENGTH: 27
<212> TYPE: DNA
<213> ORGANISM: Artificial Sequence
<220> FEATURE:
<223> OTHER INFORMATION: Synthetic Construct

<400> SEQUENCE: 256
ggcttcaaca tctattctta ttctatg                                           27

<210> SEQ ID NO 257
<211> LENGTH: 27
<212> TYPE: DNA
<213> ORGANISM: Artificial Sequence
<220> FEATURE:
<223> OTHER INFORMATION: Synthetic Construct

<400> SEQUENCE: 257
ggcttcaaca tctcttctta ttatatg                                           27

<210> SEQ ID NO 258
<211> LENGTH: 27
<212> TYPE: DNA
<213> ORGANISM: Artificial Sequence
<220> FEATURE:
<223> OTHER INFORMATION: Synthetic Construct

<400> SEQUENCE: 258
ggcttcaacc tctcttcttc ttctata                                           27

<210> SEQ ID NO 259
<211> LENGTH: 27
<212> TYPE: DNA
<213> ORGANISM: Artificial Sequence
<220> FEATURE:
<223> OTHER INFORMATION: Synthetic Construct

<400> SEQUENCE: 259
ggcttcaaca tctcttctta ttatatc                                           27

<210> SEQ ID NO 260
<211> LENGTH: 27
<212> TYPE: DNA
<213> ORGANISM: Artificial Sequence
<220> FEATURE:
<223> OTHER INFORMATION: Synthetic Construct
```

<400> SEQUENCE: 260
ggcttcaaca tctattattc ttctatc					27

<210> SEQ ID NO 261
<211> LENGTH: 27
<212> TYPE: DNA
<213> ORGANISM: Artificial Sequence
<220> FEATURE:
<223> OTHER INFORMATION: Synthetic Construct

<400> SEQUENCE: 261
ggcttcaaca tctattcttc ttctatc					27

<210> SEQ ID NO 262
<211> LENGTH: 27
<212> TYPE: DNA
<213> ORGANISM: Artificial Sequence
<220> FEATURE:
<223> OTHER INFORMATION: Synthetic Construct

<400> SEQUENCE: 262
ggcttcaacc tctcttctta ttatatg					27

<210> SEQ ID NO 263
<211> LENGTH: 30
<212> TYPE: DNA
<213> ORGANISM: Artificial Sequence
<220> FEATURE:
<223> OTHER INFORMATION: Synthetic Construct

<400> SEQUENCE: 263
tatatttctt cttcttctgg ctctacttat					30

<210> SEQ ID NO 264
<211> LENGTH: 30
<212> TYPE: DNA
<213> ORGANISM: Artificial Sequence
<220> FEATURE:
<223> OTHER INFORMATION: Synthetic Construct

<400> SEQUENCE: 264
tctatttctt cttattatgg ctctacttat					30

<210> SEQ ID NO 265
<211> LENGTH: 30
<212> TYPE: DNA
<213> ORGANISM: Artificial Sequence
<220> FEATURE:
<223> OTHER INFORMATION: Synthetic Construct

<400> SEQUENCE: 265
tatatttctt cttcttatag ctctacttct					30

<210> SEQ ID NO 266
<211> LENGTH: 30
<212> TYPE: DNA
<213> ORGANISM: Artificial Sequence
<220> FEATURE:
<223> OTHER INFORMATION: Synthetic Construct

<400> SEQUENCE: 266
tctatttatc cttcttatgg ctctacttct					30

<210> SEQ ID NO 267
<211> LENGTH: 30

-continued

<212> TYPE: DNA
<213> ORGANISM: Artificial Sequence
<220> FEATURE:
<223> OTHER INFORMATION: Synthetic Construct

<400> SEQUENCE: 267
tctatttctt cttcttatgg ctatacttat                                30

<210> SEQ ID NO 268
<211> LENGTH: 30
<212> TYPE: DNA
<213> ORGANISM: Artificial Sequence
<220> FEATURE:
<223> OTHER INFORMATION: Synthetic Construct

<400> SEQUENCE: 268
tctatttatt cttattatgg ctctacttct                                30

<210> SEQ ID NO 269
<211> LENGTH: 30
<212> TYPE: DNA
<213> ORGANISM: Artificial Sequence
<220> FEATURE:
<223> OTHER INFORMATION: Synthetic Construct

<400> SEQUENCE: 269
tatatttctc cttcttatgg ctctacttct                                30

<210> SEQ ID NO 270
<211> LENGTH: 30
<212> TYPE: DNA
<213> ORGANISM: Artificial Sequence
<220> FEATURE:
<223> OTHER INFORMATION: Synthetic Construct

<400> SEQUENCE: 270
tctatttatt cttcttctag ctatacttct                                30

<210> SEQ ID NO 271
<211> LENGTH: 30
<212> TYPE: DNA
<213> ORGANISM: Artificial Sequence
<220> FEATURE:
<223> OTHER INFORMATION: Synthetic Construct

<400> SEQUENCE: 271
tctatttctt cttattctgg ctatacttct                                30

<210> SEQ ID NO 272
<211> LENGTH: 30
<212> TYPE: DNA
<213> ORGANISM: Artificial Sequence
<220> FEATURE:
<223> OTHER INFORMATION: Synthetic Construct

<400> SEQUENCE: 272
tctatctctc cttattctgg ctatacttat                                30

<210> SEQ ID NO 273
<211> LENGTH: 30
<212> TYPE: DNA
<213> ORGANISM: Artificial Sequence
<220> FEATURE:
<223> OTHER INFORMATION: Synthetic Construct

<400> SEQUENCE: 273

```
tctatttctc cttattctgg ctatacttat                                30
```

<210> SEQ ID NO 274
<211> LENGTH: 30
<212> TYPE: DNA
<213> ORGANISM: Artificial Sequence
<220> FEATURE:
<223> OTHER INFORMATION: Synthetic Construct

<400> SEQUENCE: 274

```
tctatttctt cttcttacgg ttacacttac                                30
```

<210> SEQ ID NO 275
<211> LENGTH: 30
<212> TYPE: DNA
<213> ORGANISM: Artificial Sequence
<220> FEATURE:
<223> OTHER INFORMATION: Synthetic Construct

<400> SEQUENCE: 275

```
tctatttatc cttcttctag ctatacttat                                30
```

<210> SEQ ID NO 276
<211> LENGTH: 30
<212> TYPE: DNA
<213> ORGANISM: Artificial Sequence
<220> FEATURE:
<223> OTHER INFORMATION: Synthetic Construct

<400> SEQUENCE: 276

```
tctatttatt cttcttatag ctctacttat                                30
```

<210> SEQ ID NO 277
<211> LENGTH: 30
<212> TYPE: DNA
<213> ORGANISM: Artificial Sequence
<220> FEATURE:
<223> OTHER INFORMATION: Synthetic Construct

<400> SEQUENCE: 277

```
tctatttctc cttattctgg ctctacttat                                30
```

<210> SEQ ID NO 278
<211> LENGTH: 30
<212> TYPE: DNA
<213> ORGANISM: Artificial Sequence
<220> FEATURE:
<223> OTHER INFORMATION: Synthetic Construct

<400> SEQUENCE: 278

```
tatatttatt cttcttatgg ctatacttat                                30
```

<210> SEQ ID NO 279
<211> LENGTH: 30
<212> TYPE: DNA
<213> ORGANISM: Artificial Sequence
<220> FEATURE:
<223> OTHER INFORMATION: Synthetic Construct

<400> SEQUENCE: 279

```
tctatttctc cttattatag ctatacttat                                30
```

<210> SEQ ID NO 280
<211> LENGTH: 30
<212> TYPE: DNA
<213> ORGANISM: Artificial Sequence
<220> FEATURE:
<223> OTHER INFORMATION: Synthetic Construct

<400> SEQUENCE: 280
tatatttctt cttcttctgg ctctacttct                            30

<210> SEQ ID NO 281
<211> LENGTH: 30
<212> TYPE: DNA
<213> ORGANISM: Artificial Sequence
<220> FEATURE:
<223> OTHER INFORMATION: Synthetic Construct

<400> SEQUENCE: 281
tctatttatt cttcttatgg ctatacttct                            30

<210> SEQ ID NO 282
<211> LENGTH: 30
<212> TYPE: DNA
<213> ORGANISM: Artificial Sequence
<220> FEATURE:
<223> OTHER INFORMATION: Synthetic Construct

<400> SEQUENCE: 282
tctatttatc cttattatag ctatacttat                            30

<210> SEQ ID NO 283
<211> LENGTH: 30
<212> TYPE: DNA
<213> ORGANISM: Artificial Sequence
<220> FEATURE:
<223> OTHER INFORMATION: Synthetic Construct

<400> SEQUENCE: 283
tctatttatc cttattctgg ctatacttat                            30

<210> SEQ ID NO 284
<211> LENGTH: 30
<212> TYPE: DNA
<213> ORGANISM: Artificial Sequence
<220> FEATURE:
<223> OTHER INFORMATION: Synthetic Construct

<400> SEQUENCE: 284
tatatttctt cttcttatgg ctatacttct                            30

<210> SEQ ID NO 285
<211> LENGTH: 30
<212> TYPE: DNA
<213> ORGANISM: Artificial Sequence
<220> FEATURE:
<223> OTHER INFORMATION: Synthetic Construct

<400> SEQUENCE: 285
tctatttatc cttcttatag ctctacttat                            30

<210> SEQ ID NO 286
<211> LENGTH: 54
<212> TYPE: DNA
<213> ORGANISM: Artificial Sequence
<220> FEATURE:
<223> OTHER INFORMATION: Synthetic Construct

<400> SEQUENCE: 286
gctcgcggtt ggggtggtgg ttactggttc tacccggttt acggtattga ctac      54

```
<210> SEQ ID NO 287
<211> LENGTH: 48
<212> TYPE: DNA
<213> ORGANISM: Artificial Sequence
<220> FEATURE:
<223> OTHER INFORMATION: Synthetic Construct

<400> SEQUENCE: 287
gctcgcggtg gtggttacta ctctggtccg tacgctggtt ttgactac           48

<210> SEQ ID NO 288
<211> LENGTH: 60
<212> TYPE: DNA
<213> ORGANISM: Artificial Sequence
<220> FEATURE:
<223> OTHER INFORMATION: Synthetic Construct

<400> SEQUENCE: 288
gctcgctctt ctggtggtgg ttactaccat tggtgggttg ttccgtacgc tatggactac     60

<210> SEQ ID NO 289
<211> LENGTH: 60
<212> TYPE: DNA
<213> ORGANISM: Artificial Sequence
<220> FEATURE:
<223> OTHER INFORMATION: Synthetic Construct

<400> SEQUENCE: 289
gctcgcggtg ttgttccgtc ttactactac tggttctggc cgtacggtgc tattgactac     60

<210> SEQ ID NO 290
<211> LENGTH: 60
<212> TYPE: DNA
<213> ORGANISM: Artificial Sequence
<220> FEATURE:
<223> OTHER INFORMATION: Synthetic Construct

<400> SEQUENCE: 290
gctcgcccgt actctgctta ctactgggct tggtacggtc cgggtggtgc tttggactac     60

<210> SEQ ID NO 291
<211> LENGTH: 39
<212> TYPE: DNA
<213> ORGANISM: Artificial Sequence
<220> FEATURE:
<223> OTHER INFORMATION: Synthetic Construct

<400> SEQUENCE: 291
gctcgctctg gtccgtgggc ttggtacggt ttggactac                    39

<210> SEQ ID NO 292
<211> LENGTH: 66
<212> TYPE: DNA
<213> ORGANISM: Artificial Sequence
<220> FEATURE:
<223> OTHER INFORMATION: Synthetic Construct

<400> SEQUENCE: 292
gctcgctctg gttactactc tggtgcttac tggcattggt gggttgttcc gtacgctatg     60
gactac                                                              66

<210> SEQ ID NO 293
<211> LENGTH: 48
<212> TYPE: DNA
<213> ORGANISM: Artificial Sequence
```

```
<220> FEATURE:
<223> OTHER INFORMATION: Synthetic Construct

<400> SEQUENCE: 293
gctcgctctc cgtcttggtg ggtttcttac cattctgctt tggactac                48

<210> SEQ ID NO 294
<211> LENGTH: 48
<212> TYPE: DNA
<213> ORGANISM: Artificial Sequence
<220> FEATURE:
<223> OTHER INFORMATION: Synthetic Construct

<400> SEQUENCE: 294
gctcgctctt actcttggtg gtggtctgtt tcttacgcta tggactac                48

<210> SEQ ID NO 295
<211> LENGTH: 54
<212> TYPE: DNA
<213> ORGANISM: Artificial Sequence
<220> FEATURE:
<223> OTHER INFORMATION: Synthetic Construct

<400> SEQUENCE: 295
gctcgctact actctggttg gtactctccg gcttggtggt acggtattga ctac          54

<210> SEQ ID NO 296
<211> LENGTH: 54
<212> TYPE: DNA
<213> ORGANISM: Artificial Sequence
<220> FEATURE:
<223> OTHER INFORMATION: Synthetic Construct

<400> SEQUENCE: 296
gctcgctctt tcttcccgta ctcttactgg gtttacggtg gtggtatgga ctac          54

<210> SEQ ID NO 297
<211> LENGTH: 69
<212> TYPE: DNA
<213> ORGANISM: Artificial Sequence
<220> FEATURE:
<223> OTHER INFORMATION: Synthetic Construct

<400> SEQUENCE: 297
gctcgcggtt tctcttcttc tgctcattgg tactggtctt ggtacggtcc gggtggtggt   60
tttgactac                                                            69

<210> SEQ ID NO 298
<211> LENGTH: 69
<212> TYPE: DNA
<213> ORGANISM: Artificial Sequence
<220> FEATURE:
<223> OTHER INFORMATION: Synthetic Construct

<400> SEQUENCE: 298
gctcgcggtt ggtacgctgc ttactctgtt tactggttcg gtggtcatgc ttcttacggt   60
ttggactac                                                            69

<210> SEQ ID NO 299
<211> LENGTH: 69
<212> TYPE: DNA
<213> ORGANISM: Artificial Sequence
<220> FEATURE:
<223> OTHER INFORMATION: Synthetic Construct
```

```
<400> SEQUENCE: 299
gctcgcggtt acccgtcttc tggtgctgct tggttctggt tctctcatcc gggttctgct    60
atggactac                                                              69

<210> SEQ ID NO 300
<211> LENGTH: 54
<212> TYPE: DNA
<213> ORGANISM: Artificial Sequence
<220> FEATURE:
<223> OTHER INFORMATION: Synthetic Construct

<400> SEQUENCE: 300
gctcgctctg gtcattctgt ttactggtgg tggtctcatt tcggtatgga ctac           54

<210> SEQ ID NO 301
<211> LENGTH: 54
<212> TYPE: DNA
<213> ORGANISM: Artificial Sequence
<220> FEATURE:
<223> OTHER INFORMATION: Synthetic Construct

<400> SEQUENCE: 301
gctcgcgctg gttacttctc tgcttactac tcttcttggg gtgctatgga ctac           54

<210> SEQ ID NO 302
<211> LENGTH: 27
<212> TYPE: DNA
<213> ORGANISM: Artificial Sequence
<220> FEATURE:
<223> OTHER INFORMATION: Synthetic Construct

<400> SEQUENCE: 302
gctcgcggtg cttgggctat ggactac                                         27

<210> SEQ ID NO 303
<211> LENGTH: 54
<212> TYPE: DNA
<213> ORGANISM: Artificial Sequence
<220> FEATURE:
<223> OTHER INFORMATION: Synthetic Construct

<400> SEQUENCE: 303
gctcgctctg gtttctcttc ttggtggtgg gttgtttctt acgcttttga ctac           54

<210> SEQ ID NO 304
<211> LENGTH: 66
<212> TYPE: DNA
<213> ORGANISM: Artificial Sequence
<220> FEATURE:
<223> OTHER INFORMATION: Synthetic Construct

<400> SEQUENCE: 304
gctcgcgctg gttggtactc ttcttggtgg tggtctgctt ggggtgctgg tggtggtttg    60
gactac                                                                66

<210> SEQ ID NO 305
<211> LENGTH: 48
<212> TYPE: DNA
<213> ORGANISM: Artificial Sequence
<220> FEATURE:
<223> OTHER INFORMATION: Synthetic Construct

<400> SEQUENCE: 305
gctcgcgctg ctcattacgg ttactacgtt cattctggtt tggactac                  48
```

<210> SEQ ID NO 306
<211> LENGTH: 63
<212> TYPE: DNA
<213> ORGANISM: Artificial Sequence
<220> FEATURE:
<223> OTHER INFORMATION: Synthetic Construct

<400> SEQUENCE: 306
gctcgccatg gttacggtta cttcttctgg ggttactacg gtccgggttc tgctatggac    60
tac                                                                 63

<210> SEQ ID NO 307
<211> LENGTH: 60
<212> TYPE: DNA
<213> ORGANISM: Artificial Sequence
<220> FEATURE:
<223> OTHER INFORMATION: Synthetic Construct

<400> SEQUENCE: 307
gctcgctctg tttactcttg gtactggtct tcttggggtc cgggttctgc tttggactac    60

<210> SEQ ID NO 308
<211> LENGTH: 54
<212> TYPE: DNA
<213> ORGANISM: Artificial Sequence
<220> FEATURE:
<223> OTHER INFORMATION: Synthetic Construct

<400> SEQUENCE: 308
gctcgcggtt acccggcttc ttcttactac tacccgtctt ctgctttgga ctac          54

<210> SEQ ID NO 309
<211> LENGTH: 69
<212> TYPE: DNA
<213> ORGANISM: Artificial Sequence
<220> FEATURE:
<223> OTHER INFORMATION: Synthetic Construct

<400> SEQUENCE: 309
gctcgcgctt accattctta cttctacggt tcttactggt cttacggttg ggctggtgct    60
ttggactac                                                           69

<210> SEQ ID NO 310
<211> LENGTH: 48
<212> TYPE: DNA
<213> ORGANISM: Artificial Sequence
<220> FEATURE:
<223> OTHER INFORMATION: Synthetic Construct

<400> SEQUENCE: 310
gctcgctacg ttgttggtgg ttggtggtac cattacggta tggactac                 48

<210> SEQ ID NO 311
<211> LENGTH: 54
<212> TYPE: DNA
<213> ORGANISM: Artificial Sequence
<220> FEATURE:
<223> OTHER INFORMATION: Synthetic Construct

<400> SEQUENCE: 311
gctcgctact cttggtctcc gtactggtgg tgggcttact ctggtttgga ctac          54

<210> SEQ ID NO 312

-continued

```
<211> LENGTH: 30
<212> TYPE: DNA
<213> ORGANISM: Artificial Sequence
<220> FEATURE:
<223> OTHER INFORMATION: Synthetic Construct

<400> SEQUENCE: 312
gctcgctctg ttgcttctgc tttggactac                              30

<210> SEQ ID NO 313
<211> LENGTH: 51
<212> TYPE: DNA
<213> ORGANISM: Artificial Sequence
<220> FEATURE:
<223> OTHER INFORMATION: Synthetic Construct

<400> SEQUENCE: 313
gctcgctact cttggggttc ttctttctgg ccgggttacg gttttgacta c      51

<210> SEQ ID NO 314
<211> LENGTH: 60
<212> TYPE: DNA
<213> ORGANISM: Artificial Sequence
<220> FEATURE:
<223> OTHER INFORMATION: Synthetic Construct

<400> SEQUENCE: 314
gctcgcgctt ctggttggtt ctctcatttc tacccggctg ctgtttctgg tatggactac  60

<210> SEQ ID NO 315
<211> LENGTH: 54
<212> TYPE: DNA
<213> ORGANISM: Artificial Sequence
<220> FEATURE:
<223> OTHER INFORMATION: Synthetic Construct

<400> SEQUENCE: 315
gctcgctctt cttactctgt ttacttctgg tggtacgttt ctgctatgga ctac        54

<210> SEQ ID NO 316
<211> LENGTH: 60
<212> TYPE: DNA
<213> ORGANISM: Artificial Sequence
<220> FEATURE:
<223> OTHER INFORMATION: Synthetic Construct

<400> SEQUENCE: 316
gctcgcgctg tttctttcta ctactgggct tggtacggtc cgggtttcgc tatggactac  60

<210> SEQ ID NO 317
<211> LENGTH: 214
<212> TYPE: PRT
<213> ORGANISM: Artificial Sequence
<220> FEATURE:
<223> OTHER INFORMATION: Synthetic Construct

<400> SEQUENCE: 317

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60
```

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Leu Ile
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 318
<211> LENGTH: 684
<212> TYPE: DNA
<213> ORGANISM: Artificial Sequence
<220> FEATURE:
<223> OTHER INFORMATION: Synthetic Construct

<400> SEQUENCE: 318
gatatccaga tgacccagtc cccgagctcc ctgtccgcct ctgtgggcga tagggtcacc      60
atcacctgcc gtgccagtca gtccgtgtcc agcgctgtag cctggtatca acagaaacca     120
ggaaaagctc cgaagcttct gatttactcg gcatccagcc tctactctgg agtcccttct     180
cgcttctctg gtagccgttc cgggacggat ttcactctga ccatcagcag tctgcagccg     240
gaagacttcg caacttatta ctgtcagcaa tcttcttatt ctctgatcac gttcggacag     300
ggtaccaagg tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gtctgagctc gcccgtcaca     660
aagagcttca cagggggaga gtgt                                            684

<210> SEQ ID NO 319
<211> LENGTH: 455
<212> TYPE: PRT
<213> ORGANISM: Artificial Sequence
<220> FEATURE:
<223> OTHER INFORMATION: Synthetic Construct

<400> SEQUENCE: 319

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Tyr

```
                 20                  25                  30
Ser Ile His Trp Val Arg Gln Ala Pro Gly Lys Gly Leu Glu Trp Val
             35                  40                  45
Ala Tyr Ile Ser Ser Ser Gly Ser Thr Tyr Tyr Ala Asp Ser Val
         50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Gly Trp Gly Gly Tyr Trp Phe Tyr Pro Val Tyr Gly Ile
             100                 105                 110
Asp Tyr Trp Gly Gln Gly Thr Leu Val Thr Val Ser Ser Ala Ser Thr
             115                 120                 125
Lys Gly Pro Ser Val Phe Pro Leu Ala Pro Ser Ser Lys Ser Thr Ser
             130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                 165                 170                 175
Thr Phe Pro Ala Val Leu Gln Ser Ser Gly Leu Tyr Ser Leu Ser Ser
             180                 185                 190
Val Val Thr Val Pro Ser Ser Ser Leu Gly Thr Gln Thr Tyr Ile Cys
             195                 200                 205
Asn Val Asn His Lys Pro Ser Asn Thr Lys Val Asp Lys Lys Val Glu
             210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                 245                 250                 255
Asp Thr Leu Met Ile Ser Arg Thr Pro Glu Val Thr Cys Val Val Val
             260                 265                 270
Asp Val Ser His Glu Asp Pro Glu Val Lys Phe Asn Trp Tyr Val Asp
             275                 280                 285
Gly Val Glu Val His Asn Ala Lys Thr Lys Pro Arg Glu Glu Gln Tyr
             290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                 325                 330                 335
Pro Ala Pro Ile Glu Lys Thr Ile Ser Lys Ala Lys Gly Gln Pro Arg
             340                 345                 350
Glu Pro Gln Val Tyr Thr Leu Pro Pro Ser Arg Glu Glu Met Thr Lys
             355                 360                 365
Asn Gln Val Ser Leu Thr Cys Leu Val Lys Gly Phe Tyr Pro Ser Asp
         370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                 405                 410                 415
Lys Leu Thr Val Asp Lys Ser Arg Trp Gln Gln Gly Asn Val Phe Ser
             420                 425                 430
Cys Ser Val Met His Glu Ala Leu His Asn His Tyr Thr Gln Lys Ser
             435                 440                 445
```

```
Leu Ser Leu Ser Pro Gly Lys
    450                 455

<210> SEQ ID NO 320
<211> LENGTH: 1365
<212> TYPE: DNA
<213> ORGANISM: Artificial Sequence
<220> FEATURE:
<223> OTHER INFORMATION: Synthetic Construct

<400> SEQUENCE: 320
gaggttcagc tggtggagtc tggcggtggc ctggtgcagc caggggggctc actccgtttg    60 tcctgtgcag cttctggctt caacctctat tcttattcta tccactgggt gcgtcaggcc   120
ccgggtaagg gcctggaatg ggttgcatat atttcttctt cttctggctc tacttattat   180
gccgatagcg tcaagggccg tttcactata agcgcagaca catccaaaaa cacagcctac   240
ctacaaatga acagcttaag agctgaggac actgccgtct attattgtgc tcgcggttgg   300
ggtggtggtt actggttcta cccggtttac ggtattgact actggggtca aggaaccctg   360
gtcaccgtct cctcggctag caccaagggc ccatcggtct tccccctggc acctcctcc    420 aagagcacct ctgggggcac agcggccctg ggctgcctgg tcaaggacta cttccccgaa   480
ccggtgacgg tgtcgtggaa ctcaggcgcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aatcacaagc ccagcaacac caaggtggac   660
aagaaagttg agcccaaatc ttgtgacaaa actcacacat gcccaccgtg cccagcacct   720
gaactcctgg ggggaccgtc agtcttcctc ttccccccaa acccaaagga caccctcatg   780
atctcccgga cccctgaggt cacatgcgtg gtggtggacg tgagccacga agaccctgag   840
gtcaagttca actggtacgt ggacggcgtg gaggtgcata atgccaagac aaagccgcgg   900
gaggagcagt acaacagcac gtaccgtgtg gtcagcgtcc tcaccgtcct gcaccaggac   960
tggctgaatg gcaaggagta caagtgcaag gtctccaaca aagcccctcc agcccccatc  1020
gagaaaacca tctccaaagc caaagggcag ccccgagaac cacaggtgta caccctgccc  1080
ccatcccggg aggagatgac caagaaccag gtcagcctga cctgcctggt caaaggcttc  1140
tatcccagcg acatcgccgt ggagtgggag agcaatgggc agccggagaa caactacaag  1200
accacgcctc ccgtgctgga ctccgacggc tccttcttcc tctacagcaa gctcaccgtg  1260
gacaagagca ggtggcagca ggggaacgtc ttctcatgct ccgtgatgca tgaggctctg  1320
cacaaccact acacgcagaa gagcctctcc ctgtctccgg gtaaa              1365
```

ANTIBODIES WHICH SPECIFICALLY BIND αKLOTHO POLYPEPTIDE

CROSS REFERENCE TO RELATED APPLICATIONS

This is a U.S. national phase application based on PCT Application No. PCT/CA2017/050127, filed Feb. 3, 2017, which claims the benefit of 35 U.S.C. § 119 based on the priority of U.S. Provisional Patent Application No. 62/290,776, filed Feb. 3, 2016, which is incorporated herein by reference in its entirety.

This invention was made in part with U.S. Government support under NIH Grant Nos. R01DK091392, R01DK092461 and R01DE13686. The U.S. Government may have certain rights in this invention.

FIELD

This disclosure relates to antibodies specific for folded forms of αKlotho as well as methods and assays, for example, enzyme-linked immunosorbent assays, for detecting αKlotho.

BACKGROUND

The klotho gene was originally identified as a suppressor of premature aging [1, reviewed in 2]. Klotho is a single-pass transmembrane protein expressed predominantly in the kidney, the parathyroid gland, and the choroid plexus [1, 3, 4]. Paralogous proteins with distinct functions and expression profiles, termed βKlotho and γKlotho [5, 6] are also known.

αKlotho has diverse effects, including regulating ion transport, Wnt and insulin signaling, renin-angiotensin system, recruitment of stem cells, anti-carcinogenesis, anti-fibrosis, and antioxidation. The highest level of expression of αKlotho is in the kidney [1, 7, 8]. In addition to its transmembrane form which is a co-receptor for fibroblast growth factor (FGF) 23 [9-11], αKlotho is also released into the circulation, urine, and cerebrospinal fluid as an endocrine substance [7, 12, 13] generated by transcript splicing into a truncated peptide[2] or proteolytic release by secretases [14, 15]. A substantial portion of the circulating αKlotho is nephrogenic in origin [16]. The phenotypic similarities between genetic αKlotho ablation and chronic kidney disease (CKD) support the notion that reduced renal expression of αKlotho is pathogenic [1, 16].

Reduced renal αKlotho transcript or protein levels [12, 18-24] and serum αKlotho concentration [12, 20] was demonstrated in rodent CKD from nephron reduction surgery, ischemia reperfusion injury, immune complex glomerulonephritis, polygenic or hormonal hypertension, metabolic syndrome, and diabetes [12, 18-24]. This convergence suggests that αKlotho deficiency may be a generic consequence of nephron loss. αKlotho reduction is potentially a sensitive and early biomarker of CKD and also prognostic of CKD complications [22]. Restoration of αKlotho in experimental CKD in rodents ameliorates the kidney disease and extra-renal complications [12, 22, 23]. αKlotho deficiency has also been documented in acute kidney injury (AKI) in both rodents and humans [25]. αKlotho can potentially serve as an early biomarker for AKI as it is reduced much earlier than changes in the current known biomarkers of AKI [26].

αKlotho forms a constitutive binary complex with FGF receptors (FGFRs) to confer selective affinity to FGF23 [10, 27]. Defects in αKlotho expression result in FGF23 resistance and phosphate retention in mice [1, 28] and humans [29]. Therefore, αKlotho and FGF23 have emerged as essential components of the bone-kidney endocrine axis that regulates phosphate metabolism [30, 31].

The extracellular domain of the membrane-anchored form of αKlotho can be secreted as a soluble protein. The soluble form is generated from the membrane-anchored form by membrane-anchored proteases and is released into blood and urine [13, 15]. As noted above, membrane-anchored αKlotho functions as part of the FGF23 receptor complex, whereas secreted αKlotho functions as an endocrine factor that exerts actions on distant organs to exert highly pleiotropic actions as stated above (regulating ion transport, Wnt and insulin signaling, renin-angiotensin system, recruitment of stem cells, anti-carcinogenesis, anti-fibrosis, and antioxidation) [7].

Advanced CKD (Stages 4-5), characterized by kidney damage and decreased kidney function, affects an estimated 2.6 million Canadians, greater than 7% of the population. A recent analysis of National Vital Statistics Report, National Health and Nutrition Examination Surveys and US Renal Data System showed that the lifetime risks for white men, white women, black men, and black women, are respectively: CKD stage 3a+, 53.6%, 64.9%, 51.8%, and 63.6% [84]. The impact and burden of CKD and its associated complications on people's lives and the health care system is significant and will worsen in coming years [32-34]. Current approaches to treat CKD include modification of risk factors by diet and medication, and for end stage renal disease (ESRD) by dialysis, and organ replacement. There is an urgent need for additional therapies to arrest or delay progression of CKD at early stages, before complications arise. The majority of the complications of CKD are embraced within the entity of CKD-mineral bone disturbance (CKD-MBD) which are tied to disturbances of mineral metabolism. Phosphate retention is universally observed in CKD patients and associated with poor outcome [35, 36]. Hyperphosphatemia is usually detected only in advanced stages of CKD when the disease is destined to progress to end-stage [37]. Recently, it has been discovered that reduced renal αKlotho expression is one of the earliest events in CKD [12].

At present, there are some αKlotho antibodies and diagnostic kits available on the market, but the existing αKlotho antibodies are not of sufficient specificity and not efficient at immunoprecipitating αKlotho from human serum, and the current immune-based assays for αKlotho are costly and inadequate in sensitivity and specificity.

Low αKlotho transcript and protein levels have been described in human kidney from nephrectomy samples of end stage kidneys and biopsies from patients with CKD [21,38]. Studies using an immune-based assay have shown widely disparate results in terms of absolute values of serum αKlotho concentration (100-fold span in levels from different labs) and direction of change (increased, decreased, or no change) with CKD and age [21,39-60]. The discrepant database has thwarted progress and incapacitated the ability to determine whether the promising rodent data can be translated into meaningful human application. In addition to CKD, acute kidney injury (AKI) from a variety of causes is also associated with rapid decrease of αKlotho in the kidney [25, 61-65] and serum in rodents and in urine in humans [25]. There is no data on human serum αKlotho in AKI to date. There is a need for an early, sensitive, and/or specific marker for renal injury in humans [66].

Generating antibodies to conserved proteins is challenging, as animal immunization methods for antibody development are subject to mechanisms that protect against auto-immunity. Synthetic antibody technology offers a powerful alternative because it is applied under defined in vitro conditions, uses antibody libraries that have not been subjected to tolerance selection that remove self-reactive antibodies, and is proven to yield antibodies with high affinities and specificities [67-71]. Within an optimized antibody framework, sequence diversity is introduced into the complementary determining regions (CDR's) by combinatorial mutagenesis. These libraries are coupled with phage display, with each phage particle displaying a unique antigen-binding fragment (Fab) on its surface while carrying the encoding DNA internally, thus achieving direct phenotype-genotype relations. Fab-displaying phage that bind to an antigen of interest are enriched using binding selections with purified antigens on solid support. The CDR's of binding phage clones are identified by DNA sequencing and the Fab proteins are purified from bacteria, or converted to the full-length IgG in mammalian cells.

Barker et al. 2015 [86] describe an antibody having specific binding affinity with αKlotho, sb106, which was isolated following rounds of biopanning of a synthetic human Fab phase-displayed library. The sb106 antibody has a binding affinity to αKlotho in the single-digit nanomolar range and comprises the following CDR sequences (IMGT CDR residues are underlined, IMGT framework region residues are not underlined and residues at IMGT positions which were randomized in the selection library are shown in bold):

QSVSSA (CDR-L1), SAS (CDR-L2), QQAGYSPIT (CDR-L3),

GFNISYYSI (CDR-H1), YISPSYGYTS (CDR-H2) and

ARYYVYASHGWAGYGMDY (CDR-H3).

Additional αKlotho specific antibodies which bind a different epitope than sb106 are desirable.

SUMMARY

This present disclosure relates to an antibody and/or binding fragment thereof that comprises a light chain variable region and a heavy chain variable region, the light chain variable region comprising a complementarity determining region (CDR) CDR-L3 and the heavy chain variable region comprising CDR-H1, CDR-H2 and CDR-H3, with the amino acid sequences of said CDRs comprising one or more of the sequences set forth below:
CDR-L3: selected from any one of SEQ ID NOs: 123, 126-130, 142, 148 or 149;
CDR-H1: SEQ ID NOs: 121 or 124;
CDR-H2: SEQ ID NOs: 122 or 125; and/or
CDR-H3: selected from any one of SEQ ID NOs: 196-226.

In another embodiment, the antibody and/or binding fragment thereof comprises CDRs having amino acid sequences selected from SEQ ID NOs: 142-226, optionally as set forth below:
Light chain variable region:
CDR-L3: selected from any one of SEQ ID NOs: 142-156;
Heavy chain variable region:
CDR-H1: selected from any one of SEQ ID NOs: 157-174;
CDR-H2: selected from any one of SEQ ID NOs: 175-195; and/or
CDR-H3: selected from any one of SEQ ID NOs: 196-226.

In a further embodiment, the antibody and/or binding fragment thereof comprises a light chain variable region comprising CDR-L1 and/or CDR-L2 having the amino acid sequences of SEQ ID NO: 140 and SEQ ID NO: 141, respectively.

In an embodiment, the αKlotho polypeptide specifically bound by the antibody is a folded αKlotho polypeptide.

Another aspect includes a nucleic acid encoding an antibody and/or binding fragment thereof described herein.

A further aspect is a vector comprising a nucleic acid described herein.

Another aspect includes a recombinant cell producing an antibody and/or binding fragment thereof, nucleic acid or vector described herein.

Another aspect is an immunoassay comprising or using one or more antibodies and/or binding fragments thereof described herein.

In an embodiment, the immunoassay is an enzyme linked immunosorbent assay (ELISA).

Other aspects include a method for producing an antibody and/or binding fragment thereof, an assay for measuring the level of αKlotho polypeptide in a sample, an assay for detecting and/or measuring soluble αKlotho polypeptide as well as methods for screening, for diagnosing or for detecting a kidney condition selected from chronic kidney disease (CKD) and acute kidney injury (AKI) in a subject, and methods of prognosing disease progression and/or recovery.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 3 shows the characterization of sb106-Fab by immunoprecipitation. (A) HEK293 cells were transfected with empty vector or varying quantities (μg/dish) of vector for expression of transmembrane full length αKlotho (TM-α (Klotho) or soluble extracellular domain of αKlotho with a C-terminal FLAG epitope (s-αKlotho-FLAG). Cell lysates or cell culture medium was immunoprecipitated (IP) with either sb106-Fab or anti-FLAG MAb. Immunocomplexes were resolved by SDS-PAGE and immunoblotted (IB) with monoclonal anti-αKlotho antibody KM2076. (B) Urine from rat, mouse, or human was immunoprecipitated with sb106-Fab, resolved by SDS-PAGE and immunoblotted (IB) with KM2076 (left three lanes). Size-selected urine (100 kDa cut-off) was directly subjected to SDS-PAGE and immunoblotted (right three lanes). (C) Immunoprecipitations of endogenous αKlotho from serum. Serum samples from wild type (VVT) mouse, k/otho$^{-/-}$ mouse, normal human, and dialysis patient (ESRD) where incubated with sb106-Fab overnight at 4° C. Sepharose beads conjugated with anti-FLAG antibody were then added and incubated for 2 hours at 4° C. The beads were washed and bound proteins were eluted with 2×SDS sample loading buffer. Immunoblot was performed KM2076 followed by a standard anti-rat IgG secondary for visualization.

FIG. 6 shows human urinary αKlotho levels. αKlotho was measured in the urine of healthy volunteers or patients with chronic kidney disease stage 5 (CKD5). (A) A representative IP-IB assay using recombinant murine αKlotho (rMKl) as a calibration with four subjects in each group under steady state conditions. Equal amounts of urine creatinine were used for IP-IB. (B) Summary of the data from the IP-IB assay and the commercial ELISA. Bars and error bars represent mean and standard deviation from eight subjects in each group. The mean of the healthy volunteers was set as a reference of 100%.

FIG. 8 is a schematic of amino acid sequences of sb106. (A) Light chain sequence (SEQ ID NO: 11) of sb106. (B) Heavy chain sequence—Fab (SEQ ID NO: 12). (C) Heavy chain sequence—IgG1 (SEQ ID NO: 13). (D) Heavy chain sequence—IgG4 (SEQ ID NO: 14). IMGT CDR residues are underlined, IMGT framework region residues are not underlined, and residues at IMGT positions which were randomized in the selection library are in bold and larger font size, and italicized amino acids are constant domains.

FIG. 17 is a series of graphs of affinity estimates measured by surface plasmon resonance against human and mouse antigen for select αKlotho Fabs. Fabs were captured using an anti-IgG(H+L) antibody and serial dilutions of αKlotho were injected. Binding curves were fitted to the Langmuir model. FIG. 17(A) shows determined $K_{on}$, $K_{off}$ and $K_D$ values. FIGS. 17 (B) and (C) show binding curves for human and mouse antigen respectively.

DETAILED DESCRIPTION OF THE DISCLOSURE

I. Definitions

Figure 1:
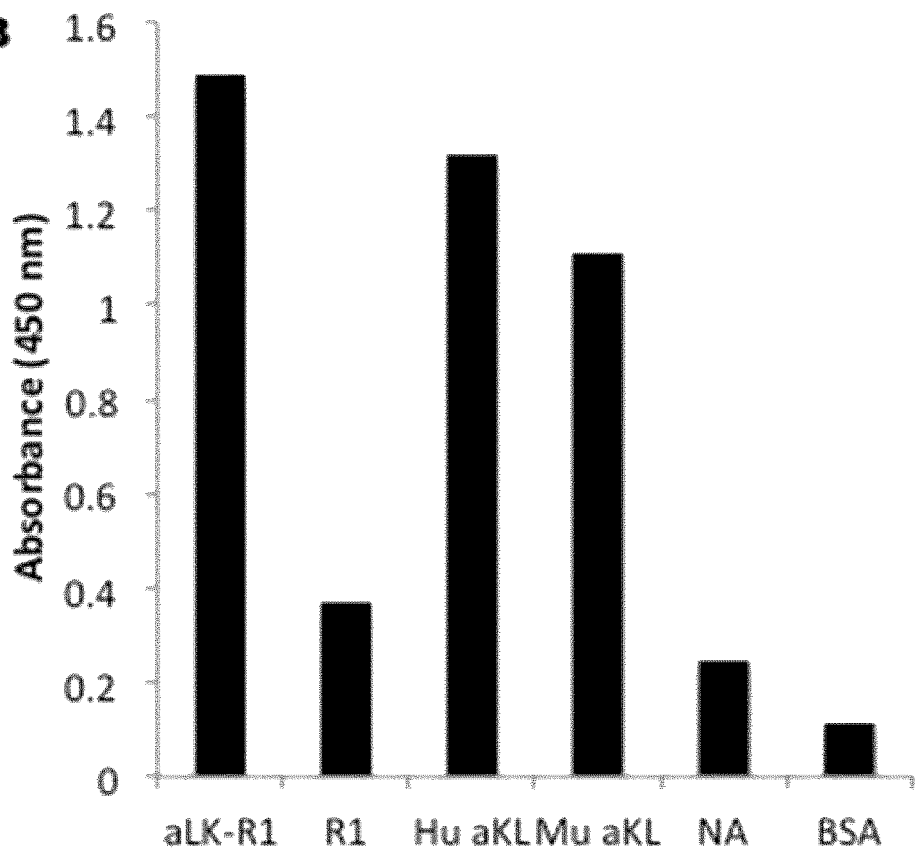
FIG. 1 shows the sequence, specificity and affinity of sb106. (A) CDR sequences and VH domain framework region residues variable in Library F for anti-αKlotho sb106, according to the IMGT (international ImMunoGeneTics database) numbering scheme. IMGT CDR residues are underlined, IMGT framework region residues are not underlined, residues at IMGT positions which were randomized in the selection library are bold. (B) Specificity determination of anti-αKlotho sb106 by Fab-phage ELISA: sb106 Fab-phage were incubated with the following immobilized antigens: a complex of FGFR1c/αKlotho complex (aKL-R1), FGFR1c alone (R1), human αKlotho (Hu aKL) and mouse αKlotho (Mu aKL), or neutravidin (NA) and bovine serum albumin (BSA) as negative controls. After washing off unbound phage, bound phages were detected using an HRP-conjugated anti-phage antibody. Colorimetric HRP reagents allow for absorbance readings at 450 nm. (C) Estimation of affinity by competitive Fab-phage ELISA. sb106 Fab-phage were pre-incubated with 50, 5, 0.5, 0.05, 0.005 and 0.0005 nM soluble human αKlotho. The binding signals to immobilized human αKlotho reported are an average of two data sets. The reduction in binding to immobilized αKlotho is indicative of the fraction bound to soluble αKlotho, thus a 50% reduction in signal occurs when the soluble αKlotho concentration is approximately equal to the KID of the interaction.
Figure 1:
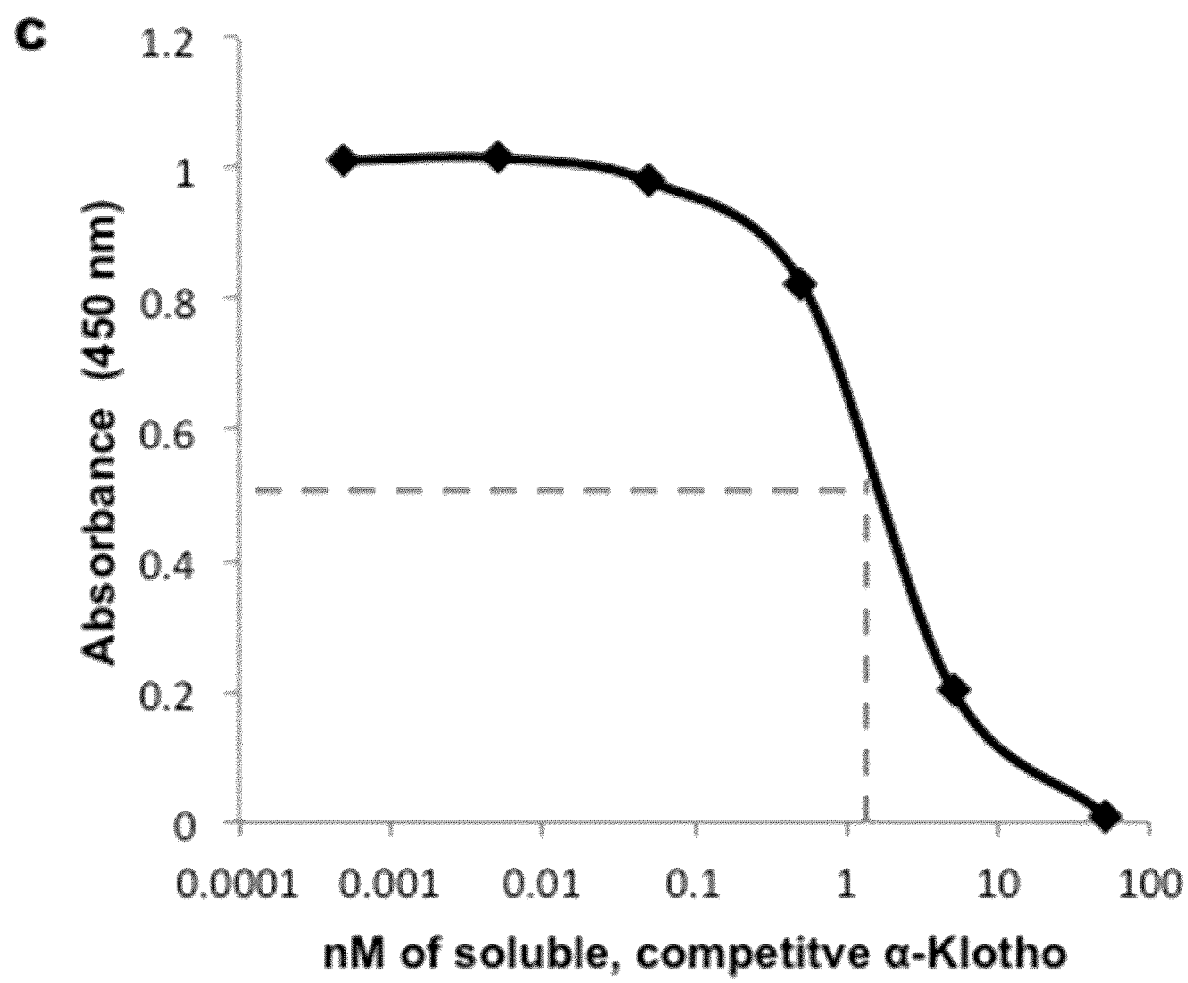

The term "αKlotho" or "alphaKlotho" as used herein refers to all known and naturally occurring αKlotho molecules including, full length αKlotho protein, fragments thereof such as ectodomain fragments, as well as nucleic acids encoding said protein and fragments, as determinable from the context used. Included are the soluble forms of αKlotho (proteolytically cleaved as well as alternatively spliced forms αKlotho, referred to as "soluble αKlotho" when present in a biological fluid such as blood or a fraction thereof, urine or cerebrospinal fluid and having a molecular weight of about 130 kDa, as well as the membrane-anchored form of αKlotho, and including but not limited to mammalian αKlotho such as human αKlotho, or rodent αKlotho including for example mouse and rat αKlotho.

The term "acute kidney injury" or "AKI" as used herein refers to an abrupt and sustained loss of kidney function for example that can lead to accumulation of urea and other chemicals in the blood, that develops within for example seven days of an insult. AKI may be caused by disease, injury such as crushing injury to skeletal muscle and medication. AKI is classified in stages varying from risk (glomerular filtration rate (GFR) decreased by 25%), injury (GFR decreased by 50%), failure (GFR decreased by 75%), loss (complete loss of kidney function for more than four weeks) and end-stage renal disease (complete loss of kidney function for more than three months). AKI can be asymptomatic.

The term "early acute kidney injury" as used herein means prior to rises in serum creatinine.

The term "amino acid" includes all of the naturally occurring amino acids as well as modified amino acids.

The term "antibody" as used herein is intended to include human antibodies, monoclonal antibodies, polyclonal antibodies, single chain and other chimeric antibodies. The antibody may be from recombinant sources and/or produced in transgenic animals. The antibody in an embodiment comprises a heavy chain variable region or a heavy chain comprising a heavy chain complementarity determining region 1, heavy chain complementarity determining region 2 and heavy chain complementarity determining region 3, as well as a light chain variable region or light chain comprising a light chain complementarity determining region 1, light chain complementarity determining region 2 and light chain complementarity determining region 3.

The term "binding fragment" as used herein is intended to include without limitations Fab, Fab', F(ab')2, scFv, scFab, dsFv, ds-scFv, dimers (e.g. Fc dimers), minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, scFab, dsFv, ds-scFv, dimers, minibodies, diabodies, bispecific antibody fragments and other fragments can also be synthesized by recombinant techniques.

The term "capture antibody" as used herein means an antibody or binding fragment thereof bound to a solid support and used to capture the target antigen in a sample, for example αKlotho polypeptide, optionally soluble αKlotho polypeptide by forming a complex with the target antigen.

The term "detection antibody" as used herein means an antibody or binding fragment thereof that binds a target antigen, for example αKlotho polypeptide, optionally soluble αKlotho polypeptide, optionally a target antigen already in a complex with a capture antibody. For example, the detection antibody binds the capture antibody: αKlotho complex at an epitope on the target antigen that is different than the one recognized by the capture antibody.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitution include:

| Conservative Substitutions | |
| --- | --- |
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "chronic kidney disease" or "CKD" refers to a disease causing a progressive loss in renal function. CDK is classified according to five stages which are determined according to a defined glomerular filtration rate (GFR). Stage 1 CKD is defined by a GFR of 90 mL/min/1.73 m², stage 2 CDK is defined by a GFR between 60-89 mL/min/1.73 m², stage 3 CKD is defined by a GFR between 30-59 mL/min/1.73 m², stage 4 CKD is defined by a GFR between 15-29 mL/min/1.73 m² and stage 5 CKD is defined by a GFR of less than 15 mL/min/1.73 m². Normal kidney function is defined by a GFR between 100-130 mL/min/1.73 m² or 90 mL/min/1.73 m² without proteinuria.

The term "control" as used herein refers to a sample from a subject or a group of subjects who are either known as having a kidney disease or not having the disease, and/or a value determined from said group of subjects, wherein subjects with αKlotho level at or below such value are likely to have the disease. The disease can be for example chronic kidney disease (CKD) or acute kidney injury (AKI). The disease can also be for example a stage of CKD such as stage 1 CKD, stage 2 CKD, stage 3 CKD, stage 4 CKD or stage 5 CKD; higher stage being more severe. In addition, the control can be for example derived from tissue of the same type as the sample of the subject being tested. In methods directed to monitoring, the control can also be tissue from the same subject taken at different a time point for example the control can be a sample from the same subject taken prior to a treatment for a kidney disease.

The term "early chronic kidney disease" refers to earlier stages of CKD, and means in an embodiment stage 1 and/or stage 2 CKD. Frequently, there are no elevations of FGF23, PTH, and phosphate. Subjects with stage 1 CKD almost never present any symptoms indicating kidney damage. Subjects with stage 2 CKD do not necessarily present symptoms indicating kidney damage but occasionally do.

The term "denatured" as used herein means a polypeptide that has lost tertiary and/or secondary structure (e.g. fully unfolded protein), for example when exposed to denaturing conditions in SDS sample loading buffer.

The term "detectable tag" as used herein refers to moieties such as peptide sequences that can be appended or introduced into recombinant protein.

The term "sandwich ELISA" as used herein refers to an ELISA comprising a solid support and a capture antibody or binding fragment thereof (specific for the antigen) immobilized onto the solid support. In such an ELISA an amount of target antigen in a sample is bound by the capture antibody (e.g. αKlotho polypeptide comprised in a sample). The bound antigen is detected by a second antibody or binding fragment thereof, i.e. a detection antibody or binding fragment thereof, which recognizes an epitope that is different from the one recognized by the capture antibody. The capture antibody:αKlotho complex) is detected by the detection antibody which can be covalently linked to an enzyme or can itself be detected by addition of a secondary antibody which is linked to an enzyme. For example, the capture antibody and/or the detection antibody can comprise CDR regions disclosed herein.

The term "epitope" as used herein refers to the site on the antigen that is recognized by the antibodies or binding fragments disclosed herein.

The term "heavy chain complementarity determining region" as used herein refers to regions of hypervariability within the heavy chain variable region of an antibody molecule. The heavy chain variable region has three complementarity determining regions termed heavy chain complementarity determining region 1 (CDR-H1), heavy chain complementarity determining region 2 (CDR-H2) and heavy chain complementarity determining region 3 (CDR-H3) from the amino terminus to carboxy terminus. All CDRs and framework regions (FRs) disclosed herein, amino acid sequences of CDRs and FRs disclosed herein, and CDR-encoding or FR-encoding nucleic acid sequences disclosed herein, are intended to be defined in accordance with IMGT numbering (85).

The term "heavy chain variable region" as used herein refers to the variable domain of the heavy chain comprising the heavy chain complementarity determining region 1, heavy chain complementarity determining region 2 and heavy chain complementarity determining region 3. One or more amino acids or nucleotides can be modified for example replaced with a conservative substitution, for example outside the CDR sequences.

The term "host cell" refers to a cell into which a recombinant DNA expression vector can be introduced to produce a recombinant cell. The host cell can be a bacterial cell such as *E. coli* but can also be any type of microbial, yeast, fungi, insect or mammalian host cell.

The term "isolated antibody or binding fragment thereof" or "isolated and purified antibody or binding fragment thereof" refers to an antibody or binding fragment thereof that is substantially free of cellular material or culture medium when produced by recombinant DNA techniques, or chemical precursors, or other chemicals when chemically synthesized and/or other antibodies, for example directed to a different epitope.

The term "$K_D$" refers to the dissociation constant of a complex for example of a particular antibody-antigen interaction.

The term "light chain complementarity determining region" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "light chain variable region" as used herein refers to the variable domain of the light chain comprising the light chain complementarity determining region 1, light chain complementarity determining region 2 and light chain complementarity determining region 3.

The term "native" or "natively folded" as used herein refers to a protein in its native conformation (e.g. 3D conformation) or in a conformation sufficient to confer functionality, including for example partially unfolded protein capable of binding a receptor or ligand. For example, folded αKlotho protein is capable of binding to a FGF receptor such as FGFR1c and can form a FGFR1c: αKlotho complex.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

The term "polypeptide" as used herein refers to a polymer consisting of a large number of amino acid residues bonded together in a chain. The polypeptide can form a part or the whole of a protein. The polypeptide may be arranged in a long, continuous and unbranched peptide chain. The polypeptide may also be arranged in a biologically functional way. The polypeptide may be folded into a specific three dimensional structure that confers it a defined activity. The term "polypeptide" as used herein is used interchangeably with the term "protein".

The term "isolated polypeptide" as used herein means substantially free of cellular material or culture medium when produced by recombinant DNA techniques, or chemical precursors, or other chemicals when chemically synthesized.

The term "reference agent" as used herein refers to an agent that can be used in an assay and that can be for example a standard amount of αKlotho protein used as a reference for example for detecting, screening or for diagnosing kidney condition such as chronic kidney disease and acute kidney disease.

The term "sample" as used herein refers to any biological fluid, cell or tissue sample from a subject, which can be assayed for αKlotho such as soluble biomarkers. For example the sample can comprise urine, serum, plasma or cerebrospinal fluid. The sample can for example be a "post-treatment" sample wherein the sample is obtained after one or more treatments, or a "base-line sample" which is for example used as a base line for assessing disease progression.

The term "sb106", "sb106 antibody" or "clone ID 48" as used herein means an antibody comprising light and heavy chain amino acid sequences set forth below:
Light chain variable region sequence (IMGT CDR sequences are underlined, IMGT framework region residues are not underlined, and residues at IMGT positions which were randomized in the selection library are shown in bold):

```
                                        (SEQ ID NO: 11)
DIQMTQSPSSLSASVGDRVTITCRASQSVSSAVAWYQQKPGKAPKLLIYS

ASSLYSGVPSRFSGSRSGTDFTLTISSLQPEDFATYYCQQAGYSPITFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Heavy chain variable region sequence (IMGT CDR sequences are underlined, IMGT framework region residues are not underlined, and residues at IMGT positions which were randomized in the selection library are shown in bold):

```
                                        (SEQ ID NO: 12)
EVQLVESGGGLVQPGGSLRLSCAASGFNISYYSIHWVRQAPGKGLEWVAY

ISPSYGYTSYADSVKGRFTISADTSKNTAYLQMNSLRAEDTAVYYCARYY

VYASHGWAGYGMDYWGQGTLVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCDKTHT
``` and comprising complementarity determining regions determined using IMGT numbering, e.g. with the amino acid sequences set forth below (IMGT CDR sequences are underlined, IMGT framework region residues are not underlined, and residues at IMGT positions which were randomized in the selection library are shown in bold):
Light chain variable region:

```
                                        (SEQ ID NO: 9)
                CDR-L1: QSVSSA (SEQ ID NO: 10)
                CDR-L2: SAS (SEQ ID NO: 5)
                CDR-L3: QQAGYSPIT
```

Heavy chain variable region:

```
                                        (SEQ ID NO: 6)
                CDR-H1: GFNISYYSI (SEQ ID NO: 7)
                CDR-H2: YISPSYGYTS (SEQ ID NO: 8)
                CDR-H3: ARYYVYASHGWAGYGMDY.
```

Sub-clones (e.g. variants) of sb106 were identified which have one or more CDRs (as shown in Table 2) which replace corresponding CDRs of sb106, and which have non-Library F-variable framework regions (i.e. all IMGT framework region positions except for IMGT VH domain positions 39, 55 and 66) which are identical to those of sb106.

Sb106 recognizes an epitope of αKlotho that is different from an epitope recognized by the antibodies and/or binding fragments herein disclosed (e.g. epitope B and epitope C). As such, sb106 and antibodies comprising the CDRs of sb106 and/or the variants of sb106 may be used in conjunction with the antibodies and/or binding fragments thereof herein described (e.g. directed to epitope B and/or epitope C) in a detection assay, for example an ELISA such as a sandwich ELISA.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm~5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "subject" as used herein refers to any member of the animal kingdom, preferably a mammal, more preferably a human being or a rodent such as a rat or a mouse. In one embodiment, the subject is suspected of having a kidney disorder such as chronic kidney disease (CKD) or acute kidney injury (AKI).

The term "variant" as used herein includes one or more amino acid and/or nucleotide modifications in a sequence (polypeptide or nucleic acid respectively) for example, one or more modifications of a light chain or a heavy chain complementarity determining region (CDR) disclosed herein that perform substantially the same function as the light chain and heavy chain CDRs disclosed herein in substantially the same way. For instance, variants of the CDRs disclosed herein have the same function of being able to specifically bind to an epitope on folded αKlotho protein or in the case of nucleotide modifications, encode CDRs that have same function of being able to specifically bind to an epitope on folded αKlotho protein. For example, codon optimized and degenerate sequences are included. Variants of CDRs disclosed herein include, without limitation, conservative amino acid substitutions as well as additions and deletions to the CDR sequences disclosed herein. For example the addition or deletion can be 1, 2, 3 or 4 amino acids and/or the corresponding number of nucleotides.

The term "level" as used herein refers to an amount (e.g. relative amount or concentration) of αKlotho protein that is detectable or measurable in a sample. For example, the soluble αKlotho level can be a concentration such as pM or a relative amount such as 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0 and/or 10 times a control level, where for example, the control level is the level of soluble αKlotho in a healthy subject.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 10%, 1-10%, or preferably 1-5%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Antibody and/or Binding Fragment Thereof

The present disclosure relates to an antibody and/or binding fragment thereof and methods of making and use for example for diagnosing and/or prognosing kidney diseases.

Figure 14:
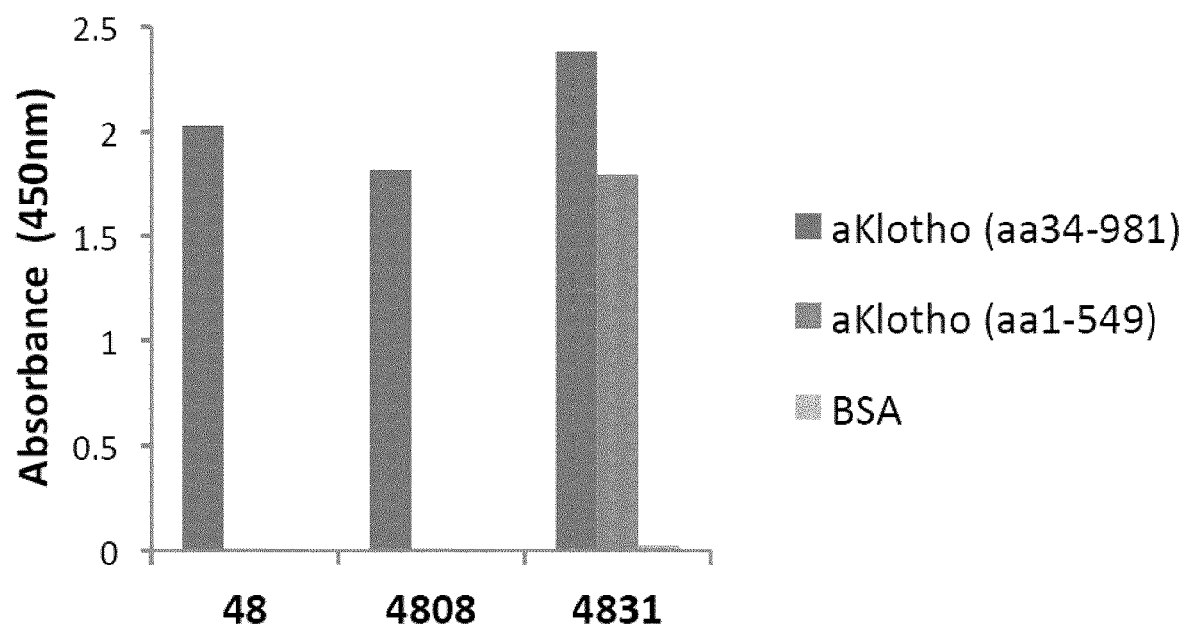
FIG. 14 is a graph showing absorbance values of capture ELISAs with IgGs representing 3 different epitopes of αKlotho.

International application No. PCT/CA2015/050728 entitled ANTIBODIES WITH HIGH AFFINITY FOR ALPHA-KLOTHO, herein incorporated by reference, disclosed sb106 antibody. Herein described are additional antibodies that specifically bind αKlotho at different epitopes. As described in FIG. 10, the additional antibodies were identified from a synthetic antibody library and were shown to bind αKlotho. As shown in Example 11 and FIG. 11, epitope grouping experiments using competitive ELISA reveal that the sb106 antibody binds a distinct epitope (identified as A), while the presently described antibodies bind at least two different epitopes, identified as epitopes B and C. It is further described in FIG. 14 that the epitopes A and B are located within amino acids 550-981 of αKlotho whereas epitope C is located within amino acids 1-549 of αKlotho. These experiments show that the 3 epitopes to which the antibodies bind can be used in a detection assay, for example an ELISA.

Accordingly, a first aspect is an antibody and/or binding fragment thereof that specifically binds αKlotho polypeptide at a different epitope than recognized by an antibody having light and heavy chain variable regions comprising the amino acid sequences of SEQ ID NO: 11 and 12, respectively.

In an embodiment, "CDR-H1" is composed of IMGT CDR-H1 and the VH domain residue at IMGT position 39 flanking the carboxy terminal residue of IMGT CDR-H1; and "CDR-H2" is composed of IMGT CDR-H2 and the VH domain residues at IMGT positions 55 and 66 flanking the amino terminal residue and flanking the carboxy terminal residue, respectively, of IMGT CDR-H2.

In an embodiment, the antibody or binding fragment thereof has a light chain variable region comprising CDR-L1, CDR-L2 and CDR-L3 and a heavy chain variable region comprising CDR-H1, CDR-H2 and CDR-H3 wherein the CDR regions are determined using IMGT numbering.

In an embodiment, the antibody and/or binding fragment thereof binds αKlotho polypeptide at a different epitope than recognized by an antibody or binding fragment thereof having a light chain variable region comprising CDR-L3 having amino acid sequences SEQ ID NO: 5, and a heavy chain variable region comprising CDR-H1, CDR-H2 and CDR-H3 having amino acid sequences SEQ ID NO: 6, 7 and 8, respectively.

In an embodiment, the antibody and/or binding fragment thereof binds αKlotho polypeptide at a different epitope than recognized by an antibody or binding fragment thereof having a light chain variable region comprising CDR-L1, CDR-L2 and CDR-L3 having amino acid sequences SEQ ID NO: 9, 10 and 5, respectively, and a heavy chain variable region comprising CDR-H1, CDR-H2 and CDR-H3 having amino acid sequences SEQ ID NO: 6, 7 and 8, respectively.

In one embodiment, the antibody and/or binding fragment thereof binds to epitope B located within amino acids 550-981 of αKlotho however does not bind to the epitope recognized by sb106 antibody.

In an embodiment, the antibody and/or binding fragment thereof specifically binds within amino acids 1 to 549 of αKlotho polypeptide.

In an embodiment, the αKlotho polypeptide is folded, optionally in native conformation (e.g. fully folded).

Accordingly another aspect is an antibody and/or binding fragment thereof, wherein the antibody and/or binding fragment thereof specifically binds to an epitope of a folded αKlotho polypeptide and specifically binds αKlotho polypeptide at a different epitope than recognized by an antibody having light and heavy chain variable regions comprising the amino acid sequences of SEQ ID NO: 11 and 12, respectively.

A further aspect is an antibody and/or binding fragment thereof, wherein the antibody and/or binding fragment thereof specifically binds to αKlotho polypeptide in an unfixed or mildly fixed sample and specifically binds αKlotho polypeptide at a different epitope than recognized by an antibody having light and heavy chain variable regions comprising the amino acid sequences of SEQ ID NO: 11 and 12, respectively.

In an embodiment, the αKlotho polypeptide in the unfixed or mildly fixed sample is folded αKlotho.

As shown in Example 12, the antibodies herein disclosed have binding affinities to αKlotho ranging from 240 pM to 8.7 nM. In an embodiment, the antibody and/or binding fragment has a dissociation constant ($K_D$) for the αKlotho polypeptide of about or less than 50 nM, about or less than 40 nM, about or less than 30 nM, about or less than 25 nM, about or less than 20 nM, about or less than 15 nM, about or less than 12 nM, about or less than 10 nM, about or less than 9 nM, about or less than 8 nM, about or less than 7 nM, about or less than 6 nM, about or less than 5 nM, about or less than 4 nM, about or less than 3 nM, about or less than 2 nM or about or less than 1 nM, as measured by competitive ELISA assay and/or SPR immunoassay.

In an embodiment, the antibody and/or binding fragment thereof comprises a light chain variable region and a heavy chain variable region, the light chain variable region comprising complementarity determining region CDR-L3 and the heavy chain variable region comprising complementarity determining regions CDR-H1, CDR-H2 and CDR-H3, with the amino acid sequences of said CDRs comprising one or more of the sequences set forth below:
CDR-L3: selected from any one of SEQ ID NOs: 123, 126-130, 142, 148 or 149;
CDR-H1: SEQ ID NOs: 121 or 124;
CDR-H2: SEQ ID NOs: 122 or 125; and/or
CDR-H3: selected from any one of SEQ ID NO: 196-226.
In an embodiment, the CDR-H1 region comprises the sequence of SEQ ID NO: 133 or 134.

In an embodiment, the CDR-H2 region comprises the sequence of SEQ ID NO: 135 or 136.

In an embodiment, the complementarity determining regions comprise the amino acid sequences selected from SEQ ID NOs: 142-226, optionally as set forth below:

CDR-L3: selected from any one of SEQ ID NOs: 142-156;

CDR-H1: selected from any one of SEQ ID NOs: 157-174;

CDR-H2: selected from any one of SEQ ID NOs: 175-195; and/or

CDR-H3: selected from any one of SEQ ID NOs: 196-226.

In an embodiment, the light chain variable region further comprises complementarity determining regions CDR-L1 and/or CDR-L2 comprising the amino acid sequences set forth below:

CDR-L1: SEQ ID NO: 140 and/or CDR-L2: SEQ ID NO: 141.

In an embodiment, the antibody and/or binding fragment thereof comprises a light chain variable region and a heavy chain variable region comprising CDR-L1, -L2, -L3, -H1, -H2 and -H3 amino acid sequences as set forth in Tables 3A and 3D-3I.

In an embodiment, the antibody and/or binding fragment thereof binds epitope B of αKlotho and comprises CDR regions as set forth in Tables 3A and/or 3D-3F.

In an embodiment, the antibody and/or binding fragment thereof that specifically binds αKlotho comprises CDR regions of an antibody identified as specific for epitope B as set forth in Table 3A.

In an embodiment, the CDRs of the antibody and/or binding fragment thereof that specifically binds αKlotho are selected from those indicated for clones 4804, 4805, 4807, 4808, 4809, 4811, 4812, 4813, 4815, 4816, 4818, 4820, 4821, 4822, 4823, 4824, 4825, 4826, 4827, 4829, 4832, 4833 and 4834, as set forth in Table 3A.

In an embodiment, the antibody and/or binding fragment thereof that specifically binds αKlotho comprises CDR regions of an antibody identified as specific for epitope C as set forth in Table 3A and/or 3G-3I.

In an embodiment, the antibody and/or binding fragment thereof that specifically binds αKlotho comprises CDR regions of an antibody identified as specific for epitope C, as set forth in Table 3A.

In an embodiment, the CDRs of the antibody and/or binding fragment thereof that specifically binds αKlotho are selected from those indicated for clones 4814, 4819, 4830 and 4831, as set forth in Table 3A.

In an embodiment, CDRs of the antibody and/or binding fragment that specifically binds αKlotho are selected from those indicated for clones 4806, 4810, 4817 and 4828, as set forth in Table 3A.

As an example, the CDR sequences of antibody sb173 (clone id 4808) in the context of the full length light and heavy variable regions are shown in Table 4. The underlined residues denoting the CDR regions may be replaced with other CDR sequences described herein, for example as set forth in Table 3A.

The antibody optionally a human antibody can be any class of immunoglobulins including: IgM, IgG, IgD, IgA or IgE; and any isotype, including: IgG1, IgG2, IgG3 and IgG4.

Any of the Fab clones can for example be inserted into a full length immunoglobulin molecule, for example by subcloning. CDRs of a Fab clone identified here can be grafted onto an antibody to make a CDR-grafted antibody.

Humanized or chimeric antibody may include sequences from one or more than one isotype or class.

Further, antibodies described herein may be produced as antigen binding fragments such as Fab, Fab' F(ab')$_2$, Fd, Fv and single domain antibody fragments, or as single chain antibodies in which the heavy and light chains are linked by a spacer. Also, the human or chimeric antibodies may exist in monomeric or polymeric form.

Chimeric antibodies can be prepared using recombinant techniques. As described in the Examples, the Fab identified in the screen was reformatted into full length IgG by subcloning the variable domains of the antibody's light and heavy chains into mammalian expression vectors and producing the IgG protein for example as shown in the Examples using human embryonic kidney cells (HEK293T). As described elsewhere any cell type suitable for expressing an antibody can be used.

In yet another embodiment, the light chain complementarity determining region CDR-L3 and heavy chain complementarity determining regions CDR-H1, CDR-H2 and CDR-H3 have at least 70%, at least 80% or at least 90% sequence identity to SEQ ID NOs: 142-156, SEQ ID NOs: 157-174, SEQ ID NOs: 175-195, and SEQ ID NOs: 196-226, respectively.

In an embodiment, the antibody, binding fragment thereof, optionally the CDR sequence has one or more conservative substitutions.

In one embodiment, the antibody and/or binding fragment thereof is selected from the group consisting of a an immunoglobulin molecule, a Fab, a Fab', a F(ab)2, a F(ab')2, a Fv, a disulfide linked Fv, a scFv, a disulfide linked scFv, a single chain domain antibody including fragment scFab, a diabody, a dimer, a minibody, a bispecific antibody fragment, a chimeric antibody, a human antibody, a humanized antibody and a polyclonal antibody.

Fab, Fab' and F(ab')$_2$, scFv, scFab, dsFv, ds-scFv, dimers, minibodies, diabodies, bispecific antibody fragments and other fragments can be synthesized or expressed by recombinant techniques.

Antibodies can also be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments.

In an embodiment, the antibody is a human antibody.

Human antibodies are optionally obtained from transgenic animals (U.S. Pat. Nos. 6,150,584; 6,114,598; and 5,770,429). In this approach the heavy chain joining region ($J_H$) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

In an embodiment, the antibody is a chimeric antibody comprising one or more CDRs selected from SEQ ID NOs: 140 to 226.

As shown in Example 15, the antibody and/or binding fragment thereof herein disclosed is cross-reactive to several species. In an embodiment, the αKlotho polypeptide bound is mammalian αKlotho polypeptide, for example, the αKlotho polypeptide is selected from human αKlotho polypeptide or rodent αKlotho polypeptide such as mouse αKlotho polypeptide or rat αKlotho polypeptide.

In an embodiment, the antibody and/or binding fragment thereof preferentially binds human αKlotho over mouse αKlotho.

In another embodiment, the folded αKlotho polypeptide is soluble folded αKlotho polypeptide. For example, the antibody and/or binding fragment thereof binds soluble folded αKlotho polypeptide found in urine, plasma, and/or serum.

As shown in Example 16, Fab fragments herein disclosed were able to bind αKlotho alone and in a complex (αKlotho-FGFR1c). In yet another embodiment, the antibody and/or binding fragment thereof binds a complex comprising folded αKlotho polypeptide. For example, the complex can comprise the folded αKlotho polypeptide with a fibroblast growth factor (FGF) receptor, optionally FGFR1c.

In a further embodiment, the antibody and/or binding fragment is labelled and/or conjugated to a tag, for example to produce a diagnostic agent. For example, the detectable tag can be a purification tag such as a His-tag, a HA-tag, a GST-tag, biotin or a FLAG-tag.

The label is preferably capable of producing, either directly or indirectly, a detectable signal. For example, the label may be radio-opaque or a radioisotope, such as $^3$H, $^{14}$C; $^{32}$P; $^{35}$S; $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase (HRP); an imaging agent; or a metal ion.

Another aspect of the disclosure relates to an antibody complex comprising the antibody and/or binding fragment thereof and αKlotho, optionally further comprising FGFR1c.

In an embodiment, the antibody complex comprises FGFR1c and optionally further comprises FGF23.

In an embodiment, the antibody and/or binding fragment thereof is an isolated antibody and/or binding fragment thereof.

Yet another aspect is a nucleic acid encoding an antibody and/or binding fragment thereof such as a binding fragment thereof described herein. In an embodiment, the nucleic acid encodes an antibody and/or binding fragment thereof comprising a light chain variable region and a heavy chain variable region, the light chain variable region comprising complementarity determining regions CDR-L1, CDR-L2 and CDR-L3 and the heavy chain variable region comprising complementarity determining regions CDR-H1 CDR-H2 and CDR-H3, with the amino acid sequences of said CDRs comprising one or more of the sequences set forth below:

CDR-L3: selected from any one of SEQ ID NOs: 123, 126-130, 142, 148 or 149;
CDR-H1: SEQ ID NOs: 121 or 124;
CDR-H2: SEQ ID NOs: 122 or 125; and/or
CDR-H3: selected from any one of SEQ ID NOs: 196-226.

In an embodiment, the nucleic acid encoding an antibody and/or binding fragment thereof further comprises the sequences set forth below:

CDR-L3: selected from any one of SEQ ID NOs: 229-243;
CDR-H1: selected from any one of SEQ ID NOs: 244-262;
CDR-H2: selected from any one of SEQ ID NOs: 263-285; and/or
CDR-H3: selected from any one of SEQ ID NOs: 286-316.

In an embodiment, the light chain variable region comprises complementarity determining regions CDR-L1 and/or CDR-L2 having the nucleic acid sequences set forth below:
CDR-L1: SEQ ID NO: 227 and/or
CDR-L2: SEQ ID NO: 228.

Variants of the CDRs that bind the different epitopes are described. In addition, the degeneracy of the genetic code allows for different nucleic acids to encode the same amino acid sequence. Accordingly, also included are nucleotide sequences that hybridize to the nucleic acid sequences encoding the antibody and/or binding fragment thereof disclosed herein under at least moderately stringent hybridization conditions and which encode an antibody that also specifically binds αKlotho polypeptide.

Also included in another embodiment are codon degenerate or optimized sequences. In another embodiment, the nucleic acid sequences have at least 70%, most preferably at least 80%, even more preferably at least 90% and even most preferably at least 95% sequence identity to nucleic acid sequences encoding SEQ ID NOs: 227-316 (as shown in Table 3B and 3C).

The antibodies described herein can comprise one or more of the features described herein.

In an embodiment, the nucleic acid is an isolated nucleic acid.

Another aspect is a vector comprising the nucleic acid herein disclosed. In an embodiment, the vector is an isolated vector.

The vector can be any vector suitable for producing an antibody and/or binding fragment thereof, including for example vectors described herein. Possible expression vectors include but are not limited to cosmids, plasmids, or modified viruses (e.g. replication defective retroviruses, adenoviruses and adeno-associated viruses).

A further aspect is a recombinant cell producing the antibody and/or binding fragment thereof herein disclosed or the vector herein disclosed.

The recombinant cell can be generated using any cell suitable for producing a polypeptide, for example suitable for producing an antibody and/or binding fragment thereof.

Suitable host cells include a wide variety of prokaryotic and eukaryotic host cells. For example, the proteins of the invention may be expressed in bacterial cells such as *E. coli*, insect cells (using baculovirus), yeast cells or mammalian cells.

More particularly, bacterial host cells suitable for producing recombinant antibody producing cells include *E. coli, B. subtilis, Salmonella typhimurium*, and various species within the genus *Pseudomonas, Streptomyces*, and *Staphylococcus*, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the R-lactamase (penicillinase) and lactose promoter system, the trp promoter and the tac promoter. Representative selectable markers include various antibiotic resistance markers such as the kanamycin or ampicillin resistance genes. Suitable expression vectors include but are not limited to bacteriophages such as lambda derivatives or plasmids such as pBR322, the pUC plasmids pUC18, pUC19, pUC118, pUC119, and pNH8A, pNH16a, pNH18a, and Bluescript M13 (Stratagene, La Jolla, Calif.).

Suitable yeast and fungi host cells include, but are not limited to *Saccharomyces cerevisiae, Schizosaccharomyces pombe*, the genera *Pichia* or *Kluyveromyces* and various species of the genus *Aspergillus*. Examples of vectors for expression in yeast S. cerivisiae include pYepSecl, pMFa, pJRY88, and pYES2 (Invitrogen Corporation, San Diego, Calif.). Protocols for the transformation of yeast and fungi are well known to those of ordinary skill in the art.

Suitable mammalian cells include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573), NS-1 cells and any derivatives of these lines.

In an embodiment, the mammalian cells used to produce a recombinant antibody are selected from CHO, HEK293 cells or Freestyle™ 293-F cells (Life technologies). FreeStyle 293-F cell line is derived from the 293 cell line and can be used with the FreeStyle™ MAX 293 Expression System, FreeStyle™ 293 Expression System or other expression systems.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences.

In an embodiment, the vector is designed for production of light chain or IgG1 heavy chain.

Suitable insect cells include cells and cell lines from Bombyx or Spodotera species. Baculovirus vectors available for expression of proteins in cultured insect cells (SF 9 cells) include the pAc series and the pVL series.

The recombinant expression vectors may also contain genes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

"Operatively linked" is intended to mean that the nucleic acid is linked to regulatory sequences in a manner which allows expression of the nucleic acid. Suitable regulatory sequences may be derived from a variety of sources, including bacterial, fungal, viral, mammalian, or insect genes. Selection of appropriate regulatory sequences is dependent on the host cell chosen and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, expression of the antibody or binding fragment thereof is under the control of an inducible promoter. Examples of inducible non-fusion expression vectors include pTrc (28) and pET 11d.

The recombinant expression vectors may also contain a marker gene which facilitates the selection of host cells transformed or transfected with a recombinant molecule of the invention. Examples of selectable marker genes are genes encoding a protein such as G418 and hygromycin which confer resistance to certain drugs, ß-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as ß-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest. Other selectable markers include fluorescent proteins such as GFP which may be cotransduced with the nucleic acid of interest.

Yet another aspect is a composition comprising the antibody and/or binding fragment thereof, the nucleic acid herein disclosed or the recombinant cell herein disclosed, optionally in combination with a suitable diluent or carrier.

The composition can be a lyophilized powder or aqueous or non-aqueous solution or suspensions, which may further contain antioxidants, buffers, bacteriostats and solutes. Other components that may be present in such compositions include water, surfactants (such as Tween), alcohols, polyols, glycerin and vegetable oils, for example.

Suitable diluents for nucleic acids include but are not limited to water, saline solutions and ethanol.

Suitable diluents for polypeptides, including antibodies or fragments thereof and/or cells include but are not limited to saline solutions, pH buffered solutions and glycerol solutions or other solutions suitable for freezing polypeptides and/or cells.

The composition can further comprise stabilizing agents, for example reducing agents, hydrophobic additives, and protease inhibitors which are added to physiological buffers.

III. Methods

Another aspect of the disclosure is a method for isolating or producing an antibody and/or binding fragment thereof described herein with specific binding affinity to αKlotho and that binds an epitope of αKlotho that is different from the epitope recognized by the sb106 antibody.

As previously mentioned, the sb106 antibody comprises a light chain variable region comprising CDR-L1, CDR-L2 and CDR-L3 having amino acid sequences SEQ ID NO: 9, 10 and 5, respectively, and a heavy chain variable region comprising CDR-H1, CDR-H2 and CDR-H3 having amino acid sequences SEQ ID NO: 6, 7 and 8, respectively.

Additional αKlotho specific antibodies that bind different epitopes are desirable for example to establish detection assays. As described herein antibodies to αKlotho were identified by antibody-phase display selections performed on the extracellular domain (ECD) of human αKlotho while in the presence of saturating levels of the original sb106 Fab. Using this method, 31 antibodies were identified as recognizing a distinct epitope of αKlotho and as binding αKlotho in the presence and absence of sb106 (Example 10 and FIG. 9). The antibodies exhibit binding affinities ($K_D$) less than 10 nM, as shown in Table 5. In one embodiment, the method comprises screening an antibody library for an antibody that binds soluble αKlotho polypeptide and isolating the antibody from an antibody library. For example, the antibody library can be an antibody phage-display library. In one embodiment, the antibody phage-display library is a human Fab phage-display library.

In an embodiment, αKlotho polypeptide is used to isolate an antibody that specifically binds αKlotho polypeptide from the antibody library. In an embodiment, αKlotho complexed with an antibody or binding fragment that has CDR regions specific for epitope A, B or C is used to isolate an antibody that specifically binds αKlotho polypeptide from the antibody library.

In another embodiment, the isolated and purified antibody and/or binding fragment thereof is affinity matured. Affinity maturation can be performed as described for the initial selection, with antigen adsorbed to plastic plates, using a for example a phage library comprising variants of the CDR sequences.

A person skilled in the art will appreciate that several methods can be used to isolate and produce antibodies and/or binding fragments thereof with specific binding affinity to folded αKlotho. A method that can be used is a phage display method. For example, a binary αKlotho-FGF1Rc complex is produced in order to isolate and characterize the antibody and/or binding fragment thereof. Phage from a human Fab phage-displayed library are selected following several rounds of panning. Phage with specific binding affinity to the binary αKlotho-FGF1Rc complex, as determined by ELISA, are sequenced and cloned into vectors designed for production of light chain or heavy chain. The heavy chain can be for example an IgG, or an IgG isotype such as an IgG1 or an IgG4. Antigen binding fragments and IgG polypeptides are then affinity purified by using, for example, Protein A affinity columns.

In another embodiment, a nucleic acid encoding an antibody described herein is expressed in a host cell to make the antibody and/or binding fragment thereof. In an embodiment, the method comprises:
  a. expressing in a host cell a nucleic acid encoding an antibody and/or binding fragment thereof herein disclosed;
  b. culturing the host cell to produce the antibody and/or binding fragment thereof; and
  c. isolating and/or purifying the antibody and/or binding fragment thereof from the host cell.

In some embodiments, a nucleic acid encoding a single chain antibody is expressed. In other embodiments, multiple nucleic acids are expressed, for example encoding a nucleic acid, encoding an antibody light chain and a nucleic acid encoding an antibody heavy chain.

Suitable host cells and vectors are described above. Vectors and nucleic acids encoding an antibody described herein may be introduced into mammalian cells via conventional techniques such as calcium phosphate or calcium chloride co-precipitation, DEAE-dextran mediated transfection, lipofectin and other liposome based transfection agents, electroporation or microinjection.

Nucleic acid encoding an antibody described herein may be directly introduced into mammalian cells using delivery vehicles such as retroviral vectors, adenoviral vectors and DNA virus vectors.

Figure 13:
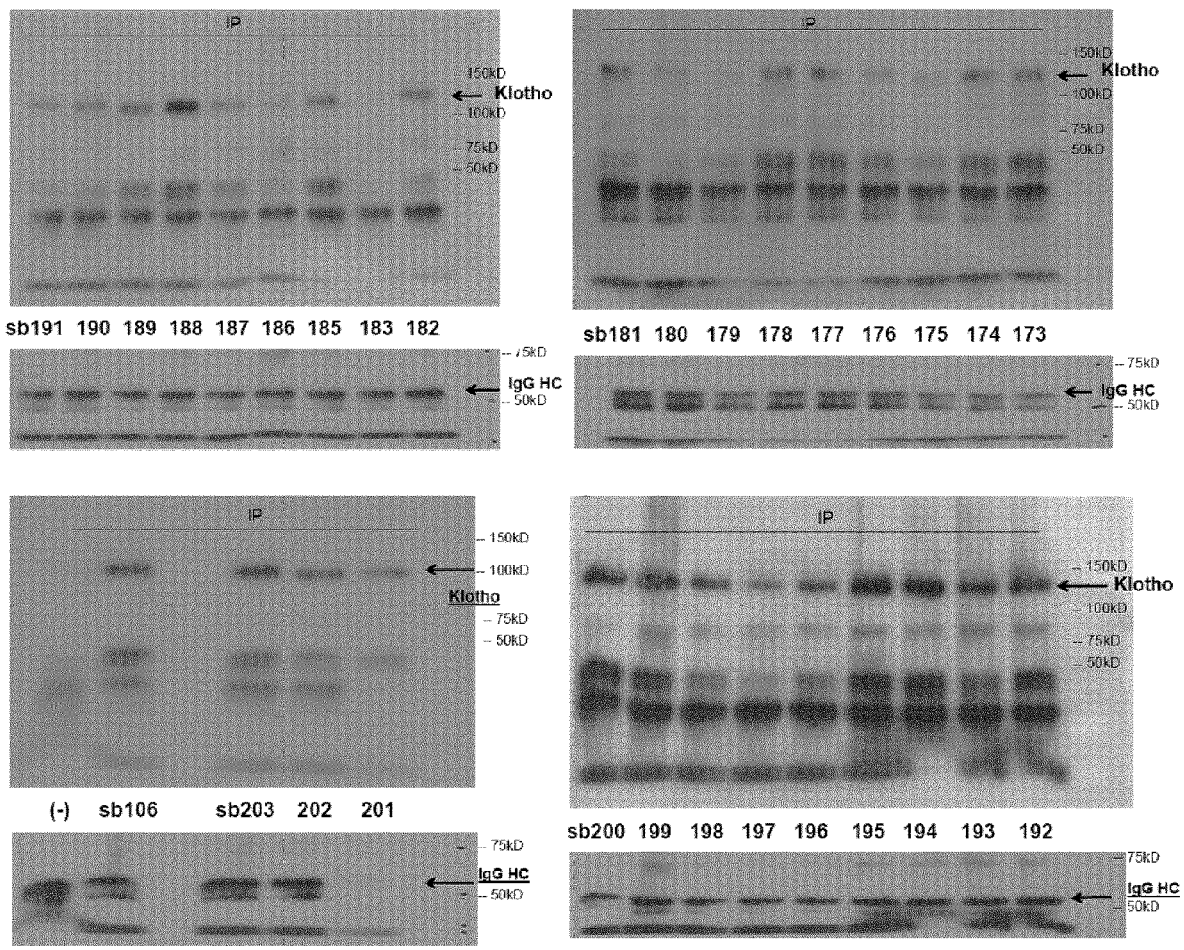
FIG. 13 is a series of immunoblots showing immunoprecipitations of αKlotho with identified Fabs.

As described in Example 13, the antibodies were tested using an immunoprecipitation-immunoblot assay as Fabs on human urine samples. The results demonstrate (FIG. 13) that the antibodies have the ability to immunoprecipitate αKlotho. The antibodies were assayed for their ability to immunoprecipitate αKlotho from human patient urine samples as Fabs.

V. Assays

The αKlotho specific antibodies disclosed herein bind different epitopes and can be used in a variety of assays for binding, detecting and measuring αKlotho in a sample. For example, the antibodies can be used in a proximity ligation assay (PLA) as well as immunoprecipitation optionally combined with immunoblot detection. The antibody based detection can also be combined with a mass spectrophometric assay, for example as in the case of a particle-based flow cytometric assay.

Immunodetection methods as described herein generally involve the detection or measuring of antibody:αKlotho complexes using antibodies and/or binding fragments thereof disclosed herein. The detection of such complexes is well known in the art and may be achieved through different methods, for example by using a detectable label or marker, such as a radioactive, fluorescent or enzymatic tag. Detection of these complexes may also involve the use of a ligand such as a secondary antibody and/or binding fragment thereof specific for αKlotho or for the antibody:αKlotho complex.

They can also be used to make detection assays, for example a sandwich ELISA, as one antibody can be used as a capture reagent to isolate the αKlotho while another antibody binding a distinct epitope can be used as a detection reagent.

Epitopes A and B are located within amino acids 550-981 αKlotho and epitope C within amino acids 1-549 of αKlotho. As shown in Example 14, FIG. 14, three antibodies binding different epitopes were incubated with two different portions of αKlotho, amino acids 1-549 and amino acids 34-981 of αKlotho. Clone 48 (sb106) which binds epitope A and clone 4808 which binds epitope B both bind within amino acids 550-981 of αKlotho whereas clone 4831 which binds epitope C binds within amino acids 1-549.

Accordingly, another aspect is an immunoassay comprising one or more antibodies and/or binding fragments thereof herein disclosed (e.g. specific for epitope B or C).

In an embodiment, the immunoassay is an enzyme linked immunosorbent assay (ELISA). Antibodies and/or binding fragments thereof may be used in the context of detection assays such as ELISAs, for example sandwich ELISAs. As shown in Example 14 and FIG. 15, the antibodies were used as capture and detection antibodies for the detection of αKlotho in solution. Full length IgGs recognizing epitopes A (sb106), B (sb177) or C (sb200) were immobilized and incubated with αKlotho. The samples were then incubated with biotinylated IgGs recognizing epitopes A, B or C.

In an embodiment, the ELISA is a sandwich ELISA comprising a capture antibody and a detection antibody, wherein the capture antibody is an antibody or binding fragment thereof that has CDRs identified herein and which specifically binds αKlotho, for example which specifically binds epitope A, B or C and/or the detection antibody is an antibody or binding fragment thereof that has CDRs identified herein and which specifically binds αKlotho, for example which specifically binds epitope A, B or C, wherein the capture antibody and the detection antibody bind different epitopes.

In one embodiment, the capture antibody and the detection antibody are selected from an antibody and/or binding fragment thereof herein disclosed, and the sb106 antibody having light and heavy chain variable regions comprising the amino acid sequences of SEQ ID NO: 11 and 12.

In another embodiment, one of the capture and detection antibodies is an antibody and/or binding fragment thereof herein disclosed having CDRs identified in Table 3 and the other of the capture and detection antibodies is an antibody with CDRs identified for sb106 antibody or a variant thereof, optionally having light and heavy chain variable regions comprising the amino acid sequences of SEQ ID NO: 11 and 12, respectively.

In one embodiment, the immunoassay comprises an antibody and/or binding fragment thereof having CDRs described herein which binds epitope B or C of αKlotho herein as well as an antibody with the CDRs of sb106 antibody or a variant thereof identified as binding epitope A.

For example, the capture antibody binds epitope A and the detection antibody binds epitope B. For example, the capture antibody binds epitope A and the detection antibody binds epitope C. For example, the capture antibody binds epitope B and the detection antibody binds epitope A. For example, the capture antibody binds epitope B and the detection antibody binds epitope C. For example, the capture antibody binds epitope C and the detection antibody binds epitope A. For example, the capture antibody binds epitope C and the detection antibody binds epitope B.

In one embodiment, the antibody or variant thereof is sb106-Fab (Fsb106).

In one embodiment, the immunoassay is for the detection and/or measuring of αKlotho polypeptide in a sample, wherein the method of making the immunoassay comprises:
 a) coating a solid support with the capture antibody;
 b) contacting the capture antibody with the sample under conditions to form a capture antibody:αKlotho complex;
 c) removing unbound sample;
 d) contacting the capture antibody:αKlotho complex with the detection antibody;
 e) removing unbound detection antibody; and
 f) detecting and/or measuring the capture antibody: αKlotho complex.

In an embodiment, the ELISA is a competitive ELISA. In an embodiment, the ELISA is a direct ELISA. In an embodiment, the ELISA is an indirect ELISA.

As used herein, "solid supports" include any material to which αKlotho polypeptide and antibodies and/or binding fragments thereof herein disclosed are capable of binding to. For example, the solid support can include plastic, glass, polystyrene, nylon, polypropylene, nylon, polyethylene, dextran, amylases, natural and modified celluloses and polyacrylamides. For example, the solid support is a microtiter plate, magnetic beads, latex beads or array surfaces.

For example, the sample is contacted with an antibody and/or binding fragment thereof under appropriate conditions, for example, at a given temperature and for a sufficient period of time, to allow effective binding of αKlotho to the antibody, thus forming an antibody:αKlotho complex, such as a capture antibody:αKlotho complex. For example, the contacting step is carried out at room temperature for about 30 minutes, about 60 minutes, about 2 hours or about 4 hours. For example, the contacting step is carried out at about 4° C. overnight.

For example, the antibody and/or binding fragment thereof disclosed herein is complexed with αKlotho in a suitable buffer. For example, the buffer has a pH of about 5.0 to about 10.0. For example, the buffer has a pH of 4.5, 6.5 or 7.4. For example, the buffer is a HBS-EP buffer, a KRH buffer or Tris-buffered saline. For example, the buffer comprises BSA and/or Tween20.

For example, any unbound sample may be removed by washing so that only the formed antibody:αKlotho complex remains on the solid support. For example, the unbound sample is washed with phosphate-buffered saline, optionally comprising bovine serum albumin (BSA).

In an embodiment, the detection antibody is labelled and/or conjugated to a tag.

For example, the detection antibody directly labelled and/or conjugated. For example, the detection antibody is indirectly labelled and/or conjugated. Indirect labels include for example fluorescent or chemiluminescent tags, metals, dyes or radionuclides attached to the antibody. Indirect labels include for example horseradish peroxidase, alkaline phosphatase (AP), beta-galactosidase and urease. For example, HRP can be used with a chromogenic substrate, for example tetramethybenzidine, which produces a soluble product in the presence of hydrogen peroxide that is detectable at 450 nm.

Yet another aspect is an assay for detecting and/or measuring level of αKlotho polypeptide in a sample, the assay comprising:
 a) contacting a sample with the antibody and/or binding fragment thereof herein described under conditions to form an antibody:αKlotho complex; and
 b) detecting and/or measuring the antibody:αKlotho complex.

A further aspect is an assay for detecting and/or measuring soluble αKlotho the method comprising:
 a) contacting a sample, the sample being a biological fluid, with the antibody and/or binding fragment thereof herein described under conditions to form an antibody:soluble αKlotho complex; and
 b) detecting and/or measuring the antibody:soluble αKlotho complex.

In an embodiment, the assay is for detecting folded αKlotho and the assay is performed under non-denaturing or mildly denaturing conditions.

In an embodiment, the complex is detected directly for example wherein the antibody is labeled with a detectable tag or fusion moiety. In an embodiment, the complex is detected indirectly using a secondary antibody specific for the antibody:αKlotho complex.

In an embodiment, the assay is an immunoprecipitation, immunoblot, immunohistochemistry or immunocytochemistry proximity ligation assay (PLA), mass spectroscopy-based techniques and fluorescence-activated cell sorting (FACS), proximity ligation assay (PLA), and mass spectroscopy-based techniques.

In an embodiment, the method is for detecting soluble αKlotho, for example wherein the sample is a biological fluid.

Detecting can be performed using methods that are qualitative or measured using quantitative methods, for example by comparing to a standard or standard curve.

In an embodiment, the biological fluid sample is blood, or a part thereof such as serum or plasma, or urine.

Yet another aspect relates to a method for screening, for diagnosing or for detecting kidney insufficiency condition selected from chronic kidney disease (CKD) and acute kidney injury (AKI) in a subject, the method comprising:
 a. measuring the level of αKlotho in a sample from a subject optionally using an antibody or assay herein disclosed; and
 b. comparing the level of αKlotho in the sample with a control,
  wherein a decreased level of αKlotho in the sample compared to the control is indicative that the subject has a kidney condition selected from CKD or AKI.

In an embodiment, the control is a control value derived from a group of subjects without CKD or AKI e.g. normal controls.

In an embodiment, the CKD is early CKD, optionally stage 1, stage 2, or stage 3, stage 4, stage 5 or stage 6 CKD.

An additional aspect of the disclosure is a method for prognosing CKD progression or AKI progression or lack thereof (e.g. recovery or worsening of disease), or extra-renal complication in CKD, which is assessed by measuring the level of αKlotho deficiency.

Accordingly an aspect is a method of prognosing a likelihood of recovery after AKI, the method comprising:
a. measuring a level of αKlotho in a sample from a subject; and
b. comparing the level of αKlotho in the sample with a control, for example a control value derived from a group of subjects that did not recover or progressed, wherein an increased level of αKlotho in the sample compared to the control is indicative that the subject has an increased likelihood of recovery after AKI.

In an embodiment, the control is a control value derived from a group of subjects that did recover and a decreased level of αKlotho in the sample compared to the control is indicative that the subject has a decreased likelihood of recovery after AKI and/or an increased likelihood of disease progression.

Another aspect is a method for prognosing a likelihood of long term complications after AKI, the method comprising:
a. measuring a level of αKlotho in a sample from a subject; and
b. comparing the level of αKlotho in the sample with a control, for example a control value derived from a group of subjects with long term complications or with increased number of long term complications, wherein an increased level of αKlotho in the sample compared to the control is indicative that the subject has an increased likelihood of having fewer long term complications after AKI.

In an embodiment, wherein the control is a control value derived from a group of subjects without long term complications or with fewer long term complications, a decreased level of αKlotho in the sample compared to the control is indicative that the subject has an increased likelihood of having long term complications or an increased number of long term complications after AKI.

A further aspect is a method for prognosing the likelihood of progression of CKD, the method comprising:
a. measuring a level of αKlotho in a sample from a subject; and
b. comparing the level of αKlotho in the sample with a control,
wherein an increased level of αKlotho in the sample compared to the control, for example wherein the control is a control value derived from a group of subjects that did not recover or progressed is indicative that the subject has an increased likelihood of recovering from CKD.

In an embodiment, the control is a control value derived from a group of subjects that did recover and a decreased level of αKlotho in the sample compared to the control is indicative that the subject has a decreased likelihood of recovery after CKD and/or an increased likelihood of disease progression.

Yet another aspect is a method for prognosing extra-renal complications in CKD, the method comprising:
a. measuring a level of αKlotho in a sample from a subject; and
b. comparing the level of αKlotho in the sample with a control,
wherein an increased level of αKlotho in the sample compared to the control is indicative that the subject has a higher likelihood of having fewer extra-renal complications related to CKD.

In an embodiment, wherein the control is a control value derived from a group of subjects without extra-renal complications or with fewer extra-renal complications, an decreased level of αKlotho in the sample compared to the control is indicative that the subject has a increased likelihood of having long term complications or an increased number of extra-renal complications after CKD.

A further aspect is a method for monitoring a subject with a kidney insufficiency condition such as CKD or AKI, the method comprising:
a. measuring a level of αKlotho in a sample from a subject; and
b. comparing the level of αKlotho in the sample with a previous reference sample other control,
wherein an increased level of αKlotho in the sample compared to the previous reference sample or other control is indicative that the subject has an ameliorating kidney condition and a decreased level of αKlotho in the sample compared to the previous reference sample or other control is indicative that the subject has a worsening kidney condition.

The sample can for example be taken after the subject has received a treatment and compared for example to a pre-treatment sample. Alternatively the patient can be monitored after a repeating interval to assess for example if treatment or other intervention is necessary. In an embodiment, the test is repeated and plotted to assess the subject's progression.

In an embodiment, the sample is a biological fluid such as blood, or a fraction thereof such as plasma or serum and the method is for example detecting soluble αKlotho. In an embodiment the biological fluid is urine.

In another embodiment, the sample is selected from a fresh sample such as a fresh biological fluid sample or tissue sample (e.g. including not frozen or one time frozen (e.g. frozen a single time at the time of obtaining the sample)) and a repeat frozen sample (e.g. frozen and thawed and frozen biological fluid sample or repeat frozen tissue sample). In an embodiment, the sample is a fixed sample such as a mildly fixed sample wherein the fixation induces limited denaturation and/or unfolding.

In an embodiment, the level of αKlotho is measured using an antibody or binding fragment described herein.

The methods disclosed herein to diagnose, detect or monitor a kidney disease or prognose a kidney disease complication, can be used in addition to or in combination with traditional diagnostic techniques for kidney disease.

Any antibody or combination of antibodies described herein or in the examples can be used in the assays.

IV. Kits

A further aspect relates to a kit comprising i) an antibody and/or binding fragment thereof, ii) a nucleic acid, iii) a composition or iv) a recombinant cell herein disclosed, comprised in a vial such as a sterile vial or other housing and optionally a reference agent and/or instructions for use thereof.

In an embodiment, the kit further comprises an additional antibody and/or binding fragment thereof having a light chain variable region comprising CDR-L1, CDR-L2 and CDR-L3 having amino acid sequences SEQ ID NO: 9, 10 and 5, respectively, and a heavy chain variable region comprising CDR-H1, CDR-H2 and CDR-H3 having amino acid sequences SEQ ID NO: 6, 7 and 8, respectively. For example, the additional antibody and/or binding fragment thereof is an sb106 antibody and/or binding fragment thereof.

In an embodiment, the kit comprises components and/or is for use in performing an assay described herein.

For example, the kit is an ELISA kit and can comprise a first antibody, e.g. a capture antibody, for example attached to a solid support, and a second antibody, e.g. a detection antibody, that binds to αKlotho and/or the capture antibody: αKlotho complex, and that is conjugated to a detectable label.

Any combination of antibodies described herein can be used.

In an embodiment, the kit is a diagnostic kit and the instructions are directed to a method described herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

A synthetic antibody library was screened and an antigen-binding fragment (Fab) with high affinity for human and rodent αKlotho was generated. This novel antibody, sb106, was characterized using recombinant proteins, cultured cells, and body fluids and tissues from humans and rodents. αKlotho levels in serum and urine in human and rodents can be accurately quantified, and it is demonstrated that both serum and urine αKlotho are dramatically reduced in early human CKD. The sb106 antibody is specific to the α-form of Klotho and is the first known one to successfully pull down αKlotho from patient serum samples, in a clean and specific manner, as compared to currently commercially available αKlotho detection reagents. In cells, it can immunoprecipitate αKlotho and label it by immunocytochemistry. In animals, the antibody is efficient at immunoprecipitating αKlotho from plasma. The ability of the sb106 antibody to detect small quantities of αKlotho from biological fluids makes it a valuable reagent for diagnosis of diseases where the level of αKlotho is abnormal. Moreover, sb106 antibody is valuable as a research reagent in studies of physiologic and pathologic states that involve any FGF23-mediated signaling pathways. It can be used in specific assays for soluble αKlotho in human and rodent samples such as serum using a variety of techniques such as enzyme-linked immunosorbent assay (ELISA), proximity ligation assay (PLA), and mass spectroscopy-based techniques.

Example 2

Preparation of the Binary αKlotho-FGFR1c Complex

The ligand-binding domain of human FGFR1c (D142 to R365) was expressed in *E. coli*, refolded in vitro from inclusion bodies, and purified by published methods [72,73]. The extracellular domain of murine αKlotho (A35 to K982) was expressed in HEK293 cells with a C-terminal FLAG tag, and the binary complex of the αKlotho ectodomain and the FGFR1c ligand-binding domain was prepared as described [9].

Isolation and Characterization of Sb106

Sb106 was isolated from a synthetic human Fab phage-displayed library (Library F) [74]. Binding selections, phage ELISAs and Fab protein purification were performed as described [67,75,76]. Briefly, phage from library F were cycled through rounds of panning with the binary complex of αKlotho extracellular domain and FGFR1c ligand-binding domain on 96-well Maxisorp Immunoplates (Fisher Scientific, Nepean, ON, Canada) as the capture target. After 5 rounds of selection, phage were produced from individual clones grown in a 96-well format and phage ELISAs were performed to detect specific binding clones. Clones that showed binding were subjected to DNA sequencing. A competitive binding ELISA was performed by pre-incubating sb106-phage with serial dilutions of soluble human αKlotho (50-0.0005 nM×1 hour) prior to binding to an ELISA plate coated with human αKlotho. The genes encoding for variable heavy and light chain domains of sb106 were cloned into vectors designed for production of light chain or IgG1 heavy chain, respectively, and sb106-IgG was expressed from 293F cells (Invivogen, San Diego, Calif. USA). Fab and IgG proteins were affinity-purified on Protein A affinity columns (GE Healthcare, Mississauga, ON, Canada).

Purification of Proteins

The binary complex of FGFR1c ligand-binding domain and murine αKlotho ectodomain (referred to as αKlotho-FGFR1c complex) was prepared by a published protocol [9]. The N-terminally hexahistidine tagged, mature form of human FGF23 (Y25 to I251) was expressed in *E. coli* and purified by published protocols [73,74,77].

Analysis of Fab Binding to αKlotho-FGFR1c Complex by SPR Spectroscopy

Real time protein-protein interactions were measured using a Biacore 2000 surface plasmon resonance (SPR) spectrometer (Biacore AB/GE Healthcare) at 25° C. in HBS-EP buffer (10 mM HEPES-NaOH, pH 7.4, 150 mM NaCl, 3 mM EDTA, 0.005% (v/v) polysorbate 20). Proteins were covalently coupled through their free amino groups to carboxymethyl (CM) dextran of research grade CM5 biosensor chips (Biacore AB/GE Healthcare). Proteins were injected over a biosensor chip at a flow rate of 50 µl min$^{-1}$, and at the end of each protein injection (180 s), HBS-EP buffer (50 µl min$^{-1}$) was flowed over the chip to monitor dissociation for 180 s. Injecting 2.0 M NaCl in 10 mM sodium acetate, pH 4.5, or 10 mM sodium/potassium phosphate, pH 6.5 regenerated the chip surface in between protein injections. The data were processed with BiaEvaluation software version 4.1 (Biacore AB/GE Healthcare). For each protein injection, the non-specific SPR responses recorded for the control flow channel were subtracted from the responses recorded for the sample flow channel.

To examine whether Fabs selected by ELISA bind to the αKlotho-FGFR1c complex, the binary receptor complex was immobilized on a CM5 chip (~42 fmol mm$^{-2}$ of chip flow channel). To control for non-specific binding, bovine β-glucuronidase (Sigma-Aldrich), which is structurally related to each of the two extracellular glycosidase-like domains of αKlotho, was coupled to the control flow channel of the chip (~45 fmol mm$^{-2}$ of flow channel). 100 nM of each Fab were injected over the chip. As a control, binding of FGF23 to the immobilized αKlotho-FGFR1c complex was examined.

To test if the Fabs can compete with FGF23 and/or binding to the αKlotho-FGFR1c complex, FGF23 was immobilized on a CM5 chip (~16 fmol mm$^{-2}$ of chip flow channel). FHF1B, which is structurally similar to FGFs but has no FGFR binding [77], was used as control for non-specific binding (~15 fmol mm$^{-2}$ of control flow channel). 100 nM of Fab mixed with 10 nM of αKlotho-FGFR1c complex (HBS-EP buffer) was injected over the chip. For control, the binding competition was carried out with FGF23 as the competitor in solution.

Cell Culture, Animal and Human Studies

Cell lines: normal rat kidney (NRK) cells with native αKlotho expression (ATCC, Manassas, Va., USA), and HEK293 cells transfected with vector only, full-length transmembrane murine αKlotho, extracellular domain of murine αKlotho with C-terminal FLAG tag, or full-length murine βKlotho[78]. Cells were cultured at 37° C. in a 95% air, 5% $CO_2$ atmosphere, passed in high-glucose (450 mg/dl) DMEM supplemented with 10% fetal bovine serum, penicillin (100 U/ml), and streptomycin (100 mg/ml).

Animal studies were approved by the University of Texas Southwestern Medical Center Institutional Animal Care and Care Committee. All animals were housed in the Animal Resource Center and experiments were performed in fully approved laboratories. Species used include: Sprague-Dawley rats (Harlan. Indianapolis, Ind.), Klotho transgenic overexpressors (Tg-Klotho; EFmKL46 line)[79], homozygous αKlotho hypomorphic mice (Kl/Kl)[80], and their wild type littermates (129sv background).

Clinical history and routine lab data were obtained from electronic charts. Blood samples from antecubital venipuncture were spun, and the serum was frozen at −80° C. Fresh urine was spun at 4,000 g and the supernatant was frozen at −80° C.

Immunocytochemistry and Immunohistochemistry

HEK293 cells transfected with vector or the stated αKlotho plasmids and seeded (1.8×10$^5$ cells/ml) on 12-well glass cover slips pre-treated with poly-lysine and grown overnight. The cells were washed (4° C. PBS×3), fixed with 3% paraformaldehyde (4° C.×10 min), washed (ice cold PBS×3), blocked with 1% BSA (PBS 44° C.×10 min), incubated with sb106-Fab (5 ug/ml in 1% BSA, PBS) washed (PBS 4° C.×5), incubated with anti-FLAG-Alexa488 (Cell Signaling; diluted 1:400 in PBS containing 1% BSA; 1 hour; 20° C.), washed (PBS; 4° C.×4), and then inverted onto glass slides containing a drop of antifade with DAPI (Invitrogen) and dried at room temperature in the dark. After 24 hours, the slides were stored at −20° C. Images were obtained on a WaveFX spinning disc confocal microscope.

The parathyroid and thyroid (en bloc with the trachea) were from adult Sprague Dawley rats. For non-fixed fresh parathyroids, tissues were embedded in OCT medium and frozen with isopentane pre-cooled in liquid $N_2$ immediately. For fixed parathyroid samples, tissue was immersed in 4% paraformaldehyde in PBS pH 7.4 at 4° C. overnight, washed with PBS, and embedded in OCT medium and frozen with isopentane pre-cooled in liquid $N_2$. Four μm thick cryostat sections were made, washed in PBS (15 min), and permeabilized in 0.1% TritonX-100 (10 min). For labeling, sections were blocked (PBS, 1.5% BSA, 10% goat serum; 40 min) and incubated with the primary antibody sb106 (21 pg/ml in blocking solution; 4° C. overnight). After washing (PBS), sections were incubated with the Alexa 546 goat anti-human IgG (1:800 dilution, Invitrogen) for 1 hour at room temperature. After additional washes with PBS, the sections were fixed with 4% paraformaldehyde in PBS, washed with PBS, and mounted and visualized with a Zeiss LSM510 microscope.

Example 3: αKlotho Assays and Detailed Methods

The ELISA was performed as instructed by the manufacturer (Immuno-Biological Laboratory, Japan). For the IP-IB assay, typically 50 μl of serum or urine were diluted with KRH buffer [25 mM Hepes-NaOH (pH 7.4), 120 mM NaCl, 5 mM KCl, 1.2 mM MgSO4, 1.3 mM CaCl2), 1.3 mM KH2PO4] to a final volume of 0.5 ml incubated with 2 pg of sb106-Fab overnight at 4° C. in low binding, siliconized tubes. Sepharose beads (50 μL) conjugated with anti-FLAG antibody (50% v/v) prewashed 3× with KRH buffer were added, incubated (4° C.×2 h), and washed (KRH-500 μl per tube×3; 22° C.). The immune complex was eluted with 2×SDS sample loading buffer (50 μl; 100° C.×3 min; 4° C.×3 min; spun), and fractionated by SDS-PAGE, transferred to nitrocellulose membranes and blotted with anti-KL1 antibody (KM2076, 1:4000 or 3.1 mg/mL, 1:10000 dilution) and diluent (Dako #53022, Carpinteria, Calif., USA) overnight (4° C., rocker). The membrane was washed (×3, Tris-buffered saline with 0.1% Tween; TBS-T), exposed to anti-rat IgG2A (LSBio cat # LS-059051, 1:20000 in 5% milk/2'Y° goat serum/TBS-T×1 h) and washed (×3 TBS-T). For chemiluminescence, the membrane was covered with SuperSignal West Femto Maximum Sensitivity substrate (Thermo Scientific, Rockford, Ill., USA) and exposed for 30-90 s. The 130-kD bands were scanned, and density was compared with internal control samples of know amount of Klotho using Adobe Photoshop CS4.

Example 4: Identification of an Anti-αKlotho Synthetic Fab

Figure 7:
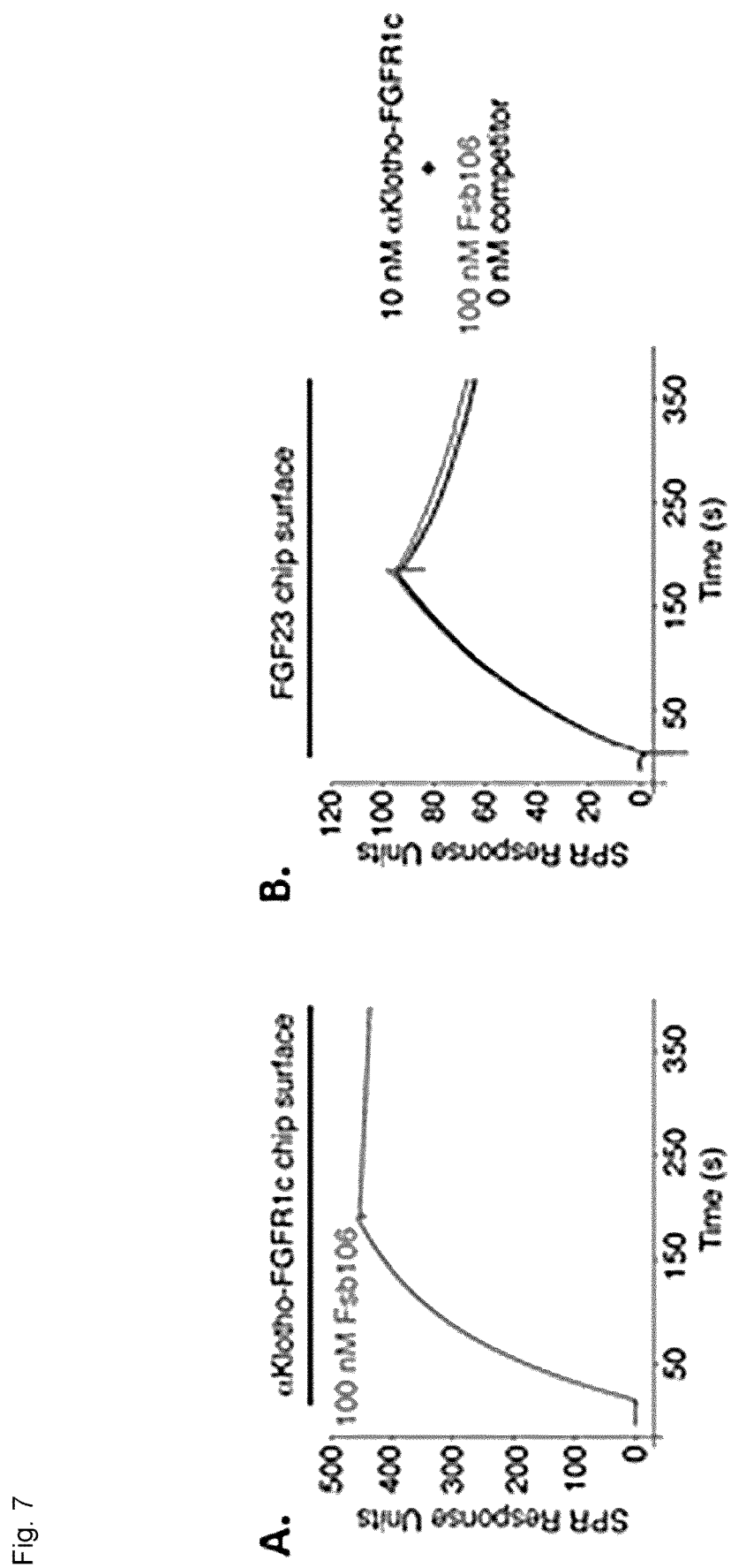
FIG. 7 shows surface plasmon resonance (SPR) sensorgrams with sb106-Fab. (A) SPR sensorgram illustrating binding of sb106-Fab (Fsb106) to the αKlotho-FGFR1c complex. The binary complex of murine αKlotho ectodomain and human FGFR1c ligand-binding domain was immobilized on a biosensor chip and 100 nM of Fsb106 were injected over the chip. Note that the Fsb106 dissociates extremely slowly from the αKlotho-FGFR1c complex. (B) Overlay of SPR sensorgrams showing that sb106-Fab does not inhibit ternary complex formation between FGF23, αKlotho, and FGFR1c. 10 nM of αKlotho-FGFR1c complex alone and a mixture of 10 nM of αKlotho-FGFR1c complex and 100 nM of Fsb106 were injected over a biosensor chip containing immobilized FGF23.

After rounds of biopanning of a phage-displayed synthetic Fab library on recombinant αKlotho ectodomain complexed with the ligand-binding domain of fibroblast growth factor receptor (FGFR)1c, several binding phages were identified. Clone sb106 (FIG. 1A) was chosen for further characterization. In phage ELISA (FIG. 1B), sb106-phage bound to both human and mouse αKlotho, demonstrating cross species reactivity, and to either αKlotho alone or in complex with FGFR1c, indicating that its epitope is not obscured by co-receptor complex formation. Sb106-phage did not bind to FGFR1c alone, neutravidin (NAV) or bovine serum albumin (BSA). Sb106 binds to human αKlotho with affinity in the single-digit nanomolar range (IC50=1.7 nM, FIG. 1C). Sb106-Fab also binds with high affinity to the binary αKlotho-FGFR1c complex immobilized on a biosensor chip (FIG. 7A) and it does not interfere with ternary complex formation between FGF23, αKlotho and FGFR1c (FIG. 7B).

Example 5: Characterization of the Anti-αKlotho Fab Sb106

Figure 2:
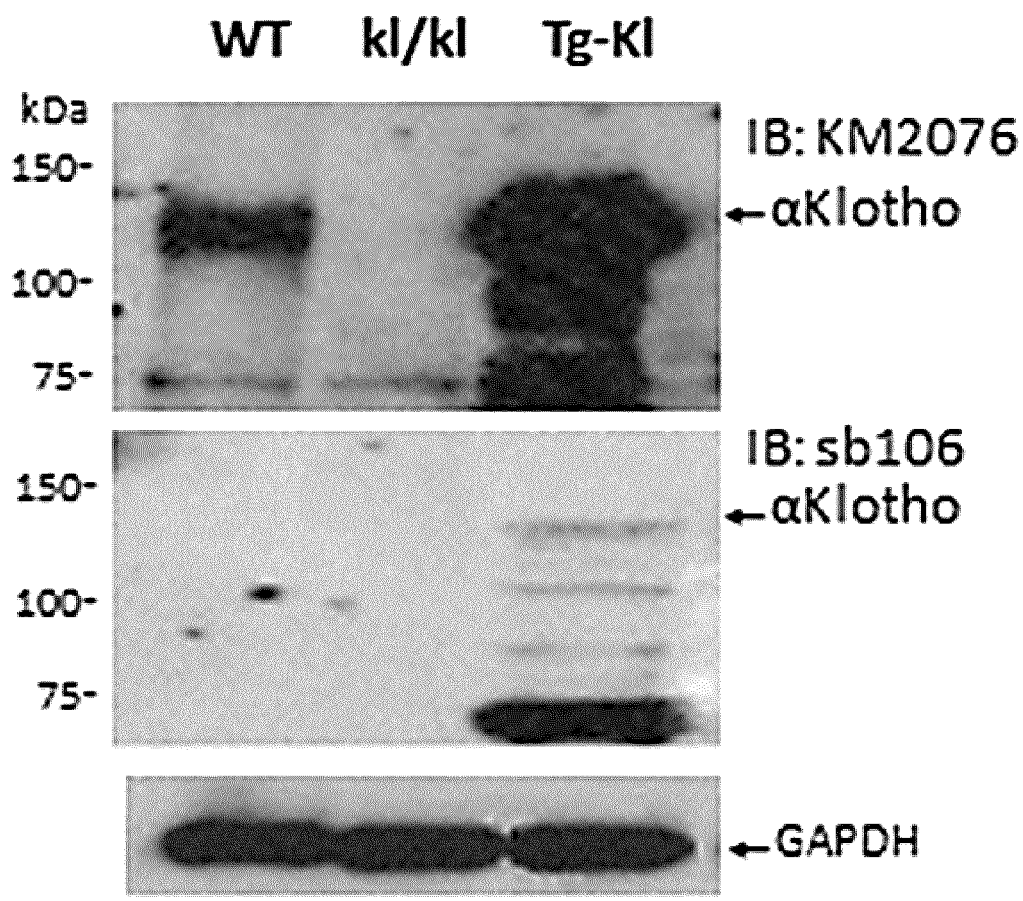
FIG. 2 shows the characterization of sb106-Fab by immunoblot, immunohistochemistry and immunocytochemistry. (A) Immunoblot of kidney lysate from wild type mice (WT), homozygous αKlotho hypomorphic mice (kl/kl) and transgenic αKlotho overexpressing mice (Tg-Kl), using the monoclonal antibody KM2076 or the sb106-Fab. GAPDH: Glyceraldehyde phosphate dehydrogenase. (B) Immunoblot of lysates from normal rat kidney (NRK) cells, human embryonic kidney (HEK) cells, and HEK cells transfected with a plasmid for over-expression of αKlotho, using the monoclonal antibody KM2076 or the sb106-Fab. (C) Fresh or fixed rat parathyroid tissue probed with phalloidin for β-actin or sb106-IgG. (D) sb106 immunostaining of HEK293T cells transfected with a vector control, or vector for over-expression for αKlotho or βKlotho. Representative cells are shown. The DAPI nuclear staining is labeled "N". (scale bar, 10 μm). αKlotho staining with Fab sb106 was only observed in cells transfected with αKlotho and not in cell transfected with βKlotho.
Figure 2:
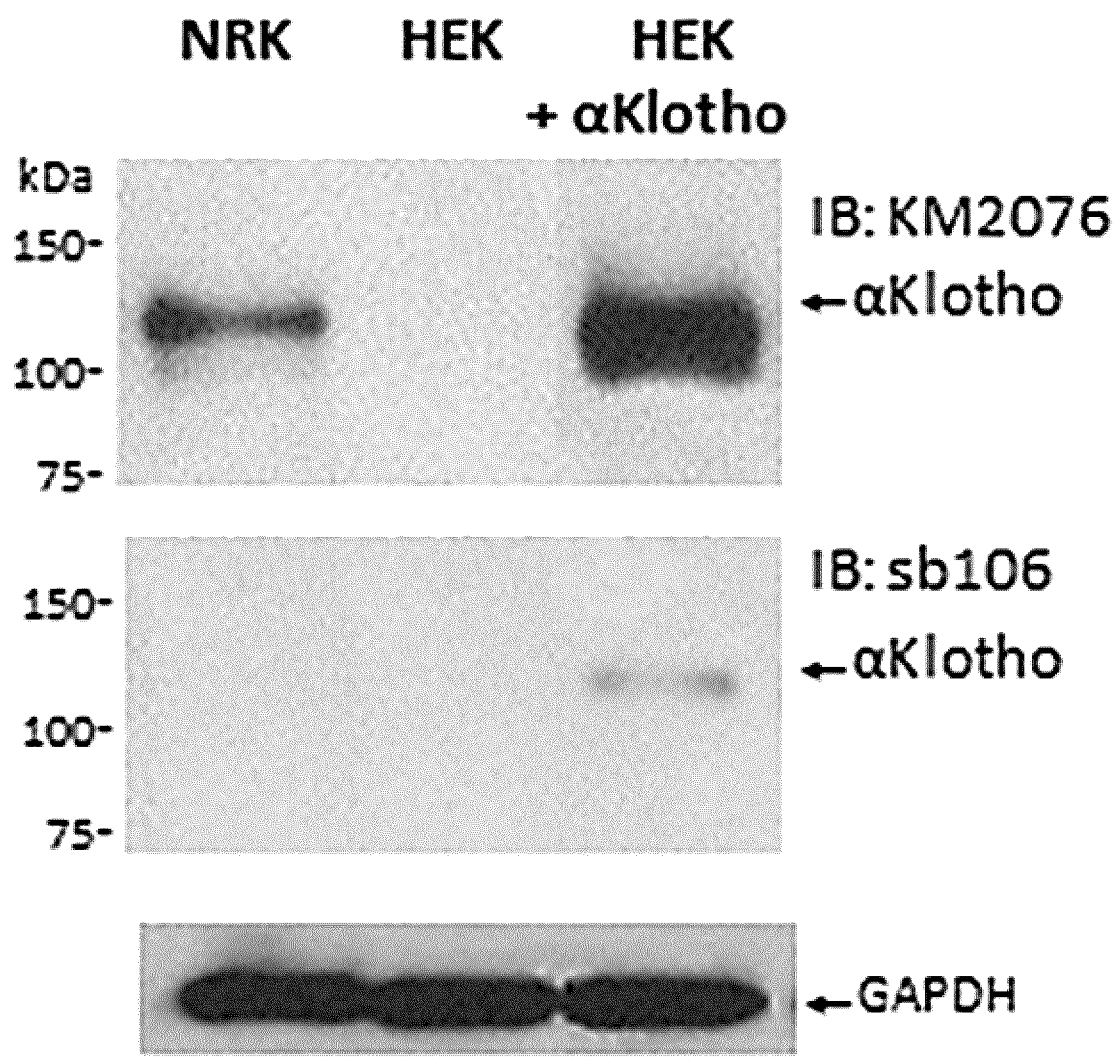
Figure 2:
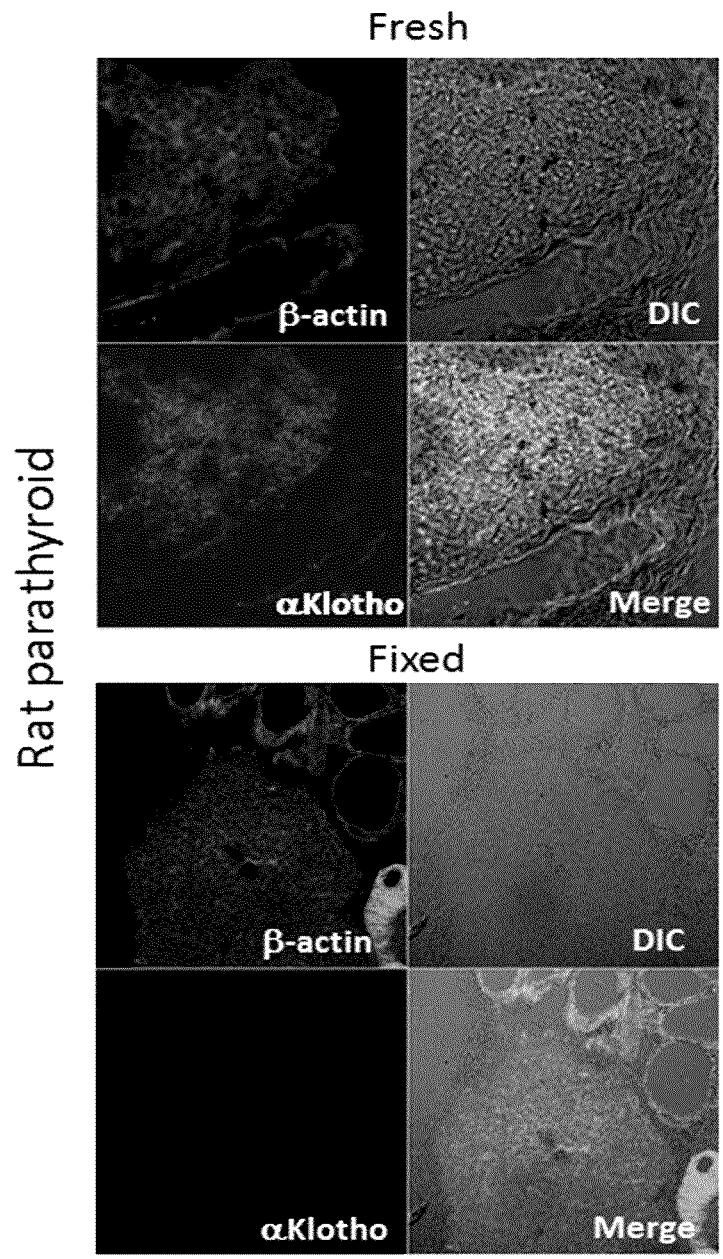
Figure 2:
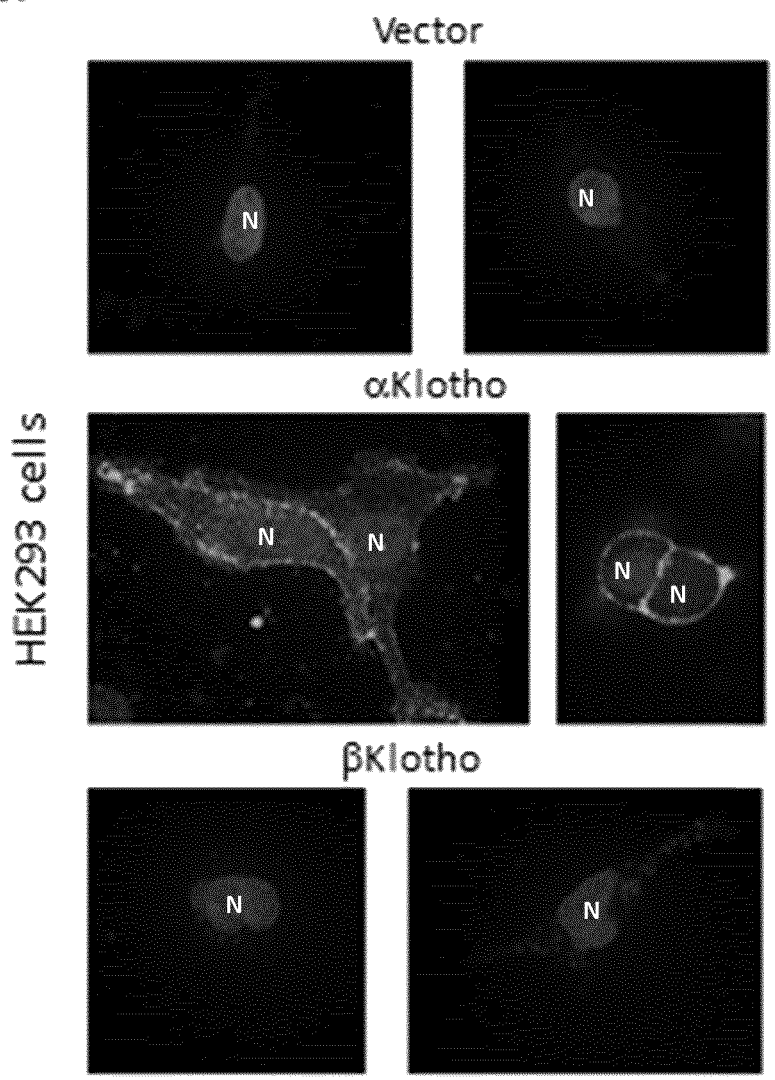

Using the unique CDR sequences of sb106 (FIG. 1A), both Fab and full-length IgG proteins were produced (e.g. Fab was produced in bacterial cells and IgG proteins in 293F cells). Sb106 was highly reactive against αKlotho under native conditions. Immunoblot signals under denaturing conditions against mouse, rat, and human kidney tissue were weak, but in samples from transgenic mice overexpressing αKlotho [79], sb106-Fab detected a band corresponding to the full-length extracellular domain of αKlotho (FIG. 2A). In cultured cells, sb106-Fab was not able to detect αKlotho in immunoblots under denaturing conditions with lysates from NRK cells expressing native αKlotho but it was able to detect overexpressed antigen in cell lysates from HEK293 cells transfected with αKlotho (FIG. 2B). In immunohistochemistry with freshly frozen unfixed rat parathyroid tissue (and other tissues known to express αKlotho, sb106-IgG detected αKlotho but the same tissue was negative when fixed (FIG. 2C), suggesting that sb106 binds to the natively folded FGFR1-αKlotho complex (FIG. 1B). In immunocytochemical stains with freshly fixed cells, unequivocal staining was obtained in HEK293 cells heterologously overexpressing αKlotho but not in cells overexpressing βKlotho (FIG. 2D). The cells were seeded at $1.8 \times 10^5$/ml on 12-well glass cover slips treated with poly-lysine and grown overnight. Cells were washed 3 times with ice cold PBS, fixed for 10 min on ice (3% paraformaldehyde), washed 3 times with cold PBS, blocked for 10 min (1% BSA in cold PBS). Cells were then incubated with sb106-Fab (5 μg/ml in 1% BSA in PBS) for 1 hr. Cells were washed 5 times with cold PBS (2 min each) and then incubated with anti-FLAG-Alexa488 (the C-terminus of the Fab light chain contains a Flag epitope tag) (1:400 in 1% BSA in PBS) for 1 hr, while being protected from light. Cells were washed 4 times with cold PBS (5 min each). The glass coverslips were then inverted onto glass slides containing a drop of antifade reagent with DAPI. Images were collected on a spinning disc confocal microscope. Even in cells overexpressing αKlotho, prolonged fixation greatly diminished or abolished the staining with sb106. These data indicate that sb106 reacts specifically with natively folded human, rat, and mouse αKlotho but not with denatured αKlotho protein.

Example 6: Immunoprecipitation of αKlotho

The ability of sb106-Fab to precipitate soluble αKlotho was tested using a sequential immunoprecipitation-immunoblot (IP-IB) assay. Sb106-Fab pulled down αKlotho from total cell lysates and conditioned cell culture medium and from αKlotho-overexpressing cells (FIG. 3A). The sb106-Fab pull-down was compared with that of an anti-FLAG antibody using soluble αKlotho with a C-terminal FLAG tag in HEK293 cells. Sb106-Fab and anti-FLAG precipitated proteins with the exact same electrophoretic mobilities.

Sb106-Fab precipitated a ~130 kDa protein from human, mouse, and rat sera that reacted with the anti-αKlotho antibody KM2076 (FIG. 3B). IP from urine also showed a ~130 kDa band (FIG. 3B), whereas the post-IP urine samples did not show such a band in immunoblot. To further support the authenticity of the IP-IB band by sb106, the intensity of this band was examined in human sera from a normal individual vs. a patient with CKD stage 5, and sera from a wild type mouse vs. a homozygous αKlotho hypomorph (FIG. 3C). Only the ~130 kDa band (FIG. 3C) was reduced in human advanced CKD and was absent in the αKlotho-deficient mice (kl/kl)[80].

Example 7: αKlotho Levels in Human CKD

The IP-IB method was tested to determine whether it can reliably determine serum αKlotho levels from a single center database of CKD patients. Recombinant human αKlotho was spiked in known amounts to test the linearity of the assay as well as the extrapolated y-intercept. IP-IB was performed with sera from a normal healthy volunteer and a patient with stage 5 CKD spiked with a range of different concentrations of recombinant αKlotho (FIG. 4A). There was graded increase in signal with the incrementally inoculated exogenous αKlotho. The serum from the CKD patient also showed increases in signal with increasing exogenous αKlotho but, at any given concentration of αKlotho, the signal intensity was lower than the normal serum.

Interestingly, the serum from the healthy volunteer gave the same signal in the absence or presence of a protease inhibitor cocktail, whereas the serum from the CKD patient displayed a marked increase in measured αKlotho levels in the presence of a protease inhibitor (FIG. 4B). These findings suggest that while endogenous αKlotho exists in a stable steady state in uremia, the exogenously added αKlotho may undergo proteolysis in uremic serum but not in normal serum. A quantitative summary of the spiking experiment is shown in FIG. 4C. Both healthy and CKD sera showed linear responses to αKlotho inoculation but the signal from CKD sera has a lower slope. When protease inhibitors were included, the slope of the CKD line approached that of the healthy subject without affecting its intercept. Extrapolation to zero inoculation showed that the serum from the normal individual had 31.1 pM αKlotho while that from the CKD patient had 8.5 pM αKlotho. Similar extrapolations were obtained from a number of other subjects with normal renal function or with CKD.

Figure 5:
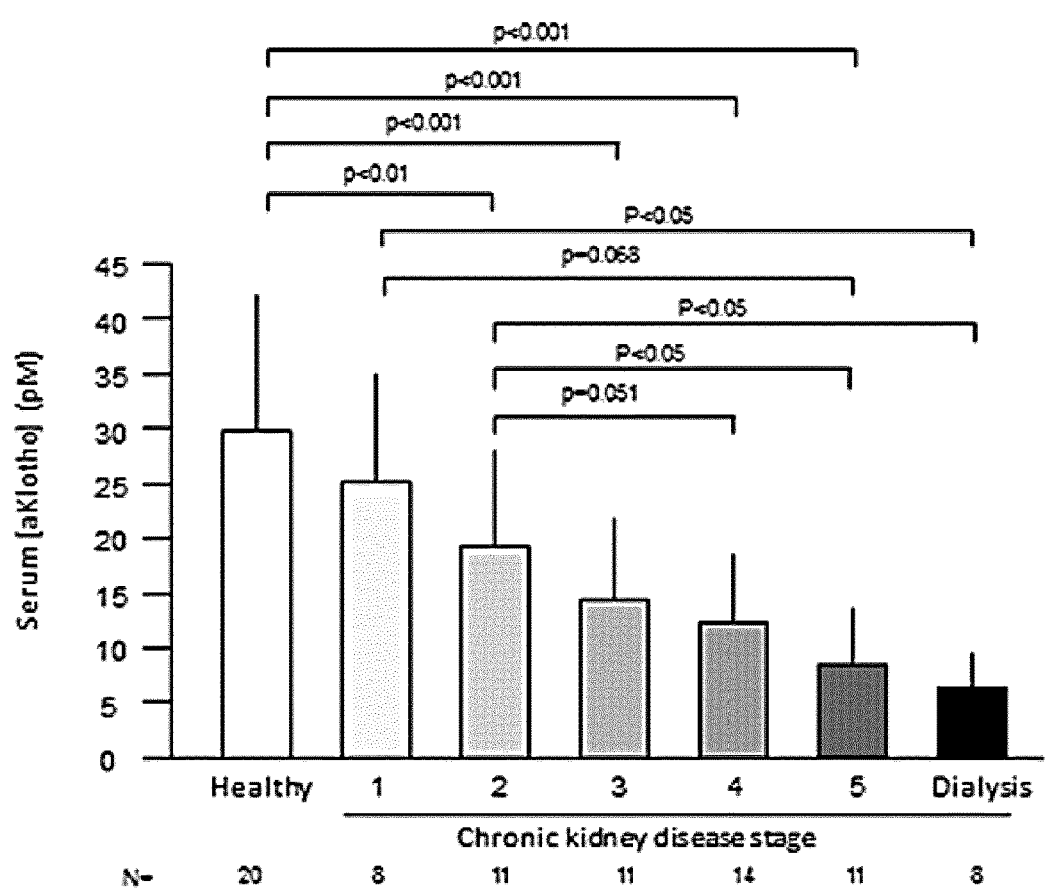
FIG. 5 shows IP-IB assay of serum αKlotho in humans with chronic kidney disease. (A) αKlotho was measured by the IP-IB assay in human sera from normal healthy volunteers and patients from a CKD clinic and dialysis unit using the conventional numerical staging using recombinant αKlotho as a calibration curve. Bars and error bars denote means and standard deviations. The data was analyzed by ANOVA followed by Student-Newman-Keuls test for pair-wise multiple comparisons. P values achieving statistical significance between groups are indicated above the brackets. The number of subjects in each group is indicated at the bottom. (B) The concentrations of αKlotho in a large variety of human sera were determined either by IP-IB (x-axis) or by a commercial ELISA (y-axis) in the same samples. The dotted line represents identity. The grey diamonds represent sera that have been through one or more freeze-thaw cycles (stored) and the black diamonds represent sera thawed only once (fresh). (C) Sera from human subjects were assayed by IP-IB and ELISA. The same sera were subjected to the indicated cycles of repeated freeze-thaw and then assayed. Results for each sample were expressed as a percentage of the reading from the same sample thawed only once. The black lines denote the mean of the different subjects.
Figure 5:
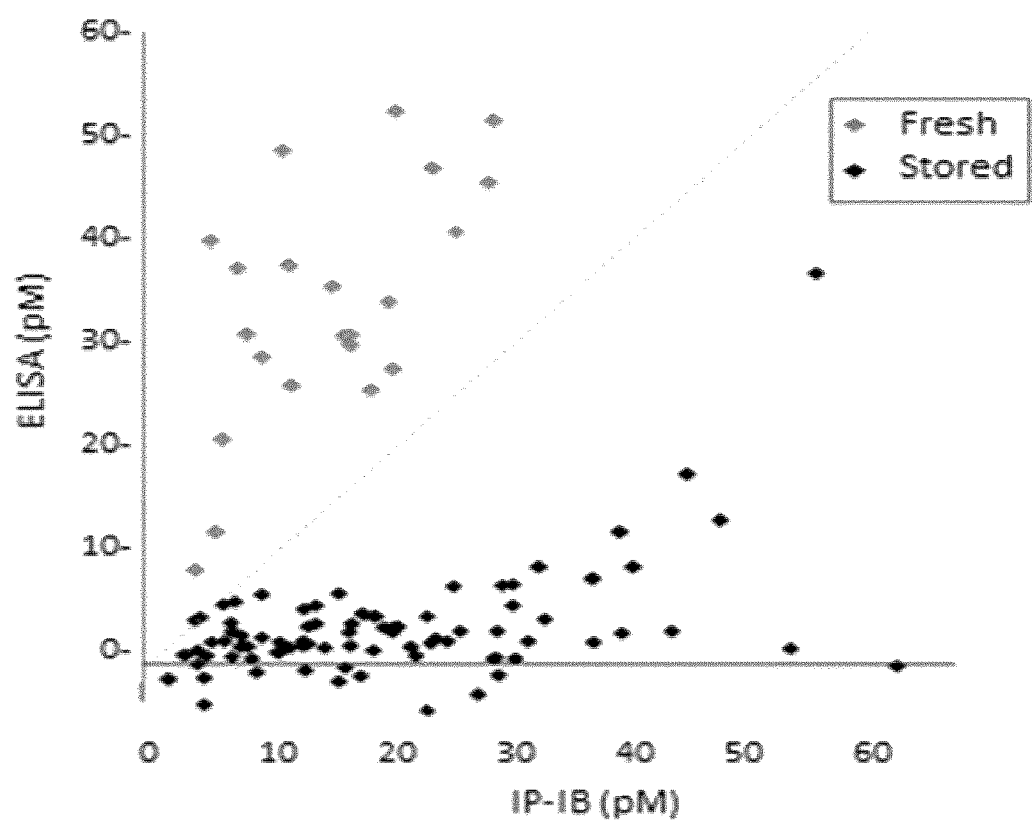
Figure 5:
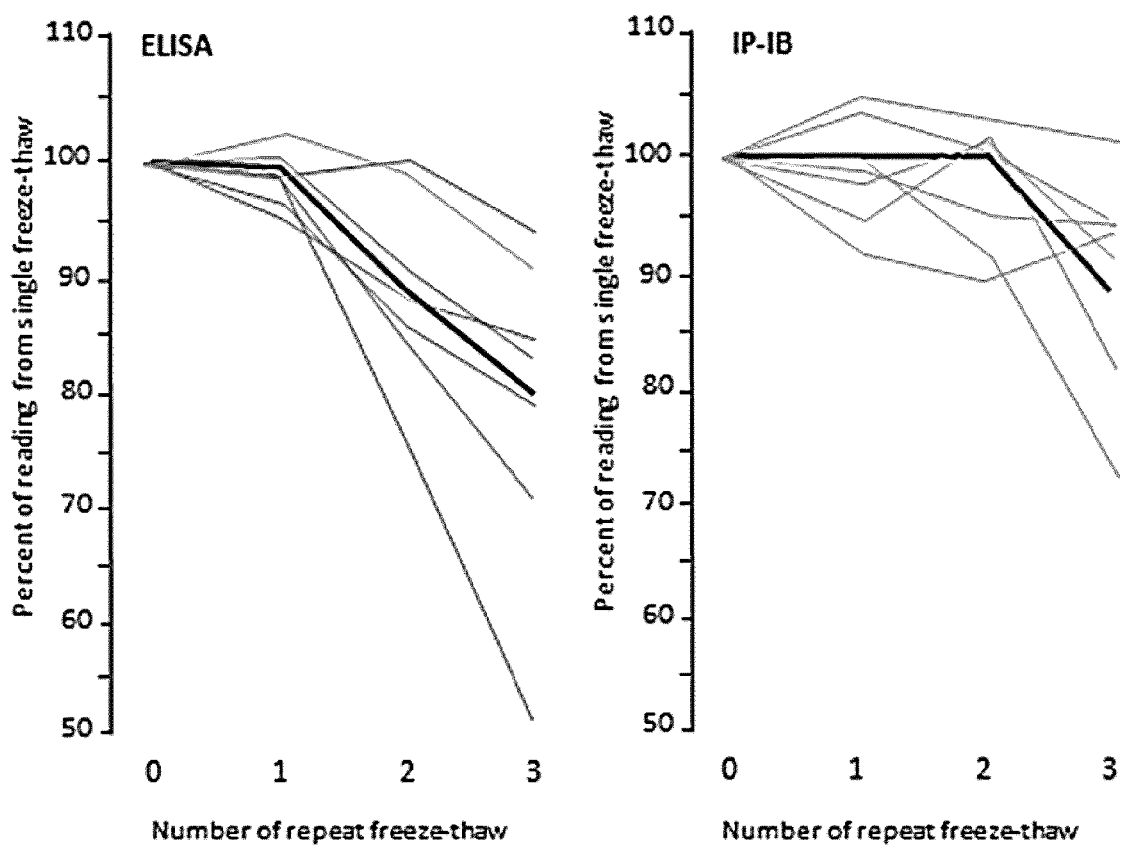

The nature of patients recruited from the CKD clinic resembles the national profile of CKD where diabetes and hypertension predominate (Table 1). Despite the scatter, there is a clear progressive decline of αKlotho with stages of CKD (FIG. 5A). The decrease in serum αKlotho occurred early in CKD, and preceded high FGF23, high PTH, and hyperphosphatemia (Table 1). The IP-IB assay was directly compared with a commercial αKlotho ELISA kit with the same samples (FIG. 5B). Overall, there is a correlation between the two but there is separation on both sides of the line of identity. In fresh samples, the ELISA shows higher values than IP-IB (grey diamonds to the left of the line of identity, FIG. 5B) but in samples that have been through one or more cycles of freeze-thaw, the ELISA values are much lower (black diamonds to the right of the line of identity, FIG. 5B). When the exact same samples were tested by the two methods before and after repeated freeze-thaw, the IP-IB assay gave more stable results while the ELISA values dropped rapidly (FIG. 5C).

Low urinary αKlotho in human CKD patients by directly immunoblotting urine was previously described[12]. The IP-IB assay with sb106-Fab showed dramatic reduction of urinary αKlotho in CKD patients (FIG. 6A). In contradistinction from serum, the ELISA yielded more comparable values to the IP-IB assay in the urine but the magnitude of decrease in αKlotho concentration is more dramatic when detected by the IP-IB assay than by ELISA (FIG. 6B). These results show that human CKD is a state of αKlotho deficiency in both serum and urine.

Hence using an immunoprecipitation-immunoblot (IP-IB) assay, both the serum and urinary levels of full-length soluble αKlotho was measured in humans and it was established that human CKD is associated with αKlotho deficiency in serum and urine. αKlotho levels were detectably lower in early CKD preceding disturbances in other parameters of mineral metabolism and levels progressively declined with CKD stages. Exogenously added αKlotho is inherently unstable in the CKD milieu.

Antibody-based reagents are valuable tools in both research and clinical settings for detection of proteins, protein isolation and purification, and numerous downstream applications. The commercial reagents available for αKlotho detection are limiting; for example there are no antibodies for specifically detecting natively folded αKlotho protein. Moreover, the commercial ELISA kit for αKlotho detection yields highly variable results.

Synthetic antibodies with designed antigen-binding sites can be fine-tuned and tailored for molecular recognition of vast repertoires of targets. Coupled with in vitro phage-display, selections are performed in the absence of tolerance mechanisms that eliminate self-reactive antibodies. Selections with an antibody library yielded sb106, an antibody with specificity for natively folded human, mouse and rat αKlotho.

In addition to its role in mineral metabolism, soluble αKlotho circulates in many bodily fluids and has multiple "house-keeping" functions that maintain cellular integrity throughout the body. Although the mechanism of action of soluble αKlotho remains poorly understood, the biologic impact of αKlotho deficiency is unequivocally shown [81]. αKlotho transcripts are present in multiple organs but the kidney by far has the highest expression [80]. CKD is a state of multiple metabolic derangements and is a complex syndrome from accumulation of under-excreted endogenous and exogenous toxins as well as deficiency in substances responsible for health maintenance.

There is evidence in experimental animals that both AKI and CKD are states of systemic αKlotho deficiency. Not only is this an early and sensitive biomarker, restoration of αKlotho can ameliorate the renal dysfunction. Independent from its renoprotective effects, αKlotho can also reduce the extrarenal complications in CKD [12,82]. Based on the preclinical data, anti-α(Klotho antibody may have both diagnostic and prognostic value.

Validation of the IP-IB Assay and Comparison with the Commercial ELISA

Available commercial assays for αKlotho have no consistent correlation between them [46, 83]. Studies in healthy humans and CKD patients based on one ELISA [58] have yielded contradictory results. The absolute levels of αKlotho in normal and CKD ranged from 0.4[47] to over 2000 pg/ml [41] with most readings in the mid to high hundreds [48, 50, 55, 58-60,83]. Based on this assay, αKlotho levels have been described to be low [48, 52, 54, 57-60], no relationship to [40, 41, 50, 51, 53] or even increased [44, 47] with decreasing glomerular filtration rate (GFR). Likewise, αKlotho levels have been reported as not changed or decreasing with age [42, 53, 58, 59]. This renders the interpretation of human αKlotho data nearly impossible, and the collective data derived from different centers will have no value.

A high affinity synthetic antibody that recognizes αKlotho in its natively folded conformation (FIGS. 1-3) was generated. Sb106-Fab or IgG pulls down αKlotho from cell lysate, culture medium, serum, and urine. Additional bands may be shorter fragments of αKlotho but the intensity of these bands did not decrease in the kl/kl mice arguing against this possibility. The ~130 kDa band has been analyzed which is full length soluble αKlotho; something that the ELISA cannot achieve.

Figure 4:
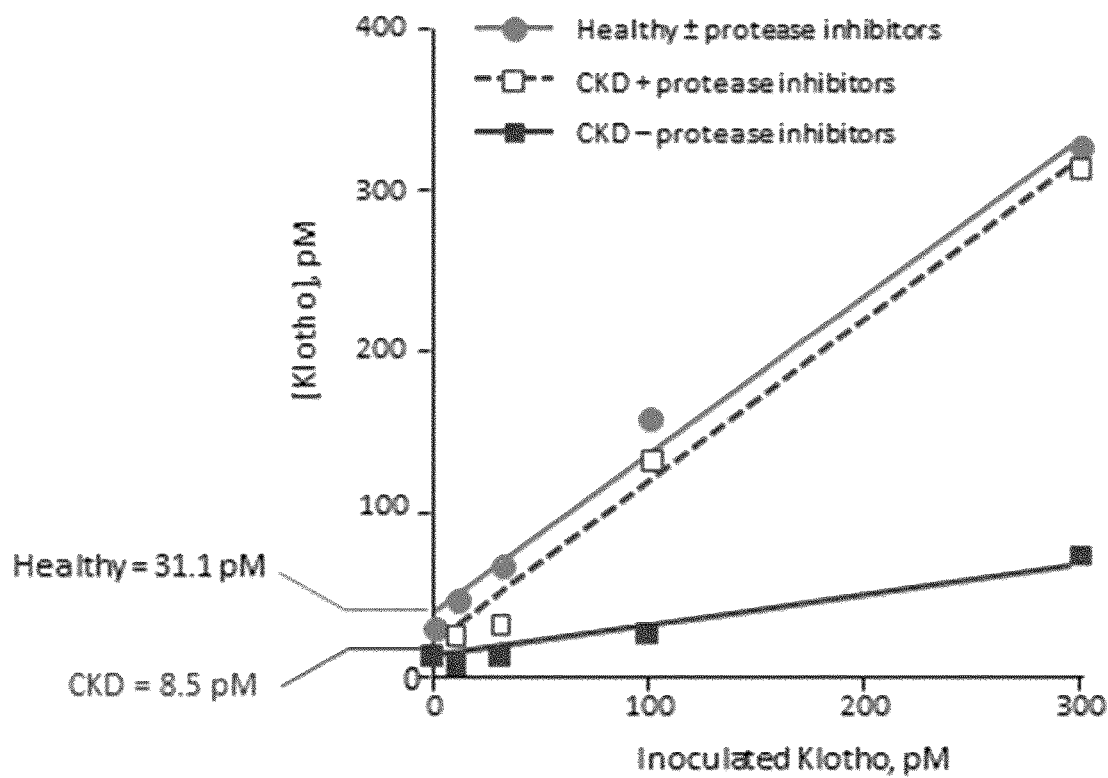
FIG. 4 shows the validation of IP-IB assay using human serum spiked with recombinant αKlotho. (A) Known amounts of soluble human αKlotho ectodomain were added to sera from a healthy volunteer or an anephric dialysis patient (CKD patient). αKlotho was measured in the sera using the IP-IB assay. (B) Similar experiment as in (A) except comparisons were made where protease inhibitors (AEBSF 0.1 mM, aprotinin 0.3 μM, bestatin 10 μM, E-64 1 μM, leupeptin 50 μM, pepstatin A 1 μM) were either included or excluded from the IP. (C) αKlotho levels determined by IP-IB (y-axis) were plotted against the added recombinant αKlotho (x-axis) in the four conditions described above. Extrapolation to zero spiking shows the level of endogenous αKlotho in the serum treated with protease inhibitors. Only one line is shown for healthy serum with or without protease inhibitors as the results were indistinguishable.

The linearity of the spiking experiment indicates that all the inoculated αKlotho is detected (FIG. 4). An unexpected finding was that exogenously added recombinant αKlotho is proteolytically degraded in uremic serum whereas no such phenomenon was observed in normal sera. This challenges the view that the low αKlotho in kidney disease stems solely from decreased production and opens up additional mechanisms and new avenues for investigation. In addition to uncovering new mechanisms of αKlotho deficiency in CKD, this may have significant implications in terms of recombinant αKlotho replacement.

There is graded reduction in serum αKlotho with advancing CKD (FIG. 5A). The coefficient of variation of the IP-IB assay was 4% for serum and 7% for urine. The IP-IB assay also showed very low urinary αKlotho in advanced CKD (FIG. 6). In fact, the reduction in urinary αKlotho is more dramatic than that in serum and may represent a more sensitive marker for CKD.

Both IP-IB and the commercial ELISA detected the low urine αKlotho in CKD, although the absolute levels of αKlotho are much higher with the ELISA assay and the percent reduction is not the same as with the IP-IB assay. With drastic reduction in urinary αKlotho levels in CKD, the two assays yielded the same conclusion with quantitative differences. The situation in serum is different. Although there is overall positive correlation, the comparison of the two assays completely segregated into two groups (FIG. 5B). The fresh samples showed higher readings for the ELISA while the stored samples yielded extremely low results with the ELISA. One possibility is that the ELISA is measuring αKlotho and some other reacting proteins in fresh samples. While the IP-IB assay did lose some efficacy with repeated freeze-thaw, this is a much more serious problem with the ELISA.

Another advantage of the IP-IB assay is that it can measure αKlotho in both humans and rodents equally well, whereas the use of the currently available ELISA in rodent can potentially be problematic as it detects very high circulating αKlotho levels in rats with CKD which is a state of pan-αKlotho deficiency. [68]

Example 8

Additional CDR sequences are provided in Table 2. Homologous mutations were introduced at each amino acid position, meaning that for each position either the original amino acid was retained or the closest "homolog" to that amino acid (e.g. conservative amino acid change) was introduced and a new Fab-phage library was constructed. Selections were performed using the new library using the alphaKlotho-FGFR1c complex as an antigen. Clones that bound to the antigen were isolated and sequenced and are shown in Table 2. The binding affinity is expected to be similar or better than Sb106.

Example 9

Human Studies

Nine human subjects (49.066.2 years) who underwent right heart catheterization were enrolled for this study. During right heart catheterization, suprarenal and infrarenal vena caval blood samples were obtained and sera were immediately separated after centrifugation at 4° C. and stored at −80° C. for future study. Serum αKlotho was determined by immunoprecipitation-immunoblot assay described herein. Briefly, 0.1 ml serum was immunoprecipitated with a synthetic anti-αKlotho Fab (sb106) and immune complex was eluted with Laemmli sample buffer, and subject to immunoblot with KM2076 antibody. The specific signals on the autoradiograms based on 130 kD mobility were quantified with ImageJ Program (National Institutes of Health (NIH), Bethesda, Md.).

Animal Studies

αKlotho hypomorphic (kl/kl) mice, kl/kl mice and their wild-type (WT) littermates were maintained at the Animal Research Center at the University of Texas Southwestern Medical Center. Currently all mice are 129 S1/SVImJ (129 SV) background age from 6 to 8 weeks. Normal Sprague- Dawley (SD) rats (220-250 g body weight) were purchased from Charles River Laboratories (Wilmington, Mass.). For αKlotho clearance study, rats underwent bilateral nephrectomy (anephric rats) or laparotomy with manual manipulation of the kidneys (sham rats). Rats or mice were intravenously or intraperitoneally injected once with labeled full extracellular domain of recombinant mouse αKlotho protein (rMKl) (R&D Systems, Minneapolis, Minn.) at a dose of 0.1 mg/kg body weight. To examine if secretases modulate blood αKlotho, doxycline hyclate (Sigma-Aldrich, St. Louis, Mo.), an α-secretase inhibitor at 25 mg/kg/day, and/or 13-secretase inhibitor III (Calbiochem, Billerica, Mass.) at 2.5 mg/kg/day were intraperitoneally injected into normal WT mice daily for 2 days, blood and kidneys were harvested at 48 hours to determine serum and renal αKlotho.

Antibodies

Rat monoclonal anti-human Klotho antibody, KM2076l,2 was used for immunoblotting and immunoelectron microscopy; and the synthetic anti-αKlotho antibody sb10663 was used for immunoprecipitation of serum Klotho.

Clearance of Labeled αKlotho in Rats and Mice

Normal Munich Wistar rats (220-250 g BW) were anesthetized with Inactin (100 mg/kg BW), and a bonus of labeled αKlotho was injected through the jugular vein (0.1 mg/kg BW). For the experiment of injection of 125I-labeled αKlotho or 125I-labeled albumin, fluid collection by freeflow micropuncture of Bowman's space, and proximal convoluted tubules was performed using published methods. In brief, the left kidney was exposed, and the left ureter was catheterized for urine collection. Proximal tubules were identified by their characteristic configuration after lissamine green dye injection and punctured with glass capillaries. The volume of fluid was measured in a calibrated constant-bore glass capillary. The radioactivity of fluids was determined by scintillation accounting and normalized to fluid volume. At specified time points, blood was drawn from retro-orbital venous sinus, and spot urine was collected. 125I-labeled αKlotho or 125I-labeled albumin in collected urine and serum was quantified by scintillation counting. Homogenates of different organs were made and radioactivity in organ homogenates was measured by scintillation counting, and normalized to protein in organ homogenates. Organ sections (10 mm) were subjected to autoradiography.

Immunoelectron Microscopy

Mouse recombinant Klotho protein (0.1 mg/kg BW) was intraperitoneally injected once into kl/kl mice and mice were sacrificed 24 hours after injection. Kidneys were harvested and fixed with 2.5% paraformaldehyde via aortic perfusion, removed, and post-fixed in 4% paraformaldehyde (4° C. for 4 hours). Immunogold labeling of ultrathin frozen tissue sections was performed as described.21 Kidney cortex was infiltrated with 2.3 M sucrose overnight, frozen in liquid nitrogen, and 70-80-nm-thick sections were made (Ultramicrotome Reichert Ultracut E; Leica Microsystems, Wetzlar, Germany) and mounted on Formvar-coated nickel grids. The sections were incubated with KM2076 antibody and followed by incubation with gold conjugated protein A (10-nm gold particles, Sigma-Aldrich) for 60 minutes. After staining with uranyl acetate, sections were visualized with Jeol 1200 EX transmission electron microscope (Jeol Ltd., Akishima, Japan).

Results

The role of the kidney in circulating αKlotho production and handling was examined. Serum levels of αKlotho protein in suprarenal and infrarenal vena cava of normal rats by direct puncture and human subjects who underwent right heart catheterization. All patients had eGFR≥60 ml/min/1.73 m². Similar infrarenal-to-suprarenal increment in caval αKlotho level was observed in both rat and human serum samples. Serum αKlotho levels were plotted against serum erythropoietin, a well-known renal-derived hormone, and it was found that as serum erythropoietin rose, and serum creatinine (SCr) decreased from infrarenal-to-suprarenal inferior vena cava, whereas αKlotho increased indicating that the kidney secretes αKlotho into the circulation.

When both kidneys were removed from rats, serum αKlotho level dropped significantly to about half the normal level in one day. The anephric state did not permit studies to continue for longer than 40-50 hours.

The method of αKlotho clearance from circulation was investigated. The levels of circulating exogenous αKlotho protein in anephric rats were similar to those in normal rats immediately after injection, but the half-life of exogenous αKlotho protein in normal rats was much shorter than that in anephric rats and the half-life of endogenous αKlotho upon nephrectomy closely approximates that of exogenous αKlotho in the anephric rats. Further experiments examining the anatomic fate of intravenous injected exogenous labeled αKlotho supported that the kidney may be a major organ of αKlotho uptake as well as its excretion.

Injected labeled αKlotho protein was prominently distributed in the kidney and spleen, sparsely in the heart, and not detectable in aorta, brain, and muscle. Further experiments tracking clearance of radioactively labelled exogenous αKlotho in serum and urine, supported that αKlotho protein is cleared from blood through the kidney to the urine.

Based on these and further experiments, it was determined that the (1) the kidney produces and releases soluble αKlotho into the systemic circulation by secretases-mediated shedding of the ectodomain of αKlotho, (2) the kidney is an important organ to clear soluble αKlotho from the circulation, (3) αKlotho traffics across renal tubules from basolateral to intracellular location and is then secreted across the apical membrane into the urinary lumen.

Example 10: Identification of Additional Antibodies that Bind αKlotho

The original antibody reagent to αKlotho, sb106 (clone 48), as well as CDR variants derived from sb106, all bind to a single common epitope. To establish a detection assay, one needs antibodies with different epitopes, as one surface/epitope is used to isolate or capture the protein while a second, distinct epitope is needed for the detection reagent. Thus another selection campaign was undertaken to identify antibodies which bind to epitopes different and distinct from that of sb106. These antibodies to αKlotho were identified by antibody-phage display selections performed on the extracellular domain (ECD) of human αKlotho while in the presence of saturating levels of sb106 Fab (50 ug/ml). The protein purchased from R&D Systems (5334-KL) covers amino acids E34-5981 with a 6-His tag attached at the C-terminus.

Figure 9:
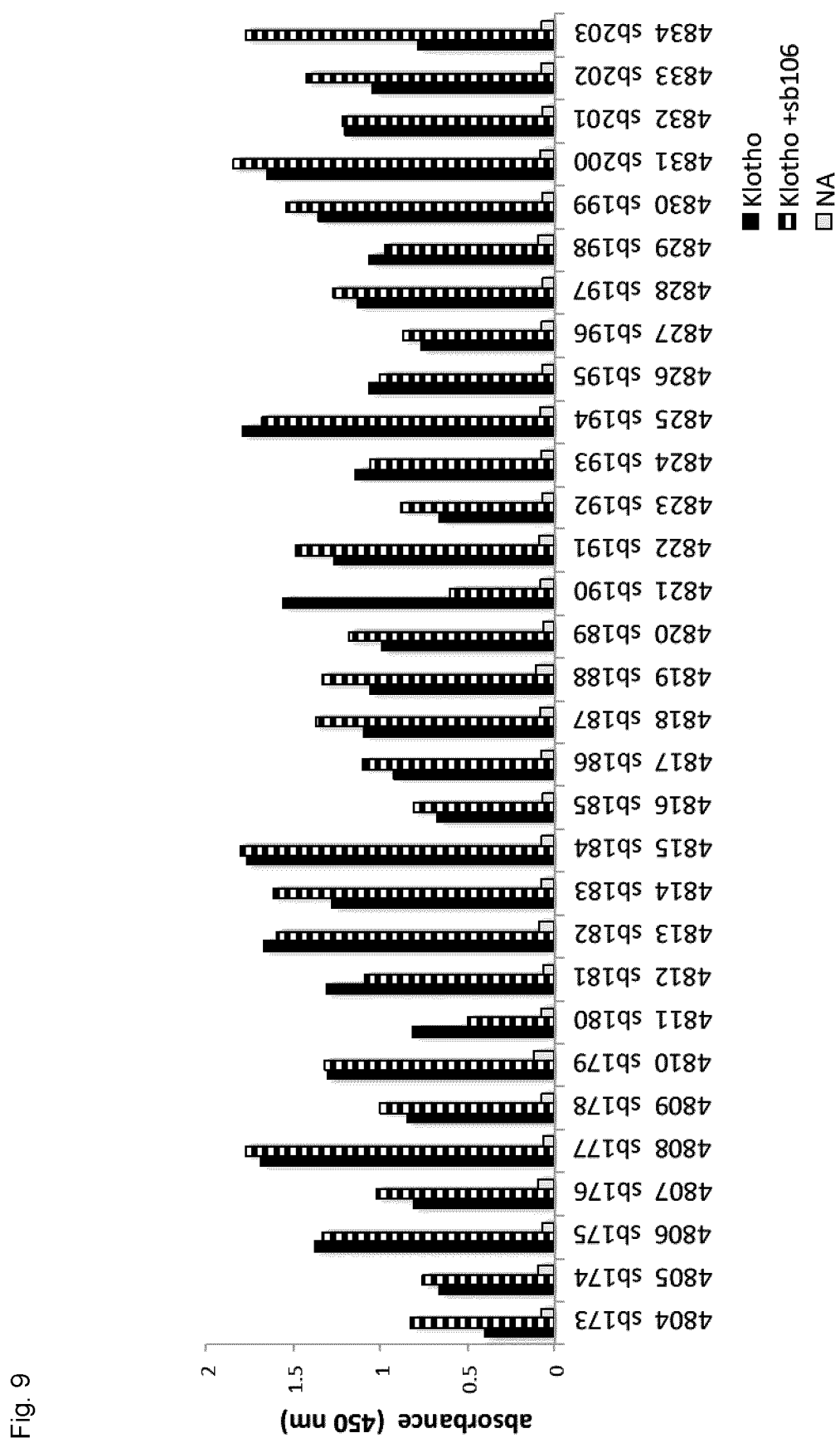
FIG. 9 is graph showing absorbance values of a Fab phage ELISA demonstrating the binding of Fab phage clones to αKlotho in the absence or presence of sb106 Fab. Fab phage clones were incubated with immobilized αKlotho in the absence or presence of sb106 Fab (25 ug/ml), or neutravidin (NA) as a negative control. After washing off unbound phage, bound phage were detected using an HRP-conjugated anti phage antibody. Colorimetric HRP reagents allow for absorbance readings at 450 nm.

In total, 31 new antibodies from a synthetic antibody library (Persson et al, 2013 J Mol Biol) were identified and shown to bind αKlotho, in the presence and absence of the first αKlotho antibody, sb106 (FIG. 9). CDRs of these clones are shown in Table 3 (amino acid sequence in 3A and nucleotide sequences in 3B & 3C) and examples of full-length sequences in Table 4. The clones were first given a name, and then ID numbers. Both are shown here for reference.

Figure 10:
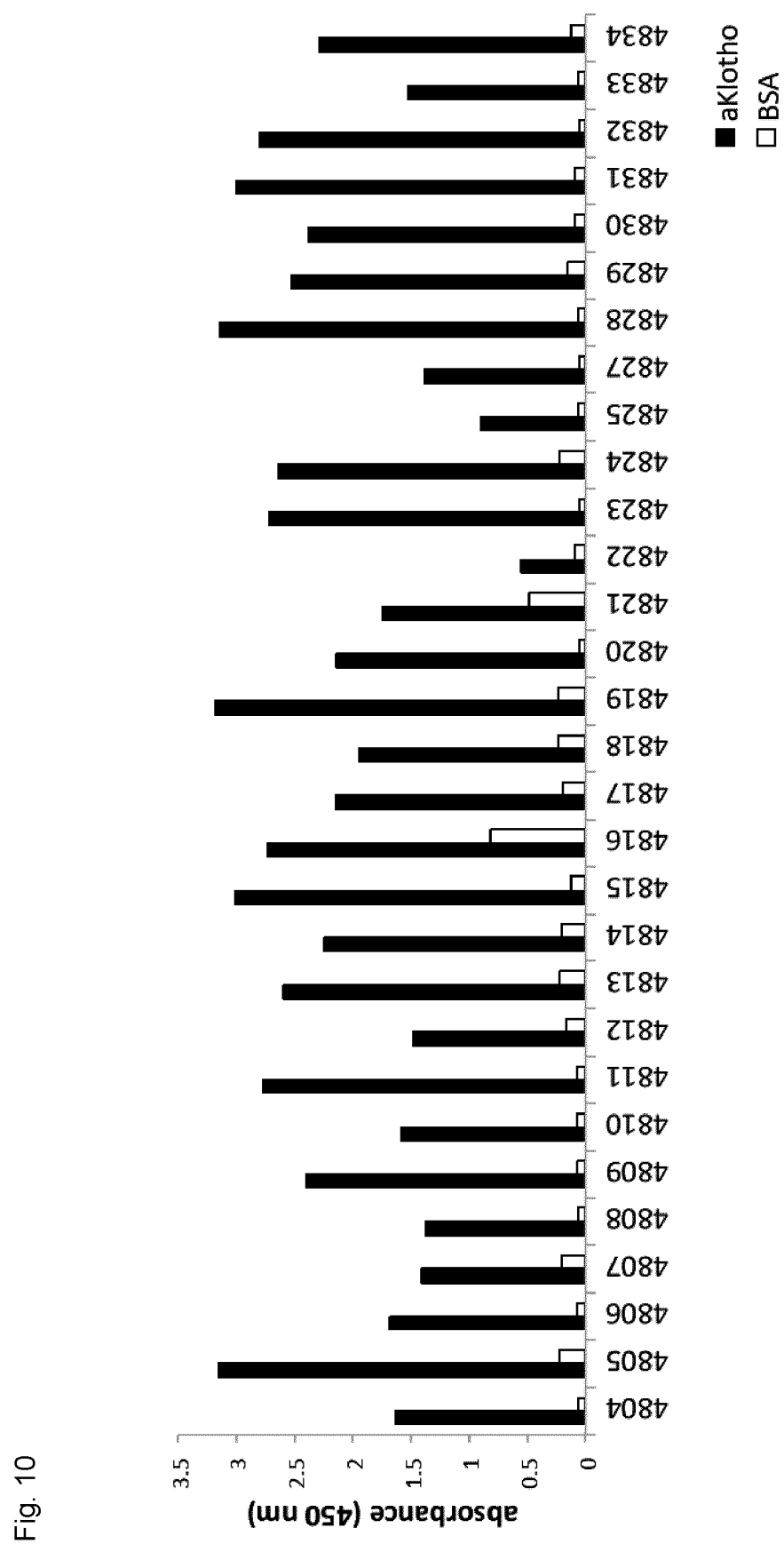
FIG. 10 is a graph showing absorbance values of Fab ELISAs with additional αKlotho antibodies. Purified Fabs [5 ug/ml] were incubated with immobilized αKlotho (1 ug/ml) or bovine serum albumin (BSA), as a negative control. After washing off unbound Fab, bound Fab were detected using an HRP-conjugated anti-Flag anti-body (Fabs have Flag-tag on the light chain). Colorimetric HRP reagents allow for absorbance readings at 450 nm.

All sequences were sub-cloned into the Fab expression vector (RH2.2), expressed and purified. As was with the phage, all Fab clones bound to the target antigen by ELISA (FIG. 10).

Example 11: Epitope Grouping

Figure 11:
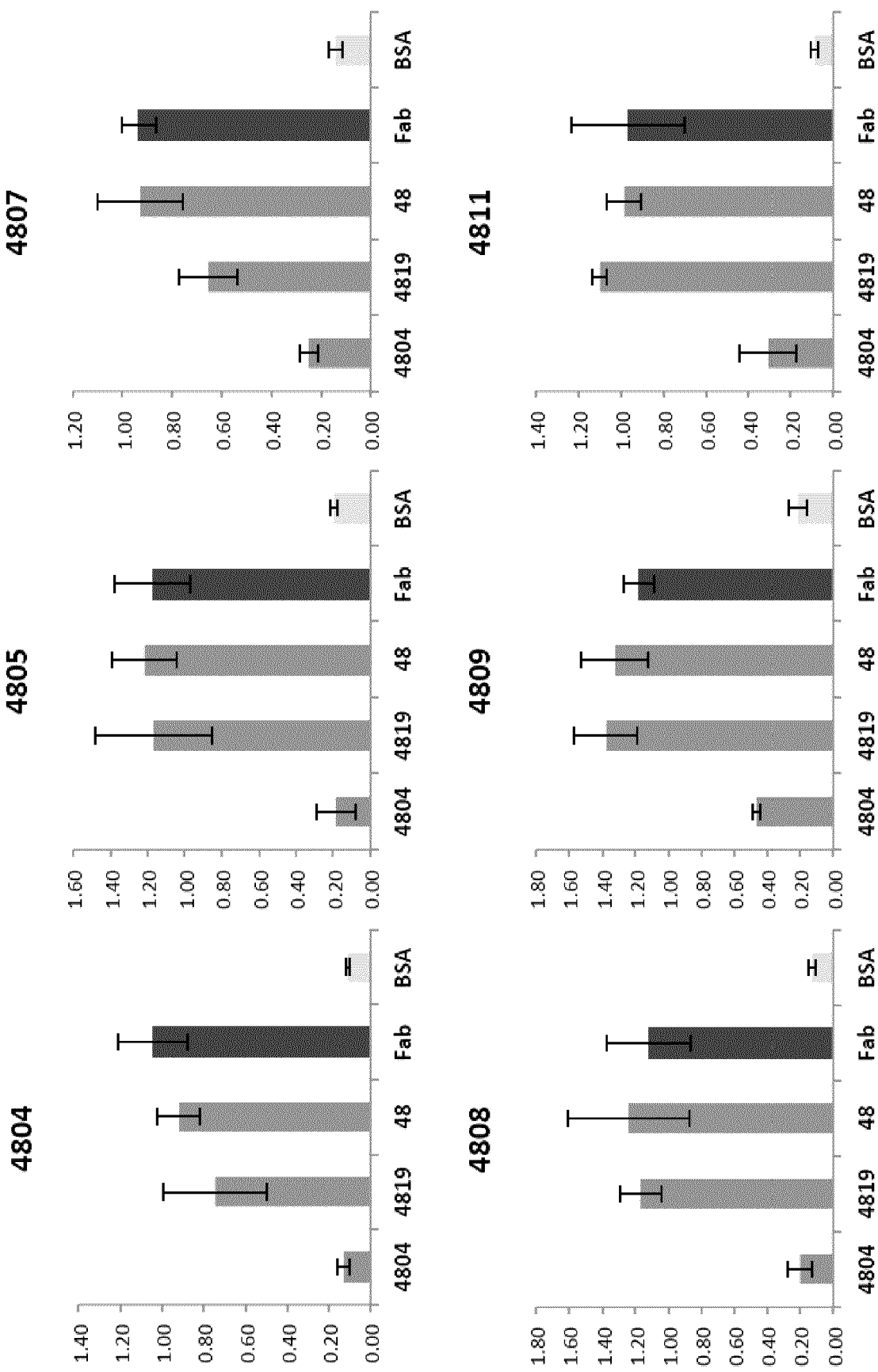
FIG. 11 is a series of graphs of epitope grouping experiments of additional αKlotho antibodies. αKlotho antigen is coated on to plates, blocked and then incubated with 10 ug/ml of Fab (as indicated on the x axis) for 1 hour. Unbound Fab is washed and then the antigen with bound Fab is exposed to Fab-phage (indicated at the top of each graph) for 20 minutes. After washing off unbound phage, bound phage were detected using an HRP-conjugated anti-phage antibody. Colorimetric HRP reagents allow for absorbance readings at 450 nm. Fab is the control, reference signal for no interference and the BSA signal is the background control.

There are at least 2 new epitopes on αKlotho within this set of additional antibodies. Epitope grouping experiments were performed using a competition ELISA strategy. Given the large number of clones within this set, preliminary studies revealed 2 distinct epitopes separate from the epitope that sb106 (48) binds. Representatives of these epitopes (4804 and 4819) were then used alongside sb106 (48) for assessment of each of the clones within the set (FIG. 11). Where sb106 (48) represents epitope A, 23 of the new clones were grouped into epitope B, and 4 clones were found for epitope C (FIG. 11 and summarized in Table 5). For 3 clones (4806, 4810 and 4817) no determination was made due to problems with the phage. Clone 4828 did not show competition with any of the 3 represented epitopes.

Example 12: Affinity Estimates

Figure 12:
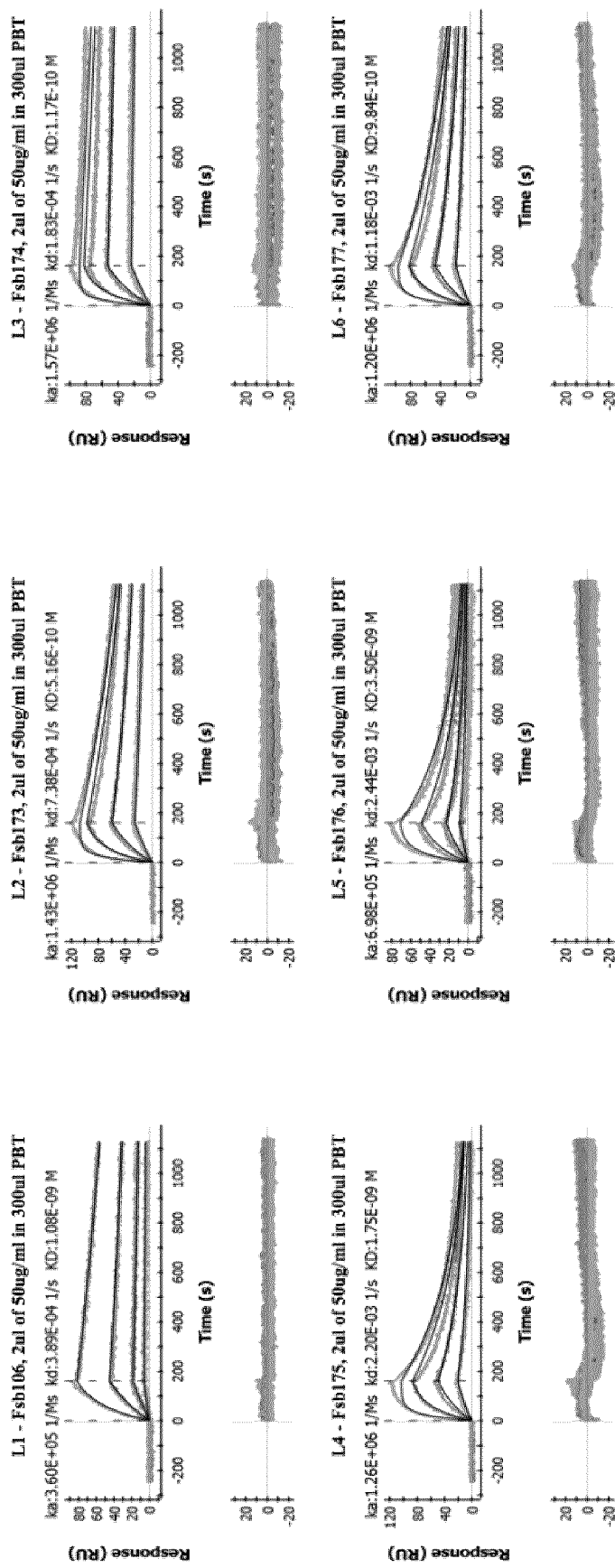
FIG. 12 is a series of graphs of affinity estimates measured by surface plasmon resonance with αKlotho Fabs. Fabs were immobilized using an anti-H+L IgG for capture. αKlotho injections were serially diluted 3 times with a two-fold reduction each time; 50 ug/ml (highest curve) was the starting concentration and 6.25 ug/ml (lowest curve) was the final concentration. Curves are fitted to the Langmuir model.

Affinity estimates for each of the antibodies were determined by surface plasmon resonance (SPR). Fabs were immobilized using an anti-H+L antibody and serial dilutions of αKlotho were injected. Binding curves are shown in FIG. 12 and the binding affinities (KDs) are summarized in Table 5. The affinities range from 240 pM to 8.7 nM.

Example 13: Immunoprecipitation

The antibodies were assayed for their ability to immunoprecipitate αKlotho from human patient urine samples as Fabs (FIG. 13). 50 ul of human urine samples from normal volunteers where incubated within 400 ul KRH buffer with 1 ug/ml of Fab (sb173-203, sb106) overnight at 4° C. 50 ul of M2 anti-FLAG Sepharose beads were then added, and incubated for 2 hrs at 4° C. (the C-terminus of the Fab light chains contains a FLAG epitope tag). The beads were washed 3 times with 500 ul KRH buffer, and bound proteins were eluted with 2×LDS sample loading buffer containing 100 mM DTT. Immunoblot was performed with a commercial primary rat anti-Klotho antibody (KM2076) followed by a standard anti-rat IgG secondary for visualization. Super Signal West Femto substrate was used as the chemiluminescent substrate. More than half of the clones behaved as well or better than sb106.

Example 14: ELISAs

Select clones, representing the new epitopes (4808 for B, and 4831 for C) were subcloned into full length IgGs, expressed and purified and further characterized alongside sb106 (48). Full length IgGs were immobilized at 1 ug/ml (capture), blocked with buffer containing 1% BSA, then incubated with either 20 ng of biotinylated αKlotho (aa34-981), 20 ng of biotinylated αKlotho (aa1-549) in capture buffer (Tris buffered saline pH 7.4+0.1% BSA+0.05% Tween20) or capture buffer only (BSA) at room temperature for 1 hour. After washing with PBS+0.05% Tween20, the captured biotinylated αKlotho was detected using an HRP-streptavidin reagent. Colorimetric HRP reagents allow for absorbance readings at 450 nm. All three IgGs predictably captured αKlotho from solution (FIG. 14), however only 4831 was able to detect a truncated version of ECD of αKlotho, further characterizing the difference in epitope recognition from sb106.

Figure 15:
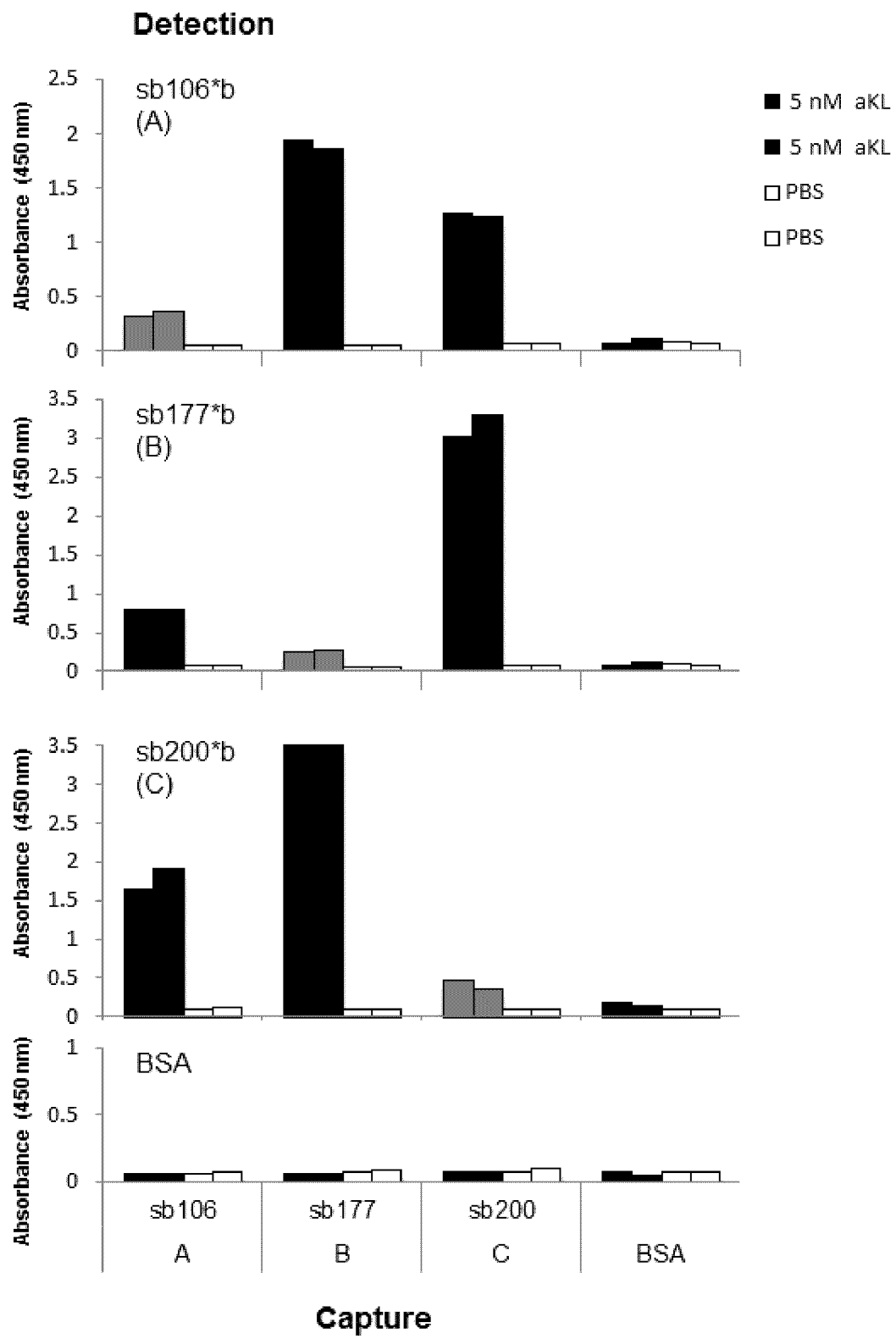
FIG. 15 is series of graphs showing absorbance values of sandwich ELISAs with IgGs representing 3 different epitopes of αKlotho.

Finally, a matrix of ELISA experiments were performed such that each of the 3 distinct epitope clones were used as capture and detection antibodies pairwise which each other for the detection of αKlotho in solution (FIG. 15). Full length IgGs were immobilized at 1 ug/ml (capture), blocked with PBS+5% BSA, then incubated with 5 nM of αKlotho at room temperature for 1 hour. After washing with PBS+ 0.05% Tween20, the samples where then incubated with biotinylated preps of the same IgGs (dectrion, *b) for 30 minutes at room temperature. After washing again, bound IgGs were detected using an HRP-streptavidin reagent. Colorimetric HRP reagents allow for absorbance readings at 450 nm. Duplicate data points are shown. Grey highlights self against self. These experiments show that the 3 epitopes the antibodies bind are suitably compatible with each other for the desired purpose of using in a diagnostic kit.

Example 15: Cross-Reactivity to Human and Mouse αKlotho

Figure 16:
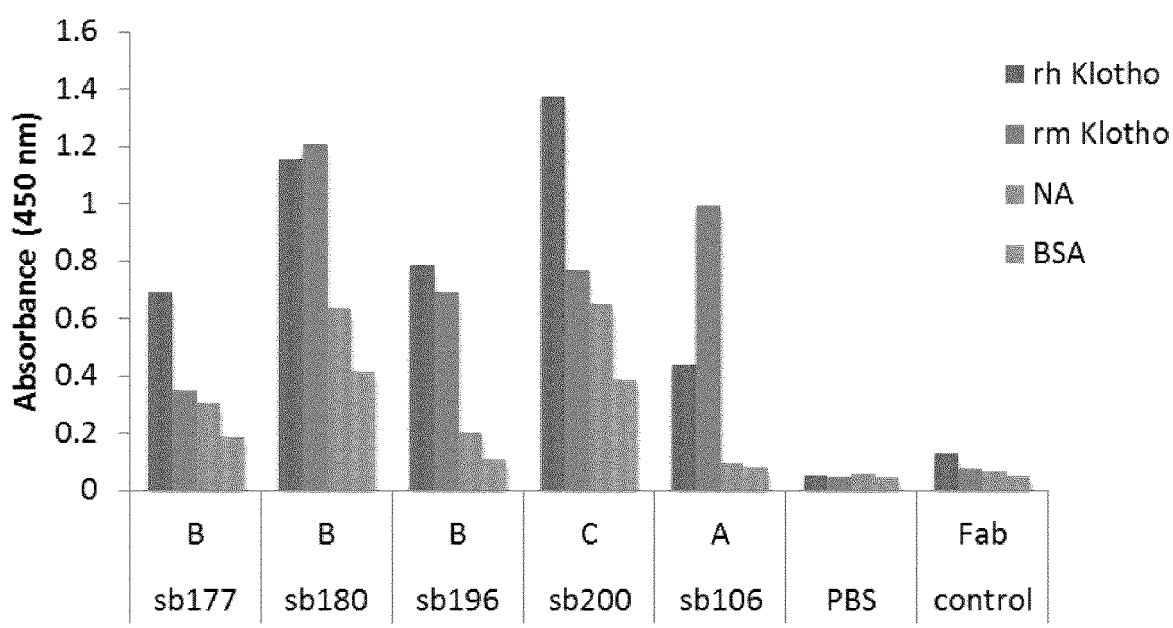
FIG. 16 is a graph showing absorbance values of a Fab ELISA using both human and mouse αKlotho.

Fab ELISA using both human and mouse αKlotho was carried out for assessing cross-reactivity to human and mouse αKlotho (FIG. 16). Fabs (5 ug/ml) were incubated with immobilized αKlotho human, mouse, or neutravidin (NA) and SBA as negative controls. After washing off unbound Fab, bound Fab were detected using an HRP-conjugated anti-Flag antibody (Fabs have Falg tag on the end of their light chains). Colorimetric HRP reagents allow for absorbance readings at 450 nm.

Estimated affinities against human and mouse antigen for select αKlotho Fabs were obtained by surface plasmon resonance on a ProteOn XPR36 (FIG. 17). Fabs were captured using an anti-IgG(H+L) antibody and serial dilutions of αKlotho were injected. Binding curves were fitted to the Langmuir model. (A) Determined Kon, Koff and KD values. (B) and (C) Binding curves for human and mouse antigen respectively.

Example 16: Fab Binding to αKlotho-FGFR1c Complex

Fab proteins (clones 4804-4824, 4826-4834) were adsorbed to an ELISA plate (Maxisorb) at a concentration of 15 ug/ml, for 1 hour at room temperature, and then blocked with PBS+0.5% BSA for 1 hour at room temperature. The plate was washed with PBS+0.05% Tween 20 and then incubated with 2 ug/ml of the following proteins: αKlotho (Fc dimer), complex of aKlotho-FGFR1c (Fc complex), Fc only, or PBS, at room temperature for 1 hour. Unbound antigen was washed away, with 6 washes of PBS+0.05% Tween 20, and then the wells were incubated with a goat-anti-mouse (mG2a, Jackson ImmunoResearch Laboratories) for 30 minutes at room temperature. Unbound anti-mouse antibody was washed away, with 6 washes of PBS+0.05% Tween 20, and then the wells were incubated with an anti-goat-HRP reagent for 30 minutes at room temperature. Unbound anti-goat-HRP antibody was washed away, with 6 washes of PBS+0.05% Tween 20, and then colourmetric HRP reagents (TMB substrate and stop solution) were used and absorbance was read at 450 nm.

The results show that the αKlotho antibodies (clones 4804-4824, 4826-4834) bind αKlotho alone and in complex (αKlotho-FGFR1c). sb106 (clone 48) was used as a control for binding to both αKlotho alone and in complex (αKlotho-FGFR1c).

TABLE 1

Characteristics of human subjects

| Subject | n | Age | Gender (M/F) | PCr (mg/dl) | Serum Pi (mg/dl) | Serum $HCO_3^-$ (mM) | Serum PTH (pg/ml) | FGF23 (pg/ml) | 25(OH) Vitamin D (ng/ml) | Etiology of CKD (number subjects*) |
|---|---|---|---|---|---|---|---|---|---|---|
| Healthy | 34 | 50 ± 17 | 14/20 | 0.8 ± 0.2 | 3.6 ± 0.6 | 23 ± 2 | 59 ± 25 | 30 ± 10 | 32 ± 10 | None |
| CKD1 | 10 | 43 ± 10 | 7/3 | 0.8 ± 0.1 | 3.9 ± 0.5 | 25 ± 2 | 47 ± 19 | 61 ± 23 | 26 ± 7 | DM (1) HTN (3) GN (7) |
| CKD2 | 11 | 50 ± 22 | 4/7 | 1.1 ± 0.2 | 3.6 ± 0.5 | 26 ± 2 | 56 ± 22 | 70 ± 27 | 21 ± 13 | DM (2), HTN (4), GN (4), RK (3) |
| CKD3 | 10 | 57 ± 17 | 5/5 | 1.7 ± 0.4# | 3.2 ± 0.8 | 25 ± 3 | 86 ± 51 | 79 ± 18# | 25 ± 8 | DM (3), HTN (7), GN (3), IN (1) |
| CKD4 | 14 | 62 ± 13 | 8/6 | 2.7 ± 0.6# | 3.5 ± 0.9 | 24 ± 3 | 202 ± 101# | 204 ± 173# | 21 ± 8 | DM (4), HTN (10), GN (3), RK (1) |
| CKD5 | 11 | 62 ± 12 | 5/6 | 4.7 ± 2.0# | 5.1 ± 3.5# | 21 ± 3 | 223 ± 188# | 580 ± 427# | 21 ± 9# | DM (7), HTN (7), GN (2) |
| Dialysis | 14 | 50 ± 12 | 6/8 | 11.9 ± 15.6# | 4.8 ± 1.7# | 22 ± 5 | 500 ± 650# | 760 ± 286# | 26 ± 8 | DM (7), HTN (10), GN (5), PKD (1) | n = number of subjects;
PCr = plasma creatinien;
GFR = estimated glomerular filtration rate;
Serum Pi = serum phosphorus;
Serum HCO3− = serum bicarbonate
PTH = parathyroid hormone;
FGF23+ Fibroblast growth factor 23;
DM = Diabetes mellitus;
HTN = hypertension;
GN = glomerulonephritis;
RK = Remnant kidney:
IN = Interstitial nephritis:
PKD = Polycystic kidney disease.
*Some patients carry more than one diagnosis.
Results are shown as mean ± standard deviation.
$p < 0.05$ compared to healthy volunteers. ANOVA

TABLE 2

CDR sequence variations (Sequences shown correspond to positions which are variable in the selection library. Sequences listed under column L3 refer to CDR-L3 but omit the first and second amino terminal amino acid residues and the carboxy terminal amino acid residue of IMGT CDR-L3. Sequences listed under column H1 refer to CDR-H1 but omit the first 3 amino terminal amino acid residues of IMGT CDR-H1 and the carboxy terminal amino acid residue thereof corresponds to IMGT VH domain position 39. Sequences listed under column H2 correspond to IMGT VH domain positions 55-66, which includes CDR-H2 and framework region residues at positions 55 and 66. Sequences listed under column H3 refer to IMGT CDR-H3, but are lacking the first two amino terminal and the last two carboxy terminal amino acids of IMGT CDR-H3. IMGT CDR amino acid residues per se are underlined. Variable FR amino acid residues are not underlined.)

| | L3 | | | | | | ID | H1 | | | | | | ID | H2 | | | | | | | | | | | ID |
|---|---|---|---|---|---|---|---|---|---|---|---|---|---|---|---|---|---|---|---|---|---|---|---|---|---|---|
| sb106 | A | G | Y | S | P | I | 5 | I | S | Y | Y | S | I | 6 | Y | I | S | P | S | Y | G | Y | T | S | | 7 |
| E12 | A | G | Y | A | P | I | 15 | I | A | Y | Y | A | V | 16 | F | I | A | P | S | Y | G | Y | S | S | | 17 |
| E2 | A | G | F | A | P | I | 19 | I | A | Y | Y | F | S | 20 | F | I | S | P | A | Y | G | F | T | A | | 21 |
| C12 | A | A | F | A | P | V | 23 | I | A | Y | Y | A | V | 24 | F | V | S | A | S | Y | G | Y | T | S | | 25 |
| E3 | S | A | F | S | P | V | 27 | V | S | F | Y | S | I | 28 | Y | V | A | P | A | Y | G | Y | S | A | | 29 |
| D7 | A | A | F | S | P | V | 31 | V | S | F | F | S | I | 32 | Y | I | S | P | S | Y | G | Y | S | S | | 33 |
| E4 | A | G | F | A | P | I | 35 | I | S | Y | Y | A | V | 36 | F | V | S | P | A | Y | G | F | S | S | | 37 |
| E6 | A | A | F | A | P | V | 39 | F | S | S | S | S | I | 40 | F | V | S | P | A | Y | G | F | T | A | | 41 |
| E10 | A | G | Y | A | P | V | 43 | I | S | Y | Y | S | I | 44 | Y | I | S | P | S | F | G | Y | T | A | | 45 |
| C9 | A | A | F | A | P | V | 47 | I | S | Y | Y | S | I | 48 | F | I | A | P | A | F | G | Y | S | S | | 49 |
| D11 | A | A | F | S | P | I | 51 | I | A | Y | F | S | I | 52 | Y | V | S | P | A | Y | G | Y | T | S | | 53 |
| E1 | A | G | Y | A | P | I | 55 | I | A | F | Y | S | I | 56 | Y | V | S | P | A | Y | A | Y | T | A | | 57 |
| D5 | A | G | F | A | P | I | 59 | V | S | F | Y | S | I | 60 | S | I | S | S | S | Y | G | Y | T | Y | | 61 |
| D12 | A | G | F | A | P | V | 63 | V | S | F | F | S | I | 64 | S | V | S | S | S | Y | G | Y | T | Y | | 65 |
| E8 | S | A | Y | A | P | V | 67 | V | A | F | Y | S | I | 68 | F | I | A | P | S | Y | G | Y | S | A | | 69 |
| E11 | A | G | F | A | P | V | 71 | I | A | F | F | S | I | 72 | F | V | S | P | A | Y | G | Y | T | A | | 73 |
| F1 | S | A | Y | S | P | V | 75 | I | A | F | Y | S | I | 76 | F | V | S | P | A | Y | A | Y | S | A | | 77 |
| D1 | A | A | F | A | P | V | 79 | F | S | S | S | S | I | 80 | Y | I | S | P | A | Y | G | Y | S | A | | 81 |
| C10 | | | | | | | | V | S | Y | Y | S | I | 83 | S | I | S | S | S | Y | G | Y | T | S | | 84 |
| D6 | S | A | F | S | P | V | 86 | I | A | F | F | S | V | 87 | F | V | S | P | S | F | G | Y | S | S | | 88 |
| D8 | A | A | F | A | P | V | 90 | I | A | F | Y | S | I | 91 | Y | I | S | P | A | Y | A | Y | S | A | | 92 |
| C11 | | | | | | | | I | S | Y | F | S | V | 94 | Y | V | S | P | S | F | A | F | S | S | | 95 |
| F2 | A | A | Y | A | P | V | 97 | V | A | F | Y | S | V | 98 | S | I | S | P | A | Y | G | Y | T | A | | 99 |
| D9 | A | A | Y | A | P | V | 101 | I | A | Y | Y | A | V | 102 | F | V | S | P | A | Y | G | F | T | S | | 103 |

TABLE 2-continued

CDR sequence variations (Sequences shown correspond to positions which are variable in the selection library. Sequences listed under column L3 refer to CDR-L3 but omit the first and second amino terminal amino acid residues and the carboxy terminal amino acid residue of IMGT CDR-L3. Sequences listed under column H1 refer to CDR-H1 but omit the first 3 amino terminal amino acid residues of IMGT CDR-H1 and the carboxy terminal amino acid residue thereof corresponds to IMGT VH domain position 39. Sequences listed under column H2 correspond to IMGT VH domain positions 55-66, which includes CDR-H2 and framework region residues at positions 55 and 66. Sequences listed under column H3 refer to IMGT CDR-H3, but are lacking the first two amino terminal and the last two carboxy terminal amino acids of IMGT CDR-H3. IMGT CDR amino acid residues per se are underlined. Variable FR amino acid residues are not underlined.)

| | | | | | | | | | | | | | | | | | | |
|---|---|---|---|---|---|---|---|---|---|---|---|---|---|---|---|---|---|---|
| E5 | A | A | F | A | P | V | 105 | I | A | F | Y | A | V | 106 | Y | V | A | P | P | Y | A | Y | S | A | 107 |
| D10 | A | A | Y | A | P | V | 109 | V | S | F | Y | S | I | 110 | Y | I | S | P | A | Y | G | Y | T | S | 111 |
| D3 | S | A | Y | S | P | V | 113 | V | A | Y | Y | S | I | 114 | Y | I | S | P | A | F | G | Y | S | S | 115 |
| D4 | A | A | Y | A | P | I | 117 | V | A | F | Y | A | V | 118 | S | I | S | S | S | Y | G | Y | T | Y | 119 |

| | H3 | | | | | | | | | | | | | | ID |
|---|---|---|---|---|---|---|---|---|---|---|---|---|---|---|---|
| sb106 | Y | Y | V | Y | A | S | H | G | W | A | G | Y | G | M | 8 |
| E12 | F | Y | V | Y | A | S | N | A | W | A | G | Y | G | M | 18 |
| E2 | F | Y | V | Y | A | A | N | G | W | A | G | Y | G | M | 22 |
| C12 | F | Y | V | Y | A | A | N | G | W | A | G | Y | G | M | 26 |
| E3 | F | Y | V | Y | A | A | H | G | W | A | G | Y | G | M | 30 |
| D7 | F | Y | V | Y | A | A | N | G | W | A | G | Y | G | M | 34 |
| E4 | F | F | V | Y | A | A | H | G | W | A | G | Y | G | M | 38 |
| E6 | F | F | V | Y | S | S | H | G | W | A | G | Y | G | M | 42 |
| E10 | F | Y | V | Y | S | S | H | G | W | A | G | Y | G | M | 46 |
| C9 | F | Y | V | Y | A | A | N | G | W | A | G | Y | G | M | 50 |
| D11 | F | Y | V | Y | S | A | N | G | W | A | G | Y | G | M | 54 |
| E1 | F | Y | V | Y | A | A | H | G | W | A | G | Y | G | M | 58 |
| D5 | F | Y | V | Y | A | S | N | G | W | A | G | Y | G | M | 62 |
| D12 | F | Y | V | Y | S | S | H | G | W | A | G | Y | G | M | 66 |
| E8 | F | F | V | Y | A | A | H | G | W | A | G | Y | G | M | 70 |
| E11 | F | Y | V | Y | S | A | N | G | W | A | G | Y | G | M | 74 |
| F1 | F | Y | V | Y | A | A | N | G | W | A | G | Y | G | M | 78 |
| D1 | F | F | V | Y | S | A | N | A | W | S | G | Y | G | M | 82 |
| C10 | F | F | V | Y | A | A | H | G | W | A | G | Y | G | M | 85 |
| D6 | F | Y | V | Y | A | A | H | G | W | A | G | Y | G | M | 89 |
| D8 | Y | F | V | Y | A | S | N | G | W | A | G | Y | G | M | 93 |
| C11 | F | F | V | Y | S | A | H | G | W | A | G | Y | G | M | 96 |
| F2 | F | Y | V | Y | A | A | H | G | W | A | G | Y | G | M | 100 |
| D9 | F | Y | V | Y | S | S | H | G | W | A | G | F | G | M | 104 |
| E5 | F | Y | V | Y | S | A | H | G | W | A | G | Y | G | M | 108 |
| D10 | F | Y | V | Y | S | A | H | G | W | A | G | Y | G | M | 112 |
| D3 | F | Y | V | Y | A | A | N | G | W | A | G | Y | G | M | 116 |
| D4 | Y | Y | V | Y | A | A | H | G | W | A | G | Y | G | M | 120 |

TABLE 2A

SEQ ID NO: 1  $X_1X_2X_3X_4PX_5$
wherein $X_1$ is A or S, $X_2$ is G or A, $X_3$ is Y or F, $X_4$ is S or A, $X_5$ is I or V SEQ ID NO: 2  $X_6X_7X_8X_9X_{10}X_{11}$
wherein $X_6$ is I or V, $X_7$ is S or A, $X_8$ is Y, F or S $X_9$ is Y, F or S, $X_{10}$ is S or A and $X_{11}$ is I or V TABLE 2A-continued SEQ ID NO: 3  $X_{12}X_{13}X_{14}X_{15}X_{16}X_{17}X_{18}X_{19}X_{20}X_{21}$
wherein $X_{12}$ is Y, F or S, $X_{13}$ is I or V, $X_{14}$ is S or A, $X_{15}$ is P or S, $X_{16}$ is S or A, $X_{17}$ is Y or F, $X_{18}$ is G or A, $X_{19}$ is Y or F, $X_{20}$ is T or S and $X_{21}$ is S, A or Y SEQ ID NO: 4  $X_{22}X_{23}VYX_{24}X_{25}X_{26}X_{27}WX_{28}GX_{29}GM$
wherein $X_{22}$ is Y or F, $X_{23}$ is Y or F, $X_{24}$ is A or S, $X_{25}$ is S or A, $X_{26}$ is H or N, $X_{27}$ is G or A, $X_{28}$ is A or S and $X_{29}$ is Y or F

TABLE 3A

CDR amino acid sequences for additional αKlotho antibodies (The carboxy terminal amino acid residue of the sequences listed under column CDR-H1 corresponds to IMGT VH domain position 39; and the amino terminal residue and the carboxy terminal residue of the sequences listed under column CDR-H2 correspond to IMGT VH domain positions 55 and 66, respectively. Amino acid residues of IMTG CDRs are underlined, amino acid residues of IMGT framework regions are not underlined, and residues at IMGT positions which were randomized in the selection library are bold.)

| clone ID | name | Epitope | CDR-L1 | SEQ ID NO: | CDR-L2 | SEQ ID NO: | CDR-L3 | SEQ ID NO: | CDR-H1 | SEQ ID NO: | CDR-H2 | SEQ ID NO: | CDR-H3 | SEQ ID NO: |
|---|---|---|---|---|---|---|---|---|---|---|---|---|---|---|
| 4804 | sb173 | B | QSVSSA | 140 | SAS | 141 | QQSSYSLIT | 141 | GFNLYSYSI | 142 | YISSSSGSTY | 157 | ARGWGGGYWFYPVYGIDY | 196 |
| 4805 | sb174 | B | QSVSSA | 140 | SAS | 141 | QQSSGWYHFLFT | 141 | GFNLSYYSM | 143 | SISSYYGSTY | 158 | ARGGGYYSGPYAGFDY | 197 |
| 4806 | sb175 | ND | QSVSSA | 140 | SAS | 141 | QQSSYSLIT | 141 | GFNISSSSI | 142 | YISSSYSTS | 159 | ARSSGGGYYHWWVVPYAMDY | 198 |
| 4807 | sb176 | B | QSVSSA | 140 | SAS | 141 | QQSSYSLIT | 141 | GFNLSSSYM | 142 | SIYPSYGSTS | 160 | ARGWPSYYYWFWPYGAIDY | 199 |
| 4808 | sb177 | B | QSVSSA | 140 | SAS | 141 | QQSSYSLIT | 141 | GFNFSSSSI | 144 | SISSSYGTS | 161 | ARPYSAYYWAWYGPGGALDY | 200 |
| 4809 | sb178 | B | QSVSSA | 140 | SAS | 141 | QQSGWAYHPIT | 141 | GFNIYSYYI | 142 | SIYSYYGSTS | 162 | ARSGPWAWYGLDY | 201 |
| 4810 | sb179 | ND | QSVSSA | 140 | SAS | 141 | QQSSYSLIT | 141 | GFNLSSSSI | 142 | YISPSYGSTS | 163 | ARSGYYSGAYWHWWVVPYAMDY | 202 |
| 4811 | sb180 | B | QSVSSA | 140 | SAS | 141 | QQGYALFT | 141 | GFNLYYSYM | 145 | SIYSSSVTS | 164 | ARSPSWWVSYHSALDY | 203 |
| 4812 | sb181 | B | QSVSSA | 140 | SAS | 141 | QQGYWLFT | 141 | GFNLSYSYM | 146 | SISSYSGVTS | 165 | ARSYSWWWSVSYAMDY | 204 |
| 4813 | sb182 | B | QSVSSA | 140 | SAS | 141 | QQAAWGGAPIT | 141 | GFNLYSSSI | 147 | SISPYSGYTY | 166 | ARYYSGWYSPAWWYGIDY | 205 |
| 4814 | sb183 | C | QSVSSA | 140 | SAS | 141 | QQSSPPIT | 141 | GFNLYYSYM | 148 | SISPYSGYTY | 167 | ARSFFPYSYWYYGGGMDY | 206 |
| 4815 | sb184 | B | QSVSSA | 140 | SAS | 141 | QQSSYSLIT | 141 | GFNFSSSSI | 142 | SISSSYGTY | 161 | ARGFSSSAHYWSWYGPGGGFDY | 207 |
| 4816 | sb185 | B | QSVSSA | 140 | SAS | 141 | QQSSYSLIT | 141 | GFNFSSSSI | 142 | SISSSYGTY | 161 | ARGWTAAYSVYWFGGHASYGLDY | 208 |
| 4817 | sb186 | ND | QSVSSA | 140 | SAS | 141 | QQSSYSLIT | 141 | GFNFSSSSI | 142 | SISSSYGTY | 161 | ARGYPSSGAAWFWFSHPGSAMDY | 209 |
| 4818 | sb187 | B | QSVSSA | 140 | SAS | 141 | QQPYSPIT | 141 | GFNIYSYSI | 149 | SISPYSGYTY | 168 | ARSGHSVYWWWSHFGMDY | 210 |
| 4819 | sb188 | C | QSVSSA | 140 | SAS | 141 | QQGSYYWWSPIT | 141 | GFNIYSSYSM | 150 | SIYPSSSYTY | 169 | ARAGYFSAYYSSWGAMDY | 211 |
| 4820 | sb189 | B | QSVSSA | 140 | SAS | 141 | QQSPWGAYLIT | 141 | GFNISSYYM | 151 | SIYSSYSSTY | 170 | ARGAWAMDY | 212 |
| 4821 | sb190 | B | QSVSSA | 140 | SAS | 141 | QQSSYSLIT | 141 | GFNLYYSYM | 145 | SISPYSGSTY | 164 | ARSGFSSWWWVVSYAFDY | 213 |
| 4822 | sb191 | B | QSVSSA | 140 | SAS | 141 | QQSSYSLIT | 141 | GFNFSSSSI | 142 | SISSSYGTY | 161 | ARAGWYSSWWWSAWGAGGGLDY | 214 |
| 4823 | sb192 | B | QSVSSA | 140 | SAS | 141 | QQSSYSLIT | 141 | GFNFSSSSI | 142 | YIYSSYGTY | 161 | ARAAHYGYYVHSGLDY | 215 |
| 4824 | sb193 | B | QSVSSA | 140 | SAS | 141 | QQSSYSLIT | 141 | GFNLSSSSI | 142 | SISSSYGTY | 163 | ARHGYCYFFWGYYGPGSAMDY | 216 |

TABLE 3A-continued

CDR amino acid sequences for additional αKlotho antibodies (The carboxy terminal amino acid residue of the sequences listed under column CDR-H1 corresponds to IMGT VH domain position 39; and the amino terminal residue and the carboxy terminal residue of the sequences listed under column CDR-H2 correspond to IMGT VH domain positions 55 and 66, respectively. Amino acid residues of IMTG CDRs are underlined, amino acid residues of IMGT framework regions are not underlined, and residues at IMGT positions which were randomized in the selection library are bold.)

| clone ID | name | Epitope | CDR-L1 | SEQ ID NO: | CDR-L2 | SEQ ID NO: | CDR-L3 | SEQ ID NO: | CDR-H1 | SEQ ID NO: | CDR-H2 | SEQ ID NO: | CDR-H3 | SEQ ID NO: |
|---|---|---|---|---|---|---|---|---|---|---|---|---|---|---|
| 4825 | sb194 | B | QSVSSA | 140 | SAS | 141 | QQSSYSLIT | 189 | GFNLYSSSI | 142 | SISPYYSYTY | 166 | ARSVYSWYWSSWGPGSALDY | 217 |
| 4826 | sb195 | B | QSVSSA | 140 | SAS | 141 | QQAGFFSYPIT | 179 | GFNISSYYM | 152 | SISSSYGYTY | 170 | ARGYPASSYYYPSSALDY | 218 |
| 4827 | sb196 | B | QSVSSA | 140 | SAS | 141 | QQSSYSLIT | 190 | GFNFSSSSI | 142 | YISSSSGSTS | 161 | ARAYHSYFYGSYWSYGWAGALDY | 219 |
| 4828 | sb197 | ND | QSVSSA | 140 | SAS | 141 | QQSSYSLIT | 179 | GFNFSSSSI | 142 | SISSSYGYTY | 161 | ARYWGGWWYHYGMDY | 220 |
| 4829 | sb198 | B | QSVSSA | 140 | SAS | 141 | QQGGLIT | 191 | GFNISSYYI | 153 | SIYSSYGYTS | 171 | ARYSWSPYWWWAYSGLDY | 221 |
| 4830 | sb199 | C | QSVSSA | 140 | SAS | 141 | QQYSWYWYSPIT | 192 | GFNIYYSSI | 154 | SIYPYYSYTY | 172 | ARSVASALDY | 222 |
| 4831 | sb200 | C | QSVSSA | 140 | SAS | 141 | QQYSYYYASPIT | 193 | GFNIYSSSI | 155 | SIYPYSGYTY | 173 | ARYSWGGSSFWPGYGFDY | 223 |
| 4832 | sb201 | B | QSVSSA | 140 | SAS | 141 | QQSSYSLIT | 194 | GFNFSSSSI | 142 | YISSSYGYTS | 161 | ARASGWFSHFYPAAVSGMDY | 224 |
| 4833 | sb202 | B | QSVSSA | 140 | SAS | 141 | QQSSHGHYPIT | 195 | GFNLSSYYM | 156 | SIYPSYSSTY | 174 | ARSSYSVYFWWVSAMDY | 225 |
| 4834 | sb203 | B | QSVSSA | 140 | SAS | 141 | QQSSYSLIT | 179 | GFNFSSSSI | 142 | SISSSYGYTY | 161 | ARAVSFYYWAWYGPGFAMDY | 226 |

TABLE 3B

Light chain CDR nucleotide sequences for additional αKlotho antibodies

| clone ID | name | Epitope | CDR-L1 | SEQ ID NO: | CDR-L2 | SEQ ID NO: | CDR-L3 | SEQ ID NO: |
|---|---|---|---|---|---|---|---|---|
| 4804 | sb173 | B | CAGTCCGTGTCCAGCGCT | 227 | TCGGCATCC | 228 | CAGCAATCTTCTTATTCTCTGATCACG | 229 |
| 4805 | sb174 | B | CAGTCCGTGTCCAGCGCT | 227 | TCGGCATCC | 228 | CAGCAATCTTCTGGTTGGTACCATTTCCTGTTCACG | 230 |
| 4806 | sb175 | ND | CAGTCCGTGTCCAGCGCT | 227 | TCGGCATCC | 228 | CAGCAATCTTCTTATTCTCTGATCACG | 229 |
| 4807 | sb176 | B | CAGTCCGTGTCCAGCGCT | 227 | TCGGCATCC | 228 | CAGCAATCTTCTTATTCTCTGATCACG | 229 |
| 4808 | sb177 | B | CAGTCCGTGTCCAGCGCT | 227 | TCGGCATCC | 228 | CAGCAATCTTCTTATTCTCTGATCACG | 229 |
| 4809 | sb178 | B | CAGTCCGTGTCCAGCGCT | 227 | TCGGCATCC | 228 | CAGCAATCTGGTTGGGCTTACCATCCGATCACG | 231 |
| 4810 | sb179 | ND | CAGTCCGTGTCCAGCGCT | 227 | TCGGCATCC | 228 | CAGCAATCTTCTTATTCTCTGATCACG | 229 |
| 4811 | sb180 | B | CAGTCCGTGTCCAGCGCT | 227 | TCGGCATCC | 228 | CAGCAAGGTTACGCTCTGTTCACG | 232 |
| 4812 | sb181 | B | CAGTCCGTGTCCAGCGCT | 227 | TCGGCATCC | 228 | CAGCAAGGTTACTGGCTGTTCACG | 233 |
| 4813 | sb182 | B | CAGTCCGTGTCCAGCGCT | 227 | TCGGCATCC | 228 | CAGCAAGCTGCTTGGGGTGGTGCTCCGATCACG | 234 |
| 4814 | sb183 | C | CAGTCCGTGTCCAGCGCT | 227 | TCGGCATCC | 228 | CAGCAATCTTCTCCGCCGATCACG | 235 |
| 4815 | sb184 | B | CAGTCCGTGTCCAGCGCT | 227 | TCGGCATCC | 228 | CAGCAATCTTCTTATTCTCTGATCACG | 229 |
| 4816 | sb185 | B | CAGTCCGTGTCCAGCGCT | 227 | TCGGCATCC | 228 | CAGCAATCTTCTTATTCTCTGATCACG | 229 |
| 4817 | sb186 | ND | CAGTCCGTGTCCAGCGCT | 227 | TCGGCATCC | 228 | CAGCAATCTTCTTATTCTCTGATCACG | 229 |
| 4818 | sb187 | B | CAGTCCGTGTCCAGCGCT | 227 | TCGGCATCC | 228 | CAGCAACCGTACTCTCCGATCACG | 236 |
| 4819 | sb188 | C | CAGTCCGTGTCCAGCGCT | 227 | TCGGCATCC | 228 | CAGCAAGGTTCTTACTACTGGTGGTCTCCGATCACG | 237 |
| 4820 | sb189 | B | CAGTCCGTGTCCAGCGCT | 227 | TCGGCATCC | 228 | CAGCAATCTCCGTGGGGTGCTTACCTGATCACG | 238 |
| 4821 | sb190 | B | CAGTCCGTGTCCAGCGCT | 227 | TCGGCATCC | 228 | CAGCAATCTTCTTATTCTCTGATCACG | 229 |
| 4822 | sb191 | B | CAGTCCGTGTCCAGCGCT | 227 | TCGGCATCC | 228 | CAGCAATCTTCTTATTCTCTGATCACG | 229 |
| 4823 | sb192 | B | CAGTCCGTGTCCAGCGCT | 227 | TCGGCATCC | 228 | CAGCAATCTTCTTATTCTCTGATCACG | 229 |
| 4824 | sb193 | B | CAGTCCGTGTCCAGCGCT | 227 | TCGGCATCC | 228 | CAGCAATCTTCTTATTCTCTGATCACG | 229 |
| 4825 | sb194 | B | CAGTCCGTGTCCAGCGCT | 227 | TCGGCATCC | 228 | CAGCAATCTTCTTATTCTCTGATCACG | 229 |
| 4826 | sb195 | B | CAGTCCGTGTCCAGCGCT | 227 | TCGGCATCC | 228 | CAGCAAGCTGGTTTCTTCTCTTACCCGATCACG | 239 |
| 4827 | sb196 | B | CAGTCCGTGTCCAGCGCT | 227 | TCGGCATCC | 228 | CAGCAATCTTCTTATTCTCTGATCACG | 229 |
| 4828 | sb197 | ND | CAGTCCGTGTCCAGCGCT | 227 | TCGGCATCC | 228 | CAGCAATCTTCTTATTCTCTGATCACG | 229 |
| 4829 | sb198 | B | CAGTCCGTGTCCAGCGCT | 227 | TCGGCATCC | 228 | CAGCAAGGTGGTGGTCTGATCACG | 240 |
| 4830 | sb199 | C | CAGTCCGTGTCCAGCGCT | 227 | TCGGCATCC | 228 | CAGCAATACTCTTGGTACTGGTACTCTCCGATCACG | 241 |
| 4831 | sb200 | C | CAGTCCGTGTCCAGCGCT | 227 | TCGGCATCC | 228 | CAGCAATACTCTTACTACTACGCTTCTCCGATCACG | 242 |
| 4832 | sb201 | B | CAGTCCGTGTCCAGCGCT | 227 | TCGGCATCC | 228 | CAGCAATCTTCTTATTCTCTGATCACG | 229 |
| 4833 | sb202 | B | CAGTCCGTGTCCAGCGCT | 227 | TCGGCATCC | 228 | CAGCAATCTTCTCATGGTCATTACCCGATCACG | 243 |
| 4834 | sb203 | B | CAGTCCGTGTCCAGCGCT | 227 | TCGGCATCC | 228 | CAGCAATCTTCTTATTCTCTGATCACG | 229 |

TABLE 3C

Heavy chain CDR nucleotide sequences for additional αKlotho antibodies (sequences encoding IMGT CDR residues are underlined, sequences encoding IMGT framework region residues are not underlined)

| clone ID | name | Epitope | CDR-H1 | SEQ ID NO: CDR-H2 | | SEQ ID NO: CDR-H3 | | SEQ ID NO: |
|---|---|---|---|---|---|---|---|---|
| 4804 | sb173 | B | GGCTTCAACCTCTATTCTTATTC<u>TATC</u> | 244 | TATATTCTCTTCTTCTCGGCTCTACTTAT | 263 | <u>GCTCGCGGTTGGGGTGGTGGTTACTGGTTACCCGGTTACGGTTATTGACTAC</u> | 286 |
| 4805 | sb174 | B | GGCTTCAACCTCTCTTATTATTC<u>TATG</u> | 245 | TATATTCTCTTCTTCTTATGGCTCTACTTAT | 264 | <u>GCTCGCGGGTGGTGGTTACTACTCTGGTCCGTACGCTGGTTTGACTAC</u> | 287 |
| 4806 | sb175 | ND | GGCTTCAACATCTCTTCTTC<u>TATC</u> | 246 | TATATTCTCTTCTTCTTATAGCTCTACTTCT | 265 | <u>GCTCGCTCTTCTCGTGGTGGTTACTACCATTGGTGGTGGTTGTTCCGTACGCTATGGACTAC</u> | 288 |
| 4807 | sb176 | B | GGCTTCAACCTCTCTTCTTCTTA<u>TATG</u> | 247 | TCTATATTCTATCCTTCTTATGGCTCTACTTCT | 266 | <u>GCTCGCGGGTGTTGTCCGTTACTACTACTGGTGTCGGCCGTACGGTGCTATTGACTAC</u> | 289 |
| 4808 | sb177 | B | GGCTTCAACTTTCTTCTTCTTC<u>TATC</u> | 248 | TCTATTCTCTTCTTCTTATGGCTATACTTAT | 267 | <u>GCTCGCCCGTACTCTGCTTACTACTGGGCTTGGTACGGTCCGGGTGGTGCTTTGGACTAC</u> | 290 |
| 4809 | sb178 | B | GGCTTCAACATCTATTCTTATA<u>TATA</u> | 249 | TCTATTATTATTCTTATGGCTCTACTTCT | 268 | <u>GCTCGCTCTGCTCCGTGGGCTTGGTACGGTTTGGACTAC</u> | 291 |
| 4810 | sb179 | ND | GGCTTCAACCTCTCCTTCTTCT<u>TATC</u> | 250 | TATATTATTATTCTTCTTATGGCTCTACTTCT | 269 | <u>GCTCGCTCGTGCTGTTACTACTCTGGTGTGCTTACTGGCATTGGGGTTGTTCCGTACGCTATGGACTAC</u> | 292 |
| 4811 | sb180 | B | GGCTTCAACCTCTCTTATTATTCTTA<u>TATG</u> | 251 | TCTATATTCTATTCTCTTCTAGCTCTACTTCT | 270 | <u>GCTCGCTCGTCTCCGTCTTGGTGGTTCTTACCATTGCTTTGGACTAC</u> | 293 |
| 4812 | sb181 | B | GGCTTCAACCTCTCTTCTTCTTA<u>TATC</u> | 252 | TCTATATTCTTCTCTTATTCTGGCTATACTTCT | 271 | <u>GCTCGCTCTTACTCTTGGTGGTCGTGTTTCTTACGCTATGGACTAC</u> | 294 |
| 4813 | sb182 | B | GGCTTCAACCTCTCTATTCTTC<u>TATC</u> | 253 | TCTATCTCTCCTTATTCTGGCTATACTTAT | 272 | <u>GCTCGCTACTACTCTGGTTGGTACTCTCCGGCTTGGTGGTACGGTATTGACTAC</u> | 295 |
| 4814 | sb183 | C | GGCTTCAACCCTCTATTCTTC<u>TATG</u> | 254 | TCTATATTCTCTCCTTATTCGGCTATACTTAT | 273 | <u>GCTCGCTCTTTTCTTCCCGTACTCTTCTGCTCATTGGTACTGGTCTTGGTACGGTGGTGGTATGG</u> | 296 |
| 4815 | sb184 | B | GGCTTCAACTTTCTTCTTCTTC<u>TATG</u> | 248 | TCTATTCTCTTCTTCTTACGGTTACACTTAT | 274 | <u>GCTCGCGGTTGGTGGTTGGTACCGCGGTCCGGGTGGTGGTTTTGACTAC</u> | 297 |
| 4816 | sb185 | B | GGCTTCAACTTTCTTCTTCTTC<u>TATA</u> | 248 | TCTATTCTCTTCTTCTTATGGCTATACTTAT | 267 | <u>GCTCGCGGGTTGGTGGTTACCTGCTTACTCTGTTTACTGGTTCGGTGGTCATGCTTCTTACGGTTTGGACTAC</u> | 298 |
| 4817 | sb186 | ND | GGCTTCAACTTTCTTCTTCTTC<u>TATA</u> | 248 | TCTATTCTCTTCTTCTTATGGCTATACTTAT | 267 | <u>GCTCGCCGGGTTACCCGTCTTCTGGTGCTGCTTGGTTCTGGTTCTCCGGGGTTCTGCTATGGACTAC</u> | 299 |
| 4818 | sb187 | B | GGCTTCAACATTTCTTACTCTTC<u>TATT</u> | 255 | TCTATTCTCTCCTTATTCTGGCTATACTTAT | 273 | <u>GCTCGCTCTGTCATTCTGTTTACTGGTGGTGGTCATTCGGTATGGACTAC</u> | 300 |

TABLE 3C-continued

Heavy chain CDR nucleotide sequences for additional αKlotho antibodies (sequences encoding IMGT CDR residues are underlined, sequences encoding IMGT framework region residues are not underlined)

| clone ID | name | Epitope | CDR-H1 | SEQ ID NO: CDR-H1 | CDR-H2 | SEQ ID NO: CDR-H2 | CDR-H3 | SEQ ID NO: CDR-H3 |
|---|---|---|---|---|---|---|---|---|
| 4819 | sb188 | C | GGCTTCAACATCTATTCTTATTC TATG | | TCTATTTATTATCCTTCTCTAGCTATACTTAT | 256 | GCTCGCGCTGGTTACTTCTGCTTACTACTCTTCTTGGGGTGCTATGG ACTAC | 275 |
| 4820 | sb189 | B | GGCTTCAACATCTCTTCTTATTA TATG | | TCTATTTATTCTTCTTTATAGCTCTACTTAT | 257 | GCTCGCGGTGCTTGGGCTATGGACTAC | 276 |
| 4821 | sb190 | B | GGCTTCAACCTCTATTATTCTTA TATG | | TCTATTTCTCCTTATTCTGGCTCTACTTAT | 251 | GCTCGCTCTGTTTCTTCTTGGTGGTGGTTGTTTCTTACGCTTTTG ACTAC | 277 |
| 4822 | sb191 | B | GGCTTCAACTTTTCTTCTTCTTC TATA | | TCTATTTCTTCTTCTTTATGGCTATACTTAT | 248 | GCTCGCGCTGGTTGGTACTCTTCTTGGTGTGGTCTGCTTGGGGTGCT GGTGGTGGTTTGGACTAC | 267 |
| 4823 | sb192 | B | GGCTTCAACTTTTCTTCTTCTTC TATA | | TATATATTTATTCTTCTTATGGCTATACTTAT | 248 | GCTCGCGCTGCTCATTACGGTTACTACGTTCATTCTGGTTTGGACTAC | 278 |
| 4824 | sb193 | B | GGCTTCAACCTCTTCTCTTCTTC TATA | | TCTATTTCTCCTTCTCTTATGGCTATACTTAT | 258 | GCTCGCCATGGTTACGGTTACTTCTTCTGGGGTTACTACGGTCCGGGT TCTGCTATGGACTAC | 267 |
| 4825 | sb194 | B | GGCTTCAACCTCTATTCTTCTTC TATC | | TCTATTTCTCCTTATATAGCTATACTTAT | 253 | GCTCGCTCTGTTTACTTCTTGGTACTACTCTTGGGGTCCGGGTTCTG CTTTGGACTAC | 279 |
| 4826 | sb195 | B | GGCTTCAACATCTCTTCTTATTA TATG | | TCTATTTCTTCTTCTTTATGGCTATACTTAT | 257 | GCTCGCGGTTACCCGGCTTCTTCTTACTACTACCCGTCTTCTGCTTGG ACTAC | 267 |

TABLE 3C-continued

Heavy chain CDR nucleotide sequences for additional αKlotho antibodies (sequences encoding IMGT CDR residues are underlined, sequences encoding IMGT framework region residues are not underlined)

| clone ID | name | Epitope | CDR-H1 | SEQ ID NO: CDR-H2 | CDR-H2 | SEQ ID NO: CDR-H3 | CDR-H3 | SEQ ID NO: |
|---|---|---|---|---|---|---|---|---|
| 4827 | sb196 | B | GGCTTCAACTTTTCTTCTTCTTC<u>TATA</u> | 248 | <u>TATATATTTCTTCTTCTTCTCTGGCTCTACTTCT</u> | 280 | GCTCGCGCTTACCATTCTTACTTCTACGGTTCTTACTGGTCTTACGGTT<u>GGGCTGGTGCTTTGGACTAC</u> | 309 |
| 4828 | sb197 | ND | GGCTTCAACTTTTCTTCTTCTTC<u>TATA</u> | 248 | <u>TATATATTTCTTCTTCTTCTCTGGCTCTACTTCT</u> | 267 | GCTCGCTACGTTGTTGGTGGTACCATTACGGTATGGACTAC | 310 |
| 4829 | sb198 | B | GGCTTCAACATCTCTTCTTC<u>TATTA</u> | 259 | <u>TCTATTTATTCTTCTTATGGCTATACTTAT</u> | 281 | GCTCGCTACTCTTGGTCTCCGTACTGGTGGTGGGCTTACTCTGGTTTG<u>GACTAC</u> | 311 |
| 4830 | sb199 | C | GGCTTCAACATCTATTATTCTTC<u>TATC</u> | 260 | <u>TCTATTTATCCTTATTATAGCTATACTTAT</u> | 282 | GCTCGCTCGTCTTGTTGCTTCTGCTTTGGACTAC | 312 |
| 4831 | sb200 | C | GGCTTCAACATCTATTCTTCTTC<u>TATC</u> | 261 | <u>TCTATTTATCCTTATTCTGGCTATACTTAT</u> | 283 | GCTCGCTACTCTTGGGGTTCTTCTTTCTGGCCGGTTACGGTTTTGACT<u>AC</u> | 313 |
| 4832 | sb201 | B | GGCTTCAACTTTTCTTCTTCTTC<u>TATA</u> | 248 | <u>TATATATTTCTTCTTCTTCTCTGGCTATACTTCT</u> | 284 | GCTCGCGCTTCTGGTTGGTTCTCTCATTTCTACCCGGCTGCTGTTTCTG<u>GTATGGACTAC</u> | 314 |
| 4833 | sb202 | B | GGCTTCAACCTCTCCTTCTTCTTA<u>TATG</u> | 262 | <u>TCTATTTATCCTTCTTATAGCTCTACTTAT</u> | 285 | GCTCGCTCGTCTTCTTACTCTGTTTACTTCTGGTGGTACGTTTCTGCTA<u>ACTAC</u> | 315 |
| 4834 | sb203 | B | GGCTTCAACTTTTCTTCTTCTTC<u>TATA</u> | 248 | <u>TATATATTTCTTCTTCTTCTATGGCTATACTTAT</u> | 267 | GCTCGCGCTGTTCTTTTCTACTACTGGGCTTGGTACGGTCCGGGTTTC<u>GCTATGGACTAC</u> | 316 |

TABLE 3D

Light chain CDR-L3 amino acid sequences - antibodies binding epitope B of αKlotho

| clone ID | name | CDR-L3 | SEQ ID NO. | Generic formula |
|---|---|---|---|---|
| 4804 | sb173 | QQSSYSLIT | 142 | |
| 4807 | sb176 | QQSSYSLIT | 142 | |
| 4808 | sb177 | QQSSYSLIT | 142 | |
| 4815 | sb184 | QQSSYSLIT | 142 | |
| 4816 | sb185 | QQSSYSLIT | 142 | |
| 4821 | sb190 | QQSSYSLIT | 142 | |
| 4822 | sb191 | QQSSYSLIT | 142 | |
| 4823 | sb192 | QQSSYSLIT | 142 | |
| 4824 | sb193 | QQSSYSLIT | 142 | |
| 4825 | sb194 | QQSSYSLIT | 142 | |
| 4827 | sb196 | QQSSYSLIT | 142 | |
| 4832 | sb201 | QQSSYSLIT | 142 | |
| 4834 | sb203 | QQSSYSLIT | 142 | |
| 4811 | sb180 | QQGYALFT | 145 | QQGX$_1$X$_2$LX$_3$T (SEQ ID NO. 126) |
| 4812 | sb181 | QQGYWLFT | 146 | wherein X$_1$ is Y or G; X$_2$ is W, A or G and X$_3$ is F or I |
| 4829 | sb198 | QQGGGLIT | 153 | |
| 4813 | sb182 | QQAAWGGAPIT | 147 | QQAX$_1$X$_2$X$_3$X$_4$X$_5$PIT (SEQ ID NO. 127) |
| 4826 | sb195 | QQAGFFSYPIT | 152 | wherein X$_1$ is A or G; X$_2$ is W or F; X$_3$ is G or F; X$_4$ is G or S and X$_5$ is A or Y |
| 4820 | sb189 | QQSPWGAYLIT | 151 | QQSX$_1$X$_2$GX$_3$YX$_4$IT (SEQ ID NO. 129) |
| 4833 | sb202 | QQSSHGHYPIT | 156 | wherein X$_1$ is S or P; X$_2$ is H or W; X$_3$ is H or A and X$_4$ is P or L |
| 4809 | sb178 | QQSGWAYHPIT | 144 | QQSX$_1$X$_2$X$_3$YHX$_4$X$_5$X$_6$T (SEQ ID NO. 130) |
| 4805 | sb174 | QQSSGVVYHFLFT | 143 | wherein X$_1$ is S or G; X$_2$ is G or W; X$_3$ W or A; X$_4$ F or P; X$_5$ L or I and X$_6$ is F or absent |
| 4818 | sb187 | QQPYSPIT | 149 | |

TABLE 3E

Heavy chain CDR-H1 amino acid sequences - antibodies binding epitope B of αKlotho (The carboxy terminal amino acid residue of the sequences listed under column CDR-H1 correspond to IMGT VH domain position 39. Amino acid residues of IMTG CDRs are underlined and amino acid residues of IMGT framework regions are not underlined. Residues at IMGT positions which were randomized in the selection library are bold.)

| clone ID | name | CDR-H1 | SEQ ID NO. | Generic formula A | Generic formula B |
|---|---|---|---|---|---|
| 4813 | sb182 | <u>GFNLYSSSI</u> | 166 | | GFNX$_1$X$_2$X$_3$X$_4$X$_5$X$_6$ (SEQ ID NO. 121) wherein X$_1$ is L, F or I; X$_2$ is Y or S; X$_3$ is S or Y; X$_4$ is S or Y; X$_5$ is S or Y and X$_6$ is I or M |
| 4825 | sb194 | <u>GFNLYSSSI</u> | 166 | | |
| 4811 | sb180 | <u>GFNLYYSYM</u> | 164 | | |
| 4821 | sb190 | <u>GFNLYYSYM</u> | 164 | | |
| 4808 | sb177 | <u>GFNFSSSSI</u> | 161 | | |
| 4815 | sb184 | <u>GFNFSSSSI</u> | 161 | | |
| 4816 | sb185 | <u>GFNFSSSSI</u> | 161 | | |
| 4822 | sb191 | <u>GFNFSSSSI</u> | 161 | | |
| 4823 | sb192 | <u>GFNFSSSSI</u> | 161 | | |
| 4827 | sb196 | <u>GFNFSSSSI</u> | 161 | | |
| 4832 | sb201 | <u>GFNFSSSSI</u> | 161 | | |
| 4834 | sb203 | <u>GFNFSSSSI</u> | 161 | | |
| 4820 | sb189 | <u>GFNISSYYM</u> | 170 | | |
| 4826 | sb195 | <u>GFNISSYYM</u> | 170 | | |
| 4809 | sb178 | <u>GFNIYSYYI</u> | 162 | GFNIX$_1$X$_2$X$_3$X$_4$I (SEQ ID NO. 133) | |
| 4818 | sb187 | <u>GFNISYSSI</u> | 168 | wherein X$_1$ is Y or S; X$_2$ is Y or S; X$_3$ is Y or S and X$_4$ is Y or S | |
| 4829 | sb198 | <u>GFNISSYYI</u> | 171 | | |
| 4804 | sb173 | <u>GFNLYSYSI</u> | 157 | GFNLX$_1$X$_2$X$_3$X$_4$X$_5$ (SEQ ID NO. 134) | |
| 4805 | sb174 | <u>GFNLSYYSM</u> | 158 | Wherein X$_1$ is Y or S; X$_2$ is Y or S; X$_3$ is Y or S; X$_4$ is Y or S and X$_5$ is M or I | |
| 4807 | sb176 | <u>GFNLSSSYM</u> | 160 | | |
| 4812 | sb181 | <u>GFNLSSYSM</u> | 165 | | |
| 4833 | sb202 | <u>GFNLSSYYM</u> | 174 | | |
| 4824 | sb193 | <u>GFNLSSSSI</u> | 163 | | |

TABLE 3F

Heavy chain CDR-H2 amino acid sequences - antibodies binding epitope B of αKlotho (The amino terminal residue and the carboxy terminal residue of the sequences listed under column CDR-H2 correspond to IMGT VH domain positions 55 and 66, respectively. Amino acid residues of IMTG CDRs are underlined and amino acid residues of IMGT framework regions are not underlined.)

| clone ID | name | CDR-H2 | SEQ ID NO. | Generic formula A | Generic formula B |
|---|---|---|---|---|---|
| 4804 | sb173 | YISSSSGSTY | 175 | YIX$_1$SSX$_2$GX$_3$TX$_4$ (SEQ ID NO. 135) wherein X$_1$ is S or Y; X$_2$ is S or Y; X$_3$ is S or Y; X$_4$ is S or Y | X$_1$IX$_2$X$_3$X$_4$X$_5$X$_6$X$_7$TX$_8$ (SEQ ID NO. 122) wherein X$_1$ is Y or S; X$_2$ is Y or S; X$_3$ is S or P; X$_4$ is S or Y; X$_5$ is S or Y; X$_6$ is G or S; X$_7$ is Y or S and X$_8$ is Y or S |
| 4823 | sb192 | YIYSSYGYTY | 188 | | |
| 4827 | sb196 | YISSSSGSTS | 190 | | |
| 4832 | sb201 | YISSSYGYTS | 194 | | |
| 4808 | sb177 | SISSSYGYTY | 179 | | |
| 4815 | sb184 | SISSSYGYTY | 179 | | |
| 4816 | sb185 | SISSSYGYTY | 179 | | |
| 4822 | sb191 | SISSSYGYTY | 179 | | |
| 4824 | sb193 | SISSSYGYTY | 179 | | |
| 4826 | sb195 | SISSSYGYTY | 179 | | |
| 4834 | sb203 | SISSSYGYTY | 179 | | |
| 4813 | sb182 | SISPYSGYTY | 184 | | |
| 4818 | sb187 | SISPYSGYTY | 184 | | |
| 4805 | sb174 | SISSYYGSTY | 176 | SIX$_1$X$_2$X$_3$X$_4$X$_5$X$_6$TX$_7$ (SEQ ID NO. 136) wherein X$_1$ is S or Y; X$_2$ is S or P; X$_3$ is Y or S; X$_4$ is Y or S; X$_5$ is G or S; X$_6$ is S or Y and X$_7$ = Y or S | |
| 4807 | sb176 | SIYPSYGSTS | 178 | | |
| 4809 | sb178 | SIYSYYGSTS | 180 | | |
| 4811 | sb180 | SIYSSSSYTS | 182 | | |
| 4812 | sb181 | SISSYSGYTS | 183 | | |
| 4820 | sb189 | SIYSSYSSTY | 186 | | |
| 4821 | sb190 | SISPYSGSTY | 187 | | |
| 4825 | sb194 | SISPYYSYTY | 189 | | |
| 4829 | sb198 | SIYSSYGYTS | 191 | | |
| 4833 | sb202 | SIYPSYSSTY | 195 | | |

TABLE 3G

Light chain CDR-L3 amino acid sequences - antibodies binding epitope C of αKlotho (Residues at IMGT positions which were randomized in the selection library are bold).

| clone ID | name | CDR-L3 | SEQ ID NO. | Generic formula |
|---|---|---|---|---|
| 4819 | sb188 | QQGSYYWWSPIT | 150 | QQX$_1$SX$_2$YX$_3$X$_4$SPIT (SEQ ID NO. 123) wherein X$_1$ is G or Y; X$_2$ is Y or W; X$_3$ is W or Y and X$_4$ is W, Y or A |
| 4830 | sb199 | QQYSWYWYSPIT | 154 | |
| 4831 | sb200 | QQYSYYYASPIT | 155 | |
| 4814 | sb183 | QQSSPPIT | 148 | |

TABLE 3H

Heavy chain CDR-H1 amino acid sequences - antibodies binding epitope C of αKlotho (The carboxy terminal amino acid residue of the sequences listed under column CDR-H1 corresponds to IMGT VH domain position 39. Amino acid residues of IMTG CDR-H1 are underlined and amino acid residues of IMGT framework regions are not underlined. Residues at IMGT positions which were randomized in the selection library are bold.)

| clone ID | name | CDR-H1 | SEQ ID NO. | Generic formula |
|---|---|---|---|---|
| 4830 | sb199 | GFNIYYSSI | 172 | GFNX$_1$YX$_2$X$_3$SX$_4$ (SEQ ID NO. 124) wherein X$_1$ is I or L, X$_2$ is Y or S; X$_3$ is S or Y and X$_4$ is I or M |
| 4831 | sb200 | GFNIYSSSI | 173 | |
| 4819 | sb188 | GFNIYSYSM | 169 | |
| 4814 | sb183 | GFNLYSYSM | 167 | |

TABLE 3I

Heavy chain CDR-H2 amino acid sequences - antibodies binding epitope C of αKlotho (The amino terminal residue and the carboxy terminal residue of the sequences listed under column CDR-H2 correspond to IMGT VH domain positions 55 and 66, respectively. Amino acid residues of IMTG CDR-H2 are underlined and amino acid residues of IMGT framework regions are not underlined.)

| clone ID | name | CDR-H2 | SEQ ID NO. | Generic formula |
|---|---|---|---|---|
| 4819 | sb188 | SIYPSSSYTY | 185 | SIX$_1$PX$_2$X$_3$X$_4$YTY (SEQ ID NO. 125) wherein X$_1$ is S or Y, X$_2$ is S or Y; X$_3$ is S or Y and X$_4$ is S or G |
| 4830 | sb199 | SIYPYYSYTY | 192 | |
| 4831 | sb200 | SIYPYSGYTY | 193 | |
| 4814 | sb183 | SISPYSGYTY | 184 | |

TABLE 4

Example of full length sequences for additional αKlotho antibodies

Light chain (hK) amino acid sequence: SEQ ID NO: 317
DIQMTQSPSSLSASVGDRVTITCRAS<u>QSVSSA</u>VAWYQQKPGKAPKLUYS<u>ASS</u>LYSGVPSRFSGSRSGTDF
TLTISSLQPEDFATYYCQQSSYSLITFGQGTKVEIKR*TVAAPSVF1FPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC*

Light Chain (hK) nucleic acid sequence: SEQ ID NO: 318
GATATCCAGATGACCCAGTCCCCGAGCTCCCTGTCCGCCTCTGTGGGCGATAGGGTCACCATCACCTGCCGTGCCAGT<u>CAGTC
CGTGTCCAGCGCTGTAGCCTGGTATCAACAGAAACCAGGAAAAGCTCCGAAGCTTCTGATTTACT<u>CGGCATCC</u>AGCCTCTAC
TCTGGAGTCCCTTCTCGCTTCTCTGGTAGCCGTTCCGGGACGGATTTCACTCTGACCATCAGCAGTCTGCAGCCGGAAGACTT
CGCAACTTATTACTGT<u>CAGCAATCTTCTTATTCTCTGATCA</u>CGTTCGGACAGGGTACCAAGGTGGAGAT*CAAACGTACGGT
GGCTGCACCATCTGTCTTCATCTTCCCGCCATCTGATGAGCAGTTGAAATCTGGAACTGCCTCTGTTGTGTGCCTGCTGAATAACT
TCTATCCCAGAGAGGCCAAAGTACAGTGGAAGGTGGATAACGCCCTCCAATCGGGTAACTCCCAGGAGAGTGTCACAGAGCAGGAC
AGCAAGGACAGCACCTACAGCCTCAGCAGCACCCTGACGCTGAGCAAAGCAGACTACGAGAAACACAAAGTCTACGCCTGCGAAGT
CACCCATCAGGGCCTGAGCTCGCCCGTCACAAAGAGCTTCAACAGGGGAGAGTGT*

Heavy chain (hG1) amino acid sequence: SEQ ID NO: 319
EVQLVESGGGLVQPGGSLRLSCAAS<u>GFNLYSYSI</u>HVVVRQAPGKGLEWVA<u>YISSSSGSTY</u>YADSVKGRFTI
SADTSKNTAYLQMNSLRAEDTAVYYCAR<u>GWGGGYWFYPVYGI</u>DYWGQGTLVTVSS*ASTKGPSVFPLA
PSSKSTSGGTAALGCLVKDYFPEPVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGK*

Heavy chain (hG1) nucleic acid sequence: SEQ ID NO: 320
GAGGTTCAGCTGGTGGAGTCTGGCGGTGGCCTGGTGCAGCCAGGGGGCTCACTCCGTTTGTCCTGTGCAGCTTCT**GGCTTCA
ACCTCTATTCTTATTCTATCCACTGGGTGCGTCAGGCCCCGGGTAAGGGCCTGGAATGGGTTGCATATATTTCTTCTTCT
TCTGGCTCTACTTAT**TATGCCGATAGCGTCAAGGGCCGTTTCACTATAAGCGCAGACACATCCAAAAACACAGCCTACCTA
CAAATGAACAGCTTAAGAGCTGAGGACACTGCCGTCTATTATTGTGCT**CGCGGTTGGGGTGGTGGTTACTGGTTCTACCC
GGTTTACGGTATT**GACTACTGGGGTCAAGGAACCCTGGTCACCGTCTCCTCGGCTAGCACCAAGGGCCCATCGGTCTTCCCCC
TGGCACCCTCCTCCAAGAGCACCTCTGGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACACCAAGGTGGACAAGAA
AGTTGAGCCCAAATCTTGTGACAAAACTCACACATGCCCACCGTGCCCAGCACCTGAACTCCTGGGGGGACCGTCAGTCTTCCTCT
TCCCCCCAAAACCCAAGGACACCCTCATGATCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAAGCCGCGGGAGGAGCAGTACAACAGCACGT
ACCGTGTGGTCAGCGTCCTCACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAGGTGTACACCCTGCCCCCATCCCGGGAGGA
GATGACCAAGAACCAGGTCAGCCTGACCTGCCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCTTCCTCTACAGCAAGCTCACCGTGGACAAG
AGCAGGTGGCAGCAGGGGAACGTCTTCTCATGCTCCGTGATGCATGAGGCTCTGCACAACCACTACACGCAGAAGAGCCTCTCCCT
GTCTCCGGGTAAA*

Underlined identifies CDR sequence;
Bold identifies residues at IMGT positions which were randomized in the selection library (Antibody #4804 shown as example here);
Italics represent constant domain sequence

TABLE 5

Summary of binding characteristics of additional αKlotho antibodies

| ID | name | affinity | epitope group |
|---|---|---|---|
| 48 | sb106 | 1.9 nM | A |
| 4804 | sb173 | 770 pM | B |
| 4805 | sb174 | 240 pM | B |
| 4806 | sb175 | 2.7 nM | nd |
| 4807 | sb176 | 6.1 nM | B |
| 4808 | sb177 | 1.6 nM | B |
| 4809 | sb178 | 845 pM | B |
| 4810 | sb179 | 1.9 nM | nd |
| 4811 | sb180 | 2.3 nM | B |
| 4812 | sb181 | 885 pM | B |
| 4813 | sb182 | 5.2 nM | B |
| 4814 | sb183 | 4.7 nM | C |
| 4815 | sb184 | 360 pM | B |
| 4816 | sb185 | 3.7 nM | B |
| 4817 | sb186 | 4.1 nM | nd |
| 4818 | sb187 | 2.1 nM | B |
| 4819 | sb188 | 550 pM | C |
| 4820 | sb189 | 2.7 nM | B |
| 4821 | sb190 | 5.1 nM | B |
| 4822 | sb191 | 8.7 nM | B |
| 4823 | sb192 | 1.6 nM | B |
| 4824 | sb193 | 3.5 nM | B |
| 4825 | sb194 | nd | B |
| 4826 | sb195 | 3.3 nM | B |
| 4827 | sb196 | 5.6 nM | B |
| 4828 | sb197 | 4.9 nM | nd |
| 4829 | sb198 | 1.8 nM | B |
| 4830 | sb199 | 2.9 nM | C |
| 4831 | sb200 | 1.6 nM | C |
| 4832 | sb201 | 515 pM | B |
| 4833 | sb202 | 1.4 nM | B |
| 4834 | sb203 | 1.1 nM | B |

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Kuro-o M, Matsumura Y, Aizawa H, et al. (1997) Mutation of the mouse klotho gene leads to a syndrome resembling ageing. *Nature* 390: 45-51.
2. Nabeshima Y. (2002) Klotho: a fundamental regulator of aging. *Ageing Res Rev* 1: 627-638.
3. Matsumura Y, Aizawa H, Shiraki-Iida T, Nagai R, Kuro-o M, Nabeshima Y. (1998) Identification of the human klotho gene and its two transcripts encoding membrane and secreted klotho protein. *Biochem Biophys Res Commun* 242: 626-630.
4. Ben-Dov I Z, Galitzer H, Lavi-Moshayoff V, Goetz R, Kuro-o M, Mohammadi M, Sirkis R, Naveh-Many T, Silver J. (2007) The parathyroid is a target organ for FGF23 in rats. *J Clin Invest* 117: 4003-4008.
5. Ito S, Kinoshita S, Shiraishi N, Nakagawa S, Sekine S, Fujimori T, Nabeshima Y I. (2000) Molecular cloning and expression analyses of mouse betaklotho, which encodes a novel Klotho family protein. *Mech Dev* 98: 115-119.
6. Kuro-o M. (2012) Klotho and betaKlotho. *Adv Exp Med Biol* 728: 25-40.
7. Hu M C, Shi M, Zhang J, et al. Klotho: a novel phosphaturic substance acting as an autocrine enzyme in the renal proximal tubule. *FASEB J* 2010; 24(9):3438-3450
8. Kato Y, Arakawa E, Kinoshita S, et al. Establishment of the anti-Klotho monoclonal antibodies and detection of Klotho protein in kidneys. *Biochem Biophys Res Commun* 2000; 267(2):597-602
9. Goetz R, Nakada Y, Hu M C, et al. Isolated C-terminal tail of FGF23 alleviates hypophosphatemia by inhibiting FGF23-FGFR-Klotho complex formation. *Proc Natl Acad Sci USA* 2010; 107(1):407-412
10. Kurosu H, Ogawa Y, Miyoshi M, et al. Regulation of fibroblast growth factor-23 signaling by klotho. *J Biol Chem* 2006; 281(10):6120-6123
11. Urakawa I, Yamazaki Y, Shimada T, et al. Klotho converts canonical FGF receptor into a specific receptor for FGF23. *Nature* 2006; 444(7120):770-774
12. Hu M C, Shi M, Zhang J, et al. Klotho deficiency causes vascular calcification in chronic kidney disease. *J Am Soc Nephrol* 2011; 22(1):124-136
13. Imura A, Iwano A, Tohyama O, et al. Secreted Klotho protein in sera and CSF: implication for post-translational cleavage in release of Klotho protein from cell membrane. *FEBS Lett* 2004; 565(1-3):143-147
14. Bloch L, Sineshchekova O, Reichenbach D, et al. Klotho is a substrate for alpha-, beta- and gamma-secretase. *FEBS Lett* 2009; 583(19):3221-3224
15. Chen C D, Podvin S, Gillespie E, et al. Insulin stimulates the cleavage and release of the extracellular domain of Klotho by ADAM10 and ADAM17. *Proc Natl Acad Sci USA* 2007; 104(50):19796-19801
16. Hu M C, Shi M, Zhang J, et al. Renal production and metabolism of circulating Klotho. Submitted
17. Hu M C, Kuro-o M, Moe O W. Secreted klotho and chronic kidney disease. *Adv Exp Med Biol* 2012; 728: 126-157
18. Aizawa H, Saito Y, Nakamura T, et al. Downregulation of the Klotho gene in the kidney under sustained circulatory stress in rats. *Biochem Biophys Res Commun* 1998; 249(3):865-871
19. Cheng M F, Chen L J, Cheng J T. Decrease of Klotho in the kidney of streptozotocin-induced diabetic rats. *J Biomed Biotechnol* 2010; 2010:513853
20. Haruna Y, Kashihara N, Satoh M, et al. Amelioration of progressive renal injury by genetic manipulation of Klotho gene. *Proc Natl Acad Sci USA* 2007; 104(7):2331-2336
21. Koh N, Fujimori T, Nishiguchi S, et al. Severely reduced production of klotho in human chronic renal failure kidney. *Biochem Biophys Res Commun* 2001; 280(4): 1015-1020
22. Mitani H, Ishizaka N, Aizawa T, et al. In vivo klotho gene transfer ameliorates angiotensin II-induced renal damage. *Hypertension* 2002; 39(4):838-843
23. Wang Y, Sun Z. Klotho gene delivery prevents the progression of spontaneous hypertension and renal damage. *Hypertension* 2009; 54:810-817
24. Zhao Y, Banerjee S, Dey N, et al. Klotho depletion contributes to increased inflammation in kidney of the db/db mouse model of diabetes via RelA (serine)536 phosphorylation. *Diabetes* 2011; 60(7):1907-1916
25. Hu M C, Shi M, Zhang J, et al. Klotho deficiency is an early biomarker of renal ischemia-reperfusion injury and its replacement is protective. *Kidney Int* 2010; 78(12): 1240-1251
26. Hu M C, Moe O W. Klotho as a potential biomarker and therapy for acute kidney injury. *Nat Rev Nephrol* 2012; 8(7):423-429
27. Goetz R, Beenken A, Ibrahimi O A, et al. (2007) Molecular insights into the klotho-dependent, endocrine mode of action of fibroblast growth factor 19 subfamily members. *Mol Cell Biol* 27: 3417-3428.
28. Shimada T, Kakitani M, Yamazaki Y, Hasegawa H, Takeuchi Y, Fujita T, Fukumoto S, Tomizuka K, Yamashita T. (2004) Targeted ablation of Fgf23 demonstrates an essential physiological role of Fgf23 in phosphate and vitamin D metabolism. *J Clin Invest* 113: 561-568.
29. Ichikawa S, Imel E A, Kreiter M L, et al. (2007) A homozygous missense mutation in human KLOTHO causes severe tumoral calcinosis. *J Clin Invest* 117: 2684-2691.
30. Kuro-o M. (2010) Overview of the FGF23-Klotho axis. *Pediatr Nephrol* 25: 583-590.
31. Kurosu H, Kuro O M. (2009) The Klotho gene family as a regulator of endocrine fibroblast growth factors. *Mol Cell Endocrinol* 299: 72-78.
32. Ayodele O E, Alebiosu C O. (2010) Burden of chronic kidney disease: an international perspective. *Adv Chronic Kidney Dis* 17: 215-224.
33. Soni R K, Weisbord S D, Unruh M L. (2010) Health-related quality of life outcomes in chronic kidney disease. *Curr Opin Nephrol Hypertens* 19: 153-159.
34. Trivedi H. (2010) Cost implications of caring for chronic kidney disease: are interventions cost-effective? *Adv Chronic Kidney Dis* 17: 265-270.
35. Ganesh S K, Stack A G, Levin N W, Hulbert-Shearon T, Port F K. (2001) Association of elevated serum PO(4), 35. CaxPO(4) product, and parathyroid hormone with cardiac mortality risk in chronic hemodialysis patients. *J Am Soc Nephrol* 12: 2131-2138.
36. Tonelli M, Curhan G, Pfeffer M, Sacks F, Thadhani R, Melamed M L, Wiebe N, Muntner P. (2009) Relation between alkaline phosphatase, serum phosphate, and all-cause or cardiovascular mortality. *Circulation* 120: 1784-1792.
37. Gutierrez O, Isakova T, Rhee E, Shah A, Holmes J, Collerone G, Juppner H, Wolf M. (2005) Fibroblast growth factor-23 mitigates hyperphosphatemia but accentuates calcitriol deficiency in chronic kidney disease. *J Am Soc Nephrol* 16: 2205-2215.
38. Asai O, Nakatani K, Tanaka T, et al. Decreased renal alpha-Klotho expression in early diabetic nephropathy in humans and mice and its possible role in urinary calcium excretion. Kidney Int 2012; 81(6):539-547
39. Akimoto T, Kimura T, Watanabe Y, et al. The impact of nephrectomy and renal transplantation on serum levels of soluble Klotho protein. Transplant Proc 2013; 45(1):134-136
40. Akimoto T, Shiizaki K, Sugase T, et al. The relationship between the soluble Klotho protein and the residual renal function among peritoneal dialysis patients. Clin Exp Nephrol 2012; 16(3):442-447
41. Akimoto T, Yoshizawa H, Watanabe Y, et al. Characteristics of urinary and serum soluble Klotho protein in patients with different degrees of chronic kidney disease. BMC Nephrol 2012; 13:155
42. Carpenter T O, Insogna K L, Zhang J H, et al. Circulating Levels of Soluble Klotho and FGF23 in X-Linked Hypophosphatemia: Circadian Variance, Effects of Treatment, and Relationship to Parathyroid Status. J Clin Endocrinol Metab 2010; 95(11):E352-357
43. Crasto C L, Semba R D, Sun K, et al. Relationship of low-circulating "anti-aging" klotho hormone with disability in activities of daily living among older community-dwelling adults. Rejuvenation Res 2012; 15(3):295-301
44. Devaraj S, Syed B, Chien A, et al. Validation of an immunoassay for soluble klotho protein: decreased levels in diabetes and increased levels in chronic kidney disease. Am J Clin Pathol 2012; 137(3):479-485
45. Fliser D, Seiler S, Heine G H, et al. Measurement of serum soluble Klotho levels in CKD 5D patients: useful tool or dispensable biomarker? Nephrol Dial Transplant 2012; 27(5):1702-1703
46. Heijboer A C, Blankenstein M A, Hoenderop J, et al. Laboratory aspects of circulating alpha-Klotho. Nephrol Dial Transplant 2013; 28(9):2283-2287
47. Kacso I M, Bondor C I, Kacso G. Soluble serum Klotho in diabetic nephropathy: relationship to VEGF-A. Clin Biochem 2012; 45(16-17):1415-1420
48. Kim H R, Nam B Y, Kim D W, et al. Circulating alpha-Klotho levels in CKD and relationship to progression. Am J Kidney Dis 2013; 61(6):899-909
49. Kitagawa M, Sugiyama H, Morinaga H, et al. A decreased level of serum soluble Klotho is an independent biomarker associated with arterial stiffness in patients with chronic kidney disease. PLoS One 2013; 8(2): e56695
50. Komaba H, Koizumi M, Tanaka H, et al. Effects of cinacalcet treatment on serum soluble Klotho levels in haemodialysis patients with secondary hyperparathyroidism. Nephrol Dial Transplant 2012; 27(5):1967-1969
51. Pavik I, Jaeger P, Ebner L, et al. Soluble klotho and autosomal dominant polycystic kidney disease. Clin J Am Soc Nephrol 2012; 7(2):248-257
52. Pavik I, Jaeger P, Ebner L, et al. Secreted Klotho and FGF23 in chronic kidney disease Stage 1 to 5: a sequence suggested from a cross-sectional study. Nephrol Dial Transplant 2013; 28(2):352-359
53. Seiler S, Wen M, Roth H J, et al. Plasma Klotho is not related to kidney function and does not predict adverse outcome in patients with chronic kidney disease. Kidney Int 2013; 83(1):121-128
54. Shimamura Y, Hamada K, Inoue K, et al. Serum levels of soluble secreted alpha-Klotho are decreased in the early stages of chronic kidney disease, making it a probable novel biomarker for early diagnosis. Clin Exp Nephrol 2012; 16(5):722-729
55. Siahanidou T, Garatzioti M, Lazaropoulou C, et al. Plasma soluble alpha-Klotho protein levels in premature and term neonates: correlations with growth and metabolic parameters. Eur J Endocrinol 2012; 167(3):433-440
56. Sugiura H, Tsuchiya K, Nitta K. Circulating levels of soluble alpha-Klotho in patients with chronic kidney disease. Clin Exp Nephrol 2011; 15(5):795-796
57. Wan M, Smith C, Shah V, et al. Fibroblast growth factor 23 and soluble klotho in children with chronic kidney disease. Nephrol Dial Transplant 2013; 28(1):153-161
58. Yamazaki Y, Imura A, Urakawa I, et al. Establishment of sandwich ELISA for soluble alpha-Klotho measurement: Age-dependent change of soluble alpha-Klotho levels in healthy subjects. Biochem Biophys Res Commun 2010; 398(3):513-518
59. Yokoyama K, Imura A, Ohkido I, et al. Serum soluble alpha-Klotho in hemodialysis patients. Clin Nephrol 2012; 77(5):347-351
60. Semba R D, Cappola A R, Sun K, et al. Plasma klotho and mortality risk in older community-dwelling adults. J Gerontol A Biol Sci Med Sci 2011; 66(7):794-800
61. Doi S, Zou Y, Togao O, et al. Klotho inhibits transforming growth factor-beta1 (TGF-beta1) signaling and suppresses renal fibrosis and cancer metastasis in mice. J Biol Chem 2011; 286(10):8655-8665
62. Ohyama Y, Kurabayashi M, Masuda H, et al. Molecular cloning of rat klotho cDNA: markedly decreased expression of klotho by acute inflammatory stress. Biochemical And Biophysical Research Communications 1998; 251(3):920-925
63. Sugiura H, Yoshida T, Mitobe M, et al. Klotho reduces apoptosis in experimental ischaemic acute kidney injury via HSP-70. Nephrol Dial Transplant 2010; 25(1):60-68
64. Sugiura H, Yoshida T, Tsuchiya K, et al. Klotho reduces apoptosis in experimental ischaemic acute renal failure. Nephrol Dial Transplant 2005; 20(12):2636-2645
65. Moreno J A, Izquierdo M C, Sanchez-Nino M D, et al. The inflammatory cytokines TWEAK and TNFalpha reduce renal klotho expression through NFkappaB. J Am Soc Nephrol 2011; 22(7):1315-1325
66. Goldstein S L. Acute kidney injury biomarkers: renal angina and the need for a renal troponin I. BMC Med 2011; 9:135
67. Fellouse F A, Esaki K, Birtalan S, et al. High-throughput generation of synthetic antibodies from highly functional minimalist phage-displayed libraries. J Mol Biol 2007; 373(4):924-940
68. Gao J, Sidhu S S, Wells J A. Two-state selection of conformation-specific antibodies. Proc Natl Acad Sci USA 2009; 106(9):3071-3076
69. Koellhoffer J F, Chen G, Sandesara R G, et al. Two synthetic antibodies that recognize and neutralize distinct proteolytic forms of the ebola virus envelope glycoprotein. Chembiochem 2012; 13(17):2549-2557

70. Li B, Russell S J, Compaan D M, et al. Activation of the proapoptotic death receptor DR5 by oligomeric peptide and antibody agonists. J Mol Biol 2006; 361(3):522-536
71. Uysal S, Vasquez V, Tereshko V, et al. Crystal structure of full-length KcsA in its closed conformation. Proc Natl Acad Sci USA 2009; 106(16):6644-6649
72. Ibrahimi O A, Zhang F, Eliseenkova A V, et al. Biochemical analysis of pathogenic ligand-dependent FGFR2 mutations suggests distinct pathophysiological mechanisms for craniofacial and limb abnormalities. Hum Mol Genet 2004; 13(19):2313-2324
73. Plotnikov A N, Hubbard S R, Schlessinger J, et al. Crystal structures of two FGF-FGFR complexes reveal the determinants of ligand-receptor specificity. Cell 2000; 101(4):413-424
74. Persson H, Ye W, Wernimont A, et al. CDR-H3 diversity is not required for antigen recognition by synthetic antibodies. J Mol Biol 2013; 425(4):803-811
75. Rajan S, Sidhu S S. Simplified synthetic antibody libraries. Methods Enzymol 2012; 502:3-23
76. Colwill K, Graslund S. A roadmap to generate renewable protein binders to the human proteome. Nat Methods 2011; 8(7):551-558
77. Olsen S K, Garbi M, Zampieri N, et al. Fibroblast growth factor (FGF) homologous factors share structural but not functional homology with FGFs. J Biol Chem 2003; 278(36):34226-34236
78. Kurosu H, Choi M, Ogawa Y, et al. Tissue-specific expression of betaKlotho and fibroblast growth factor (FGF) receptor isoforms determines metabolic activity of FGF19 and FGF21. J Biol Chem 2007; 282(37):26687-26695
79. Kurosu H, Yamamoto M, Clark J D, et al. Suppression of aging in mice by the hormone Klotho. Science 2005; 309(5742):1829-1833
80. Kuro-o M, Matsumura Y, Aizawa H, et al. Mutation of the mouse klotho gene leads to a syndrome resembling ageing. Nature 1997; 390(6655):45-51
81. Hu M C, Shiizaki K, Kuro-o M, et al. Physiology and pathophysiology of an endocrine network of mineral metabolism. Ann Rev Phys 2013; 75:503-533
82. Hu M C, Kuro-o M, Moe O W. Renal and extrarenal actions of Klotho. Semin Nephrol 2013; 33(2)118-129
83. Pedersen L, Pedersen S M, Brasen C L, et al. Soluble serum Klotho levels in healthy subjects. Comparison of two different immunoassays. Clin Biochem 2013; 46(12):1079-1083
84. Grams M E, Chow E K, Segev D L, Coresh J. Lifetime incidence of CKD stages 3-5 in the United States. Am J Kidney Dis. 2013 August; 62(2):245-52.
85. Lefranc et al. IMGT unique numbering for immunoglobulin and T cell receptor variable domains and Ig superfamily V-like domains. Development and Comparative Immunology. 2003; 27:55-77.
86. Barker S L, Pastor J, Carranza D, et al. The demonstration of αKlotho deficiency in human chronic kidney disease with a novel synthetic antibody. Nephrology Dialysis Transplantation. 2015 February; 30(2):223-33.

The invention claimed is:

1. An antibody or binding fragment thereof that specifically binds an αKlotho polypeptide, wherein the antibody or binding fragment thereof comprises:
- a VL domain, wherein the VL domain comprises a complementarity determining region (CDR) L1, a CDR-L2 and a CDR-L3, and wherein the CDR-L1, the CDR-L2 and the CDR-L3 comprise the amino acid sequences QSVSSA (SEQ ID NO: 140), SAS (SEQ ID NO: 141), and QQSSYSLIT (SEQ ID NO: 142), respectively; and
- a VH domain, wherein the VH domain comprises a CDR-H1, a CDR-H2 and a CDR-H3; and wherein the VH domain is selected from the group consisting of:
  - (i) a VH domain wherein the CDR-H1, the CDR-H2 and the CDR-H3 comprise amino acid sequences GFNLYSYS (residues 1 to 8 of SEQ ID NO: 157), ISSSSGST (residues 2 to 9 of SEQ ID NO: 175), and ARGWGGGYWFYPVYGIDY (SEQ ID NO: 196), respectively;
  - (ii) a VH domain wherein the CDR-H1, the CDR-H2 and the CDR-H3 comprise amino acid sequences GFNISSSS (residues 1 to 8 of SEQ ID NO: 159), ISSYSST (residues 2 to 9 of SEQ ID NO: 177), and ARSGGGYYHWWVVPYAMDY (SEQ ID NO: 198), respectively;
  - (iii) a VH domain wherein the CDR-H1, the CDR-H2 and the CDR-H3 comprise amino acid sequences GFNLSSSY (residues 1 to 8 of SEQ ID NO: 160), IYPSYGST (residues 2 to 9 of SEQ ID NO: 178), and ARGVVPSYYYWFWPYGAIDY (SEQ ID NO: 199), respectively;

(iv) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARPYSAYYWAWYGPGGALDY (SEQ ID NO: 200), respectively;

(v) a VH domain wherein the CDR-H1, the CDR-H2 and the CDR-H3 comprise amino acid sequences GFNLSSSS (residues 1 to 8 of SEQ ID NO: 163), ISPSYGST (residues 2 to 9 of SEQ ID NO: 181), and ARSGYYSGAYWHWWVVPYAMDY (SEQ ID NO: 202), respectively;

(vi) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARGFSSSAHWYWSWYGPGGGFDY (SEQ ID NO: 207), respectively;

(vii) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARGWYAAYSVYWFGGHASYGLDY (SEQ ID NO: 208), respectively;

(viii) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARGYPSSGAAWFWFSHPGSAMDY (SEQ ID NO: 209), respectively;

(ix) a VH domain wherein the CDR-H1, the CDR-H2 and the CDR-H3 comprise amino acid sequences GFNLYYSY (residues 1 to 8 of SEQ ID NO: 164), ISPYSGST (residues 2 to 9 of SEQ ID NO: 187), and ARSGFSSWWWVVSYAFDY (SEQ ID NO: 213), respectively;

(x) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARAGWYSSWWWSAWGAGGGLDY (SEQ ID NO: 214), respectively;

(xi) a VH domain wherein the CDR-H1, the CDR-H2 and the CDR-H3 comprise amino acid sequences GFNFSSSS (residues 1 to 8 of SEQ ID NO: 161), IYSSYGYT (residues 2 to 9 of SEQ ID NO: 188), and ARAAHYGYYVHSGLDY (SEQ ID NO: 215), respectively;

(xii) a VH domain wherein the CDR-H1, the CDR-H2 and the CDR-H3 comprise amino acid sequences GFNLSSSS (residues 1 to 8 of SEQ ID NO: 163), ISSSYGYT (residues 2 to 9 of SEQ ID NO: 179), and ARHGYGYFFWGYYGPGSAMDY (SEQ ID NO: 216), respectively;

(xiii) a VH domain wherein the CDR-H1, the CDR-H2 and the CDR-H3 comprise amino acid sequences GFNLYSSS (residues 1 to 8 of SEQ ID NO: 166), ISPYYSYT (residues 2 to 9 of SEQ ID NO: 189), and ARSVYSWYWSSWGPGSALDY (SEQ ID NO: 217), respectively;

(xiv) a VH domain wherein the CDR-H1, the CDR-H2 and the CDR-H3 comprise amino acid sequences GFNFSSSS (residues 1 to 8 of SEQ ID NO: 161), ISSSSGST (residues 2 to 9 of SEQ ID NO: 190), and ARAYHSYFYGSYWSYGWAGALDY (SEQ ID NO: 219), respectively;

(xv) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARYVVGGWWYHYGMDY (SEQ ID NO: 220), respectively;

(xvi) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 194), and ARASGWFSHFYPAAVSGMDY (SEQ ID NO: 224), respectively; and (xvii) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARAVSFYYWAWYGPGFAMDY (SEQ ID NO: 226), respectively.

2. The antibody or binding fragment thereof of claim 1, wherein the antibody or binding fragment thereof is selected from the group consisting of a monoclonal antibody, an immunoglobulin molecule, a Fab, a Fab', a F(ab)2, a F(ab')2, a Fv, a disulfide linked Fv, a scFv, a disulfide linked scFv, a single chain domain antibody, scFab, a diabody, a dimer, a minibody, a bispecific antibody fragment, a chimeric antibody, a humanized antibody and a polyclonal antibody.

3. The antibody or binding fragment thereof of claim 1, wherein the αKlotho polypeptide is mammalian αKlotho polypeptide, optionally human αKlotho polypeptide.

4. The antibody or binding fragment thereof of claim 1, wherein the αKlotho polypeptide is folded αKlotho polypeptide or soluble αKlotho polypeptide.

5. The antibody or binding fragment thereof of claim 4, wherein the antibody or binding fragment thereof binds soluble folded αKlotho polypeptide found in urine, plasma, and/or serum.

6. The antibody or binding fragment thereof of claim 1, wherein the antibody or binding fragment thereof binds a complex comprising folded αKlotho polypeptide.

7. The antibody or binding fragment thereof according to claim 6, wherein the folded αKlotho polypeptide forms a complex with a fibroblast growth factor (FGF) receptor, optionally FGFR1c.

8. An antibody complex comprising the antibody or binding fragment thereof of claim 1 and αKlotho polypeptide, optionally further comprising FGFR1c.

9. A composition comprising the antibody or binding fragment thereof of claim 1.

10. A kit comprising an antibody or binding fragment thereof that specifically binds an αKlotho polypeptide, a reference agent and optionally instructions for use thereof and/or b) an antibody or binding fragment having light and heavy chain variable regions comprising the amino acid sequences of SEQ ID NO: 11 and 12, respectively, wherein the antibody or binding fragment thereof comprises:
a VL domain, wherein the VL domain comprises a complementarity determining region (CDR) L1, a CDR-L2 and a CDR-L3, and wherein the CDR-L1, the CDR-L2 and the CDR-L3 comprise the amino acid sequences QSVSSA (SEQ ID NO: 140), SAS (SEQ ID NO: 141), and QQSSYSLIT (SEQ ID NO: 142), respectively; and
a VH domain, wherein the VH domain comprises a CDR-H1, a CDR-H2 and a CDR-H3; and wherein the VH domain is selected from the group consisting of:
(i) a VH domain wherein the CDR-H1, the CDR-H2 and the CDR-H3 comprise amino acid sequences GFNLYSYS (residues 1 to 8 of SEQ ID NO: 157), ISSSSGST (residues 2 to 9 of SEQ ID NO: 175), and ARGWGGGYWFYPVYGIDY (SEQ ID NO: 196), respectively;
(ii) a VH domain wherein the CDR-H1, the CDR-H2 and the CDR-H3 comprise amino acid sequences GFNISSSS (residues 1 to 8 of SEQ ID NO: 159), ISSSYSST (residues 2 to 9 of SEQ ID NO: 177), and ARSSGGGYYHWWVVPYAMDY (SEQ ID NO: 198), respectively;
(iii) a VH domain wherein the CDR-H1, the CDR-H2 and the CDR-H3 comprise amino acid sequences GFNLSSSY (residues 1 to 8 of SEQ ID NO: 160), IYPSYGST (residues 2 to 9 of SEQ ID NO: 178), and ARGVVPSYYYWFWPYGAIDY (SEQ ID NO: 199), respectively;
(iv) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARPYSAYYWAWYGPGGALDY (SEQ ID NO: 200), respectively;
(v) a VH domain wherein the CDR-H1, the CDR-H2 and the CDR-H3 comprise amino acid sequences GFNLSSSS (residues 1 to 8 of SEQ ID NO: 163), ISPSYGST (residues 2 to 9 of SEQ ID NO: 181), and ARSGYYSGAYWHWWVVPYAMDY (SEQ ID NO: 202), respectively;
(vi) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARGFSSSAHWYWSWYGPGGGFDY (SEQ ID NO: 207), respectively;
(vii) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARGWYAAYSVYWFGGHASYGLDY (SEQ ID NO: 208), respectively;
(viii) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARGYPSSGAAWFWFSHPGSAMDY (SEQ ID NO: 209), respectively;
(ix) a VH domain wherein the CDR-H1, the CDR-H2 and the CDR-H3 comprise amino acid sequences GFNLYYSY (residues 1 to 8 of SEQ ID NO: 164), ISPYSGST (residues 2 to 9 of SEQ ID NO: 187), and ARSGFSSWWWVVSYAFDY (SEQ ID NO: 213), respectively;
(x) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARAGWYSSWWWSAWGAGGGLDY (SEQ ID NO: 214), respectively;
(xi) a VH domain wherein the CDR-H1, the CDR-H2 and the CDR-H3 comprise amino acid sequences GFNFSSSS (residues 1 to 8 of SEQ ID NO: 161), IYSSYGYT (residues 2 to 9 of SEQ ID NO: 188), and ARAAHYGYYVHSGLDY (SEQ ID NO: 215), respectively;
(xii) a VH domain wherein the CDR-H1, the CDR-H2 and the CDR-H3 comprise amino acid sequences GFNLSSSS (residues 1 to 8 of SEQ ID NO: 163), ISSSYGYT (residues 2 to 9 of SEQ ID NO: 179), and ARHGYGYFFWGYYGPGSAMDY (SEQ ID NO: 216), respectively;
(xiii) a VH domain wherein the CDR-H1, the CDR-H2 and the CDR-H3 comprise amino acid sequences GFNLYSSS (residues 1 to 8 of SEQ ID NO: 166), ISPYYSYT (residues 2 to 9 of SEQ ID NO: 189), and ARSVYSWYWSSWGPGSALDY (SEQ ID NO: 217), respectively;
(xiv) a VH domain wherein the CDR-H1, the CDR-H2 and the CDR-H3 comprise amino acid sequences GFNFSSSS (residues 1 to 8 of SEQ ID NO: 161), ISSSSGST (residues 2 to 9 of SEQ ID NO: 190), and ARAYHSYFYGSYWSYGWAGALDY (SEQ ID NO: 219), respectively;
(xv) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARYVVGGWWYHYGMDY (SEQ ID NO: 220), respectively;
(xvi) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 194), and ARASGWFSHFYPAAVSGMDY (SEQ ID NO: 224), respectively; and
(xvii) a VH domain wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARAVSFYYWAWYGPGFAMDY (SEQ ID NO: 226), respectively.

11. An antibody or binding fragment thereof that specifically binds an αKlotho polypeptide, wherein the antibody or binding fragment thereof comprises:
a VL domain, wherein the VL domain comprises a complementarity determining region (CDR) L1, a CDR-L2 and a CDR-L3, and wherein the CDR-L1, the CDR-L2 and the CDR-L3 comprise the amino acid sequences QSVSSA (SEQ ID NO: 140), SAS (SEQ ID NO: 141), and QQSSYSLIT (SEQ ID NO: 142), respectively; and a VH domain, wherein the VH domain comprises a CDR-H1, a CDR-H2 and a CDR-H3; and wherein the CDR-H1, the CDR-H2 and the CDR-H3 comprise amino acid sequences GFNFSSSS (residues 1 to 8 of SEQ ID NO: 161), ISSSYGYT (residues 2 to 9 of SEQ ID NO: 179), and ARPYSAYYWAWYGPGGALDY (SEQ ID NO: 200), respectively.

12. The antibody or binding fragment thereof of claim 11, wherein the amino acids at international ImMunoGeneTics database (IMGT) positions 39, 55 and 66 of the VH domain are Ile, Ser and Tyr, respectively.

\* \* \* \* \*

UNITED STATES PATENT AND TRADEMARK OFFICE
CERTIFICATE OF CORRECTION

PATENT NO. : 10,663,474 B2
APPLICATION NO. : 16/075033
DATED : May 26, 2020
INVENTOR(S) : Sachdev S. Sidhu et al.

Page 1 of 1

It is certified that error appears in the above-identified patent and that said Letters Patent is hereby corrected as shown below:

In the Specification

Column 1, Lines 13–16, delete "This invention was made in part with U.S. Government support under NIH Grant Nos. R01DK091392, R01DK092461 and R01DE13686. The U.S. Government may have certain rights in this invention." and insert --This invention was made with government support under grant numbers DK079328 and DK091392 awarded by The National Institutes of Health. The government has certain rights in the invention.--

Signed and Sealed this
Thirtieth Day of June, 2020

Andrei Iancu
*Director of the United States Patent and Trademark Office*